United States Patent
Thomas et al.

(10) Patent No.: US 8,044,186 B2
(45) Date of Patent: Oct. 25, 2011

(54) HETEROLOGOUS PRODUCTION OF CAPREOMYCIN AND GENERATION OF NEW CAPREOMYCIN DERIVATIVES THROUGH METABOLIC ENGINEERING

(75) Inventors: Michael George Thomas, Madison, WI (US); Elizabeth Anne Felnagle, Madison, WI (US); Michelle Renee Rondon, Madison, WI (US); Andrew David Berti, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 542 days.

(21) Appl. No.: 12/118,362

(22) Filed: May 9, 2008

(65) Prior Publication Data

US 2009/0104658 A1    Apr. 23, 2009

Related U.S. Application Data

(60) Provisional application No. 60/917,628, filed on May 11, 2007.

(51) Int. Cl.
  C07H 21/02    (2006.01)
  C12P 19/62    (2006.01)
  C12N 1/12    (2006.01)
(52) U.S. Cl. .................. 536/23.1; 435/76; 435/252.1
(58) Field of Classification Search .................. None
  See application file for complete search history.

(56) References Cited

U.S. PATENT DOCUMENTS

| | | | |
|---|---|---|---|
| 4,551,433 A | 11/1985 | DeBoer | |
| 5,605,793 A | 2/1997 | Stemmer | |
| 5,811,238 A | 9/1998 | Stemmer et al. | |
| 5,830,727 A | 11/1998 | Wang et al. | |
| 5,834,252 A | 11/1998 | Stemmer et al. | |
| 5,837,458 A | 11/1998 | Minshull et al. | |
| 5,848,956 A | 12/1998 | Grettner | |
| 7,326,782 B2 | 2/2008 | Thomas et al. | |

FOREIGN PATENT DOCUMENTS

| WO | WO 93/16094 | 8/1993 |
|---|---|---|
| WO | WO 02/059322 | 8/2002 |
| WO | WO 2005/021586 | 3/2005 |
| WO | WO 2006/052499 | 5/2006 |

OTHER PUBLICATIONS

Taxonomy Browser (last viewed on Dec. 28, 2010).*
Bibb et al. (1985) "Nucleotide Sequences Encoding and Promoting Expression of Three Antibiotic Resistance Genes Indigenous to Streptomyces," *Mol. Gen. Genet.* 199:26-36.
Carter et al. (1974) "Biosynthesis of Viomycin. I. Origin of Alpha, Beta-Dianunopropionic Acid and Serine," *Biochemistry* 13:1221-1227.
Carter et al. (1974) "Biosythesis of Viomycin. II. Origin of Beta-Lysene and Viomycidine," *Biochemistry* 13:1227-1233.

(Continued)

*Primary Examiner* — Alexander Kim
(74) *Attorney, Agent, or Firm* — Greenlee Sullivan P.C.

(57) ABSTRACT

Provided are nucleic acid molecules comprising at least a functional fragment of the capreomycin biosynthetic gene cluster, polypeptides encoded by the cluster and recombinant host cells transformed with any of the nucleic acid molecules disclosed herein. Various methods using any of the vectors or expression cassettes that encode one or more of the gene products of the cluster are provided for heterologous production of capreomycin and capreomycin derivatives.

25 Claims, 5 Drawing Sheets

Capreomycin

Figure 1:
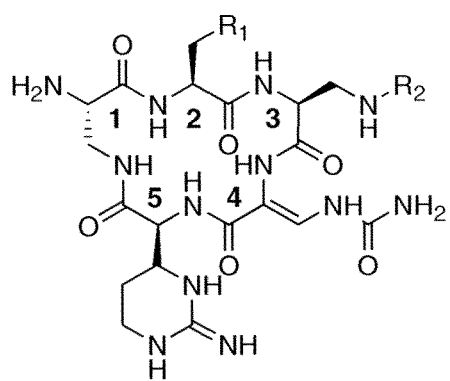
Figure 1:
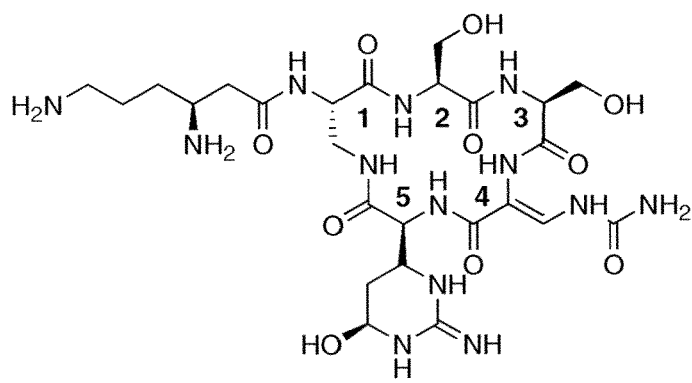

IA: $R_1 = OH$; $R_2 = H$
IB: $R_1 = H$; $R_2 = H$
IIA: $R_1 = OH$; $R_2 = \beta$-Lysine
IIB: $R_1 = H$; $R_2 = \beta$-Lysine

Viomycin

OTHER PUBLICATIONS

Chalis et al. (2000) "Predictive, Structure-Based Model of Amino Acid Recognition by Nonribosomal Peptide Synthetase Adenylation Domains," *Chem. Biol.* 7:211-224.
Copeland et al. (Apr. 2008) "Molybdopterin-guanine Dinucleotide Biosynthesis Protein B," NCBI Accession No. ABP62761.
Dirlam et al. (1997) "Cyclic Homopentapeptides 1. Analogs of Tuberactinomycins and Capreomycin with Activity Against Vancomycin-Resistant *Enterococci* and *Pasteurella*," *Biorg. Med. Chem. Lett.* 7(9):1139-1144.
Fei et al. (2007) "Roles of VioG and VioQ in the Incorporation and Modification of the Capreomycidine Residue in the Peptide Antibiotic Viomycin," *J. Nat. Prod.* 70:618-622.
Felnagle et al. (Jul. 2007) "Identification of the Biosynthetic Gene Cluster and an Additional Gene for Resistance to the Antituberculosis Drug Capreomycin," *Appl. Environ. Microbiol.* 73(13):4162-4170.
GenBank Accession No. AY225601S1, Aug. 29, 2003 [Yin].
GenBank Accession No. AY225601S2, Aug. 29, 2003 [Yin].
GenBank Accession No. AY225601S1, Aug. 5, 2003 [Yin].
GenBank Accession No. AY225601S2, Aug. 5, 2003 [Yin].
GenBank Accession No. AA066425, Aug. 29, 2003 [Yin].
GenBank Accession No. AA066425, Aug. 5, 2003 [Yin].
GenBank Accession No. AA066426, Aug. 29, 2003 [Yin].
GenBank Accession No. AA066427, Aug. 29, 2003 [Yin].
GenBank Accession No. AA066428, Aug. 29, 2003 [Yin].
GenBank Accession No. AAP92509, Aug. 25, 2003 [Thomas].
GenBank Accession No. AAP92510, Aug. 25, 2003 [Thomas].
GenBank Accession No. AY263398, Aug. 25, 2003 [Thomas].
Gould et al. (1992) "Biosynthesis of Capreomycin: 1. Incorporation of Arginine," *J. Org. Chem.* 57:5214-5217.
Heifets et al. (2005) "Capreomycin is Active Against non-Replicating *M. tuberculosis*," *Ann. Clin. Microbiol. Antimicrob.* 1:6.
International Search Report, Corresponding to International Application No. PCT/US2008/063258, Mailed Aug. 29, 2008.
International Search Report, Corresponding to International Application No. PCT/US2004/027427, Mailed Aug. 11, 2005.
Johansen et al. (2006) "Capreomycin Binds Across the Ribosomal Subunit Interface Using *tylA*-Encoded 2'-O-methylations in 16S and 23S rRNAs," *Mol. Cell* 23:173-182.
Ju et al. (2004) "Conversion of (2S)-Arginine to (2S,3R)-Capreomycidine by VioC and VioD from the Viomycin Biosynthetic Pathway of *Streptomyces* sp. Strain ATCC11861," *ChemBioChem* 5:1281-1285.
Kieser et al. (2000) "Introduction of DNA into *Streptomyces*," In; *Practical Streptomyces Genetics*, The John Innes Foundation, Norwich, UK, pp. 229-252.
Linde II et al. (1997) "Cyclic Homopentapeptides 3. Synthetic Modifications to the Capromycins and Tuberactinomycins: Compounds with Activity Against Methicillin-Resistant *Staphylococcus aureus* and Vancomycin-Resistant *Enterococci*," *Biorg. Med. Chem. Lett.* 7(9):1149-1152.
Lyssikatos et al. (1997) "Cyclic Homopentapeptides 2. Synthetic Modifications of Viomycin," *Biorg. Med. Chem. Lett.* 7(9):1145-1148.
Maus et al. (2005) "Mutation of *TlyA* Confers Capreomycin Resistance in *Mycobacterium tuberculosis*," *Antimicrob. Agents Chemother.* 49(2):571-577.
Mizuguchi et al. (1974) "Genetic and Biochemical Studies on Drug-Resistant Mutants in *Mycobacterium smematis*," *Jpn. J. Microbiol.* 18:457-462.
Mizuguchi et al. (1979) "Interaction Between 30 S Ribosomal Components in a Viomycin Resistant Mutant of *Mycobacterium smegmatis*," *Microbiol. Immunol.* 23:595-604.
Patten et al. (Dec. 1997) "Application of DNA Shuffling to Pharmaceuticals and Vaccines," *Curr. Opin. Biotech.* 8(6):724-733.
Saugar et al. (2002) "Identification of a set of Genes Involved in the Biosynthesis of the Aminonucleoside Moiety of Antibiotic A201A from *Streptomyces capreolus*," *Eur. J. Biochem.* 269:5527-5535.
Skinner et al. (1980) "Resistance to the Antibiotics Viomycin and Capreomycin in the *Streptomyces* Species which Produced them," *J. Gen. Microbiol.* 120:95-104.
Smirnova et al. (2001) "Engineered Fatty Acid Biosynthesis in *Streptomyces* by Altered Catalytic Function of Beta-Ketoacyl-Acyl Carrier Protein Synthase III," *J. Bacteriol.* 183(7):2335-2342.
Stachelaus et al. (1999) "The Specificity-Conferring Code of adenylation Domains in Nonribosomal Peptide Synthetases," *Chem. Biol.* 6:493-505.
Steffensky et al. (2000) "Identification of the Novobiocin Biosynthetic Gene Cluster of *Streptomyces spheroids* NCIB 11891," *Antimicrob. Agents Chemother.* 44:1214-1222.
Tam et al. (1972) "Laboratory Production and $^{14}$C-Labelling of Viomycin," *J. Antibiot.* 25:524-529.
Taniguchi et al. (Aug. 1997) "Molecular Analysis of Kanamycin and Viomycin Resistance in *Mycobacterium smegmatis* by Use of the Conjunction System," *J. Bacteriol.* 179:4795-4801.
Thiara et al. (1995) "Analysis of Two Capreomycin-Resistance Determinants from *Streptomyces capreolus* and Characterization of the Action of their Products," *Gene* 167:121-126.
Thiara et al. (Mar. 13, 1996) "*Streptomyces capreolus* NCIB9801 Capreomycin Phosphotransferase (cph) gene, Complete cds," Gene Bank Accession No. U13078.
Thomas et al. (2002) Conversion of L-Proline to Pyrrolyl-2-Carboxyl-S-PCP During Undecylprodigiosin and Pyoluteorin Biosynthesism, *Chem. Biol.* 9:171-184.
Thomas et al (2003) "Deciphering tuberactinomycin Biosynthesis: Isolation, Sequencing, and Annotation of the Viomycin Biosynthetic Gene Cluster," *Antimicrob. Agents Chemother.* 47(9):2823-2830.
Trauger et al. (2000) "Heterologous Expression in *Escherichia coli* of the First Module of the Nonribosomal Peptide Synthetase of Chloroeremomycin, an Vancomycin-Type Glycopeptide Antibotic," *Proc. Nat. Acad. Sci.* USA 97(7):3112-3117.
Wang et al. (1993) "Biosynthesis of Capreomycin. 2. Incorporation of L-Serine, L-Alanin, and L-2,3-diaminopropionic Acid," *J. Org. Chem.* 58:5176-5180.
Written Opinion, Corresponding to International Application No. PCT/US2008/063258, Mailed Aug. 29, 2008.
Written Opinion, Corresponding to International Application No. PCT/US2004/027427, Mailed Aug. 11, 2005.
Yamada, T. (1987) "The Role of Ribosomes in Sensitivity of Mycobacteria to Tuberactinomycin," *Microbiol. Immunol.* 31:179-181.
Yamada et al. (1978) "Viomycin Favours the Formation of 70S Ribosome Couples," *Mol. Gen. Genet.* 161:261-265.
Yamada et al. (1976) "Altered Ribosomes in Antibiotic-Resistant Mutants of *Mycobacterium smegmatis*," *Antimicrob. Agents Chemother.* 9(5):817-823.
Yamada et al. (1972) "Analysis of Ribosomes from Viomycin-Sensitive and -Resistant *Mycobecterium smegmatis*," *J. Bacteriol.* 112:1-6.
Yamada et al. (1978) "Resistance to Viomycin Conferred by RNA of Either Ribosomal Subunit," *Nature* 275:460-461.
Yamada et al. (1976) "Localization of Co-resistance to *Streptomyces*, Kanamycin, Capreomycin and Tuberctinomycin in Core Particles Derived from Ribosomes of Viomycin Resistant *Mycobacterium smegmatis*," *J. Antibiot.* 229:1124-1126.
Yamada et al. (1985) "Alteration of Ribosomes and RNA Polymerase in Drug-Resistant Clinical Isolated of *Mycobacterium tuberculosis*," *Antimicrob. Agents Chemother.* 27:921-924.
Yamada et al. (Dec. 1981) "Activity of Di-β-Lysyl-Capreomycin IIA and Palmitoyl Tuberactinamine N Against Drug-Resistant Mutants with Altered Ribosomes," *Antimicrob. Agents Chemother.* 20(6):834-836.
Yin et al. (2003) "Identification and Cloning of Genes Encoding Viomycin Biosynthesis from *Streptomycees vinaceus* and Evidence for Involvement of a Rare Oxygenase," *Gene* 312:215-224.
Yin et al. (2004) "Formation of the Nonproteinogenic Amino Acid 2S, 3R-capreomycidine by VioD from the Viomycin Biosynthesis Pathway," *ChemBioChem.* 5:1278-1281.
Yin et al. (2004) "VioC is a Non-Heme Iron, A-Ketoglutarate-Dependent Oxygenase that Catalyzes the Formation of 3S-Hydroxy-L-Arginine During Viomycin Biosynthesis," *ChemBioChem* 5:1274-1277.
Zoller et al. (1983) "Oligonucleotide-Directed Mutagenesis of DNA Fragments Cloned into M13 Vectors," *Methods Enzymol.* 100:468-500.
Barkei et al. (Dec. 22, 2009) "Investigations into Viomycon Biosynthesis by Using Heterologous Production in *Streptomyces lividans*," *ChemBioChem* 10(2):366-376.

* cited by examiner

Capreomycin

IA: $R_1$ = OH; $R_2$ = H
IB: $R_1$ = H; $R_2$ = H
IIA: $R_1$ = OH; $R_2$ = β-Lysine
IIB: $R_1$ = H; $R_2$ = β-Lysine

Viomycin

SEQUENCE LISTING

<160> NUMBER OF SEQ IDS: 52

<210> SEQ ID NO 1
<211> LENGTH: 44141
<212> TYPE: DNA
<213> ORGANISM: Saccharothrix mutabilis

<400> SEQUENCE: 1
cttatcgatg ataagcggtc aaacatgaga attcgcggcc gcataatacg actcactata    60
gggatccgca gcgcgccggg ctcggtcggg tccgggtggt cgtccacggc cggcaggcta   120
ccggaccgga gcaccggtga tcatcggcct tgtgccgggg tgtcgcccca cgtctgcgcg   180
ggcgccacgt gcgagggacg gctctgaccg gcgaggagga cctccgccca caccgtcttg   240
tgctccgggt ggcggaccac gccccagtcg gtggacagcg cctgcacgat caccaggccg   300

-continued

```
cgaccaccgg aggcgtccgc ggtgcggatg cggggctggc cggagccggc gtcgtccacc      360
tcgacgcgca ggcgctgccc ggcccggacc aggcggcacc ggcggggcgg ctcgccgtgc      420
cgcaacgcgt tgctgaccag ttcgtccacc acgagcacgg cgtcgtccac cgcgaccccg      480
gcgcggtccg agagcagatc acgcacaagg tcacgcacct cgcgcacggc gaccccgtcc      540
agcgcgagca ccacctcgtc gccagactcg tctcccgcgt cccacgactg cgaggacatg      600
accacatcac ccccatcggg catcccgccg caccagcggc tcacgcgacg acatacccg      660 cgcggcgacc cgcgaatccg ccgggatgcg gactgcggcc cctctcacgc cctcgacgtg      720
cgtgcggctg accgggtgag ggcgggttcc cgatccggtg atcttgcttg cccgcaccca      780
ccgccgaccc gagactccgc cctatgacct ccacggagaa cgacctgctc tcgacaaga      840 tcgggcgggg attcgaccac ctcgacgccg acggtgacgg gctgctcgac gagcgggacc      900
acgtcctcat gggcgagcgc gtcgcggcgg cgctcgggca cgggtccggg tcggcggaag      960
aggagcggat cgtggacatg tacgtccgcg tctggacga cgtgcacctc ccccacctgc     1020
cggccgggac caccgccatc ggccgggacg agttcatcgc cgccaccgc gacctcgccg     1080 acgaccggc cgccgcggac gccacgctcg gcgcccctcgc ccgggagttc ctccggatcg     1140
ccgacatcga cgccgacggc cgggtcacgc ccgccgagtt cctgaccttc agcgcggcc      1200 acttcccga cctgagcgac gaggacgccg ccgccgcgtt cgagcacctc gacaccgacg     1260
gcgacggctc gctgtccccg gaggagttca tccgggccac cgtcgagtac tggaccagca     1320
ccgaccccga ctcgcccgcc aactggtgga tcggtcggcc gcggccgacc gcctgaggcg     1380
gatcagcagc cgggtttcgg gcagggcaac cgggacgccg cgccggtgag cagccgcagg     1440
gcgccctcgc ggctctcgtc ggcgggcatg ccctgcggtc tggcgttgcc gttcgccccg     1500
ccgtactcga ccgtcaggaa cacgttgtgg tccacggccc tgacccggct gtagctctgc     1560
accccgttgt acttgtgcat gacgtcgccg tcgtccaggc cggcgcccgt gatgccgggg     1620
tccttcgcct gcgggtccga cgcgaggtgg tggcgggcgt tcccggtggc cgaccggccg     1680
tcgccggcgc ggtagcgcat gaccgtgacc gtgacgtagc ggtacagggg agtgccgggc     1740
gtgtcgggcg cccagtcgtc gtgcggcaac accggcacgt tgccggaatc gccgaactcg     1800
tggcggcact cgaccatgtc gacccggtcg tcagaaaacc ggaccggctc ccggctcggc     1860
ggtgcggcgg ggaggccgcg cgacagcgcg gtgaccgtcc ccgggtccac gaggtcgcac     1920
gcctcgatga gcgaaacgta ctcgggctct tccgccgcgc aggccgatgc caccgtcgcc     1980
aacaacaggg cgacgacccc cagtctcacc atgccgcgaa ccctagcgcg atcacgctcc     2040
agatgcggct gaccaccgat agtaggtgtt gatcgtgacc gggtcggccc catactcgcg     2100
agcggagcgg cggtcacccc caccctgcac cgaccgccgg ctcgtctgga ggtcttccat     2160
gaaactacgg gcgggacttc tcaccgcggc cctgttgctg ctgggaacca acgcgatggc     2220
cgccgcaccg gactcgacgc cgttctactg gcaggtcccg ggagccgatg agcgcacgct     2280
ccaggacgcc gggttcgacg tcgaacacgg cgtggacggc ggcgtgcagg tggtcgggga     2340
cgcgcgggtg gccggccggc tgaccgcgct gggctaccag ccgaagaagt tcgacaccgt     2400
ctacaagccg gtgccgcccg gccgcagcgg cgacatcggc gtccagacgt tctacggcgg     2460
ctaccacacg gtcgccgagc acgagaagca cctgaccgac gtggccgccg cgtacccgc      2520 gctgacgcag gtgttcgaca tcggcgacag ttggcgcaag acccgcggcc tgggcgggca     2580
cgacatcaag gccatctgca tcaccaagaa gcaggccggc gactgcgcgt tgagcccac      2640 ctcccccaag ccccggttcg ccatgatcgc gcagttgcac gcgcgggaac tggccaccgg     2700
```

```
tgaactcgcg tggcgctgga tcgaccatgt cacccgcggc tacggcaccg acgccgaggt    2760
gacgtccatc ctggacacca ccgagctgtg ggtggtcccg atcgtcaacc ccgacggcgt    2820
ggacatcgtc gcctccggcg gcagccggcc gctgatgcag cgcaagaacg ccaacaacac    2880
cggcgcgtcc tgctcggtgc cgagctacgg cgtggacctc aaccgcaact ccacgttcaa    2940
gtggggcggc gcgggcacga accggtgcgg cgagacctac cagggcacgg cggccgggtc    3000
ggagccggag accagggcgc tggaggcgtg gttcaagcag ctgttccccg accagcgcgg    3060
ccccggtgac accgaccccg cgccggtgac caccaagggc gtgatgatca cgatccacag    3120
ctacggcaac ctgatcatgc cgccgtgggg ctggacgtgg aacgcgaacc cgaacgccgc    3180
gcaactggcc gcgctgggca agaagatggc ggcgttcaac gggtacacgg tggtggccga    3240
gggcgacacg acgggcacga ccgacgactt cacctacggc accctgggca tcgccagcta    3300
cacgttcgag atcgggtcca gcagcggcag ctgcggcggg ttcttcccgc agtactcgtg    3360
cgtggacagc ctgttctggc cgcggaacaa gggcgctttc ctgacggcgg cgaaggccgc    3420
caaggcccct tacgcgagct gacgccggcg gccggtggac gctaccccgc cgcgggtgcg    3480
tccgccggcc gcgcgacgga caggatgacc tcgcgcagcc ggtccacgta gaggcggatg    3540
ttcttgtacg ccacgtcgtt gtccgggtac cggcacgcga actggagccc ttcgtgcagc    3600
cgggtcaccc acacgcacac ctggtcgccg taggacacgc ggatcagccc gtacgccttc    3660
atgtcccgcc agcgctccga acccggcgtg gggcgggcgt ccatgaacga cgacgatcgag  3720
tacaggtcgg gcgaggtggg gcggaagtcg tcgcccagca ggcgcagcac gcgcgcgacc    3780
ggcacccgcg acgccgggcg gctcgcgcgc agttcggcct gggccgcgcg cagcaggccg    3840
tcgaaaccgc ccgccgtggc cacgggcagt tccaccggca cgccgccgac gtaccagccg    3900
accgagtccg accaccgcga cttggcccgc gtgtggaacg gcacgaccgt gcggtagacg    3960
tcgtcgccgg tcatctcgcg catgatcagc gcggtggcgg cgaggacgcc gaccagggaa    4020
ccgccgtagg gccggcagtg ccgctcgaac gccgccgcgt cggcgtcgtc caccagcatc    4080
tcgtgcaacg acttctgcgt gggcagcggg ccgcccggcg ccaggcccag gtcgaacggg    4140
aagttcggca tccggccgtc gcagcgcgcc acgaaccgcc gccaccggtc caccaccggg    4200
tggtcggcgt ccacctcgtc ggcgtcggcg cgctcggtgg cgcagaagtc gacgtagctg    4260
gcgatcggcg cggcgtccac ggtgcggccg tcgagcgcgg cggcgtacag ctcgtgcagc    4320
tcggcgggga cgcggtacat ggagtaggcg tcgacgttgc tgtggtcgaa cgcgaggtag    4380
acgtcgtgc tgtcctcgcg ggccacggcc gcgtagatga agttgggcca ggtgagggtg     4440
tcggcggcga cgtcgaaccg gtcctggagg tgctgcacga gcacgtcggc gtcggtgaac    4500
tcgccgacgt cctctcggtg cagcgcgacg gcgtcggcgt cgagggtgaa ccggcgcatc    4560
tcgccgtcct cccaccggaa accgctgcgc agcgtctcgt gccgcaacgt ccacacccgc    4620
aacgcctcct ccagggcgtc gaggtccacc gcgcccggca ggtcgaacgc gacgcccagc    4680
cacgtcggga cgaacaggcc gtcctcgcgc aggctccggg ccgtgcgcac gtgcgactcc    4740
tgcaggtacg ccggcggtcg cgcgtcgtcc ggcgcgccgt tcgcggcggc cacggggcgc    4800
agcacccact ccacgacgcg ccctggccgg acctcacaac gctggacatc ggtgatgcgc    4860
atgaccttct ccgtctgcct gccggtgcgg cacaaggcgc gcgcaggcg tacctgaaac     4920
cttcgggggg agggtggctc gtctcacgac cacacggcgg aatgtcgccg tacccgagcg    4980
aggaccttaa cgacgcccg atcaagaaac caccgccgaa gacccgagcc acgctatcga     5040
gtgaactcgt gatgtgactg ccgtcacaga tcaccggcaa ccggaatgac catgaccgat    5100
```

```
ctaacggttg gaccctaggt caaacgttag aacgcgcccg gaggccgaga tgaccagccg    5160
cttcgcccaa gtcatgttca ccccggacgt ccagctccac caggagcggc acggcagccg    5220
cgacgcctac gcccggatgg ccgacgccgc gccggtccgg gaccgcatcg ccccgacga    5280
ggcggcgttc atcgccgagc gcgacagctt ctacctggcc accgtcgggg agaccgggtg    5340
gccctacatc cagcaccgcg gcggcccgcc cgggttcctg cgcgtgctgg acgagcacac    5400
gctcggcttc gccgacttcc gcggcaaccg gcagtacatc acccgcggca acctcgacca    5460
cgacgaccgc gtggcgctgt tcctgatgga ctacgccaac cgcacgcgcc tcaagctcat    5520
cggccacgcc cgcgccgacg actcgcccga ggtcgtcgaa cggctcgcgc tgccggacta    5580
ccgggcgaag gtcgaacgcg cggtgctcat cgaggtcgag gctacgatct ggaactgccg    5640
ccagcacatc ccgcaactgt tcccgcgcga cgccgtggaa caggccgtcg gcgcgctgcg    5700
cgaccggatc accgagctgg aacaggaaaa cgcccgcctg cgcgcgaggt gacgcgggcc    5760
ggccgggggc gtcgccgggg ccggccggat cggccggggt cgccgggtca ggcggggcg    5820
tcaccgggtc aggcgggacg tcaccggac agccggggcg tcatcgggac agccgccacc    5880
ggacctcgcc gtcgtgcacc tcgtcggtgg gcgcgagtcc ggcggcggtc gcgacggcgg    5940
ccgacgcgtg gtggtcgggg tggacgtggg cgacgaccgt gcgcacgccc tgccgcccga    6000
gccagtccac gagcccccgg gcggcttcac gggcgatccc ccgcccctgg aacgcgtcc    6060
ccaccaccca ggcgacctcc gcgaccgggc cctggtccgt ggggccgacc gtcgcctgga    6120
ccgtgccccgc caggcgggac tcctcgcgca gccggacgac ccagttcagc caggagaccg    6180
cgggatcggg cgagccggcg agcatgcgtt cgtagcgtga ccgcagggct cgcgggtcgt    6240
ccggggtgcc gccggtgaac gtgtgcaacg cgggatcggc caacacgacg gccatctcct    6300
ccgcgtggtc cacccgcaac ggcaccaggt cgaggcgggc ggtgccgatg gctggggcgt    6360
ggaggcggcc ggacatgtgg gccaacagta gtgctcaccc cacggtcacc acccgggccc    6420
acgccggcgg tgggtccggt cggtagtcgc ccggtttcgg tgggcggcgg aacaggccca    6480
cgaccgttcg gcacggcggt cgcacggtgg gccacggggt ctggccgtcg gtcagggcga    6540
cgatgacgtc cgggcgggtg cgcagggccc gggtgaagcc ggtgcgcagg tcggtcccgc    6600
cgccgcccat caggggatg ccctcggctc ggcacagcgg gtgcgtcacg tgggcggcgg    6660
cgtcgcagga caggaccgac accaggtcgc gccggccgcc cacggcgcgg gcgatggcgg    6720
cgatctccag cagcgcgctg cccagttccg cgtcgctcac cgaccggag gtgtccacga    6780
ccacgcacac gcgcggcggc ctgcggcgca ggctgggcag cacgacaccg ggcagggcgg    6840
tggaccggcg cgccgggcgg ccgtaggtgt agtcgtcgcc cgcgcccgcg ccgacgcgg    6900
ccgagcggac cgccgcgccc agcaggtcgc gccacggctg gggcgggtgg aacgcccgct    6960
ccgcccaccg ccgccagccc agcggcacgt cgcccggccg gccggtgatg gcctcggcga    7020
cccggaaccg caccgcgtcc cgctcctgct cgctgagccc gtgcgcgccg tccggcccca    7080
ggtcccactc gcgctccagg ccgtccgcgc cgctgccgca gtccagccac gtgaacgcgt    7140
cggtgtacgg gccgagccgg aactggcgca ggtagtcctc catcaactgc ccctcgcgca    7200
actgcagcag ttccggctcc accgcgccct cgggccgtgc caacccgtcg ccgaacacgt    7260
cgtcgttgat ctcgcagtca gcggcgatgt tcatccgcaa ccgctccccc ggcccggtca    7320
gcccgtgctc cgcggcgaac cggtcgccgc gccgtggtg gtcgcgcagc aggtgcgaca    7380
cctcgtgcac ccacaccccg gccaactcct cctccgcgt gcggtccacg aaggccgggg    7440
agacgtaaca acgccagtgc cggtccacgg ccatcgtcgg cacccgccgc gactccacca    7500
```

```
cgtgcagcgc gaacaacgcc gtcgccaggt acggccggca gcgcaccgcg tgcagccggg    7560
cggcgaacag cttgcgctcg tccaggctca ccggcccgcc ccgacgcgcg ccgccgtccg    7620
gtcggccagc cgcgacaccg acaccgcgcc ggagagccgc tcgatcgccg ccggcacctc    7680
ccagtcgtcg cggcgcaacg cggcgagcgt cgccgccggc acgacgacca ggtccggcgc    7740
gccggtgtcc aacgcccgca ccaacaacgc ccacgccgcg tcccaccgcg ccgcctccgg    7800
acgtcgccgc accgcctcca ccacaccgtc gagcaccgct ggcgcaggt cgccgcgctc     7860 gggcagcacg gccgccgccg ggttcgcgag cagcgactcg ggtcgggca ggtccatccg     7920 gtccaggctc gccagcagct ccaggcccgg cccgtcgccc acggtccccc gcacgagcat    7980
cgacagcacg tcccgggaca cgtccgccgc ggtggcgaag gcgatcagcc gcaacgccat    8040
ctcccagctg cgcggcgacg gccacggacc accgcgccgg gtctcgtcct tgggcagttg    8100
gtgcaccagg ttggggcggg cggccagcag ttcgcacacc gcccgacgcg cgtaggccac    8160
ggcgtccggc aagcggcccg gtccaggcg cggcagctcg gccgcggcc acgtcccgcc      8220 cagcccgcgg accaccacgt cgtggtcgtg ggcccactgg aggtggacga accggttggc    8280
cagcggcggg ctgagctccc agccgtcggc ggcggacgag gcgcggttgg cggcggccac    8340
gatccgcacg cccggcggga gggtcagcgc gccgatccgg cgttcgagga cgacccgcag    8400
gagcgcggcc tggaccgccg gcggcgcggt ggacagctcg tccaggaaca gcagtccgcg    8460
gccggcgcgg accaggcgca ccgcccagtc cggcggggcc atcggaacgc cctgcaccgc    8520
cgggtcgtcg ccgacgacgg gcaggccggc gaagtcggac ggttcgtgca cgctcgcgat    8580
gaccgtggtc agcggcaggt cgagggcgtc ggcgagctgg gtgagggcgg cggtcttgcc    8640
gatccccggc tcgccccaca gcagcaccgg caggtcggcg gacacggcca gggtcagggc    8700
ttcgagctgg gcgtcggaac gggtttcggt ggtcgtgcgg ccgagcaggg cgagcaggtc    8760
ggcggcgacg tcgagcggtc gcgcggacag ggaagtgggc atattcgggc accctcgggt    8820
tgcgtaggga cgtgcgtcgg ccgagcgagc acgcggggg attcagcgag agaacgcgtg     8880
gcgcgggcgg acccgtcgcc gaccgtcctt tgtggaggga gccgggccgc cggcgagtcc    8940
ggcccggtac aggccgtgcg ccagccggcg gcggaccgcc gcgtccagct cgtcgcgcag    9000
cgcgccggcg cgcaggagcg cctccggggcc gagcagggct tcgacggccg cgacggcgcc    9060
ggcggtgtcg ccgtggtcga gccgggcgcg aacgtccaca agggactccg gttgtcggtg    9120
cacgtcgtcg atcgcccgca ggcacggcaa cggcggaccg ccccactcgg ccagcagctc    9180
ctcgcggcgg acctcgtcgg ggtcgtggtc cagcggcacc aggaccccgt ccacgacgcc    9240
gatccggtgc gtcgcgccgc ggcactcgac caggcgcgga cccgttgcgg ggtcgggact    9300
tccggttgtt cgccggtggc cggggaccag ggccgacgcg accagcgggt gcagccggtc    9360
ggcgtcgacc aggccggcgc ggagcaggtc gaggtcgggt ggtgtgcggg tggcggcgtc    9420
gggcaggacg ggccgggtgg ggtctcgtcg gggagcggcc gtgagcacgg gtgtcggctc    9480
gtccggggcc agcgccaacc accgaccggc gttgagccgc acggtgatca cgcggtcggc    9540
gcaccggtcc gcgcgcagga ggagcaaggc ctccggcacc caacgaccga cagcgaaacc    9600 ctcccctcg acggcccacg gcgcggcggg tccctcggct ggcggcgcc cgacggccca     9660 cgaacgcggc gggcccctcg gctgccgcg acccgacggc ccgcgagccg gctgcgcgca    9720
gcgcggtggt caaacccggg cgggggatcg ccgcccgcgg accgttcccg cagctcgccg    9780
gcccggcgcg cgtcccacag gtggcggtgc aggtccaggc ggaaccgccg gtccggccgg    9840
gggtgcgggt gcgtgcccgc gccggcccgg ggttcggccg ggtcccacca cgccaggctg    9900
```

```
atccgctgcc cggctgccgc ccacgccggt ggcgtgcgcg ccacgagdtg cgggcccgcc    9960
gcgtaccggg ccagggacac ggtgagcccc gggcgcagca agccgtccgg accgatcctc   10020
gggaagtgcc agcgcagcag gtcggggcc aggtgccgca ggtcggcgcg gacctgtgcc    10080
gcgagctgcc gaccgtgggt ccggcccacg gcccgcaggt ccaggtccac gtcgaagcgc   10140
gcggcggcac aggccccggc ccagtcgccc accgagcggc gggcggtcgc tgtctcgacc   10200
atcgacggcg gcacggcgaa ctcgcgcacg cgcgtccaga agtgaaggcg aaggttctca   10260
tccgcggtgg tgtggtgcat cagcactcac cttgcgcgaa tgaaaccccc gatctaccag   10320
agaaggtgat catcgcggcc gagcgtacca gcaaacggcg ctcaggtgtg cgagacgacg   10380
agccggaaac cggcgtccca ctggtcgagg tcgagcaggt cgcggtggtc gtcgtgccac   10440
cggccgctgt cgaggtccgc gcgcaggcgg cggacgccgc ggtccacggc ggcggggtcg   10500
gtctgggcca gggcggagca cgcgcggcgg acgcgcgggt cgaggtaggc gtccgggcgt   10560
cgccagtacg cggggaagac gccgtcgacg aagtcccacg gcagcggcag cggcgtgacg   10620
ctgtccgcgc ccagttcgcc cgcgatgtcg gccgccgacg ggcgggtgcg ttccaggtcg   10680
gcgatctcgg gcacgtactc gcggacgaac cagaactcgg tgtgcaggct cgtgtcgtag   10740
gccagcacga cccggcgcgg cgcgatccgg cgcagttcgg cgagcccggc ccgccagtcg   10800
gtccagtggt ggacggtgag cacggccagc gcggcgtcca cggcgtggtc gcgcagcggc   10860
agggcctcgg cgaccgcgcg cacggccggt ccgacctccg gcgggcgttg gcggatcatc   10920
tccgtggacg gttcgagggc gaccaccgtc cggtcgtccg gctcgtagga gccggtgccc   10980
gcgcccacgt tggcgatcgt ccgcgcgccg ccgagcgcgt cgaggatcgc ggtcatccac   11040
cgcgggtcgg tgcggcggcc cagcgcgtaa cccgtgccga tgtcgtcgta gagatccgtg   11100
ccggccactg tccccccagt gctcaagcgg aaagtttcga cgtgggcggc gacgggccgg   11160
tccgggaggg cccggatcgg ccgtcgtcac ccgcgggttc ggccccggcg gtcacgccga   11220
cgcgcccggg ggcttcacca cctcgggggc ctcgcgcgcg gtcaccaggc ccaggcgcca   11280
ggccagcaga gcggcctgga cgcggtctcg cagctccagc ttggccagca cccgggacac   11340
gtggctcttc accgtggtct cgctgacctc gaactcgcgg gcgatctcgc ggttggaccg   11400
ccctggccg atggcgcgca gcacctggcc ctcccgttcg gtcaacgaca gcagggccgg   11460
cgccgacggg tcgggcagcg ggatgatctg gaagctctcg aacacccgct tggtgacgtg   11520
cgcgggcagg tacgcgccgc cctcggccac cgcccggatc gcgcgcggga actcctcccc   11580
cggcgacccc agcggcaggt agccgctcac acccgccgcg atcgcggaca ccagcagctc   11640
gtccgagtcg tcctgggtgg ccaccacgac ccgctgcccc gccagcagcc gcgccacccg   11700
gaaatcgtcc acccgcaaca cgacgcccc gaccagcacc acgtccggct ggtcgcggcc   11760
gatccggtcc agcagttccg gcacgccgtg caccgcgccg accacggtga tcgcgtcgtc   11820
ccgcgcgagc acggcccgca ggccgtccag gatcacctcg tggtcgtcgg cgagcagcac   11880
ggcgatcccc cgccgcgccc gccccgccc ggcggcgtc agcacgctta tcgccccggt   11940
ctcccgacgg taccggggcc cgactgaata tcgtccgac acttctccgg tcacgttctt   12000
ccgacccct cggccacggg ttttccccac ggcgtttcga acagtcgcg gcggcgcga    12060
aaacaccacc ggaaccgcga gccgcccggg accaccgacc cgcggcaccc cggccgtctg   12120
cttcaccatc cccaggcgcc gccggcaatc cggatcgacg ccaccccagt tgcaaacaat   12180
atgcattaac acccaaccta ccggaccacc ggacgggcgg caacgtccgc acggtgtgtg   12240
cacgcactca cactaacgcg ccaattaggc ggggagacat gccgctttag aagtaatccc   12300
```

```
ggcaacgccg ggcgtcgatc cgccacgcgc cgcgccctcc acgccgagca cgtcgaactc   12360
ctcccggcag gccccagcc gacgggtcca cgtgctggtc aactcgctcg cgccgacatc    12420
ggccaggtac ccggcccggg taacgcgcag gcccgcctcg cgtagacgt gggccagttc    12480 ccggcgcacc cattcgggtg tcggttcggc gatcccggtg acggcggggg ccgccggccg   12540
ccaggcgtgg aggttcacgg tgatgtggaa ccggggcgcg cgcggcacg cgcccgccag    12600 gccggcgagc acggcggggt cgcgcccgag gacaccgcgc agcaggctgc cccacggcat   12660
caacacgtgc atttcgtcca catcgcccag acagggcggc atctcctcgg cggcggcgtg   12720
gaccagcacc aggttgggca gcccgccgcg cgcgggtttg gcggcggcgc gcgcggacac   12780
gccccgcatc cggtcgggt tggcgtccac gccgaccacc agccggtcgg ggtcggcgcg   12840
ggcgagccgg taggcgtgct tgccgtcgcc ggtgcccacg tcgagcagga ccgaccggtg   12900
acgggcgcgc aactcggcga actcggcgtc ggcgagcggc acgaccgct tgccgacgac    12960 cttgaccaga ccttcggaag gcatgacggg gcccttcgcg tgagtgggtg aggacctgcg   13020
ggaaacggcc ggcgacggac cgcagaatta cggggaaaca ccctccggga catcgccgga   13080
ggacccttgt caatcgttgc cggaaatacc ggccgctgcc caccctccg gagcagcgcg    13140 gagcccggtc ctgggaaaat gtggccgtaa atcacgccaa tggggggaagt gaacccgtc   13200 aaaatcactc tgcgtgatta gttttctcct accagcggac gagacgtcac cctacttcgg   13260
aaggaacggt gctcgttcga aatatccgca ccgggcattc gccggaatga gccggcgggc   13320
cacccaaaga agtctgtcga aaacggcgga gtcgctcata ggctgagcgg cgtccccaat   13380
tcgcgacgac cggagggcca tttgcccggg ccgggtcgga tcgacatcag ccggagacgc   13440
caccatgacc gttgaccca cgatcgagct gcgcctgacg ctgaacggcg acccggacgt    13500
gcccgcgctg acccgggcgt gggcggcgct gcgcgcccgg caccgcgccc tggccggtcc   13560
gctgggtgcg caccgggacg tcgccgcgtt cgaggacgcg gtgcgcgcgg gccccggctg   13620
ccacctgctg cgcgccccg gccggcacga gttcgcgctg accgccgggt gcgacgcggc   13680
gtcggtgccc gcggtcctgg ccgagctgtc cgcgctctac gcccgcgagc tgggccaccc   13740
ctccgagggg ctgcccgcgc cggccccggc cgtcccgcac gaccgcccgc cgcacgacgt    13800
tcccccgccc ggaccggagc tgccgggcct ggagctgttc gggcgcggcg aacgggccc    13860 gcgcgtggtg accgcgtgg acctcggcca cccgaccccgc cggcacgtct ccgcgctggc   13920
ccgccggcac ggcgtgaccc gcgaggtcgt cgtggtcacc gcgtgggcgc tgctgctggg   13980
cgagctggcc gagcgggacg agttcgtgct gggcctggtc accgatcccc gcgacccggc   14040
cgcgcaccga cccgccgtgg gcgcgctgcg cgaggcccgc ccgctgcggg tggacctgac   14100
cggccggccg tcgttcgccg acgcggtgcg ccgcaccacc gccgccgtgg cgaccgcccg   14160
gtcccgcccc ggtgacgcgc ccgccgacgt ggcggtgcag tacggcgagc agccggcggc   14220
ggcgctgcgg ctggccggcc tcgacccccgc cgaggtcccc gccgccttct ggctggccga   14280
cgacctcccc ggcccgcacc gggtcgtgct gcgcctgctg gacacccccg acgggctgct   14340
cgccggcgtc gcgcaccacc ccgacgccct ggacgggccc ggcgcgcggc gctgggtgtc   14400
ccggctggcc gcgctgctgg ccggcgcgca cgacgagtcg cccgagcccg tggtgatgtc   14460
cgaggacgag caccgccggg tcgtgctcgc gcccaacgcg accgcgtgg acctcggcgc   14520 gcccgcgacg gtccacgacc tggtcgccga gcaggcccgc cgcacccgg accgaccgc    14580 gctggtcttc gccggcgccg aggtcggcta cgccgagctg gacgcccgcg ccaaccgcct   14640
cgcccacgag ctgcgcgagc gcggcgtgcg gcgggagacg ccggtcgcgg tgtgcctgga   14700
```

```
acgcgagacg ggcctggtgg tcgcgctgct ggcggtgctc aaggcgggcg gcgcgttcgt    14760
gccgctggac ccgcagtacc cgcggcagcg cctggcccac atgctcgccg actcgggcgc    14820
ggccgtggtg ctcacccagg gtcggctgcg cgaccggttc gccgccgacg gcccgcccgt    14880
gctggtgacc gacgacgacg cgacccggtt cgcccaccac ccgagcagcg cgccgccggc    14940
gtcgtccggc ccggacgacc tcgcctacgt cgtctacacc tcgggatcga ccggcgggcc    15000
caagggcgtg atggtcgagc accggggcat cgcgtcctac ctgcgcggaa tgcagcacga    15060
cttcccgctc acgcccgagg accgcgtgct ccaggcgacc tcgctgtcct tcgacgtgtc    15120
ggtgtacgag atcttctggc cgttgcaggt gggcgcggcg gtggtgctgc ccgcgcccgg    15180
cgggcacacc gacccgtacc acctgtcgga gctgatccag cggcacggcg tgacgtgcct    15240
gcacttcgtg ccgtcgctga tgcggttgtt cgtggaggag gccgacccgg gggcgggcgc    15300
cgggctgcgg cgggtgttcg tgtccggtga ggcgctggac ccgtcgctgg tggcgctggt    15360
gcacgagcgg acctcggcgg agctggtgaa cctgtacggg gcgacggagg tgtcggtcga    15420
ctcgacctac tggaccgccg accgcgccaa gcccgaccgc ccggtgctgg tggggcggcc    15480
gatggccaac gccacggcgt acgtgctgga ccagcggttg cgacccaagc ccgcgggcgt    15540
ggtcggcgag gtcttcctgg gcggcgcgag cgtcacccgc ggctaccacg cgcggccggc    15600
gctgacggcg gagcggttcg tgcccgaccc gttcgggcca cccgggtcgc ggctgtaccg    15660
gaccggcgac ctgggccggg tgaccccgga cggcgagctg gagttcctgg ggcggcgcga    15720
ccaccagttc aagctgcgcg ggtggcgggt ggaggccggc gagatcgagg cggcgatcac    15780
cgcgcacccc ggcgtgaacg cgcggtcgt ggtgaccgag ggggcgcacg agcacgcgac    15840
cctgctggcc tacgtgggcg cggacgcggg gctggaccag gcggcgctgc gggagttcct    15900
ggcgcggcgc ctgccccgac cgctggtgcc ggcgcggttc atccgcctgg accgcctgcc    15960
gatctccccc aacggcaagg tggaccgcgc cgccctgccc aagcccgacc aggcgcccgc    16020
cgagcccgcg ccgaccaccg cggcaccgcc gacgcacgcc gcggacggtc ggcccgcgtt    16080
ggagcacgcc gcggacggtc ggccggcgct ggagcgcggc tcggacggtc ggccggtgtt    16140
ggaggtggtg ctggcggtcg cggccgaggt gctgggcgcg ccgatcgggc cggaggacag    16200
cttcttcggc tccggcggca actccatcca ggcacccgg ctggccgccc gcctgcgcgc    16260
cgccctgcgc accgacgtcc cggtgcggct ggcgttcgag gcgcccacgc cggccgcgat    16320
ggcggcgctg ctgtccccgc cgtccccga gcccgtcgcc gaggtctccc gggccgagca    16380
acggatctgg ctgctcagcc ggctcggcgg ccacccgcc gagtacgcga tccccgtggc    16440
gctgcgcctg gccggcccgc tggacgtcgc caagctcaag aacgccgtgg acgcggtcgt    16500
gcgccgccac gaaggcctgc ggcacgtctt ccccgaggtc gacggctccc cgacgcgggc    16560
cgtgctcgac ccgggctcga tcaccgtggc cgaggaggcg aaccggtcgg tgcgcgaggt    16620
gctcgccgag ggtgtcgccg cgctggaccc cgcgaccggc ccactggccc gcttcacgct    16680
ggtcaaccag ggcccgcagg accacgtgct ggccatcgtg ctgcaccacc tcatcgccga    16740
cggctggtcg gtgacgtgc tgctgcgcga catcgccgcc cactacaccg gcgcgccgac    16800 cgccacccc ggccgctacg ccgactacct cgccctggaa cgggccgagg agcaggacgg    16860
cgccctgggc cgcgccctgg agcacttcgt caccgcgctg gacggcgtgc cgacgaggt    16920 cagcttcccg cccgaccacc cccgccccgc gcaacgcacc gggcgcggcg acgtcgtgcg    16980
ccaccggatc gacgccgcgc cggtcaccgc gctggccgaa cgcctgcgca ccacgccgtt    17040
cgcggtgctg ctggcggcgg tgggcgtgct gctgcaccgc gtcggcggcc accggacgt    17100
```

-continued

```
ggtggtcggc acggccgtcg cccgccggcc cgacgccggg ctggaccacc tggtcggcct    17160
gtgcctgaac acgctcgccc tgcgctggcc cgtgcagccg cacgacacgc tgggcgaggt    17220
ggtccgcgcc gtgaccgacc ggctcgccga cggcctccag cacgacgccg cgtcgttcga    17280
ccgggtggtg gacaagctcg cccccgcccg cgacagcggt cgcaccccgg tgttccaggt    17340
gatggccctg tacgaggagc cgtacgagac cgcgctggcg ctgccggacg tgacgaccac    17400
cgacgtgacc gtccactgtg gatccgcgca ggcggacgcg gcgttcgggt tcgtgccgcg    17460
cgagggcggg atcgacctca ccctccagtt ctccaccgac gtgttcaccc gcgccacggc    17520
gagccggtgg gcgcgccgcc tggcgaccct gctggccggc gcgcgggcgg acaccagggt    17580
cgcggacctg ccgctgctgc cggaggacga aagccaggac ctggaacgct ggagcggcac    17640
cacaggggaa gcgccgacca ccacgctgca cgccctcgcc cacgagatcg cccaacgcca    17700
ccccgaccgc ccggcgatcc acttcggaca gaacagcctg acctacggcg agttcgacgc    17760
gcgatccgct cagctcgccc acgagttgcg cgcccgcggc gtccgagccg aaaccccggt    17820
cgtggtgtgc ctggaacgct ctcccgaggc gctgatcgcc gtctacggcg tgctgaaggc    17880
cggcggcgcg tacgtgccgg tggagaccag caaccccgac ctgcggatcg ccgagctgat    17940
cgccgactcc ggagcggcgc tggtcctcac ccagcggcga ctcgccgacc gcctggccgc    18000
gctgggcgcg gaggtcgtgg tggtggacga ccgctgcccc cggcaccccca ccaccgaccc    18060 ggagccgctc accggtcccg accacctggc gtacgtgatc tacacgtccg gctccaccgg    18120
ccgccccaag ggcgtgatgg tgcagcacgg gtcggtgctg aacttcctcg acgcgctgga    18180
ccgccgcttc gacctcaccc ccgacgaccg gctgctgcac aagtccccgc tggcgttcga    18240
cgtgtcggtg cgcgaggtct tctgggcgct gacccggggc gcgtcggtcg tcgtcgcga    18300 acccggccgg cacgccgacc ccggccacct ggtggacctg gtcgagcggg agcgggtcac    18360
cgtcgcgcac ttcgtgccca gctcgctggc ggtgttcctg gagggcctgc ccggaccggg    18420
ccggtgcccg accctgcggc acgtcctcac cagcggcgag acgctgcccg tgaccacggc    18480
ccgagccgcg cgcgacctgc tgggagcccg gctgcgcaac atgtacggcc ccaccgagac    18540
cacagtcgag atgaccgacc acgacgtcgt ggacgacacc gtggaccggc tgccgatcgg    18600
ccacccgttc gagggcgcgg tcgtgcgcgt gctggacgcg gacctgccgc cggtgccgcc    18660
gggcagcacc ggtgagctgt gcgtcggcgg cctgccggtg gcgcgcggct acctgggccg    18720
cccggcgctg accgccgagc ggttcgtgcc cgacccgctg gggccggcgg gcgcgcggct    18780
gtaccgcacc ggcgacctgg cccggctgct gcccgacggg caactggact tcctgggccg    18840
caacgacttc caggtcaagg tgcgcgggca ccggatcgag ccggcgagg tcgaggcggt    18900 gctcggcgcg ctgcccggcg tgcacggggc gctggtcacc gcgcacgacg accggctcat    18960
cggctacgcc gtcaccgacc gggacggcga ggagctgcgg acggcgctgg ccgagcggct    19020
gcccgagcac ctggtgccct cggtggtgct gaccctggac cggttcccgt tgaccggcaa    19080
cggcaagctc gaccgcgcgg cgctgcccac cccaccggc cggcacaccg gcgacagccg    19140
cccgctgacc gcgaccgagg cggcgctggc cgcgatctgg cgcgacctgc tggacgtgcc    19200
ggaggtgcgg gcggacgacc acttcttcgc gctgggcggc cactcgctgc tcgcggcccg    19260
ggtcgccgcc cgcgccggcg ccgcgctggg cgtggcgctg cccttgccga ccgtgctgcg    19320
cttccccgcg ctccggacc tggcgaccgc ggtggacggc acgcgcgccg accgcgaacc    19380
cgtccggccc cggcccgacc ggcggcgccg cgcgccgctc tcgtccgcgc agcgccggct    19440
gtggatcgag gagaacctgc gacccggcac cgccacctac accgtggccg aggcgttccg    19500
```

```
cctgcgcggc gagctggacg aggaggcgtt cgcggcggcc gtggacgacg tgctgcgccg   19560
ccacgacgcg ctgcgcgccc acgtcgagtc cgtcgaggac ggtgaaccgg agctggtggt   19620
cgcgcccgag ccgcgcaccg cgctgcgcgt cggcgacctg ccggccgacc gggtgcggga   19680
cgcgctggcc gccgagtcgg cccgggtgtt cgacccggcc ggcccgctgg tggccacgag   19740
cctgcaccgg ctcgcgcccg acgagtggct gttccagttc accgcgcacc acctggtggt   19800
ggacggctgg tcgctggacg tgctgtggcg cgacctggcc gcctgctacc acgaccgccg   19860
cgcaggccgc gcgccgcgac cgcgcgacgg gctgaccttc accgactaca cgtggtggga   19920
gcgggacgtg cggtcccgcg acctggaacc gcacctggcg ttctggcgcg gggaactggc   19980
cgggttgcgc ccgcagcccc cggccgacgc gcacggcccc ggcgcggtgc tggacttcgc   20040
gctcggcgcg gcgctgtccg acgagctgcg cgccaccgcc gccggcctgg gcgtctcgcc   20100
gttcgtgctc gggctgaccg cgttcgcgct ggcgctgggc gaggactcgc cgggcgcgat   20160
cggcgtggag gtggccaacc gggcctccgc cgagaccgcc gacctggtgg ggctgttcgt   20220
caaccacgtg ccggtgcggg tggcgccgcg cggcaccggc cgggcggcgg tggcggcggt   20280
ggacgaggcc cgccggcgcg tcctgccgca cgagcacgtg ccgttcgacc tggtggtgga   20340
cctgctgggg cccgggaggg cgccgacgag cgtggcgttc tcgcacctgg acgtgcgcgg   20400
gcactcgccg cggctggacg gcgtcaccgc caccccggctc accccgccgc acaacgcac   20460 cgccaagttc gacctcctgc tggaggtgct ggacaccgag cacggcctga ccggggcgtt   20520
cgagtaccgg cccgagcggt tcaccgccgc ccgcgtcgcg caggtccgca accactggga   20580
ggccgcgctg ctgacgctgc tggccgaccc ggacctgccg gtggacgccc gccgacccga   20640
tttcgcgtga tgtcgagggg gaacgacgtg ctgtcaacgg tcgatccggc ggcggagctg   20700
agcaccaccg ccgccgaggt cctggaacac gtggacgccg cggtggcggc gtacccggag   20760
gtgccgatcg cccgcgtgcg ggtcgaggtc gcgggcatcc cgcgcaccct gctgctgaag   20820
ctggagggcc gctcgccgtg gcggtccatc aagggccgca ccgcgctggg cctggtccgc   20880
tcgatcgcgc cgcgcatggc gtcgcgggac gtcacggtcg tggagtccac ctcgggcaac   20940
ctgggcgtgg cgctgtcggc gatctgccgc gacctgggcc tgccgttcgt ggccgtggtg   21000
gacctcaagc agtcgccggt gatccaggcg gcgatcgagg ccaacggcgc gcggctggag   21060
gtcgtgcgga cgccggcggc ggccaccacg cacctgctgg accggctgga ccgggtgcgc   21120
aagctggtcg ccgagatccc cggcgcggtg tggcccaacc agtacgagaa cgacgccaac   21180
cggcacgtgc acgagacgtg gaccgcgccg gagatcgacc gccaggtcgg cggcgaggcg   21240
caggcggtgt tcgtcgcggt gtccaccggg ggcacgctgg cgggcctggc cgcccacttc   21300
cgccgcgccc gccggcgac gcgcctggtg gccgtggacg tcgagggctc gacggtgttc   21360
ggcggcgtgc ccggcgggcg cgtgctgacc ggcatcggcg cgagccgccg ctccaccttc   21420
ctgacccgcg ccgagtgcga cgacctggtg tacgtgcggg aggcggcggc gatcgccgcg   21480
tgccacgtgc tgcgcgccga caccgggatc gcggtcggcg ggtccagcgg cgcggtcgtc   21540
gcaggcgcgc tggaccacct cgccgcccac cccgggctga ccaccgccgt gtgcgtgtgc   21600
gccgacctcg gcgagaacta cgcgcgcacg gtctacgacc ccgactggct ggcgccgctg   21660
cgcctcaccg acgaccccgg actcctgcgg tcccgcctgc gcggggcgcg cttccaccac   21720
gccgaaccgg acaccggaca ggagagcacc ccatgaccgc catccgcgag atccggctca   21780
gcgagccgga gtccgcgcag gccgcgctgc tcgcgctgga gtgcgcgcag cgctacgccg   21840
aacccgactc cgccgacttc ctcgccgacg ccgccgtgct ggcccacgac ctgccccggg   21900
```

```
cggtgcgccg ggaggtcgag cgcgcccgcc tggacgaccg gctgcacgcg ctggtcgtgc   21960
gcggcaacga cgtcgaccag gacgcgctcg gcccgacccc gccgcattgg cggcaggcgc   22020
gcaccgccgc gtcccgccgc tacggcttcc tcctggtgct ctacgcctcg ctgctcggcg   22080
acgtggtcgg ctgggccacc cagcaggacg gccgcgtggt gaccgacgtg ctgcccatcg   22140
aggggcagga ggactcgctg gtcagctcca gcagcagcgt ggagctgggc tggcacaccg   22200
aggacgcgtt ctcccctac cgggccgact acgtgggcct gttctcgctg cgcaaccccg    22260
actcggtggc caccaccgtg gccgggctgg accccgacct ggtcgggccg gccgtggtgg   22320
acgtgctgtt cggcgagcgc ttccacatcc gccccgacaa ctcccacctg cccacgcaca   22380
acagcggcgg ccggttgagc gactacttcg ccggcatcgt cgaggcggtg gagaacccgc   22440
gcgcggtgtc gatcctgcgc gggcaccgcg acgcgccgca gttgtgcgtg gacagcgact   22500
tcaccaccgc cgtggacggc gacgccgagg ccgcgggcgc gttggacacg ctcatcaagc   22560
acctcggcgg cgcgctgtac gaggtggtgc tgggcccggg tgacgtggcg ttcctggaca   22620
accgcaacgt cgtgcacggc cgccgcccgt tccgggcccg gttcgacggc acggaccgct   22680
ggctcaagcg catcaacgtg accgcggacc tgcgcaagtc gcgggcggcg cggcgcgacg   22740
cccaggcgcg cgtgctgggt gaggcgtgat ggtgcgcgac ctgccggccg ccgcgctgga   22800
ggactggttg cgcgagcggt acttcaccgc ccgcgtggac gtctccagca gcggtgtggc   22860
cgaccaccgg ctggcggacc tgcggcggtt gggcgggatc accgtcgagg agctggacgc   22920
ggtggtgttc cgcgacgggc cgtcgctggg cgcggagcgg ctgcgggcgg cgctggcgga   22980
ccggctgcgg cccggacccg accacgtcgt gatgaccgcg cacgggtcca gcgaggcgtt   23040
gttcctggcg atgaccgcgc tggtgcgcc cggtgacgag gtggtggtgc ccgacccgc     23100 ctaccactcg ctgtcggcgc tggcgcgggc gtgcggggcg gtgctgcggc cgtggccggt   23160
gctgggcgcg gcaccgcacc cggcggacct gcgggcgttg ttgacgcccc gcacccggct   23220
ggtcgtggtg aacttcccgc acaaccccac cgggggtgacc gtggacgcgg cggtgcaggc   23280
cgaactgctc gacgtggtcg ggcgcagcgg ggcgtacctg ttgtgggaca acgcgttccg   23340
cgacctggtc tacgacgcgc cgccgctgcc ggagccgacc gcgctgggcg ggcgggtgct   23400
gtccaccggc acgctgtcca aggcccacgg gctgcccggc ctgcgggtcg ggtggtgcgt   23460
gctgcccgcc gacctcgcgc cggagctggt ccgcgtccgg gactacctga cgctgagcct   23520
gtcgccgctg accgaactgc tcgccgcggt cgccgtggag cacgccgacg agctgatcgc   23580
gccccggctg gcggaggcga ccgccaaccg gcggcggctg ctggactggg ccgccgcgca   23640
cggcgtggac tgccccgcgc cgggcggcgg ggtgaccgcg ttccccggtt tcccgggggt   23700
ggccgacgtg acgccgctgt gcgaccggct gatgtccgaa cacggcgtcc tgaccgttcc   23760 gggcggtttgt ttcggattcc ccgatcgaat gcgatcgga ttcggctgcg accccgcggt    23820
gttcgcggcc gggttgaccg cgctgggcgc cgtgctggcg gaaaacggt tgccggcaaa    23880 actgtgactg gttgactacg cagcgcaaca tcgccgtttc gagaggaatc accgtggcag   23940
ccatcgagaa cgcgccacgc aggctgcgcg acaacaggga cttccggttc tggtggggcg   24000
gcaccgtgct gtcggccatc ggcgacgagg tcacgctgat cgcgtttccc ctgctcgtgc   24060
tgttcctgac cgggtcgccg acgcacgcgg gcctggtcgg cggcgtggcg gccgtgccgc   24120
cgctgctgct gagcgtgccg atcggcgtgc tggccgaccg gacgtccggg cgggcgctca   24180
tgctcggcgg ttcggtggtc agcgcgatct ccatcacgtc cattccggtc gtgcacctcc   24240
tgggtgaact caccccttccg catttgtacg tggtcgcatt tgtcaacagc gttgcggcga   24300
```

```
ccgtgtaccg gatcgccgac accgccgcgc tgccccggat cgcgggcgag gagaaactgg    24360
gcgaggcggc gtcccagagc gagacgatct ggggcatctc ggccatcgtc gcgccgccgc    24420
tggccggtct gctgttcgag accgccgggc cgacctcgcc gttctggatc gacgccgtgt    24480
cgttcgtcgc gatcatggtg tgcgtcctgg cgatccgggc ccggctcggc gcggacaagc    24540
cctacccgga ggtgtcctgg cggcaggacc tcaccaccgg cgcgcgcgtc acgttgagcc    24600
ggccgctggt gcgggccctg acgatcctga ccgtcgcggg cgacttcctg ttcgcgggca    24660
tcggcctgct gctgatcgtc atggtgcggg agaacggcgc gtcggggctg agaccggca    24720
cggtgttcac cgccgccgcg gtgggcggca tcctcggctc gatgctcgcc ggccgggtcg    24780
aggaccggat cgggatggtc ccggccgtgc tgaccaagca ctggctgacc gccgcgctgt    24840
tcccgctgct gctggtggac ctgccccggct gggccaccgg gctggtctgg ggcctgatct    24900
cgttccagat ctcgatcctc aacgtgatcc agatgaagta cctgatgagc gtcatcccca    24960
acagcaagct cggccgcgtc gaggggttcc tgacgttcat cgagcagggc agcctgccgc    25020
tgggctacgc gctcaccggc gtgctgctgg gcctgctcgg caccacgtcc acgctgctgg    25080
cctacgaggc cgtgctgctg gtcctggccg tcttcgcgac ggtcagccgg ggcctgcgca    25140
cccccgcgca ccccgacgag cccgcccgat catcgggctg acgccaggag agctgatgac    25200
ccaggtcgac ttcacccggt gggacctgcg caccgacgcc gagaagcacg ccaccccgac    25260
cgtcctgagt ggaccgccgc cggcgtggtc gccggacacc acgttggcgc ggctggtgct    25320
ggaccaggcc gaccgcaccc cggacgcgga cgcggtccgc atcggccgg acgccctgac    25380
ctaccgcgag ttggccgccg gcgcgcggcg ggtcgcggcc tgggtggccc ggcagccgca    25440
caccgggccg ccgcgcgtcg gcgtgctcgg cgagcggtcc cttgcgacct acccggtgct    25500
gctgggggtg ctgctggcgg gcggcgcgta cgtgccgctg gacccggcgg cgccgcccgc    25560
ccggctgcgc gcggtgctgt cccggccga cgcgcacgcc gtggtgacga ccgcggagag    25620
ctgggcgttg ttggagcagc cggggctgcc ccgcgctgctg accgaccagc cgctgccgtt    25680
ccagcggtcc aaggtggaca gcgggcgggt cgcggtgctg gcgggcctgc ccgacgcggg    25740
cgagccggtc gggccgacgc cggacgacgt ggcctacgtg atcttcacgt ccggttcgac    25800
cggcacgccc aagggtgtgg tggtgcagca ccggggcggc gtgaacctga cctgctgggc    25860
ccgcgacctg gtgccgatgg ggccgggcag ccgggtcacc cagaacgcgt cgctgcactt    25920
cgacgcctcg gtgcaacaga tcttcccggc gctggcctcg ggggcgacgc tgttcccggt    25980
gccggagcgg gtgcgactgt ccgggccgga gctggccgcg tggctggccc ggcaccggat    26040
cacgcactgg gactcggtgc cctcgctgtg gacgcccgtg gtggagcacc tggccgaccg    26100
gatcgccgcg ggacaacggg tgctgcccga cctgcgggcc gtgctgctgg ccggcgagcc    26160
gctgccggcg cggcaggtgg accggtggcg gtcgtgggag cagggcaccg gctgttcaa    26220
cgtctacggg cccaccgagg tgaccgtgaa cgcgaccgcg ttcgaggtga ccgggccggt    26280
gggcgcggtg gtgccgatcg gcggccgtt ccggggatc accgcgtccg tgctggacgc    26340
gcacggcaac ccctgcccgg tggacgccga cggtgagctg ttcctgggcg gggtggggct    26400
ggcgcgcggc tacctggacg acccggaggg caccgcgcgg tcgttcgtgg agcgcggcgg    26460
cgagcggttc taccggaccg gtgacgtggt gcgggtcggc gcggacggcc tgctggtgtt    26520
cgtgggccgc cgggacgacc aggtgaagct caacggcgtc gcgtcgagc cggccgagat    26580
cgagcacgcc ctgctggcgc accccggcgt gaccgaggcg gtggcggtgg tgctgcgcga    26640
ggagggccgg gcggagctgg tggcctgcgt ggcctcggcg gtcgagctgt ccacggagga    26700
```

```
catccgggcc gggctggcgg aagagctgcc ggcggcgctg gtgccgtcgc gggtggtggt   26760
cgtggagtcg ttgccgcaca cgccaacgg caagctggac cgggccgcgt gcgcggagct   26820
ggcgcgcgac ctgtccggcc cgtcgggcgg cgccggggcg ctcggggcga cggcggcgac   26880
gctgctgggc atctggcgga gcgtgctggg ccgtgacgac atcggcccgg acgacgagtt   26940
cttccaggtc ggcggcaact cgatcaccag catccggctg cgccgggagt gcgtggaggc   27000
ggggttgccg atccgggcgg tggacgtgtt cctgcacccg accgtgcggc ggctggcccg   27060
gtacgtggac gacaaccgga ccacgctggc cgcccgcgcc cgtcccgcgc cggaggagtc   27120
gccgaccgac ggcgagttcc ccctgctgcc cgcccaacgg ccgctcgccc tgacggcgct   27180
gctcagcgac ggcggcgcgc agcgcggtct ggtgcaggag accgtcacct accgggtgcc   27240
gctggacgtg gacgccgtgc gcggcgcgct ggaggtgctg ctggagcggc acgaagtgct   27300
gcggacggcg gtcacgccgg ggctggcgca gcgggtgctg ccgaaggtgc cggtgccgtt   27360
ggaggtggtg gacctgaccg gcgtggccga ccagtggggt gcggtgctgg aggccgccga   27420
ccgggactac gcgacccgt tcgacctggc cgagccgccg ctggtgcggg tgcgggcgtt   27480
cgaccggggc gaggtgttct cgctgacctg gaccctgcac cacgtcatct cggacggggtg   27540
gtcgtgggag atcgtgcaac gcgagttcga ccggctgcac gtggccctgc gagcgggccg   27600
gttccgcccg ctgccgccac cggtgctgcc cctgcgcgcg ctggcccgcc gcctggggtc   27660
gggcgggacg ccggacccgg agtgggtggc gcgcctggcc gccacgcccg ccctgctgct   27720
gcccgccgac ggcagcggcg tcggcggtga gcacatcgag tggccgatcg accccgggac   27780
gcaccgcgag ttggccgccc gcgcgcaggc cgcggaggcg tcgccggccg cgatccacct   27840
cctcgccttc accgaggccc tgcggcgggt gtgccggcag gactcgttcg ccgtcggcgt   27900
cgtgtcgtcg ggccgcaacg tggacgtgcc gggcgtcgag gaggccgtcg cgtgcctggc   27960
ccggaccgtg ccgctgccgg tggacgccgt gggcggcgcc gaggcccgcc tggcgcggct   28020
gcaccgcgac ctcgccgtgg tggtcggcat ggacgacgtg gacaccgacg tgctcccggc   28080
cgacgtgccc gccggcgtcc gccacccggt ggcgaccttc gtcttccaga actacccgga   28140
cgccgccgtg ccgcccggcc accggccgct gcccgaggtg cccgaggagg ccgctggcg   28200
cgaggccggg tccgacccgc tggcgctggt gtgcttcgag gacgacgcg tgcccggctg   28260
ccggctggag ttcgacaccg ccgcggtgtc ccgggcgacc gccgagctgg tcgccaggga   28320
ggtccgccgg gcccagaacc gactcgcgaa ggggatgcag ccgtgaccgc ggacgccgcg   28380
ctcgaacccg acgaacgggc cgcctggctg gcctacaacg acaccgccga ggacttcccc   28440
ggcccgcacc tgctcgcccg cctcgacgcc gtggcgcgcg agcacccga ccgcccgcc   28500
gtgcacgccg tcgacggcgt gtggacctac cgcgaactgc accgccgcgc cgacgcggtg   28560
gccgccttcc tggccgcgcg gggcgtccgg ccgggttcgg tggtggcgat cgcggccacc   28620
cgcgcgctcg ccccgtacgc cgcgctgctc ggcgtcctga aggccgggtg cgcctacgtg   28680
ccggtcaacc cggacgaccc cgccgaccgg gtggcgttcg tgctggccga cgccggcgcc   28740
acgccgctgc tgctggacac cgaccgcg agcctgcccg ccgcgccgc gccggacgtg   28800
ccgcacgagc cggaccgggt ctgctacgtc atctacacct ccggcagcac cggccgcccc   28860
aagggcgtgg tgatggccga acgcgccgtg gacaacctca cgcactgggt ggtgcggcgg   28920
cacgacgtgc gcccgacga ccggctgggc cagaccgcgc gctgacgtt cgacccgtcc   28980
gtgcaacagg tcttccccgc ctgggcgacc ggcgcgtgcc tggtcaccgt gcccgacgac   29040
gtccagcgcg acccggccgc cttcctggac tggctgcgcg ccgagcgcgt cacccacctg   29100
```

```
gacctggtga cctcgcactg ggtccacctg ctcaacgccg ccgaggcgcg cccggcggag   29160
ctgccggacc tgcgctggat catcatcggc ggcgagacgt actactacca ccagacccac   29220
cgctggcacc gggtcgtgtc ctcccccgcg cggctgaaca cgatctacgg ccccaccgag   29280
gcggccgtca acgccaccga gcacctcacc gaacccgacc tggaccacgg ccaggtgccc   29340
atcggcgtcc cgctgcccaa ctaccgcctc tacgccctgg acgacgacgg gcggctgtgc   29400
ccgccgggca tcaccggcga gatccacatc gccggcgccg gcctcgcgcg cggctaccgg   29460
tccgccgagg ccaccgcgaa ggcgttccac gagctggaag tccacagtgg acggaccgag   29520
cggctgtacc ggaccggcga cctcgcccgg ctggtgcgcc acgccgaccg gtgggcgctg   29580
gagttccagg gccgggtgga cagccaggtc aagatctccg gctaccgcgt cgagctggag   29640
gaggtggacg cggcggtcaa ggccgtgccg ggcgtgcggg acgcggccgt cgtggtcgcg   29700
ggcgaaccgg ccgagcagct cgtgtgctgc tacgtcggcg acgtgccgcc ggaccggctg   29760
cggtcgcgcc tgaccgagcg gttgcccgcc tacctggtgc cgcacctgct ggtgccggtg   29820
gaggcgttgc cgttcacccg caacgggaag atggacaccg ccgagctggc cgagctggtg   29880
cggcggttcg cgcgcgactc cgccggccgc gcgccgcgcc ccggcgtgga gtccgtggtc   29940
gcggcggtgt gggccgaggt gctggacctg ccggaggtgt cggcggacgc ggacttcctg   30000
ggccacggcg ggtcgtcgct gctggcgttc cgggtcgtgg accggctgcg ccggcgcggg   30060
atccgggtgc ggccggccga cgtgctgcgc gagcgcacgg tcgcgggcct ggccgccgtc   30120
gccgaagagg acctggtgct gacgcccctcg acgcggctgg cgctgcgccg gccgggcggc   30180
aacgccaccc tcgacatcgg cctccccgcc gacgtgcccg ccgaacgggt ccgcgccgtg   30240
ctggaggaca tcgtgcggcg gcaccccgtg ctgcgcgccc ggatcgacga cgacggcccg   30300
cgcgcggtgc cggtggaccg gttcgagctg cacaccccccg acggcccggt ggacgacgcc   30360
aaggcccggc tcgccgagtc caccgacctg acgaccgggc tgcccacggc agccgcgctg   30420
gtggcgggcc ggctgctggt gtcgatccgg cacgaactgg tcgacggcgc ggcgctgcgc   30480
cgggtcgccg aggaggtcgc ggccggcctg ggtcgcgcgc cgcggccccg cccggtcgtg   30540
cccgtggccg accagccgct gggcggaccg gccccggacg ggctgcgcgg gcacctggtc   30600
cgcttccttg aggccgagaa ggccgcgttg gccgcgctgc cgcgcgagca ccgcgaccgg   30660
gtggtggagg tggacctggg gcacgcgccc gacgcgctgc tggacacccc gccgacccgg   30720
tggcacgccc gcctggtcgc cgccgccgcg acggccgcgc ggtcctggct ggggctggtc   30780
gacgtgccgg tgggcgtgcc ccggcactgg ccggcgcgg cggggtcggt cgcgaacctg   30840
gccgacgtgc tgcccctggt cgtcgcggac gacgacgagg ccgacgcgca gtggcggcgc   30900
ttcgccgacc cggccgtgca ctgggcgcg gcgctgctgg acgcctgccc cgacctcgcc   30960
gacgactggc ccgcgcccg gatcgcgccg cagggctcgt tccggctcgt ggtgaccgcc   31020
gacgacgaac cgctcgcgcc cgacctcccg ctgcacgaga gccgaccgc gttcgacccg   31080 gcgtcgcgg gcgcggtgga gttcgcggtc gtcgcgggcg accgcctgcg gctgcacgtc   31140
accggctggg acctgcccgc cgacgaggtc aaggccgtgg ccgccggctg ggtcgaggcg   31200
ttggcgggtg agcggcggtg acgccggacc cgcactggct gcgcccggtg ggcgggcggt   31260
ccggcggccc ggtgctgctg tgcctgccgc acgcgggcgc cggcgccttc gcctacgccg   31320
gctgggaccg gcaggacgcg ttcgacgtcg tggccgtgca accgccggc cgggaggacc   31380 ggttcgccga gcagccgatc accgaccccg agcacctcgt ccgcgagatc gccgacgcgc   31440
tgggcgacct cgccgagcag ccgctggcgc tgttcgggca cagcctgggc gcgctgatcg   31500
```

```
cccacgacct ggcccgcgag ctggaccgcc ggggcgcgcc cgaccgctg ctgctcgcgg      31560 tgtccgggca cgtgccgccg caccggctcg accccgaccg ggcgcgcgac cggtccgacg      31620
ccgaactggt cgagcacgtc cgcgaactcg acgacgaccc cctggacgac gtgctggccg      31680
acccggagtg gcgcgcgatg ctgctgcgcc cgctgcgcgg cgacctggcc ctgcacgacg      31740
cccacaccca ccgccccggc ccccggctgc gcgtgcccgt gctcgcgctg accggcgcgg      31800
acgacgacgc caccccggcc gaggacacgg cggcgtgggc ggagctgacc gagggcccct      31860
tcgcccaccg ggtccacccc ggcgggcact tctacctccg cgccgccagg tcggccgtcc      31920
tcgacgacct cgcgcaccac ctcgaaggag cgtggcgacc atgaccaccg agaccccagc      31980
gaccaccggc gccccggcga ccaccggcgc ccccgcccca ccgggccggg ccagatcgt      32040 cgccgccgtg ctgccggtat cgccgaggt gctcgacgcg ccggacctca cccccgacag      32100
cgacttcttc gtccacggcg gcaactcgct gctggccatc cgggtcgccg ggcgggtggg      32160
ccgcaggctg ggcggcagg tcccgcccgc cggcgtgctc aagcaccga ccccggacct      32220 gctggccgcc cacctggagg aggagttccg cggcggcggc gcgccgccga tccccgcgcc      32280
gcgcgccggg gcggaggccg accgccggcc gtccaccgcc caggaacggg tgtggctgct      32340
gcaccagctc gaccccgacc ggctcgacca cctggtcacc gtggcgctgg acgtggccgg      32400
gacggtggac ccgcggcgt tcaccgcggc gtggaccgcg gtcgtgcgcc ggcacgaggc      32460
gctgcgcagc cggttcgtca aggccgacga cgaccgggtc gcggtcgtcg tggacgccga      32520
ggccgcgccg gagatcagcg tgctggacct cgcccgcttc cccgcccgg tgcgcgaccg      32580 gctcgccgag gaacgggtcc ggctcctgcg caccaccccg atccggctgg acaccggccc      32640
gctcgcccgg ttcgcgctgc tgcgcctggc cgaccggcgg taccggatcg agctggccgt      32700
gcaccacatc gtgtgcgacg gctggagcct ggacaccctg ctcgccgact cctcgacgc      32760 ctacggccgc gcgctggcgg gccgctcccc gcgcgctgccg ccgccggcgg tgggcttcgc      32820
cgactacgtg gcgtgggagc gggacgtgga gtcctcgcgg tggccggaca tggccgtgcg      32880 gctggccgc cggttcgccg accggcccgc cgacctgccg ctgccggtgg acccggtgga      32940
cgtgccggcg cacgaggacg gcgacgacgt gaccgtgcac gccccgcccg gcctcgcggc      33000
ggcggtggag cgggcccgga cctccttcgg gcacaccgcg ctgacgttcc acctgaccgc      33060
gctgggcgtc ctgctcgccc ggatcaccgg ggtggacgac ctggtggtgg cggtgccggt      33120
cgcgggccgc gcgcagaccg agcacgagga cctggtgggg ctgttcgtca acacggccct      33180
ggcgcgggtg cggctgggcg gcacctcgga cgtgcgggtg ctgctggagc gcaaccgcga      33240
cgaggtggac gagctggtgg actgccagac cttcccgttc gaccgcctgg tggacctgct      33300
cggcgcgcgc gcgcgcggca ccagggtgcc gctggcccgg gtgtcgctgg cggtgcagaa      33360
cttcgacgac cccggcacgc ccgcgcccga gctgggcttc acctggcagt ccgcgaccc      33420 gccgagcgg cagagcaagt tcgacctggc cttcaccgtc tccgacaccg acggcctgcg      33480
gttgacggtc acctaccggc cgtcgctgtt ccgccgggcc accgtcgccg cgtgggccgg      33540
ccagtacctc gtggcgctgg agcacgtcgt gcgcggcgtc ccgacccgg aggggagcgc      33600 gcggtgaagc tcaaccggca gcacgagttg ttccgcgagt ccgtgcggat ggtgctcgac      33660
cgcgagtgcg tcgagctggt cgacgactgg gagcgcgacg gcgtcatgcc cgtgcaccag      33720
ctgtgcaaga ccctggccgc cgaagggctg ctgggcctga ccatgccggt ggaggacggc      33780
gggctggccc tggacctggg ctactcctac gtgtgggcgc aggagctggg ccgcgtcccg      33840
gccggcgcgc ccgcgatggc gctgtccgtg cagaccgaca tcgtcgcgcc gctgctggcc      33900
```

```
cgcgccggca cgcccgaggt gcgccgggac gtgctgcggc cggccatccg gggcgagctg   33960
gtggcggcgc tggccgcgac cgagccggcg ggcgggtccg acctgggcgc gctcaccacc   34020
accgccgtgc gcaccgagcg cggcttcacc gtcaacggca ccaaggcgtt catcaccaac   34080
gggtcggtcg cggacttcgc cgtggtgctg tgccgcaccg gcgaggcggc cggcatcggc   34140
gacctggcgc tgctggtggt gccgaccaac ctggccgggg tgcggcaggt ccgccacacc   34200
ggcaagctcg gccaccgctc gtgcgaccac ggcacgctga ccttcaccga cgtggaggtg   34260
cccgcggcct acctgctggg cgaggtcggc gagggctacg agctgcagac ccgcacgttc   34320
acccgggagc gctgcttcct ggccgtggtc gcgctcggcc aggccgaacg ggtgctgcgc   34380
gcgaccgtgc accacgcgcg ccgccgccgc gtcctgggcc gcgcgctgac cgaccaccag   34440
gcgatcgggt tccggctcgc cgaactcgac gccgaactcg acctcgtgcg cagctacgcg   34500
ggcgaggcct accaactgct cgccgacggc gcgcagtgcc tgcgcgaggc cagcatcgcc   34560
aagctgcgcg ccacccgcct gctgcgcgag gtcgccgacg tcgggctcca ggtccggggc   34620
gcggcgggct acctgggcgt ggacgacgtc gagcgcacct accgcgacgc ccgcgcgggc   34680
agcttcgcgg gcggcgcgga cgaagcgctg ctgcacctca tcgcgggcca cctgaccggc   34740
accgaacagg agtgaccatg acgccgagcg aagaactgct gttcctggac cgcgagaccg   34800
tgcgggcctg cgtcgcgggc gtggaccccg tcgaggtggt cgagtccgtg ctgcgcagcc   34860
acgccgccgg ccgcaccacc ctgcccgccg agggctacct gccgtgggag aacgaccagg   34920
gcgcgtactg ccggtccatc gccatgctgg gcgcggtgga cggcgaacgc ggccccacct   34980
acggcatcaa gctgatcaac gccgccgtct ccaacccctc gatcggcctg gaccgggccg   35040
gcggctgcgg gttcctgttc gacccgcgga ccgcccggcc cgtggtgctg gcggaggcgg   35100
cctacctgtc gggactgcgc accgccgcct acacgatggc gagcctgcgg cacctggggc   35160 cggtgggggtt cgacgcggtg agcttcatcg gcacgggggc gcaggcgcgc gtgcacgccg   35220
cgctgctggc ccgctacttc ccggccgtgc gggacctgca cgtgttcgac accgagcgct   35280
ccagggccga ggcgttcacc ggcgcgtccg ggcacaccgt gcacgtgcac gacaccgccg   35340
aggccgccgt gcgcgcgagt cacgtcctgg tcaccctgac caccgtcgac gacgggtaca   35400
tcccgcacga ctggttccgg cccgggtcgt tcgtcgcgca cgtgtcgctg gacgacctgc   35460
tgcccgaggt gttcttcaag tccgaggcgc tgttcgtgga cgacctggag ctgatccggg   35520
agaacccgcg ccggggtgctg ggcgcgctgc tggccgacgg cgacgtcccg gtcaccgggt   35580
cgctgggcgg ggtgctgacc ggggcggtgg ccccggtgcg gccccgggac ggggtggtgg   35640
tcagcaaccc gttcggcatg gccgtgctgg acgtgggcct gctggcggag gtcgccgcgc   35700
acgcccgctc cgccgggctg gcacgacccc tcgacctgct gggcgcggcc cgatgaccgg   35760
cctgtactcg ctggcggacc tgtccccggc ggacgtcctc gccctggcgg accggtcggt   35820
gcagctgcac cgcgaccgga ccgcgcacga ccgcccgctg accgacctgg tggtgggcac   35880
cctgttcacc aagacctcca cccgcaccag gaccgcgttc accacggcgg cgctgcggct   35940
gggcgcgtcg gtggtcgcgt tcggcccgga cgagctgcag accgccaccg gcgagtccac   36000
cgcggacacc ggccgggtcc tggcgtccat gctggacggg ctggtcgtgc gcaccgccgg   36060
gccggtcgcg cggcaacggg agttgtccgg cggcggcgtg ctgccggtgg tcaacgccat   36120
gagccgcgag gagcacccca cccagggcct gaccgacctc gcggtgctgc gccaccactt   36180
cggcgacctg gcgggcgtgc gggtgctgta cgtgggcgag ggcaacaaca ccgccgcgc   36240 cctggtgcac gcgctggccg ccgtcccggg ctgcgagctg gtgctggcct gccccaaggg   36300
```

```
ctacgggccg cgcgacecceg geccgtggeg ggaggtcgcg gacctcgcgg aggtcaccgg   36360
ggacgtggac gtcgtctaca ccacccggtg gcagaccacc ggcacggcca aggccgaccc   36420
ggactgcgcc gaggcgttcc ggcccttcca cgtggacacc gcgctgatgg accggtggcc   36480
ggacgcggtg ttcctgcacg acctgcccgc ccaccggggc gaggaggtgg ccggcgcggt   36540
gctggacggc gcgcgtcgc tggcctggac gcaggccgcg atgaaggcgg cgagcgcgat   36600
ggcggtgctg gagcggttcg tcgggggtcg tcgtgcttga cctctccccc gcgcagcgca   36660
gcctgtgggt gctgcaccaa ctggacgaca ccgggttcac gctgtcgtcg gcgcaccggc   36720
tgcgcgggcc gttcgacctc ggcgcgttca cggcggcggt ggacgcggtg gtggcccggc   36780
actcgccgtt gcgcacccgg ttcccggtcg gacggacgg cgggcccgac ccgtggtgg    36840 accogccggg gccggtggtg gtcgaggcgg tcgcggcgga ggggttcacg gccgcgcacg   36900
ccgaagccgc gcggttctgc gcccggccgt tcgacctggc gcgggagtgg ccgctacggg   36960
tgctcgtggt gcgtctgtcc acagaggacc atgtggtggc gttggcggtg caccacatct   37020
cctgtgacgg cgtgtcgctg gggctgttgc acgacgagct gtcccggctc tacgacggtg   37080
cggagctgcc gccggtcgcc gaccaccggg agctggtggc tcggcgcgcg gtggaccgg    37140 cggcggtggc ccggtgccgg gaccggctgg cgggcgtgcc gccgctggcc gccgaccggc   37200
ccgcggtgcg gtcgggcaag ggcgaccagg tgtggttcac cgtgcccgcc gacctgaccg   37260
gcgcggtgcg ggcgtgcgcg cggcggcacc gcgtcaccgc gttcatggtg ttgctggccg   37320
cgttccagct cgtcctgcac cggcggaccg ggcagaccga cttcgcggtc ggcgtgccgg   37380
tggccgggcg cggcgacccg gacagcgaga acgtcatcgg cctgttcacc aacaccgtcg   37440
tggtgcgggc cgacctggcc ggcgagccgg gcccggcgga ggtgctgcgc cgggtgcggg   37500
aggccgcgtt cgacgcgttc gccgaccagg acgtcccgct gggcgcggtg gtggcggccg   37560
tgggcgaacc gcccgacccg gcgcgcaccc cgttgttcca ggccctgttc accttccagg   37620
acgcgccggt cgggcggctg gcgctgcccg gcgtgcggtg cgtggaactg gacctgccca   37680
ccggcgccgc cgcctccgac ctggagctgg agctggtgcg cgacggcgac gagctggccg   37740
ggtccctgga gtactcgacc gacctgcacg acagcggcac ggccgcggcg ctgaccgccg   37800
acttcctggc cgtgctggac gagatccacg cggaataggg ggaaacgtgg acacgtacct   37860
ggtggtcgtc aaccacgagg agcagtactc ggtgtggccg gccgaccggc cgctgcccgc   37920
cgggtggcgt gccgagggca cgtccggcga caaggagcag tgcctcgcgc acatcgagac   37980
cgtgtggacc gacatgcgcc cgctcagcgt gcgccgccgc gcggaggcgg tgtgaccgcg   38040
ctgcaccgcc tcgaccagct cgccggcgcg cggcccgacg cgccggcgtt gctggacgag   38100
gcggagacgg tgtcctacgg gcggctgtgg cgcgagctga ccggcgtggc gggcgcgttg   38160
cgggcggcgg gcgtgcggcg cggggaccgg gtggtggtgc cggcggaccg gacgtggcag   38220
ggcatcgtgt cgatgctcgg tgtgctgcgg gcggggcgg cgtacgtgcc ggtggacgcc   38280
ggcgacccgg tcgagcggtt gcggcacgtc gtgcggacgg cgggcgcggc gtgggtgacc   38340
gggcgggcgg aggcgctggc ggcgttgccg gacctgggcc tgcaccccgat cccgttcggc   38400 tcggccccag actcgccctc acgctcggcc tcaggctcgg actcgggttc gcactcggct   38460 tccgaggcg tcggcgggtt gcccgatccg gaggacttgg cgtacgtgat gttcacctcc   38520
gggtccacgg gcacggcgaa ggcggtcatg gtgccgcacc ggtcgatcgc gcacgccgcc   38580
ccgtcgctgg cgcggcggtg cgggatcacg ccggacgacc ggttcctgag ctgggcgtcg   38640
ctcgtgtggg acaccagcgg cgaggagctg tactcgacgc tgctgtccgg cgcgggcctg   38700
```

```
gtgctcgacc gcgaggccac ctccgggtcg gtcccggcgc tgctgcgcgc ggtcgaacgc    38760
cggtcggtgt cggtcgtgga cctgccgacc gcgttctgga accaggtggt cgactacctg    38820
gagacgaccg gcgaggcggt gccggagtgc ctgcggctgg tcgtcgtggg cggcgaggag    38880
gtgcgggcgc ggcaggtgcg ggtctgggcc gagcgcgcgc cggacgtccg gctgctcaac    38940
acctacgggc agaccgagac cgtcatggtc acccacgcgg ccgacatcgg cggtctcgcg    39000
ccgccggacg ggggcgcggt gccgatcggg cacccgctgc cgcacgtccg ccagcacctc    39060
gaaccggtcg gcgacggcct gttcgagctg cacgtcggcg gtcccacccct cgcgtggggc    39120 taccgggacc ggcccgcggc gaccgccgag cggttcccgc ccgacgagcg cgggcggcgg    39180
ttccgcaccg gggacctggt gcgggtggcc gacgacggcg cactggtgtt cgtgggtcgg    39240
gcggaccggc aggtcaaggt gcgcggggtg cgggtcgagc cggccgaggt ggaacgcgcg    39300
ctcatggcgt gccccggggt gaccgcggcg cggcgttcg tggtggacaa cgcgtcggac    39360
ggcgtcctgc tggtcggcgc gttcgtgccc ggcgacggcc acgccacgcc cgcgacggtc    39420
gcggcggccc tgcgcaccag gttgtcgccc gcgctgctgc cgcaccgcct ggtgtccgtg    39480
cccagcatgc cgctgctcac cacgggcaag atcgaccagg ccgcgctggt ggagcggttc    39540
gcgcggtccg acgtcgcgcc gggcgccggc ctggcggggc agctcgcggt ggtgttcagc    39600
gaagtcctgg gcacgccgtg cgcggccgac gacgacttct tcgaccaggg cggtgactcc    39660
gtggtcgcga cccggctgct gacgcgcatc cggcgcagct accgggtgga gctgacgttc    39720
cgcgacgtgt tcgaccaccc gagcccgacc gcgttggcgg gcctgatcag ccggacccccg    39780 aggtgagcgc ggtgcccgtc cagccgcacg agcacgtccg gcgcacgccg gtggagccgt    39840
cctggcggcg gttccccggc tggcgggacg tgacgcggga gcagtggcgc gacccgcggt    39900
ggcagcgcgt gcactgcgtc cggaacaccc ggcagttgcg cgcggtcgtc ggtgacctgc    39960
tcgacgagcg gttctacgac gacctggcgg ccgaccagga gtcgttcgcc acgatgtcga    40020
tgctgctgcc cccgcagatg ctcaacacga tggtgcccga gggggcggcg gacttcaccg    40080
gggcgttcta cgccgacccg gtgcgccggt acatgctgcc ggtgcggtcc gaccgcgacc    40140
ccgagtggcc gagccacccg tactcgtcac gggactcgtt gcacgaggcc gagatgtggg    40200
tggtggaggg cctgacccac cggtaccga cgaaggtgct ggcggagctg gtgtccacgt    40260
gcccccagta ctgcgggcac tgcacgcgga tggacctggt cggcaactcg accccgcagg    40320
tgcgcaagca caagctggag ctcaaaccgg tggaccggca ggaccggatg ctggactacc    40380
tgcgccggac gccggccgtg cgggacgtgg tggtctccgg cggtgacgtg gcgaacgtgc    40440
cgtggccgca actggagtcg ttcctggcgc ggctgctgga gatcgagacc gtgcgcgaca    40500
tccggttggc caccaaggcg ctcgccggcc tgccccagca ctggctccaa ccgcaggtgg    40560
tggagggcat gtcccgcgtc gcccgcacgg ccgcgagccg gggcgtgaac ctggccgtgc    40620
acacgcacgt gaaccacgcc cagtccgtga cgccgttggt ggccgaggcg gcgcgggcgc    40680
tgctggacgc gggggtgcgg gacgtgcgca accaggcgt gctgatgagg ggcgtgaacg    40740
cgacgccgga cgacctgctg gagctgtgct tcgcgttgca gggcgaggcg aacatcctgc    40800
cgtactactt ctacctgtgc gacatgatcc cgaacgccga gcactggcgg acgtcggtgg    40860
ccgaggcgca ggacctgcag gcggcgatca tgggttactt acccggctac gcgacgcgcg    40920
gcatcgtgtg cgacgtgccg tacgtgggga agcggtgggt gcaccaggtg gtcgagtacg    40980
accgcgagct gggcgtctcg tactggacga agaactaccg gacgggtatc gaatcagacg    41040
acccgaacgc cctggaccgc cggtacccct actacgaccc gatctccacg ttgggcgaga    41100
```

```
cgggccggcg gtggtggcgc aaacacgaac gagcctgacc cgcacgcgcc ccgacggctc   41160
aacggtcgtc ggggcgcggc accggcacgg gcgggcgcgg ggtgggccgg cctggcgtgc   41220
gcgggcctgc ggcgagtgtg ggcgtgcggg tgggctatgg cggagcggtg gactcagcgg   41280
taggcggtca ggccgtcttc cagttcttcg tcgtcgccgt cctcggcacc cgccagcgcc   41340
tgctgcaacg cgaacgtccc ctggtaagcc cggatccgcg ccacaggtc ccccgccccg    41400 agcagcgcga ccacccgctc caccagctca ggcccataac tggcccccac cgccgccagg   41460
tcctccgccg ggtcgcccac cttggcctcg tcccagtcca cgatcccggt cagccgcggc   41520
agctcctcga cctgctgcca caacacgttc tccccgccga gatcccgtg caccaacccg    41580 gtggcgacgt ggtccatcgc cacggccgcc gccaactcgc gctcggcccg cgccggccg    41640 tcctccgaca tcagcgggaa cagcgtcgcc cggacccgcc cggcgaaccc gcgccaccgc   41700
ccggcgtcgg cgaccggcag caccagccga aacttctcca catcagcgcc ggccatcgcc   41760
cgcaacaccc gcgcgaactc ggcggccacg acgtcgatca cctcgggcga cgtcgcgtcc   41820
ccccgctcca acggcgtgcc gtgcagccgg ctgagcacca ggaacccgtg cggaccgccg   41880
tcccgcacct ccgacagcgg aaccggcacc cccaccccca gctccaccgc gtcgaccgcc   41940
gtcagcaccg ccacccgacc cggcagctcc gccgccgcgc cagccgtctt gggaaaccgg   42000
aacacccggt cacgcgcgat caacacgtcg tggaactggc cggagtgcac accggcaccc   42060
tcaagatcga catccgggtg ggcacgccga accacgtcaa caaggtggga caaggtcatg   42120
cccccacata gtgccgaccc accgaagcca ccgcgaccga tttatctcac ggtccgcacc   42180
cgtcccacta ctcagtgaaa tcccttacaa cgatcgggtg aatcgccgca cagcacccga   42240
accgaaccca cgcccgcgca cgaaccactg gagccgtccg gcgcacggcg gaatcgtgcg   42300
ccggacgggc ctgcgcgtgc cgccggttag agttcgcggg tggggaatgg cgagcggatc   42360
ggggtgttct acgacggcac ctggttcgcg tatttgagcg actacttcgc gtccgtgcac   42420
ccgcgggccg cccgggtctc gctggacggg ttccacgacg ccctgcgctg gtacgtgcac   42480
accgtcaccc accagccgtt ggacgagtgc gtggtcagtg aggcgcatta cgtccgcggc   42540
cggatcgaca cgccggcggt ggcgttcgac gccgtgttgg cggcggccgg ggtggtgcgg   42600
cacgacctgc cgctgcacgc gggcaaggag aagggggtgg acgtccacct cgcgctggag   42660
gcctgggagc gggccacctc cgtgccgttg cggtgggtcg tgctggtgac cggcgacgcg   42720
gacttcgcac ccctcgccac ccgcctcaag acacgcggcg tccgggtcgt ggtgccggtc   42780
gtggacggcg gggtcgtcgc gccggcgtgg atgccgcgca cggcggcgcc gctgcgcgcg   42840
gcggcgtcgg ccacgcccac gttcgacgac ctgttcacac ccgcgaacg cgacgactac   42900 ccgctgcggg cgccgttcgt gcggacctcc ggggcggcg cgtccgtcgc cggcgaaccc    42960
cgcggccggc gcaagggcac cgtcaccggg tggaaaaccg gccagccgca cgggttcatc   43020
accgacacgc gcggcgcgtc ctggttcgtc tcgcgcgacg acctcccgct ggggctggtg   43080
gccctgccgg tcggcacgtc cgtgtcgttc tccggcccgt ccactccccc ggccggacgc   43140
aagtacccgc gggcgtacgc ggtgcagacg gagtgatcag cccttcttga acagcagctt   43200
ccacggcatg accgcggact ccaactgcac cccgaagctc atcttggacg cgccctccgc   43260
ccgctcctcg aaccggatcg gcacctcggc gatgcgcatc ccgcgcttga ccacgcggtg   43320
gttcatctcg acctggaagg cgtaccgtt gctgcggatc gagccgacgt cgatcctgcg    43380
gagcgtcgcg gcgcgccagc acttgaagcc ggcggtggcg tccttgacgc gcagccgcag   43440
gatcgcgttg acgtagacgt tggcccacag ggaaagcgcc ttgcggtgcc acttccactc   43500
```

```
gccggacacc gacccgccgg gcacgtaacg cgaaccgatg acgaccgccg cgtccgacgt   43560
ccgcagcacc tcgatcatcg tcgggatggc gctcgccggg tgcgacaggt cggcgtccat   43620
ctggacgacc aggtcggcgc cgtcgtccag ggccttcagg atccccgcga cgtacgcgcg   43680
cccgaggccg tccttctccg tgcggtgcaa cacggaaagc ggaagcgggc cttcgagcgc   43740
caacttgtcc gcgaggtcgc cggtgccgtc gggggaattg tcgtcgacca ccaggacgtg   43800
caggcccggc acacccaggt cggcgagcag gtcgaccagg acgggcaggt tgtcccgctc   43860
gttgtaggtc ggcacgacga cggtggtcct gagcgagtcc ggttgtttcg acattccccc   43920
gagcttaccc gcgcgcggac gccgggaagt gcgcgaccgc ctcagtcgtg ccaggggagt   43980
tcgtcacgta gtccggtgtg gatcgcataa gcgttcttga tggcggcttt caccgagcct   44040
tccgcccaac gccggtgccg gcggtcacag gcgtcgttgg cgaaccacac ccggttcacc   44100
gggcggatcc ctttagtgag ggttaattgc ggccgcgaat t                      44141
```

<210> SEQ ID NO 2
<211> LENGTH: 2401
<212> TYPE: PRT
<213> ORGANISM: Saccharothrix mutabilis

<400> SEQUENCE: 2

```
Met Thr Val Asp Pro Thr Ile Glu Leu Arg Leu Thr Leu Asn Gly Asp
1               5                   10                  15

Pro Asp Val Pro Ala Leu Thr Arg Ala Trp Ala Ala Leu Arg Ala Arg
                20                  25                  30

His Arg Ala Leu Ala Gly Pro Leu Gly Ala His Arg Asp Val Ala Ala
            35                  40                  45

Phe Glu Asp Ala Val Arg Ala Gly Pro Gly Cys His Leu Leu Arg Ala
        50                  55                  60

Pro Gly Arg His Glu Phe Ala Leu Thr Ala Gly Cys Asp Ala Ala Ser
65                  70                  75                  80

Val Pro Ala Val Leu Ala Glu Leu Ser Ala Leu Tyr Ala Arg Glu Leu
                85                  90                  95

Gly His Pro Ser Glu Gly Leu Pro Ala Pro Ala Pro Ala Val Pro His
            100                 105                 110

Asp Arg Pro Pro His Asp Val Pro Pro Gly Pro Glu Leu Pro Gly
        115                 120                 125

Leu Glu Leu Phe Gly Arg Gly Glu Pro Gly Pro Arg Val Val Thr Arg
    130                 135                 140

Val Asp Leu Gly His Pro Thr Arg Arg His Val Ser Ala Leu Ala Arg
145                 150                 155                 160

Arg His Gly Val Thr Arg Glu Val Val Val Thr Ala Trp Ala Leu
                165                 170                 175

Leu Leu Gly Glu Leu Ala Glu Arg Asp Glu Phe Val Leu Gly Leu Val
            180                 185                 190

Thr Asp Pro Arg Asp Pro Ala Ala His Arg Pro Ala Val Gly Ala Leu
        195                 200                 205

Arg Glu Ala Arg Pro Leu Arg Val Asp Leu Thr Gly Arg Pro Ser Phe
    210                 215                 220

Ala Asp Ala Val Arg Arg Thr Thr Ala Ala Val Ala Thr Ala Arg Ser
225                 230                 235                 240

Arg Pro Gly Asp Ala Pro Ala Asp Val Ala Val Gln Tyr Gly Glu Gln
                245                 250                 255

Pro Ala Ala Ala Leu Arg Leu Ala Gly Leu Asp Pro Ala Glu Val Pro
```

-continued

```
            260                 265                 270
Ala Ala Phe Trp Leu Ala Asp Asp Leu Pro Gly Pro His Arg Val Val
            275                 280                 285

Leu Arg Leu Leu Asp Thr Pro Asp Gly Leu Leu Ala Gly Val Ala His
            290                 295                 300

His Pro Asp Ala Leu Asp Gly Pro Gly Ala Arg Arg Trp Val Ser Arg
305                 310                 315                 320

Leu Ala Ala Leu Leu Ala Gly Ala His Asp Glu Ser Pro Glu Pro Val
                    325                 330                 335

Val Met Ser Glu Asp Glu His Arg Arg Val Val Leu Ala Pro Asn Ala
                    340                 345                 350

Thr Ala Val Asp Leu Gly Ala Pro Ala Thr Val His Asp Leu Val Ala
                    355                 360                 365

Glu Gln Ala Arg Arg Thr Pro Asp Arg Thr Ala Leu Val Phe Ala Gly
            370                 375                 380

Ala Glu Val Gly Tyr Ala Glu Leu Asp Ala Arg Ala Asn Arg Leu Ala
385                 390                 395                 400

His Glu Leu Arg Glu Arg Gly Val Arg Arg Glu Thr Pro Val Ala Val
                    405                 410                 415

Cys Leu Glu Arg Glu Thr Gly Leu Val Val Ala Leu Leu Ala Val Leu
                    420                 425                 430

Lys Ala Gly Gly Ala Phe Val Pro Leu Asp Pro Gln Tyr Pro Arg Gln
            435                 440                 445

Arg Leu Ala His Met Leu Ala Asp Ser Gly Ala Ala Val Val Leu Thr
            450                 455                 460

Gln Gly Arg Leu Arg Asp Arg Phe Ala Ala Asp Gly Pro Pro Val Leu
465                 470                 475                 480

Val Thr Asp Asp Ala Thr Arg Phe Ala His His Pro Ser Ser Ala
                    485                 490                 495

Pro Pro Ala Ser Ser Gly Pro Asp Leu Ala Tyr Val Tyr Thr
            500                 505                 510

Ser Gly Ser Thr Gly Arg Pro Lys Gly Val Met Val Glu His Arg Gly
            515                 520                 525

Ile Ala Ser Tyr Leu Arg Gly Met Gln His Asp Phe Pro Leu Thr Pro
            530                 535                 540

Glu Asp Arg Val Leu Gln Ala Thr Ser Leu Ser Phe Asp Val Ser Val
545                 550                 555                 560

Tyr Glu Ile Phe Trp Pro Leu Gln Val Gly Ala Ala Val Val Leu Pro
                    565                 570                 575

Ala Pro Gly Gly His Thr Asp Pro Tyr His Leu Ser Glu Leu Ile Gln
            580                 585                 590

Arg His Gly Val Thr Cys Leu His Phe Val Pro Ser Leu Met Arg Leu
            595                 600                 605

Phe Val Glu Glu Ala Asp Pro Gly Ala Gly Ala Gly Leu Arg Arg Val
            610                 615                 620

Phe Val Ser Gly Glu Ala Leu Asp Pro Ser Leu Val Ala Leu Val His
625                 630                 635                 640

Glu Arg Thr Ser Ala Glu Leu Val Asn Leu Tyr Gly Ala Thr Glu Val
                    645                 650                 655

Ser Val Asp Ser Thr Tyr Trp Thr Ala Asp Arg Ala Lys Pro Asp Arg
                    660                 665                 670

Pro Val Leu Val Gly Arg Pro Met Ala Asn Ala Thr Ala Tyr Val Leu
            675                 680                 685
```

-continued

```
Asp Gln Arg Leu Arg Pro Lys Pro Ala Gly Val Val Glu Val Phe
690                 695                 700
Leu Gly Gly Ala Ser Val Thr Arg Gly Tyr His Ala Arg Pro Ala Leu
705                 710                 715                 720
Thr Ala Glu Arg Phe Val Pro Asp Pro Phe Gly Pro Pro Gly Ser Arg
                725                 730                 735
Leu Tyr Arg Thr Gly Asp Leu Gly Arg Val Thr Pro Asp Gly Glu Leu
                740                 745                 750
Glu Phe Leu Gly Arg Arg Asp His Gln Phe Lys Leu Arg Gly Trp Arg
            755                 760                 765
Val Glu Ala Gly Glu Ile Glu Ala Ala Ile Thr Ala His Pro Gly Val
770                 775                 780
Asn Gly Ala Val Val Thr Glu Gly Ala His Glu His Ala Thr Leu
785                 790                 795                 800
Leu Ala Tyr Val Gly Ala Asp Ala Gly Leu Asp Gln Ala Ala Leu Arg
                805                 810                 815
Glu Phe Leu Ala Arg Arg Leu Pro Arg Pro Leu Val Pro Ala Arg Phe
            820                 825                 830
Ile Arg Leu Asp Arg Leu Pro Ile Ser Pro Asn Gly Lys Val Asp Arg
        835                 840                 845
Ala Ala Leu Pro Lys Pro Asp Gln Ala Pro Ala Glu Pro Ala Pro Thr
850                 855                 860
Thr Ala Ala Pro Pro Thr His Ala Ala Asp Gly Arg Pro Ala Leu Glu
865                 870                 875                 880
His Ala Ala Asp Gly Arg Pro Ala Leu Glu Arg Gly Ser Asp Gly Arg
                885                 890                 895
Pro Val Leu Glu Val Val Leu Ala Val Ala Glu Val Leu Gly Ala
            900                 905                 910
Pro Ile Gly Pro Glu Asp Ser Phe Phe Gly Ser Gly Asn Ser Ile
        915                 920                 925
Gln Ala Thr Arg Leu Ala Ala Arg Leu Arg Ala Ala Leu Arg Thr Asp
930                 935                 940
Val Pro Val Arg Leu Ala Phe Glu Ala Pro Thr Pro Ala Ala Met Ala
945                 950                 955                 960
Ala Leu Leu Ser Pro Pro Ser Pro Glu Pro Val Ala Glu Val Ser Arg
                965                 970                 975
Ala Glu Gln Arg Ile Trp Leu Leu Ser Arg Leu Gly Gly His Pro Ala
            980                 985                 990
Glu Tyr Ala Ile Pro Val Ala Leu Arg Leu Ala Gly Pro Leu Asp Val
        995                 1000                1005
Ala Lys Leu Lys Asn Ala Val Asp Ala Val Val Arg Arg His Glu
    1010                1015                1020
Gly Leu Arg His Val Phe Pro Glu Val Asp Gly Ser Pro Thr Arg
    1025                1030                1035
Ala Val Leu Asp Pro Gly Ser Ile Thr Val Ala Glu Glu Ala Asn
    1040                1045                1050
Arg Ser Val Arg Glu Val Leu Ala Glu Gly Val Ala Ala Leu Asp
    1055                1060                1065
Pro Ala Thr Gly Pro Leu Ala Arg Phe Thr Leu Val Asn Gln Gly
    1070                1075                1080
Pro Gln Asp His Val Leu Ala Ile Val Leu His His Leu Ile Ala
    1085                1090                1095
Asp Gly Trp Ser Val Asp Val Leu Leu Arg Asp Ile Ala Ala His
    1100                1105                1110
```

Tyr Thr Gly Ala Pro Thr Ala Thr Pro Gly Arg Tyr Ala Asp Tyr
    1115                1120                1125

Leu Ala Leu Glu Arg Ala Glu Glu Gln Asp Gly Ala Leu Gly Arg
    1130                1135                1140

Ala Leu Glu His Phe Val Thr Ala Leu Asp Gly Val Pro Asp Glu
    1145                1150                1155

Val Ser Phe Pro Pro Asp His Pro Arg Pro Ala Gln Arg Thr Gly
    1160                1165                1170

Arg Gly Asp Val Val Arg His Arg Ile Asp Ala Ala Pro Val Thr
    1175                1180                1185

Ala Leu Ala Glu Arg Leu Arg Thr Thr Pro Phe Ala Val Leu Leu
    1190                1195                1200

Ala Ala Val Gly Val Leu Leu His Arg Val Gly Gly His Arg Asp
    1205                1210                1215

Val Val Val Gly Thr Ala Val Ala Arg Arg Pro Asp Ala Gly Leu
    1220                1225                1230

Asp His Leu Val Gly Leu Cys Leu Asn Thr Leu Ala Leu Arg Trp
    1235                1240                1245

Pro Val Gln Pro His Asp Thr Leu Gly Glu Val Val Arg Ala Val
    1250                1255                1260

Thr Asp Arg Leu Ala Asp Gly Leu Gln His Asp Ala Ala Ser Phe
    1265                1270                1275

Asp Arg Val Val Asp Lys Leu Ala Pro Ala Arg Asp Ser Gly Arg
    1280                1285                1290

Thr Pro Val Phe Gln Val Met Ala Leu Tyr Glu Glu Pro Tyr Glu
    1295                1300                1305

Thr Ala Leu Ala Leu Pro Asp Val Thr Thr Thr Asp Val Thr Val
    1310                1315                1320

His Cys Gly Ser Ala Gln Ala Asp Ala Ala Phe Gly Phe Val Pro
    1325                1330                1335

Arg Glu Gly Gly Ile Asp Leu Thr Leu Gln Phe Ser Thr Asp Val
    1340                1345                1350

Phe Thr Arg Ala Thr Ala Ser Arg Trp Ala Arg Arg Leu Ala Thr
    1355                1360                1365

Leu Leu Ala Gly Ala Arg Ala Asp Thr Arg Val Ala Asp Leu Pro
    1370                1375                1380

Leu Leu Pro Glu Asp Glu Ser Gln Asp Leu Glu Arg Trp Ser Gly
    1385                1390                1395

Thr Thr Gly Glu Ala Pro Thr Thr Thr Leu His Ala Leu Ala His
    1400                1405                1410

Glu Ile Ala Gln Arg His Pro Asp Arg Pro Ala Ile His Phe Gly
    1415                1420                1425

Gln Asn Ser Leu Thr Tyr Gly Glu Phe Asp Ala Arg Ser Ala Gln
    1430                1435                1440

Leu Ala His Glu Leu Arg Ala Arg Gly Val Arg Ala Glu Thr Pro
    1445                1450                1455

Val Val Val Cys Leu Glu Arg Ser Pro Glu Ala Leu Ile Ala Val
    1460                1465                1470

Tyr Gly Val Leu Lys Ala Gly Gly Ala Tyr Val Pro Val Glu Thr
    1475                1480                1485

Ser Asn Pro Asp Leu Arg Ile Ala Glu Leu Ile Ala Asp Ser Gly
    1490                1495                1500

Ala Ala Leu Val Leu Thr Gln Arg Arg Leu Ala Asp Arg Leu Ala

```
                1505                1510                1515

Ala Leu Gly Ala Glu Val Val Val Asp Pro Leu Pro Arg
    1520                1525                1530

His Pro Thr Thr Asp Pro Glu Pro Leu Thr Gly Pro Asp His Leu
    1535                1540                1545

Ala Tyr Val Ile Tyr Thr Ser Gly Ser Thr Gly Arg Pro Lys Gly
    1550                1555                1560

Val Met Val Gln His Gly Ser Val Leu Asn Phe Leu Asp Ala Leu
    1565                1570                1575

Asp Arg Arg Phe Asp Leu Thr Pro Asp Asp Arg Leu Leu His Lys
    1580                1585                1590

Ser Pro Leu Ala Phe Asp Val Ser Val Arg Glu Val Phe Trp Ala
    1595                1600                1605

Leu Thr Arg Gly Ala Ser Val Val Val Ala Glu Pro Gly Arg His
    1610                1615                1620

Ala Asp Pro Gly His Leu Val Asp Leu Val Glu Arg Glu Arg Val
    1625                1630                1635

Thr Val Ala His Phe Val Pro Ser Ser Leu Ala Val Phe Leu Glu
    1640                1645                1650

Gly Leu Pro Gly Pro Gly Arg Cys Pro Thr Leu Arg His Val Leu
    1655                1660                1665

Thr Ser Gly Glu Thr Leu Pro Val Thr Thr Ala Arg Ala Ala Arg
    1670                1675                1680

Asp Leu Leu Gly Ala Arg Leu Arg Asn Met Tyr Gly Pro Thr Glu
    1685                1690                1695

Thr Thr Val Glu Met Thr Asp His Asp Val Val Asp Asp Thr Val
    1700                1705                1710

Asp Arg Leu Pro Ile Gly His Pro Phe Glu Gly Ala Val Val Arg
    1715                1720                1725

Val Leu Asp Ala Asp Leu Arg Pro Val Pro Pro Gly Ser Thr Gly
    1730                1735                1740

Glu Leu Cys Val Gly Gly Leu Pro Val Ala Arg Gly Tyr Leu Gly
    1745                1750                1755

Arg Pro Ala Leu Thr Ala Glu Arg Phe Val Pro Asp Pro Leu Gly
    1760                1765                1770

Pro Ala Gly Ala Arg Leu Tyr Arg Thr Gly Asp Leu Ala Arg Leu
    1775                1780                1785

Leu Pro Asp Gly Gln Leu Asp Phe Leu Gly Arg Asn Asp Phe Gln
    1790                1795                1800

Val Lys Val Arg Gly His Arg Ile Glu Pro Gly Glu Val Glu Ala
    1805                1810                1815

Val Leu Gly Ala Leu Pro Gly Val His Gly Ala Leu Val Thr Ala
    1820                1825                1830

His Asp Asp Arg Leu Ile Gly Tyr Ala Val Thr Asp Arg Asp Gly
    1835                1840                1845

Glu Glu Leu Arg Thr Ala Leu Ala Glu Arg Leu Pro Glu His Leu
    1850                1855                1860

Val Pro Ser Val Val Leu Thr Leu Asp Arg Phe Pro Leu Thr Gly
    1865                1870                1875

Asn Gly Lys Leu Asp Arg Ala Ala Leu Pro Thr Pro Thr Gly Arg
    1880                1885                1890

His Thr Gly Asp Ser Arg Pro Leu Thr Ala Thr Glu Ala Ala Leu
    1895                1900                1905
```

-continued

Ala Ala Ile Trp Arg Asp Leu Leu Asp Val Pro Glu Val Arg Ala
1910                1915                1920

Asp Asp His Phe Phe Ala Leu Gly Gly His Ser Leu Leu Ala Ala
1925                1930                1935

Arg Val Ala Ala Arg Ala Gly Ala Ala Leu Gly Val Ala Leu Pro
1940                1945                1950

Leu Pro Thr Val Leu Arg Phe Pro Arg Leu Ala Asp Leu Ala Thr
1955                1960                1965

Ala Val Asp Gly Thr Arg Ala Asp Arg Glu Pro Val Arg Pro Arg
1970                1975                1980

Pro Asp Arg Arg Arg Ala Pro Leu Ser Ser Ala Gln Arg Arg
1985                1990                1995

Leu Trp Ile Glu Glu Asn Leu Arg Pro Gly Thr Ala Thr Tyr Thr
2000                2005                2010

Val Ala Glu Ala Phe Arg Leu Arg Gly Glu Leu Asp Glu Glu Ala
2015                2020                2025

Phe Ala Ala Ala Val Asp Asp Val Leu Arg Arg His Asp Ala Leu
2030                2035                2040

Arg Ala His Val Glu Ser Val Glu Asp Gly Glu Pro Glu Leu Val
2045                2050                2055

Val Ala Pro Glu Pro Arg Thr Ala Leu Arg Val Gly Asp Leu Pro
2060                2065                2070

Ala Asp Arg Val Arg Asp Ala Leu Ala Ala Glu Ser Ala Arg Val
2075                2080                2085

Phe Asp Pro Ala Gly Pro Leu Val Ala Thr Ser Leu His Arg Leu
2090                2095                2100

Ala Pro Asp Glu Trp Leu Phe Gln Phe Thr Ala His His Leu Val
2105                2110                2115

Val Asp Gly Trp Ser Leu Asp Val Leu Trp Arg Asp Leu Ala Ala
2120                2125                2130

Cys Tyr His Asp Arg Arg Ala Gly Arg Ala Pro Arg Pro Arg Asp
2135                2140                2145

Gly Leu Thr Phe Thr Asp Tyr Thr Trp Trp Glu Arg Asp Val Arg
2150                2155                2160

Ser Arg Asp Leu Glu Pro His Leu Ala Phe Trp Arg Gly Glu Leu
2165                2170                2175

Ala Gly Leu Arg Pro Gln Pro Pro Ala Asp Ala His Gly Pro Gly
2180                2185                2190

Ala Val Leu Asp Phe Ala Leu Gly Ala Ala Leu Ser Asp Glu Leu
2195                2200                2205

Arg Ala Thr Ala Ala Gly Leu Gly Val Ser Pro Phe Val Leu Gly
2210                2215                2220

Leu Thr Ala Phe Ala Leu Ala Leu Gly Glu Asp Ser Pro Gly Ala
2225                2230                2235

Ile Gly Val Glu Val Ala Asn Arg Ala Ser Ala Glu Thr Ala Asp
2240                2245                2250

Leu Val Gly Leu Phe Val Asn His Val Pro Val Arg Val Ala Pro
2255                2260                2265

Arg Gly Thr Gly Arg Ala Ala Val Ala Ala Val Asp Glu Ala Arg
2270                2275                2280

Arg Arg Val Leu Pro His Glu His Val Pro Phe Asp Leu Val Val
2285                2290                2295

Asp Leu Leu Gly Pro Gly Arg Ala Pro Thr Ser Val Ala Phe Ser
2300                2305                2310

```
His Leu Asp Val Arg Gly His Ser Pro Arg Leu Asp Gly Val Thr
    2315                2320                2325

Ala Thr Arg Leu Thr Pro Pro His Asn Gly Thr Ala Lys Phe Asp
    2330                2335                2340

Leu Leu Leu Glu Val Leu Asp Thr Glu His Gly Leu Thr Gly Ala
    2345                2350                2355

Phe Glu Tyr Arg Pro Glu Arg Phe Thr Ala Ala Arg Val Ala Gln
    2360                2365                2370

Val Arg Asn His Trp Glu Ala Ala Leu Leu Thr Leu Leu Ala Asp
    2375                2380                2385

Pro Asp Leu Pro Val Asp Ala Arg Arg Pro Asp Phe Ala
    2390                2395                2400

<210> SEQ ID NO 3
<211> LENGTH: 362
<212> TYPE: PRT
<213> ORGANISM: Saccharothrix mutabilis

<400> SEQUENCE: 3

Met Leu Ser Thr Val Asp Pro Ala Ala Glu Leu Ser Thr Ala Ala
1               5                   10                  15

Glu Val Leu Glu His Val Asp Ala Ala Val Ala Tyr Pro Glu Val
                20                  25                  30

Pro Ile Ala Arg Val Arg Val Glu Val Ala Gly Ile Pro Arg Thr Leu
                35                  40                  45

Leu Leu Lys Leu Glu Gly Arg Ser Pro Trp Arg Ser Ile Lys Gly Arg
50                  55                  60

Thr Ala Leu Gly Leu Val Arg Ser Ile Ala Pro Arg Met Ala Ser Arg
65                  70                  75                  80

Asp Val Thr Val Val Glu Ser Thr Ser Gly Asn Leu Gly Val Ala Leu
                85                  90                  95

Ser Ala Ile Cys Arg Asp Leu Gly Leu Pro Phe Val Ala Val Val Asp
                100                 105                 110

Leu Lys Gln Ser Pro Val Ile Gln Ala Ala Ile Glu Ala Asn Gly Ala
                115                 120                 125

Arg Leu Glu Val Val Arg Thr Pro Ala Ala Thr Thr His Leu Leu
    130                 135                 140

Asp Arg Leu Asp Arg Val Arg Lys Leu Val Ala Glu Ile Pro Gly Ala
145                 150                 155                 160

Val Trp Pro Asn Gln Tyr Glu Asn Asp Ala Asn Arg His Val His Glu
                165                 170                 175

Thr Trp Thr Ala Pro Glu Ile Asp Arg Gln Val Gly Gly Glu Ala Gln
                180                 185                 190

Ala Val Phe Val Ala Val Ser Thr Gly Gly Thr Leu Ala Gly Leu Ala
                195                 200                 205

Ala His Phe Arg Arg Ala Arg Pro Ala Thr Arg Leu Val Ala Val Asp
    210                 215                 220

Val Glu Gly Ser Thr Val Phe Gly Gly Val Pro Gly Gly Arg Val Leu
225                 230                 235                 240

Thr Gly Ile Gly Ala Ser Arg Arg Ser Thr Phe Leu Thr Arg Ala Glu
                245                 250                 255

Cys Asp Asp Leu Val Tyr Val Arg Glu Ala Ala Ile Ala Ala Cys
                260                 265                 270

His Val Leu Arg Ala Asp Thr Gly Ile Ala Val Gly Gly Ser Ser Gly
                275                 280                 285
```

```
Ala Val Val Ala Gly Ala Leu Asp His Leu Ala Ala His Pro Gly Leu
    290                 295                 300

Thr Thr Ala Val Cys Val Cys Ala Asp Leu Gly Glu Asn Tyr Ala Arg
305                 310                 315                 320

Thr Val Tyr Asp Pro Asp Trp Leu Ala Pro Leu Arg Leu Thr Asp Asp
                325                 330                 335

Pro Gly Leu Leu Arg Ser Arg Leu Arg Gly Ala Arg Phe His His Ala
            340                 345                 350

Glu Pro Asp Thr Gly Gln Glu Ser Thr Pro
            355                 360

<210> SEQ ID NO 4
<211> LENGTH: 338
<212> TYPE: PRT
<213> ORGANISM: Saccharothrix mutabilis

<400> SEQUENCE: 4

Met Thr Ala Ile Arg Glu Ile Arg Leu Ser Glu Pro Glu Ser Ala Gln
1               5                   10                  15

Ala Ala Leu Leu Ala Leu Glu Cys Ala Gln Arg Tyr Ala Glu Pro Asp
            20                  25                  30

Ser Ala Asp Phe Leu Ala Asp Ala Ala Val Leu Ala His Asp Leu Pro
        35                  40                  45

Arg Ala Val Arg Arg Glu Val Glu Arg Ala Arg Leu Asp Asp Arg Leu
    50                  55                  60

His Ala Leu Val Val Arg Gly Asn Asp Val Asp Gln Asp Ala Leu Gly
65                  70                  75                  80

Pro Thr Pro Pro His Trp Arg Gln Ala Arg Thr Ala Ala Ser Arg Arg
                85                  90                  95

Tyr Gly Phe Leu Leu Val Leu Tyr Ala Ser Leu Leu Gly Asp Val Val
            100                 105                 110

Gly Trp Ala Thr Gln Gln Asp Gly Arg Val Val Thr Asp Val Leu Pro
        115                 120                 125

Ile Glu Gly Gln Glu Asp Ser Leu Val Ser Ser Ser Ser Val Glu
    130                 135                 140

Leu Gly Trp His Thr Glu Asp Ala Phe Ser Pro Tyr Arg Ala Asp Tyr
145                 150                 155                 160

Val Gly Leu Phe Ser Leu Arg Asn Pro Asp Ser Val Ala Thr Thr Val
                165                 170                 175

Ala Gly Leu Asp Pro Asp Leu Val Gly Pro Ala Val Val Asp Val Leu
            180                 185                 190

Phe Gly Glu Arg Phe His Ile Arg Pro Asp Asn Ser His Leu Pro Thr
        195                 200                 205

His Asn Ser Gly Gly Arg Leu Ser Asp Tyr Phe Ala Gly Ile Val Glu
    210                 215                 220

Ala Val Glu Asn Pro Arg Ala Val Ser Ile Leu Arg Gly His Arg Asp
225                 230                 235                 240

Ala Pro Gln Leu Cys Val Asp Ser Asp Phe Thr Thr Ala Val Asp Gly
                245                 250                 255

Asp Ala Glu Ala Ala Gly Ala Leu Asp Thr Leu Ile Lys His Leu Gly
            260                 265                 270

Gly Ala Leu Tyr Glu Val Val Leu Gly Pro Gly Asp Val Ala Phe Leu
        275                 280                 285

Asp Asn Arg Asn Val Val His Gly Arg Arg Pro Phe Arg Ala Arg Phe
    290                 295                 300
```

Asp Gly Thr Asp Arg Trp Leu Lys Arg Ile Asn Val Thr Ala Asp Leu
305                 310                 315                 320

Arg Lys Ser Arg Ala Ala Arg Arg Asp Ala Gln Ala Arg Val Leu Gly
            325                 330                 335

Glu Ala

<210> SEQ ID NO 5
<211> LENGTH: 373
<212> TYPE: PRT
<213> ORGANISM: Saccharothrix mutabilis

<400> SEQUENCE: 5

Met Met Val Arg Asp Leu Pro Ala Ala Ala Leu Glu Asp Trp Leu Arg
1               5                   10                  15

Glu Arg Tyr Phe Thr Ala Arg Val Asp Val Ser Ser Gly Val Ala
            20                  25                  30

Asp His Arg Leu Ala Asp Leu Arg Arg Leu Gly Gly Ile Thr Val Glu
        35                  40                  45

Glu Leu Asp Ala Val Val Phe Arg Asp Gly Pro Ser Leu Gly Ala Glu
    50                  55                  60

Arg Leu Arg Ala Ala Leu Ala Asp Arg Leu Arg Pro Gly Pro Asp His
65                  70                  75                  80

Val Val Met Thr Ala His Gly Ser Ser Glu Ala Leu Phe Leu Ala Met
                85                  90                  95

Thr Ala Leu Val Arg Pro Gly Asp Glu Val Val Val Pro Asp Pro Ala
            100                 105                 110

Tyr His Ser Leu Ser Ala Leu Ala Arg Ala Cys Gly Ala Val Leu Arg
        115                 120                 125

Pro Trp Pro Val Leu Gly Ala Ala Pro Asp Pro Ala Asp Leu Arg Ala
    130                 135                 140

Leu Leu Thr Pro Arg Thr Arg Leu Val Val Asn Phe Pro His Asn
145                 150                 155                 160

Pro Thr Gly Val Thr Val Asp Ala Ala Val Gln Ala Glu Leu Leu Asp
                165                 170                 175

Val Val Gly Arg Ser Gly Ala Tyr Leu Leu Trp Asp Asn Ala Phe Arg
            180                 185                 190

Asp Leu Val Tyr Asp Ala Pro Pro Leu Pro Glu Pro Thr Ala Leu Gly
        195                 200                 205

Gly Arg Val Leu Ser Thr Gly Thr Leu Ser Lys Ala His Gly Leu Pro
    210                 215                 220

Gly Leu Arg Val Gly Trp Cys Val Leu Pro Ala Asp Leu Ala Pro Glu
225                 230                 235                 240

Leu Val Arg Val Arg Asp Tyr Leu Thr Leu Ser Leu Ser Pro Leu Thr
                245                 250                 255

Glu Leu Leu Ala Ala Val Ala Val Glu His Ala Asp Glu Leu Ile Ala
            260                 265                 270

Pro Arg Leu Ala Glu Ala Thr Ala Asn Arg Arg Leu Leu Asp Trp
        275                 280                 285

Ala Ala Ala His Gly Val Asp Cys Pro Ala Pro Gly Gly Val Thr
    290                 295                 300

Ala Phe Pro Arg Phe Pro Gly Val Ala Asp Val Thr Pro Leu Cys Asp
305                 310                 315                 320

Arg Leu Met Ser Glu His Gly Val Leu Thr Val Pro Gly Gly Cys Phe
                325                 330                 335

```
Gly Phe Pro Asp Arg Met Arg Ile Gly Phe Gly Cys Asp Pro Ala Val
                340                 345                 350

Phe Ala Ala Gly Leu Thr Ala Leu Gly Ala Val Leu Ala Glu Lys Arg
                355                 360                 365

Leu Pro Ala Lys Leu
            370

<210> SEQ ID NO 6
<211> LENGTH: 415
<212> TYPE: PRT
<213> ORGANISM: Saccharothrix mutabilis

<400> SEQUENCE: 6

Met Ala Ala Ile Glu Asn Ala Pro Arg Arg Leu Arg Asp Asn Arg Asp
1               5                   10                  15

Phe Arg Phe Trp Trp Gly Gly Thr Val Leu Ser Ala Ile Gly Asp Glu
                20                  25                  30

Val Thr Leu Ile Ala Phe Pro Leu Leu Val Leu Phe Leu Thr Gly Ser
            35                  40                  45

Pro Thr His Ala Gly Leu Val Gly Gly Val Ala Val Pro Pro Leu
        50                  55                  60

Leu Leu Ser Val Pro Ile Gly Val Leu Ala Asp Arg Thr Ser Arg Arg
65                  70                  75                  80

Ala Leu Met Leu Gly Gly Ser Val Val Ser Ala Ile Ser Ile Thr Ser
                85                  90                  95

Ile Pro Val Val His Leu Leu Gly Glu Leu Thr Leu Pro His Leu Tyr
            100                 105                 110

Val Val Ala Phe Val Asn Ser Val Ala Ala Thr Val Tyr Arg Ile Ala
                115                 120                 125

Asp Thr Ala Ala Leu Pro Arg Ile Ala Gly Glu Glu Lys Leu Gly Glu
        130                 135                 140

Ala Ala Ser Gln Ser Glu Thr Ile Trp Gly Ile Ser Ala Ile Val Ala
145                 150                 155                 160

Pro Pro Leu Ala Gly Leu Leu Phe Glu Thr Ala Gly Pro Thr Ser Pro
                165                 170                 175

Phe Trp Ile Asp Ala Val Ser Phe Val Ala Ile Met Val Cys Val Leu
            180                 185                 190

Ala Ile Arg Ala Arg Leu Gly Ala Asp Lys Pro Tyr Pro Glu Val Ser
                195                 200                 205

Trp Arg Gln Asp Leu Thr Thr Gly Ala Arg Val Thr Leu Ser Arg Pro
        210                 215                 220

Leu Val Arg Ala Leu Thr Ile Leu Thr Val Ala Gly Asp Phe Leu Phe
225                 230                 235                 240

Ala Gly Ile Gly Leu Leu Leu Ile Val Met Val Arg Glu Asn Gly Ala
                245                 250                 255

Ser Gly Leu Glu Thr Gly Thr Val Phe Thr Ala Ala Val Gly Gly
                260                 265                 270

Ile Leu Gly Ser Met Leu Ala Gly Arg Val Glu Asp Arg Ile Gly Met
            275                 280                 285

Val Pro Ala Val Leu Thr Lys His Trp Leu Thr Ala Ala Leu Phe Pro
        290                 295                 300

Leu Leu Val Asp Leu Pro Gly Trp Ala Thr Gly Leu Val Trp Gly
305                 310                 315                 320

Leu Ile Ser Phe Gln Ile Ser Ile Leu Asn Val Ile Gln Met Lys Tyr
                325                 330                 335
```

```
Leu Met Ser Val Ile Pro Asn Ser Lys Leu Gly Arg Val Glu Gly Phe
            340                 345                 350

Leu Thr Phe Ile Glu Gln Gly Ser Leu Pro Leu Gly Tyr Ala Leu Thr
            355                 360                 365

Gly Val Leu Leu Gly Leu Leu Gly Thr Thr Ser Thr Leu Leu Ala Tyr
370                 375                 380

Glu Ala Val Leu Leu Val Leu Ala Val Phe Ala Thr Val Ser Arg Gly
385                 390                 395                 400

Leu Arg Thr Pro Ala His Pro Asp Glu Pro Ala Arg Ser Ser Gly
            405                 410                 415

<210> SEQ ID NO 7
<211> LENGTH: 1056
<212> TYPE: PRT
<213> ORGANISM: Saccharothrix mutabilis

<400> SEQUENCE: 7

Met Thr Gln Val Asp Phe Thr Arg Trp Asp Leu Arg Thr Asp Ala Glu
1               5                   10                  15

Lys His Ala Thr Pro Thr Val Leu Ser Gly Pro Pro Ala Trp Ser
            20                  25                  30

Pro Asp Thr Thr Leu Ala Arg Leu Val Leu Asp Gln Ala Asp Arg Thr
            35                  40                  45

Pro Asp Ala Asp Ala Val Arg Ile Gly Pro Asp Ala Leu Thr Tyr Arg
50                  55                  60

Glu Leu Ala Ala Gly Ala Arg Arg Val Ala Ala Trp Val Ala Arg Gln
65                  70                  75                  80

Pro His Thr Gly Pro Pro Arg Val Gly Val Leu Gly Glu Arg Ser Leu
            85                  90                  95

Ala Thr Tyr Pro Val Leu Leu Gly Val Leu Leu Ala Gly Gly Ala Tyr
            100                 105                 110

Val Pro Leu Asp Pro Ala Ala Pro Pro Ala Arg Leu Arg Ala Val Leu
            115                 120                 125

Ser Arg Ala Asp Ala His Ala Val Val Thr Thr Ala Glu Ser Trp Ala
130                 135                 140

Leu Leu Glu Gln Pro Gly Leu Pro Ala Leu Leu Thr Asp Gln Pro Leu
145                 150                 155                 160

Pro Phe Gln Arg Ser Lys Val Asp Ser Gly Arg Val Ala Val Leu Ala
            165                 170                 175

Gly Leu Pro Asp Ala Gly Glu Pro Val Gly Pro Thr Pro Asp Asp Val
            180                 185                 190

Ala Tyr Val Ile Phe Thr Ser Gly Ser Thr Gly Thr Pro Lys Gly Val
            195                 200                 205

Val Val Gln His Arg Ala Ala Val Asn Leu Thr Cys Trp Ala Arg Asp
210                 215                 220

Leu Val Pro Met Gly Pro Gly Ser Arg Val Thr Gln Asn Ala Ser Leu
225                 230                 235                 240

His Phe Asp Ala Ser Val Gln Gln Ile Phe Pro Ala Leu Ala Ser Gly
            245                 250                 255

Ala Thr Leu Phe Pro Val Pro Glu Arg Val Arg Leu Ser Gly Pro Glu
            260                 265                 270

Leu Ala Ala Trp Leu Ala Arg His Arg Ile Thr His Trp Asp Ser Val
            275                 280                 285

Pro Ser Leu Trp Thr Pro Val Val Glu His Leu Ala Asp Arg Ile Ala
            290                 295                 300
```

-continued

```
Ala Gly Gln Arg Val Leu Pro Asp Leu Arg Ala Val Leu Leu Ala Gly
305                 310                 315                 320

Glu Pro Leu Pro Ala Arg Gln Val Asp Arg Trp Arg Ser Trp Glu Gln
                325                 330                 335

Gly His Arg Leu Phe Asn Val Tyr Gly Pro Thr Glu Val Thr Val Asn
            340                 345                 350

Ala Thr Ala Phe Glu Val Thr Gly Pro Val Gly Ala Val Val Pro Ile
        355                 360                 365

Gly Arg Pro Leu Pro Gly Ile Thr Ala Ser Val Leu Asp Ala His Gly
    370                 375                 380

Asn Pro Cys Pro Val Asp Ala Asp Gly Glu Leu Phe Leu Gly Gly Val
385                 390                 395                 400

Gly Leu Ala Arg Gly Tyr Leu Asp Asp Pro Glu Gly Thr Ala Arg Ser
                405                 410                 415

Phe Val Glu Arg Gly Glu Arg Phe Tyr Arg Thr Gly Asp Val Val
                420                 425                 430

Arg Val Gly Ala Asp Gly Leu Val Phe Val Gly Arg Arg Asp Asp
            435                 440                 445

Gln Val Lys Leu Asn Gly Val Arg Val Glu Pro Ala Glu Ile Glu His
    450                 455                 460

Ala Leu Leu Ala His Pro Gly Val Thr Glu Ala Val Ala Val Val Leu
465                 470                 475                 480

Arg Glu Glu Gly Arg Ala Glu Leu Val Ala Cys Val Ala Ser Ala Val
                485                 490                 495

Glu Leu Ser Thr Glu Asp Ile Arg Ala Gly Leu Ala Glu Glu Leu Pro
                500                 505                 510

Ala Ala Leu Val Pro Ser Arg Val Val Val Glu Ser Leu Pro His
            515                 520                 525

Asn Ala Asn Gly Lys Leu Asp Arg Ala Ala Cys Ala Glu Leu Ala Arg
530                 535                 540

Asp Leu Ser Gly Pro Ser Gly Gly Ala Gly Pro Leu Gly Ala Thr Ala
545                 550                 555                 560

Ala Thr Leu Leu Gly Ile Trp Arg Ser Val Leu Gly Arg Asp Asp Ile
                565                 570                 575

Gly Pro Asp Asp Glu Phe Phe Gln Val Gly Gly Asn Ser Ile Thr Ser
            580                 585                 590

Ile Arg Leu Arg Arg Glu Cys Val Glu Ala Gly Leu Pro Ile Arg Ala
    595                 600                 605

Val Asp Val Phe Leu His Pro Thr Val Arg Arg Leu Ala Arg Tyr Val
    610                 615                 620

Asp Asp Asn Arg Thr Thr Leu Ala Ala Arg Ala Arg Pro Ala Pro Glu
625                 630                 635                 640

Glu Ser Pro Thr Asp Gly Glu Phe Pro Leu Leu Pro Ala Gln Arg Pro
                645                 650                 655

Leu Ala Leu Thr Ala Leu Leu Ser Asp Gly Gly Ala Gln Arg Gly Leu
            660                 665                 670

Val Gln Glu Thr Val Thr Tyr Arg Val Pro Leu Asp Val Asp Ala Val
    675                 680                 685

Arg Gly Ala Leu Glu Val Leu Leu Glu Arg His Glu Val Leu Arg Thr
690                 695                 700

Ala Val Thr Pro Gly Leu Ala Gln Arg Val Leu Pro Lys Val Pro Val
705                 710                 715                 720

Pro Leu Glu Val Val Asp Leu Thr Gly Val Ala Asp Gln Trp Gly Ala
                725                 730                 735
```

Val Leu Glu Ala Ala Asp Arg Asp Tyr Ala Thr Pro Phe Asp Leu Ala
                740                 745                 750

Glu Pro Pro Leu Val Arg Val Arg Ala Phe Asp Arg Gly Glu Val Phe
            755                 760                 765

Ser Leu Thr Trp Thr Leu His His Val Ile Ser Asp Gly Trp Ser Trp
770                 775                 780

Glu Ile Val Gln Arg Glu Phe Asp Arg Leu His Val Ala Leu Arg Ala
785                 790                 795                 800

Gly Arg Phe Arg Pro Leu Pro Pro Val Leu Pro Leu Arg Ala Leu
                805                 810                 815

Ala Arg Arg Leu Gly Ser Gly Thr Pro Asp Pro Glu Trp Val Ala
                820                 825                 830

Arg Leu Ala Ala Thr Pro Ala Leu Leu Pro Ala Asp Gly Ser Gly
                835                 840                 845

Val Gly Gly Glu His Ile Glu Trp Pro Ile Asp Pro Gly Thr His Arg
850                 855                 860

Glu Leu Ala Ala Arg Ala Gln Ala Ala Glu Ala Ser Pro Ala Ala Ile
865                 870                 875                 880

His Leu Leu Ala Phe Thr Glu Ala Leu Arg Val Cys Arg Gln Asp
                885                 890                 895

Ser Phe Ala Val Gly Val Val Ser Ser Gly Arg Asn Val Asp Val Pro
                900                 905                 910

Gly Val Glu Glu Ala Val Ala Cys Leu Ala Arg Thr Val Pro Leu Pro
                915                 920                 925

Val Asp Ala Val Gly Gly Ala Glu Ala Arg Leu Ala Arg Leu His Arg
                930                 935                 940

Asp Leu Ala Val Val Val Gly Met Asp Asp Val Asp Thr Asp Val Leu
945                 950                 955                 960

Pro Ala Asp Val Pro Ala Gly Val Arg His Pro Val Ala Thr Phe Val
                965                 970                 975

Phe Gln Asn Tyr Pro Asp Ala Ala Val Pro Pro Gly His Arg Pro Leu
                980                 985                 990

Pro Glu Val Pro Glu Glu Gly Arg Trp Arg Glu Ala Gly Ser Asp Pro
            995                 1000                1005

Leu Ala Leu Val Cys Phe Glu Asp Asp Gly Val Pro Gly Cys Arg
            1010                1015                1020

Leu Glu Phe Asp Thr Ala Ala Val Ser Arg Ala Thr Ala Glu Leu
            1025                1030                1035

Val Ala Arg Glu Val Arg Arg Ala Gln Asn Arg Leu Ala Lys Gly
            1040                1045                1050

Met Gln Pro
            1055

<210> SEQ ID NO 8
<211> LENGTH: 952
<212> TYPE: PRT
<213> ORGANISM: Saccharothrix mutabilis

<400> SEQUENCE: 8

Met Thr Ala Asp Ala Ala Leu Glu Pro Asp Glu Arg Ala Ala Trp Leu
1               5                   10                  15

Ala Tyr Asn Asp Thr Ala Glu Asp Phe Pro Gly Pro His Leu Leu Ala
                20                  25                  30

Arg Leu Asp Ala Val Ala Arg Glu His Pro Asp Arg Pro Ala Val His
                35                  40                  45

```
Ala Val Asp Gly Val Trp Thr Tyr Arg Glu Leu His Arg Arg Ala Asp
         50                  55                  60

Ala Val Ala Ala Phe Leu Ala Ala Arg Gly Val Arg Pro Gly Ser Val
 65                  70                  75                  80

Val Ala Ile Ala Ala Thr Arg Ala Leu Ala Pro Tyr Ala Ala Leu Leu
                 85                  90                  95

Gly Val Leu Lys Ala Gly Cys Ala Tyr Val Pro Val Asn Pro Asp Asp
                100                 105                 110

Pro Ala Asp Arg Val Ala Phe Val Leu Ala Asp Ala Gly Ala Thr Pro
                115                 120                 125

Leu Leu Leu Asp Thr Asp Pro Ala Ser Leu Pro Ala Ala Pro Ala Pro
         130                 135                 140

Asp Val Pro His Glu Pro Asp Arg Val Cys Tyr Val Ile Tyr Thr Ser
145                 150                 155                 160

Gly Ser Thr Gly Arg Pro Lys Gly Val Val Met Ala Glu Arg Ala Val
                165                 170                 175

Asp Asn Leu Thr His Trp Val Val Arg Arg His Asp Val Arg Pro Asp
                180                 185                 190

Asp Arg Leu Gly Gln Thr Ala Pro Leu Thr Phe Asp Pro Ser Val Gln
        195                 200                 205

Gln Val Phe Pro Ala Trp Ala Thr Gly Ala Cys Leu Val Thr Val Pro
        210                 215                 220

Asp Asp Val Gln Arg Asp Pro Ala Ala Phe Leu Asp Trp Leu Arg Ala
225                 230                 235                 240

Glu Arg Val Thr His Leu Asp Leu Val Thr Ser His Trp Val His Leu
                245                 250                 255

Leu Asn Ala Ala Glu Ala Arg Pro Ala Glu Leu Pro Asp Leu Arg Trp
                260                 265                 270

Ile Ile Ile Gly Gly Glu Thr Tyr Tyr Tyr His Gln Thr His Arg Trp
        275                 280                 285

His Arg Val Val Ser Ser Pro Ala Arg Leu Asn Thr Ile Tyr Gly Pro
        290                 295                 300

Thr Glu Ala Ala Val Asn Ala Thr Glu His Leu Thr Glu Pro Asp Leu
305                 310                 315                 320

Asp His Gly Gln Val Pro Ile Gly Val Pro Leu Pro Asn Tyr Arg Leu
                325                 330                 335

Tyr Ala Leu Asp Asp Asp Gly Arg Leu Cys Pro Pro Gly Ile Thr Gly
                340                 345                 350

Glu Ile His Ile Ala Gly Ala Gly Leu Ala Arg Gly Tyr Arg Ser Ala
        355                 360                 365

Glu Ala Thr Ala Lys Ala Phe His Glu Leu Glu Val His Ser Gly Arg
        370                 375                 380

Thr Glu Arg Leu Tyr Arg Thr Gly Asp Leu Ala Arg Leu Val Arg His
385                 390                 395                 400

Ala Asp Arg Trp Ala Leu Glu Phe Gln Gly Arg Val Asp Ser Gln Val
                405                 410                 415

Lys Ile Ser Gly Tyr Arg Val Glu Leu Glu Val Asp Ala Ala Val
                420                 425                 430

Lys Ala Val Pro Gly Val Arg Asp Ala Val Val Arg Gly Glu
        435                 440                 445

Pro Ala Glu Gln Leu Val Cys Cys Tyr Val Gly Asp Val Pro Pro Asp
450                 455                 460

Arg Leu Arg Ser Arg Leu Thr Glu Arg Leu Pro Ala Tyr Leu Val Pro
```

-continued

```
            465                 470                 475                 480
His Leu Leu Val Pro Val Glu Ala Leu Pro Phe Thr Arg Asn Gly Lys
                    485                 490                 495

Met Asp Thr Ala Glu Leu Ala Glu Leu Val Arg Arg Phe Ala Arg Asp
                500                 505                 510

Ser Ala Gly Arg Ala Pro Arg Pro Gly Val Glu Ser Val Val Ala Ala
                515                 520                 525

Val Trp Ala Glu Val Leu Asp Leu Pro Glu Val Ser Ala Asp Ala Asp
            530                 535                 540

Phe Leu Gly His Gly Gly Ser Ser Leu Leu Ala Phe Arg Val Val Asp
545                 550                 555                 560

Arg Leu Arg Arg Arg Gly Ile Arg Val Arg Pro Ala Asp Val Leu Arg
                565                 570                 575

Glu Arg Thr Val Ala Gly Leu Ala Ala Val Ala Glu Glu Asp Leu Val
                580                 585                 590

Leu Thr Pro Ser Thr Arg Leu Ala Leu Arg Arg Pro Gly Gly Asn Ala
                595                 600                 605

Thr Leu Asp Ile Gly Leu Pro Ala Asp Val Pro Ala Glu Arg Val Arg
                610                 615                 620

Ala Val Leu Glu Asp Ile Val Arg Arg His Pro Val Leu Arg Ala Arg
625                 630                 635                 640

Ile Asp Asp Asp Gly Pro Arg Ala Val Pro Val Asp Arg Phe Glu Leu
                645                 650                 655

His Thr Pro Asp Gly Pro Val Asp Asp Ala Lys Ala Arg Leu Ala Glu
                660                 665                 670

Ser Thr Asp Leu Thr Thr Gly Leu Pro Thr Ala Ala Ala Leu Val Ala
                675                 680                 685

Gly Arg Leu Leu Val Ser Ile Arg His Glu Leu Val Asp Gly Ala Ala
            690                 695                 700

Leu Arg Arg Val Ala Glu Glu Val Ala Ala Gly Leu Gly Arg Ala Pro
705                 710                 715                 720

Arg Pro Arg Pro Val Val Pro Val Ala Asp Gln Pro Leu Gly Gly Pro
                725                 730                 735

Ala Pro Asp Gly Leu Arg Gly His Leu Val Arg Phe Leu Glu Ala Glu
                740                 745                 750

Lys Ala Ala Leu Ala Ala Leu Pro Arg Glu His Arg Asp Arg Val Val
            755                 760                 765

Glu Val Asp Leu Gly His Ala Pro Asp Ala Leu Leu Asp Thr Pro Pro
        770                 775                 780

Thr Arg Trp His Ala Arg Leu Val Ala Ala Ala Thr Ala Ala Arg
785                 790                 795                 800

Ser Trp Leu Gly Leu Val Asp Val Pro Val Gly Val Pro Arg His Trp
                805                 810                 815

Pro Gly Ala Gly Gly Ser Val Ala Asn Leu Ala Asp Val Leu Pro Leu
                820                 825                 830

Val Val Ala Asp Asp Glu Ala Asp Ala Gln Trp Arg Arg Phe Ala
            835                 840                 845

Asp Pro Ala Val His Trp Gly Ala Ala Leu Leu Asp Ala Cys Pro Asp
                850                 855                 860

Leu Ala Asp Asp Trp Pro Ala Pro Arg Ile Ala Pro Gln Gly Ser Phe
865                 870                 875                 880

Arg Leu Val Val Thr Ala Asp Asp Glu Pro Leu Ala Pro Asp Leu Pro
                885                 890                 895
```

Leu His Glu Ser Pro Thr Ala Phe Asp Pro Ala Ser Ala Gly Ala Val
                900                 905                 910

Glu Phe Ala Val Val Ala Gly Asp Arg Leu Arg Leu His Val Thr Gly
            915                 920                 925

Trp Asp Leu Pro Ala Asp Glu Val Lys Ala Val Ala Ala Gly Trp Val
    930                 935                 940

Glu Ala Leu Ala Gly Glu Arg Arg
945                 950

<210> SEQ ID NO 9
<211> LENGTH: 248
<212> TYPE: PRT
<213> ORGANISM: Saccharothrix mutabilis

<400> SEQUENCE: 9

Met Thr Pro Asp Pro His Trp Leu Arg Pro Val Gly Gly Arg Ser Gly
1               5                   10                  15

Gly Pro Val Leu Leu Cys Leu Pro His Ala Gly Ala Gly Ala Phe Ala
            20                  25                  30

Tyr Ala Gly Trp Asp Arg Gln Asp Ala Phe Asp Val Val Ala Val Gln
        35                  40                  45

Pro Pro Gly Arg Glu Asp Arg Phe Ala Glu Gln Pro Ile Thr Asp Pro
    50                  55                  60

Glu His Leu Val Arg Glu Ile Ala Asp Ala Leu Gly Asp Leu Ala Glu
65                  70                  75                  80

Gln Pro Leu Ala Leu Phe Gly His Ser Leu Gly Ala Leu Ile Ala His
                85                  90                  95

Asp Leu Ala Arg Glu Leu Asp Arg Arg Gly Ala Pro Asp Pro Leu Leu
            100                 105                 110

Leu Ala Val Ser Gly His Val Pro Pro His Arg Leu Asp Pro Asp Arg
        115                 120                 125

Ala Arg Asp Arg Ser Asp Ala Glu Leu Val His Val Arg Glu Leu
    130                 135                 140

Asp Asp Asp Pro Leu Asp Val Leu Ala Asp Pro Glu Trp Arg Ala
145                 150                 155                 160

Met Leu Leu Arg Pro Leu Arg Gly Asp Leu Ala Leu His Asp Ala His
                165                 170                 175

Thr His Arg Pro Gly Pro Arg Leu Arg Val Pro Val Leu Ala Leu Thr
            180                 185                 190

Gly Ala Asp Asp Asp Ala Thr Pro Ala Glu Asp Thr Ala Ala Trp Ala
        195                 200                 205

Glu Leu Thr Glu Gly Pro Phe Ala His Arg Val His Pro Gly Gly His
    210                 215                 220

Phe Tyr Leu Arg Ala Ala Arg Ser Ala Val Leu Asp Asp Leu Ala His
225                 230                 235                 240

His Leu Glu Gly Ala Trp Arg Pro
                245

<210> SEQ ID NO 10
<211> LENGTH: 548
<212> TYPE: PRT
<213> ORGANISM: Saccharothrix mutabilis

<400> SEQUENCE: 10

Met Thr Thr Glu Thr Pro Ala Thr Thr Gly Ala Pro Ala Thr Thr Gly
1               5                   10                  15

Ala Pro Ala Pro Pro Gly Arg Ala Glu Ile Val Ala Ala Val Leu Pro

-continued

```
                20                  25                  30
Val Phe Ala Glu Val Leu Asp Ala Pro Asp Leu Thr Pro Asp Ser Asp
                35                  40                  45

Phe Phe Val His Gly Gly Asn Ser Leu Leu Ala Ile Arg Val Ala Gly
        50                  55                  60

Arg Val Gly Arg Leu Gly Arg Gln Val Pro Ala Gly Val Leu
65                  70                  75                  80

Lys His Pro Thr Pro Asp Leu Leu Ala Ala His Leu Glu Glu Glu Phe
                85                  90                  95

Arg Gly Gly Gly Ala Pro Pro Ile Pro Ala Pro Arg Ala Gly Ala Glu
                    100                 105                 110

Ala Asp Arg Arg Pro Ser Thr Ala Gln Glu Arg Val Trp Leu Leu His
            115                 120                 125

Gln Leu Asp Pro Asp Arg Leu Asp His Leu Val Thr Val Ala Leu Asp
        130                 135                 140

Val Ala Gly Thr Val Asp Pro Ala Ala Phe Thr Ala Ala Trp Thr Ala
145                 150                 155                 160

Val Val Arg Arg His Glu Ala Leu Arg Ser Arg Phe Val Lys Ala Asp
                165                 170                 175

Asp Asp Arg Val Ala Val Val Asp Ala Glu Ala Ala Pro Glu Ile
            180                 185                 190

Ser Val Leu Asp Leu Ala Arg Phe Pro Ala Pro Val Arg Asp Arg Leu
        195                 200                 205

Ala Glu Glu Arg Val Arg Leu Leu Arg Thr Thr Pro Ile Arg Leu Asp
        210                 215                 220

Thr Gly Pro Leu Ala Arg Phe Ala Leu Leu Arg Leu Ala Asp Arg Arg
225                 230                 235                 240

Tyr Arg Ile Glu Leu Ala Val His His Ile Val Cys Asp Gly Trp Ser
                245                 250                 255

Leu Asp Thr Leu Leu Ala Asp Phe Leu Asp Ala Tyr Gly Arg Ala Leu
            260                 265                 270

Ala Gly Arg Ser Pro Ala Leu Pro Pro Pro Ala Val Gly Phe Ala Asp
        275                 280                 285

Tyr Val Ala Trp Glu Arg Asp Val Glu Ser Ser Arg Trp Pro Asp Met
        290                 295                 300

Ala Val Arg Leu Ala Arg Phe Ala Asp Arg Pro Ala Asp Leu Pro
305                 310                 315                 320

Leu Pro Val Asp Pro Val Asp Val Pro Ala His Glu Asp Gly Asp Asp
                325                 330                 335

Val Thr Val His Ala Pro Pro Gly Leu Ala Ala Ala Val Glu Arg Ala
            340                 345                 350

Arg Thr Ser Phe Gly His Thr Ala Leu Thr Phe His Leu Thr Ala Leu
        355                 360                 365

Gly Val Leu Leu Ala Arg Ile Thr Gly Val Asp Leu Val Val Ala
        370                 375                 380

Val Pro Val Ala Gly Arg Ala Gln Thr Glu His Glu Asp Leu Val Gly
385                 390                 395                 400

Leu Phe Val Asn Thr Ala Leu Ala Arg Val Arg Leu Gly Gly Thr Ser
                405                 410                 415

Asp Val Arg Val Leu Leu Glu Arg Asn Arg Asp Glu Val Asp Glu Leu
            420                 425                 430

Val Asp Cys Gln Thr Phe Pro Phe Asp Arg Leu Val Asp Leu Leu Gly
        435                 440                 445
```

```
Ala Arg Arg Ala Gly Thr Arg Val Pro Leu Ala Arg Val Ser Leu Ala
        450                 455                 460
Val Gln Asn Phe Asp Asp Pro Gly Thr Pro Ala Pro Glu Leu Gly Phe
465                 470                 475                 480
Thr Trp Gln Phe Arg Asp Pro Pro Glu Arg Gln Ser Lys Phe Asp Leu
                485                 490                 495
Ala Phe Thr Val Ser Asp Thr Asp Gly Leu Arg Leu Thr Val Thr Tyr
            500                 505                 510
Arg Pro Ser Leu Phe Arg Arg Ala Thr Val Ala Ala Trp Ala Gly Gln
        515                 520                 525
Tyr Leu Val Ala Leu Glu His Val Val Arg Gly Val Ala Asp Pro Glu
530                 535                 540
Gly Ser Ala Arg
545

<210> SEQ ID NO 11
<211> LENGTH: 383
<212> TYPE: PRT
<213> ORGANISM: Saccharothrix mutabilis

<400> SEQUENCE: 11

Met Lys Leu Asn Arg Gln His Glu Leu Phe Arg Glu Ser Val Arg Met
1               5                   10                  15
Val Leu Asp Arg Glu Cys Val Glu Leu Val Asp Asp Trp Glu Arg Asp
            20                  25                  30
Gly Val Met Pro Val His Gln Leu Cys Lys Thr Leu Ala Ala Glu Gly
        35                  40                  45
Leu Leu Gly Leu Thr Met Pro Val Glu Asp Gly Gly Leu Gly Leu Asp
50                  55                  60
Leu Gly Tyr Ser Tyr Val Trp Ala Gln Glu Leu Gly Arg Val Pro Ala
65                  70                  75                  80
Gly Ala Pro Ala Met Ala Leu Ser Val Gln Thr Asp Ile Val Ala Pro
                85                  90                  95
Leu Leu Ala Arg Ala Gly Thr Pro Glu Val Arg Arg Asp Val Leu Arg
            100                 105                 110
Pro Ala Ile Arg Gly Glu Leu Val Ala Leu Ala Ala Thr Glu Pro
        115                 120                 125
Ala Gly Gly Ser Asp Leu Gly Ala Leu Thr Thr Thr Ala Val Arg Thr
130                 135                 140
Glu Arg Gly Phe Thr Val Asn Gly Thr Lys Ala Phe Ile Thr Asn Gly
145                 150                 155                 160
Ser Val Ala Asp Phe Ala Val Val Leu Cys Arg Thr Gly Glu Ala Ala
                165                 170                 175
Gly Ile Gly Asp Leu Ala Leu Leu Val Val Pro Thr Asn Leu Ala Gly
            180                 185                 190
Val Arg Gln Val Arg His Thr Gly Lys Leu Gly His Arg Ser Cys Asp
        195                 200                 205
His Gly Thr Leu Thr Phe Thr Asp Val Glu Val Pro Ala Ala Tyr Leu
    210                 215                 220
Leu Gly Glu Val Gly Glu Gly Tyr Glu Leu Gln Thr Arg Thr Phe Thr
225                 230                 235                 240
Arg Glu Arg Cys Phe Leu Ala Val Val Ala Leu Gly Gln Ala Glu Arg
                245                 250                 255
Val Leu Arg Ala Thr Val His His Ala Arg Arg Arg Val Leu Gly
            260                 265                 270
```

```
Arg Ala Leu Thr Asp His Gln Ala Ile Gly Phe Arg Leu Ala Glu Leu
            275                 280                 285

Asp Ala Glu Leu Asp Leu Val Arg Ser Tyr Ala Gly Glu Ala Tyr Gln
290                 295                 300

Leu Leu Ala Asp Gly Ala Gln Cys Leu Arg Glu Ala Ser Ile Ala Lys
305                 310                 315                 320

Leu Arg Ala Thr Arg Leu Leu Arg Glu Val Ala Asp Val Gly Leu Gln
            325                 330                 335

Val Arg Gly Ala Ala Gly Tyr Leu Gly Val Asp Asp Val Glu Arg Thr
                340                 345                 350

Tyr Arg Asp Ala Arg Ala Gly Ser Phe Ala Gly Gly Ala Asp Glu Ala
            355                 360                 365

Leu Leu His Leu Ile Ala Gly His Leu Thr Gly Thr Glu Gln Glu
            370                 375                 380
```

<210> SEQ ID NO 12
<211> LENGTH: 332
<212> TYPE: PRT
<213> ORGANISM: Saccharothrix mutabilis

<400> SEQUENCE: 12

```
Met Thr Pro Ser Glu Glu Leu Leu Phe Leu Asp Arg Glu Thr Val Arg
1               5                   10                  15

Ala Cys Val Ala Gly Val Asp Pro Glu Val Val Glu Ser Val Leu
                20                  25                  30

Arg Ser His Ala Ala Gly Arg Thr Thr Leu Pro Ala Glu Gly Tyr Leu
            35                  40                  45

Pro Trp Glu Asn Asp Gln Gly Ala Tyr Cys Arg Ser Ile Ala Met Leu
50                  55                  60

Gly Ala Val Asp Gly Glu Arg Gly Pro Thr Tyr Gly Ile Lys Leu Ile
65                  70                  75                  80

Asn Ala Ala Val Ser Asn Pro Ser Ile Gly Leu Asp Arg Ala Gly Gly
                85                  90                  95

Cys Gly Phe Leu Phe Asp Pro Arg Thr Ala Arg Pro Val Val Leu Ala
            100                 105                 110

Glu Ala Ala Tyr Leu Ser Gly Leu Arg Thr Ala Ala Tyr Thr Met Ala
        115                 120                 125

Ser Leu Arg His Leu Gly Pro Val Gly Phe Asp Ala Val Ser Phe Ile
130                 135                 140

Gly Thr Gly Ala Gln Ala Arg Val His Ala Ala Leu Leu Ala Arg Tyr
145                 150                 155                 160

Phe Pro Ala Val Arg Asp Leu His Val Phe Asp Thr Glu Arg Ser Arg
                165                 170                 175

Ala Glu Ala Phe Thr Gly Ala Ser Gly His Thr Val His Val His Asp
            180                 185                 190

Thr Ala Glu Ala Ala Val Arg Ala Ser His Val Leu Val Thr Leu Thr
        195                 200                 205

Thr Val Asp Asp Gly Tyr Ile Pro His Asp Trp Phe Arg Pro Gly Ser
210                 215                 220

Phe Val Ala His Val Ser Leu Asp Asp Leu Leu Pro Glu Val Phe Phe
225                 230                 235                 240

Lys Ser Glu Ala Leu Phe Val Asp Asp Leu Glu Leu Ile Arg Glu Asn
                245                 250                 255

Pro Arg Arg Val Leu Gly Ala Leu Leu Ala Asp Gly Asp Val Pro Val
            260                 265                 270
```

```
Thr Gly Ser Leu Gly Gly Val Leu Thr Gly Ala Val Ala Pro Val Arg
        275                 280                 285

Pro Arg Asp Gly Val Val Ser Asn Pro Phe Gly Met Ala Val Leu
290                 295                 300

Asp Val Gly Leu Ala Glu Val Ala Ala His Ala Arg Ser Ala Gly
305                 310                 315                 320

Leu Gly Thr Thr Leu Asp Leu Leu Gly Ala Ala Arg
                325                 330

<210> SEQ ID NO 13
<211> LENGTH: 295
<212> TYPE: PRT
<213> ORGANISM: Saccharothrix mutabilis

<400> SEQUENCE: 13

Met Thr Gly Leu Tyr Ser Leu Ala Asp Leu Ser Pro Ala Asp Val Leu
1               5                   10                  15

Ala Leu Ala Asp Arg Ser Val Gln Leu His Arg Asp Arg Thr Ala His
            20                  25                  30

Asp Arg Pro Leu Thr Asp Leu Val Val Gly Thr Leu Phe Thr Lys Thr
        35                  40                  45

Ser Thr Arg Thr Arg Thr Ala Phe Thr Thr Ala Ala Leu Arg Leu Gly
    50                  55                  60

Ala Ser Val Val Ala Phe Gly Pro Asp Glu Leu Gln Thr Ala Thr Gly
65                  70                  75                  80

Glu Ser Thr Ala Asp Thr Gly Arg Val Leu Ala Ser Met Leu Asp Gly
                85                  90                  95

Leu Val Val Arg Thr Ala Gly Pro Val Ala Arg Gln Arg Glu Leu Ser
            100                 105                 110

Gly Gly Gly Val Leu Pro Val Val Asn Ala Met Ser Arg Glu Glu His
        115                 120                 125

Pro Thr Gln Gly Leu Thr Asp Leu Ala Val Leu Arg His His Phe Gly
    130                 135                 140

Asp Leu Ala Gly Val Arg Val Leu Tyr Val Gly Glu Gly Asn Asn Thr
145                 150                 155                 160

Ala Ala Ala Leu Val His Ala Leu Ala Ala Val Pro Gly Cys Glu Leu
                165                 170                 175

Val Leu Ala Cys Pro Lys Gly Tyr Gly Pro Arg Asp Pro Gly Pro Trp
            180                 185                 190

Arg Glu Val Ala Asp Leu Ala Glu Val Thr Gly Asp Val Asp Val Val
        195                 200                 205

Tyr Thr Thr Arg Trp Gln Thr Thr Gly Thr Ala Lys Ala Asp Pro Asp
    210                 215                 220

Trp Arg Glu Ala Phe Arg Pro Phe His Val Asp Thr Ala Leu Met Asp
225                 230                 235                 240

Arg Trp Pro Asp Ala Val Phe Leu His Asp Leu Pro Ala His Arg Gly
                245                 250                 255

Glu Glu Val Ala Gly Ala Val Leu Asp Gly Ala Arg Ser Leu Ala Trp
            260                 265                 270

Thr Gln Ala Ala Met Lys Ala Ala Ser Ala Met Ala Val Leu Glu Arg
        275                 280                 285

Phe Val Gly Gly Arg Arg Ala
    290                 295

<210> SEQ ID NO 14
<211> LENGTH: 401
```

```
<212> TYPE: PRT
<213> ORGANISM: Saccharothrix mutabilis

<400> SEQUENCE: 14
```

| | | | | | | | | | | | | | | |
|---|---|---|---|---|---|---|---|---|---|---|---|---|---|---|
|Met|Leu|Asp|Leu|Ser|Pro|Ala|Gln|Arg|Ser|Leu|Trp|Val|Leu|His|Gln|
|1| | | |5| | | | |10| | | | |15|

Leu Asp Asp Thr Gly Phe Thr Leu Ser Ser Ala His Arg Leu Arg Gly
               20                   25                 30

Pro Phe Asp Leu Gly Ala Phe Thr Ala Ala Val Asp Ala Val Val Ala
        35                   40                 45

Arg His Ser Pro Leu Arg Thr Arg Phe Pro Val Gly Thr Asp Gly Gly
50                    55                   60

Pro Asp Pro Val Val Asp Pro Gly Pro Val Val Glu Ala Val
65                  70                75             80

Ala Ala Glu Gly Phe Thr Ala Ala His Ala Glu Ala Arg Phe Cys
            85               90                 95

Ala Arg Pro Phe Asp Leu Ala Arg Glu Trp Pro Leu Arg Val Leu Val
        100                105              110

Val Arg Leu Ser Thr Glu Asp His Val Val Ala Leu Ala Val His His
        115                120              125

Ile Ser Cys Asp Gly Val Ser Leu Gly Leu Leu His Asp Glu Leu Ser
130                   135                140

Arg Leu Tyr Asp Gly Ala Glu Leu Pro Pro Val Ala Asp His Arg Glu
145                  150               155             160

Leu Val Ala Arg Arg Ala Val Asp Pro Ala Val Ala Arg Cys Arg
              165              170              175

Asp Arg Leu Ala Gly Val Pro Pro Leu Ala Ala Asp Arg Pro Ala Val
        180                185              190

Arg Ser Gly Lys Gly Asp Gln Val Trp Phe Thr Val Pro Ala Asp Leu
        195              200              205

Thr Gly Ala Val Arg Ala Cys Ala Arg Arg His Arg Val Thr Ala Phe
210                   215                220

Met Val Leu Leu Ala Ala Phe Gln Leu Val Leu His Arg Arg Thr Gly
225                   230               235             240

Gln Thr Asp Phe Ala Val Gly Val Pro Val Ala Gly Arg Gly Asp Pro
              245              250              255

Asp Ser Glu Asn Val Ile Gly Leu Phe Thr Asn Thr Val Val Val Arg
        260                265              270

Ala Asp Leu Ala Gly Glu Pro Gly Pro Ala Glu Val Leu Arg Arg Val
        275              280              285

Arg Glu Ala Ala Phe Asp Ala Phe Ala Asp Gln Asp Val Pro Leu Gly
        290              295              300

Ala Val Val Ala Ala Val Gly Glu Pro Pro Asp Pro Ala Arg Thr Pro
305                   310               315             320

Leu Phe Gln Ala Leu Phe Thr Phe Gln Asp Ala Pro Val Gly Arg Leu
              325              330              335

Ala Leu Pro Gly Val Arg Cys Val Glu Leu Asp Leu Pro Thr Gly Ala
        340              345              350

Ala Ala Ser Asp Leu Glu Leu Glu Leu Val Arg Asp Gly Asp Glu Leu
        355              360              365

Ala Gly Ser Leu Glu Tyr Ser Thr Asp Leu His Asp Ser Gly Thr Ala
        370              375              380

Ala Ala Leu Thr Ala Asp Phe Leu Ala Val Leu Asp Glu Ile Thr Ala
385                   390               395             400

Glu

<210> SEQ ID NO 15
<211> LENGTH: 62
<212> TYPE: PRT
<213> ORGANISM: Saccharothrix mutabilis

<400> SEQUENCE: 15

```
Met Asp Thr Tyr Leu Val Val Asn His Glu Glu Gln Tyr Ser Val
1               5                   10                  15

Trp Pro Ala Asp Arg Pro Leu Pro Ala Gly Trp Arg Ala Glu Gly Thr
            20                  25                  30

Ser Gly Asp Lys Glu Gln Cys Leu Ala His Ile Glu Thr Val Trp Thr
        35                  40                  45

Asp Met Arg Pro Leu Ser Val Arg Arg Ala Glu Ala Val
    50                  55                  60
```

<210> SEQ ID NO 16
<211> LENGTH: 584
<212> TYPE: PRT
<213> ORGANISM: Saccharothrix mutabilis

<400> SEQUENCE: 16

```
Met Thr Ala Leu His Arg Leu Asp Gln Leu Ala Gly Ala Arg Pro Asp
1               5                   10                  15

Ala Pro Ala Leu Leu Asp Glu Ala Glu Thr Val Ser Tyr Gly Arg Leu
            20                  25                  30

Trp Arg Glu Leu Thr Gly Val Ala Gly Ala Leu Arg Ala Ala Gly Val
        35                  40                  45

Arg Arg Gly Asp Arg Val Val Val Pro Ala Asp Arg Thr Trp Gln Gly
    50                  55                  60

Ile Val Ser Met Leu Gly Val Leu Arg Ala Gly Ala Ala Tyr Val Pro
65                  70                  75                  80

Val Asp Ala Gly Asp Pro Val Glu Arg Leu Arg His Val Val Arg Thr
                85                  90                  95

Ala Gly Ala Ala Trp Val Thr Gly Arg Ala Glu Ala Leu Ala Ala Leu
            100                 105                 110

Pro Asp Leu Gly Leu His Pro Ile Pro Phe Gly Ser Ala Pro Asp Ser
        115                 120                 125

Ala Ser Arg Ser Ala Ser Gly Ser Asp Ser Gly Ser His Ser Ala Ser
    130                 135                 140

Gly Gly Val Gly Gly Leu Pro Asp Pro Glu Asp Leu Ala Tyr Val Met
145                 150                 155                 160

Phe Thr Ser Gly Ser Thr Gly Thr Ala Lys Ala Val Met Val Pro His
                165                 170                 175

Arg Ser Ile Ala His Ala Ala Pro Ser Leu Ala Arg Arg Cys Gly Ile
            180                 185                 190

Thr Pro Asp Asp Arg Phe Leu Ser Trp Ala Ser Leu Val Trp Asp Thr
        195                 200                 205

Ser Gly Glu Glu Leu Tyr Ser Thr Leu Leu Ser Gly Ala Gly Leu Val
    210                 215                 220

Leu Asp Arg Glu Ala Thr Ser Gly Ser Val Pro Ala Leu Leu Arg Ala
225                 230                 235                 240

Val Glu Arg Arg Ser Val Ser Val Val Asp Leu Pro Thr Ala Phe Trp
                245                 250                 255

Asn Gln Val Val Asp Tyr Leu Glu Thr Thr Gly Glu Ala Val Pro Glu
            260                 265                 270
```

-continued

```
Cys Leu Arg Leu Val Val Gly Gly Glu Val Arg Ala Arg Gln
         275                 280                 285

Val Arg Val Trp Ala Glu Arg Ala Pro Asp Val Arg Leu Leu Asn Thr
     290                 295                 300

Tyr Gly Gln Thr Glu Thr Val Met Val Thr His Ala Ala Asp Ile Gly
305                 310                 315                 320

Gly Leu Ala Pro Pro Asp Gly Ala Val Pro Ile Gly His Pro Leu
                 325                 330                 335

Pro His Val Arg Gln His Leu Glu Pro Val Gly Asp Gly Leu Phe Glu
             340                 345                 350

Leu His Val Gly Gly Pro Thr Leu Ala Trp Gly Tyr Arg Asp Arg Pro
         355                 360                 365

Ala Ala Thr Ala Glu Arg Phe Pro Pro Asp Glu Arg Gly Arg Arg Phe
     370                 375                 380

Arg Thr Gly Asp Leu Val Arg Val Ala Asp Asp Gly Ala Leu Val Phe
385                 390                 395                 400

Val Gly Arg Ala Asp Arg Gln Val Lys Val Arg Gly Val Arg Val Glu
                 405                 410                 415

Pro Ala Glu Val Glu Arg Ala Leu Met Ala Cys Pro Gly Val Thr Ala
             420                 425                 430

Ala Ala Ala Phe Val Val Asp Asn Ala Ser Asp Gly Val Leu Leu Val
         435                 440                 445

Gly Ala Phe Val Pro Gly Asp Gly Asp Ala Thr Pro Ala Thr Val Ala
     450                 455                 460

Ala Ala Leu Arg Thr Arg Leu Ser Pro Ala Leu Leu Pro His Arg Leu
465                 470                 475                 480

Val Ser Val Pro Ser Met Pro Leu Leu Thr Thr Gly Lys Ile Asp Gln
                 485                 490                 495

Ala Ala Leu Val Glu Arg Phe Ala Arg Ser Asp Val Ala Pro Gly Ala
             500                 505                 510

Gly Leu Ala Gly Gln Leu Ala Val Val Phe Ser Glu Val Leu Gly Thr
         515                 520                 525

Pro Cys Ala Ala Asp Asp Asp Phe Phe Asp Gln Gly Gly Asp Ser Val
     530                 535                 540

Val Ala Thr Arg Leu Leu Thr Arg Ile Arg Arg Ser Tyr Arg Val Glu
545                 550                 555                 560

Leu Thr Phe Arg Asp Val Phe Asp His Pro Ser Pro Thr Ala Leu Ala
                 565                 570                 575

Gly Leu Ile Ser Arg Thr Pro Arg
             580

<210> SEQ ID NO 17
<211> LENGTH: 448
<212> TYPE: PRT
<213> ORGANISM: Saccharothrix mutabilis

<400> SEQUENCE: 17

Met Pro Val Gln Pro His Glu His Val Arg Arg Thr Pro Val Glu Pro
1               5                   10                  15

Ser Trp Arg Arg Phe Pro Gly Trp Arg Asp Val Thr Glu Gln Trp
             20                  25                  30

Arg Asp Pro Arg Trp Gln Arg Val His Cys Val Arg Asn Thr Arg Gln
         35                  40                  45

Leu Arg Ala Val Val Gly Asp Leu Leu Asp Glu Arg Phe Tyr Asp Asp
     50                  55                  60
```

Leu Ala Ala Asp Gln Glu Ser Phe Ala Thr Met Ser Met Leu Leu Pro
65                  70                  75                  80

Pro Gln Met Leu Asn Thr Met Val Pro Glu Gly Ala Ala Asp Phe Thr
            85                  90                  95

Gly Ala Phe Tyr Ala Asp Pro Val Arg Arg Tyr Met Leu Pro Val Arg
            100                 105                 110

Ser Asp Arg Asp Pro Glu Trp Pro Ser His Pro Tyr Ser Ser Arg Asp
            115                 120                 125

Ser Leu His Glu Ala Glu Met Trp Val Val Glu Gly Leu Thr His Arg
            130                 135                 140

Tyr Pro Thr Lys Val Leu Ala Glu Leu Val Ser Thr Cys Pro Gln Tyr
145                 150                 155                 160

Cys Gly His Cys Thr Arg Met Asp Leu Val Gly Asn Ser Thr Pro Gln
                165                 170                 175

Val Arg Lys His Lys Leu Glu Leu Lys Pro Val Asp Arg Gln Asp Arg
            180                 185                 190

Met Leu Asp Tyr Leu Arg Arg Thr Pro Ala Val Arg Asp Val Val Val
            195                 200                 205

Ser Gly Gly Asp Val Ala Asn Val Pro Trp Pro Gln Leu Glu Ser Phe
210                 215                 220

Leu Ala Arg Leu Leu Glu Ile Glu Thr Val Arg Asp Ile Arg Leu Ala
225                 230                 235                 240

Thr Lys Ala Leu Ala Gly Leu Pro Gln His Trp Leu Gln Pro Gln Val
            245                 250                 255

Val Glu Gly Met Ser Arg Val Ala Arg Thr Ala Ala Ser Arg Gly Val
            260                 265                 270

Asn Leu Ala Val His Thr His Val Asn His Ala Gln Ser Val Thr Pro
            275                 280                 285

Leu Val Ala Glu Ala Ala Arg Ala Leu Leu Asp Ala Gly Val Arg Asp
290                 295                 300

Val Arg Asn Gln Gly Val Leu Met Arg Gly Val Asn Ala Thr Pro Asp
305                 310                 315                 320

Asp Leu Leu Glu Leu Cys Phe Ala Leu Gln Gly Glu Ala Asn Ile Leu
            325                 330                 335

Pro Tyr Tyr Phe Tyr Leu Cys Asp Met Ile Pro Asn Ala Glu His Trp
            340                 345                 350

Arg Thr Ser Val Ala Glu Ala Gln Asp Leu Gln Ala Ile Met Gly
            355                 360                 365

Tyr Leu Pro Gly Tyr Ala Thr Pro Arg Ile Val Cys Asp Val Pro Tyr
370                 375                 380

Val Gly Lys Arg Trp Val His Gln Val Val Glu Tyr Asp Arg Glu Leu
385                 390                 395                 400

Gly Val Ser Tyr Trp Thr Lys Asn Tyr Arg Thr Gly Ile Glu Ser Asp
            405                 410                 415

Asp Pro Asn Ala Leu Asp Arg Arg Tyr Pro Tyr Tyr Asp Pro Ile Ser
            420                 425                 430

Thr Leu Gly Glu Thr Gly Arg Arg Trp Trp Arg Lys His Glu Arg Ala
            435                 440                 445

<210> SEQ ID NO 18
<211> LENGTH: 237
<212> TYPE: PRT
<213> ORGANISM: Saccharothrix mutabilis

<400> SEQUENCE: 18

```
Met Leu Thr Pro Ala Gly Ala Gly Arg Ala Arg Gly Ile Ala Val
1               5                   10                  15

Leu Leu Ala Asp Asp His Glu Val Ile Leu Asp Gly Leu Arg Ala Val
            20                  25                  30

Leu Ala Arg Asp Asp Ala Ile Thr Val Val Gly Ala Val His Gly Val
            35                  40                  45

Pro Glu Leu Leu Asp Arg Ile Gly Arg Asp Gln Pro Asp Val Val Leu
        50                  55                  60

Val Gly Ala Ser Leu Leu Arg Val Asp Asp Phe Arg Val Ala Arg Leu
65                  70                  75                  80

Leu Ala Gly Gln Arg Val Val Ala Thr Gln Asp Asp Ser Asp Glu
                85                  90                  95

Leu Leu Val Ser Ala Ile Ala Ala Gly Val Ser Gly Tyr Leu Pro Leu
                100                 105                 110

Gly Ser Pro Gly Glu Glu Phe Pro Arg Ala Ile Arg Ala Val Ala Glu
            115                 120                 125

Gly Gly Ala Tyr Leu Pro Ala His Val Thr Lys Arg Val Phe Glu Ser
            130                 135                 140

Phe Gln Ile Ile Pro Leu Pro Asp Pro Ser Ala Pro Ala Leu Leu Ser
145                 150                 155                 160

Leu Thr Glu Arg Glu Gly Gln Val Leu Arg Ala Ile Gly Gln Gly Arg
                165                 170                 175

Ser Asn Arg Glu Ile Ala Arg Glu Phe Glu Val Ser Glu Thr Thr Val
            180                 185                 190

Lys Ser His Val Ser Arg Val Leu Ala Lys Leu Glu Leu Arg Asp Arg
            195                 200                 205

Val Gln Ala Ala Leu Leu Ala Trp Arg Leu Gly Leu Val Thr Ala Arg
        210                 215                 220

Glu Ala Pro Glu Val Val Lys Pro Arg Gly Ala Ser Ala
225                 230                 235

<210> SEQ ID NO 19
<211> LENGTH: 239
<212> TYPE: PRT
<213> ORGANISM: Saccharothrix mutabilis

<400> SEQUENCE: 19

Met Pro Ser Glu Gly Leu Val Lys Val Val Gly Lys Arg Cys Val Pro
1               5                   10                  15

Leu Ala Asp Ala Glu Phe Ala Glu Leu Arg Ala Arg His Arg Ser Val
            20                  25                  30

Leu Leu Asp Val Gly Thr Gly Asp Gly Lys His Ala Tyr Arg Leu Ala
            35                  40                  45

Arg Ala Asp Pro Asp Arg Leu Val Val Gly Val Asp Ala Asn Pro Asp
        50                  55                  60

Arg Met Arg Gly Val Ser Ala Arg Ala Ala Lys Pro Ala Arg Gly
65                  70                  75                  80

Gly Leu Pro Asn Leu Val Leu Val His Ala Ala Glu Glu Met Pro
                85                  90                  95

Pro Cys Leu Gly Asp Val Asp Glu Met His Val Leu Met Pro Trp Gly
            100                 105                 110

Ser Leu Leu Arg Gly Val Leu Gly Arg Asp Pro Ala Val Leu Ala Gly
            115                 120                 125

Leu Ala Gly Ala Cys Arg Ala Gly Ala Arg Phe His Ile Thr Val Asn
            130                 135                 140
```

-continued

Leu His Ala Trp Arg Pro Ala Ala Pro Ala Val Thr Gly Ile Ala Glu
145                 150                 155                 160

Pro Thr Pro Glu Trp Val Arg Arg Glu Leu Ala His Val Tyr Ala Glu
                165                 170                 175

Ala Gly Leu Arg Val Thr Arg Ala Gly Tyr Leu Ala Asp Val Gly Ala
            180                 185                 190

Ser Glu Leu Thr Ser Thr Trp Thr Arg Arg Leu Gly Ala Cys Arg Glu
            195                 200                 205

Glu Phe Asp Val Leu Gly Val Glu Gly Ala Ala Arg Gly Gly Ser Thr
210                 215                 220

Pro Gly Val Ala Gly Ile Thr Ser Lys Ala Ala Cys Leu Pro Ala
225                 230                 235

<210> SEQ ID NO 20
<211> LENGTH: 281
<212> TYPE: PRT
<213> ORGANISM: Saccharothrix mutabilis

<400> SEQUENCE: 20

Met Thr Leu Ser His Leu Val Asp Val Val Arg Ala His Pro Asp
1               5                   10                  15

Val Asp Leu Glu Gly Ala Gly Val His Ser Gly Gln Phe His Asp Val
                20                  25                  30

Leu Ile Ala Arg Asp Arg Val Phe Arg Phe Pro Lys Thr Ala Gly Ala
            35                  40                  45

Ala Ala Glu Leu Pro Gly Arg Val Ala Val Leu Thr Ala Val Asp Ala
50                  55                  60

Val Glu Leu Gly Val Gly Val Pro Val Pro Leu Ser Glu Val Arg Asp
65                  70                  75                  80

Gly Gly Pro His Gly Phe Leu Val Leu Ser Arg Leu His Gly Thr Pro
                85                  90                  95

Leu Glu Arg Gly Asp Ala Thr Ser Pro Glu Val Ile Asp Val Val Ala
            100                 105                 110

Ala Glu Phe Ala Arg Val Leu Arg Ala Met Ala Gly Ala Asp Val Glu
        115                 120                 125

Lys Leu Arg Leu Val Leu Pro Val Ala Asp Ala Gly Arg Trp Arg Gly
130                 135                 140

Phe Ala Gly Arg Val Arg Ala Thr Leu Phe Pro Leu Met Ser Glu Asp
145                 150                 155                 160

Gly Arg Ala Arg Ala Glu Arg Glu Leu Ala Ala Val Ala Met Asp
                165                 170                 175

His Val Ala Thr Gly Leu Val His Gly Asp Leu Gly Gly Glu Asn Val
            180                 185                 190

Leu Trp Gln Gln Val Glu Glu Leu Pro Arg Leu Thr Gly Ile Val Asp
        195                 200                 205

Trp Asp Glu Ala Lys Val Gly Asp Pro Ala Glu Asp Leu Ala Ala Val
210                 215                 220

Gly Ala Ser Tyr Gly Pro Glu Leu Val Glu Arg Val Val Ala Leu Leu
225                 230                 235                 240

Gly Ala Gly Asp Leu Trp Pro Arg Ile Arg Ala Tyr Gln Gly Thr Phe
                245                 250                 255

Ala Leu Gln Gln Ala Leu Ala Gly Ala Glu Asp Gly Asp Glu Glu
            260                 265                 270

Leu Glu Asp Gly Leu Thr Ala Tyr Arg
        275                 280

<210> SEQ ID NO 21
<211> LENGTH: 167
<212> TYPE: PRT
<213> ORGANISM: Saccharothrix mutabilis

<400> SEQUENCE: 21

```
Met Ser Arg Trp Cys Gly Gly Met Pro Asp Gly Gly Asp Val Val Met
1               5                   10                  15

Ser Ser Gln Ser Trp Asp Ala Gly Asp Glu Ser Gly Asp Glu Val Val
            20                  25                  30

Leu Ala Leu Asp Gly Val Ala Val Arg Glu Val Arg Asp Leu Val Arg
        35                  40                  45

Asp Leu Leu Ser Asp Arg Ala Gly Val Ala Val Asp Asp Ala Val Leu
    50                  55                  60

Val Val Asp Glu Leu Val Ser Asn Ala Leu Arg His Gly Glu Pro Pro
65                  70                  75                  80

Arg Arg Cys Arg Leu Val Arg Ala Gly Gln Arg Leu Arg Val Glu Val
                85                  90                  95

Asp Asp Ala Gly Ser Gly Gln Pro Arg Ile Arg Thr Ala Asp Ala Ser
            100                 105                 110

Gly Gly Arg Gly Leu Val Ile Val Gln Ala Leu Ser Thr Asp Trp Gly
        115                 120                 125

Val Val Arg His Pro Glu His Lys Thr Val Trp Ala Glu Val Leu Leu
    130                 135                 140

Ala Gly Gln Ser Arg Pro Ser His Val Ala Pro Ala Gly Thr Trp Gly
145                 150                 155                 160

Asp Thr Pro Ala Gln Gly Arg
                165
```

<210> SEQ ID NO 22
<211> LENGTH: 190
<212> TYPE: PRT
<213> ORGANISM: Saccharothrix mutabilis

<400> SEQUENCE: 22

```
Met Thr Ser Thr Glu Asn Asp Leu Leu Leu Asp Lys Ile Gly Arg Gly
1               5                   10                  15

Phe Asp His Leu Asp Ala Asp Gly Asp Gly Leu Leu Asp Glu Arg Asp
            20                  25                  30

His Val Leu Met Gly Glu Arg Val Ala Ala Leu Gly His Gly Ser
        35                  40                  45

Gly Ser Ala Glu Glu Glu Arg Ile Val Asp Met Tyr Val Arg Val Trp
    50                  55                  60

His Asp Val His Leu Pro His Leu Pro Ala Gly Thr Thr Ala Ile Gly
65                  70                  75                  80

Arg Asp Glu Phe Ile Ala Ala Thr Arg Asp Leu Ala Asp Pro Ala
                85                  90                  95

Ala Ala Asp Ala Thr Leu Gly Ala Leu Ala Arg Glu Phe Leu Arg Ile
            100                 105                 110

Ala Asp Ile Asp Ala Asp Gly Arg Val Thr Pro Ala Glu Phe Leu Thr
        115                 120                 125

Phe Gln Arg Gly His Phe Pro Asp Leu Ser Asp Glu Asp Ala Ala Ala
    130                 135                 140

Ala Phe Glu His Leu Asp Thr Asp Gly Asp Gly Ser Leu Ser Pro Glu
145                 150                 155                 160
```

```
Glu Phe Ile Arg Ala Thr Val Glu Tyr Trp Thr Ser Thr Asp Pro Asp
                165                 170                 175

Ser Pro Ala Asn Trp Trp Ile Gly Arg Pro Arg Pro Thr Ala
            180                 185                 190

<210> SEQ ID NO 23
<211> LENGTH: 246
<212> TYPE: PRT
<213> ORGANISM: Saccharothrix mutabilis

<400> SEQUENCE: 23

Met Gly Val Thr Ala Ala Pro Leu Ala Ser Met Gly Pro Thr Arg Ser
1               5                   10                  15

Arg Ser Thr Pro Thr Ile Gly Gly Gln Pro His Leu Glu Arg Asp Arg
            20                  25                  30

Ala Arg Val Arg Gly Met Val Arg Leu Gly Val Val Ala Leu Leu Leu
        35                  40                  45

Ala Thr Val Ala Ser Ala Cys Ala Ala Glu Pro Glu Tyr Val Ser
    50                  55                  60

Leu Ile Glu Ala Cys Asp Leu Val Asp Pro Gly Thr Val Thr Ala Leu
65                  70                  75                  80

Ser Arg Gly Leu Pro Ala Ala Pro Pro Ser Arg Glu Pro Val Arg Phe
                85                  90                  95

Ser Asp Asp Arg Val Asp Met Val Glu Cys Arg His Glu Phe Gly Asp
            100                 105                 110

Ser Gly Asn Val Pro Val Leu Pro His Asp Asp Trp Ala Pro Asp Thr
        115                 120                 125

Pro Gly Thr Pro Leu Tyr Arg Tyr Val Thr Val Thr Val Met Arg Tyr
    130                 135                 140

Arg Ala Gly Asp Gly Arg Ser Ala Thr Gly Asn Ala Arg His His Leu
145                 150                 155                 160

Ala Ser Asp Pro Gln Ala Lys Asp Pro Ala Ile Thr Gly Ala Gly Leu
                165                 170                 175

Asp Asp Gly Asp Val Met His Lys Tyr Asn Gly Val Gln Ser Tyr Ser
            180                 185                 190

Arg Val Arg Ala Val Asp His Asn Val Phe Leu Thr Val Glu Tyr Gly
        195                 200                 205

Gly Ala Asn Gly Asn Ala Arg Pro Gln Gly Met Pro Ala Asp Glu Ser
    210                 215                 220

Arg Glu Gly Ala Leu Arg Leu Leu Thr Gly Ala Ala Ser Arg Leu Pro
225                 230                 235                 240

Cys Pro Lys Pro Gly Cys
                245

<210> SEQ ID NO 24
<211> LENGTH: 427
<212> TYPE: PRT
<213> ORGANISM: Saccharothrix mutabilis

<400> SEQUENCE: 24

Met Lys Leu Arg Ala Gly Leu Leu Thr Ala Ala Leu Leu Leu Leu Gly
1               5                   10                  15

Thr Asn Ala Met Ala Ala Ala Pro Asp Ser Thr Pro Phe Tyr Trp Gln
            20                  25                  30

Val Pro Gly Ala Asp Glu Arg Thr Leu Gln Asp Ala Gly Phe Asp Val
        35                  40                  45

Glu His Gly Val Asp Gly Gly Val Gln Val Val Gly Asp Ala Arg Val
```

```
                     50                  55                  60
Ala Gly Arg Leu Thr Ala Leu Gly Tyr Gln Pro Lys Lys Phe Asp Thr
 65                  70                  75                  80

Val Tyr Lys Pro Val Pro Gly Arg Ser Gly Asp Ile Gly Val Gln
                 85                  90                  95

Thr Phe Tyr Gly Gly Tyr His Thr Val Ala Glu His Glu Lys His Leu
                100                 105                 110

Thr Asp Val Ala Ala Tyr Pro Ala Leu Thr Gln Val Phe Asp Ile
                115                 120                 125

Gly Asp Ser Trp Arg Lys Thr Arg Gly Leu Gly His Asp Ile Lys
130                 135                 140

Ala Ile Cys Ile Thr Lys Lys Gln Ala Gly Asp Cys Ala Leu Ser Pro
145                 150                 155                 160

Thr Ser Pro Lys Pro Arg Phe Ala Met Ile Ala Gln Leu His Ala Arg
                165                 170                 175

Glu Leu Ala Thr Gly Glu Leu Ala Trp Arg Trp Ile Asp His Val Thr
                180                 185                 190

Arg Gly Tyr Gly Thr Asp Ala Glu Val Thr Ser Ile Leu Asp Thr Thr
                195                 200                 205

Glu Leu Trp Val Val Pro Ile Val Asn Pro Asp Gly Val Asp Ile Val
210                 215                 220

Ala Ser Gly Gly Ser Arg Pro Leu Met Gln Arg Lys Asn Ala Asn Asn
225                 230                 235                 240

Thr Gly Ala Ser Cys Ser Val Pro Ser Tyr Gly Val Asp Leu Asn Arg
                245                 250                 255

Asn Ser Thr Phe Lys Trp Gly Ala Gly Thr Asn Arg Cys Gly Glu
                260                 265                 270

Thr Tyr Gln Gly Thr Ala Ala Gly Ser Glu Pro Glu Thr Arg Ala Leu
                275                 280                 285

Glu Ala Trp Phe Lys Gln Leu Phe Pro Asp Gln Arg Gly Pro Gly Asp
                290                 295                 300

Thr Asp Pro Ala Pro Val Thr Thr Lys Gly Val Met Ile Thr Ile His
305                 310                 315                 320

Ser Tyr Gly Asn Leu Ile Met Pro Pro Trp Gly Trp Thr Trp Asn Ala
                325                 330                 335

Asn Pro Asn Ala Ala Gln Leu Ala Leu Gly Lys Lys Met Ala Ala
                340                 345                 350

Phe Asn Gly Tyr Thr Val Val Ala Glu Gly Asp Thr Thr Gly Thr Thr
                355                 360                 365

Asp Asp Phe Thr Tyr Gly Thr Leu Gly Ile Ala Ser Tyr Thr Phe Glu
                370                 375                 380

Ile Gly Ser Ser Gly Ser Cys Gly Gly Phe Phe Pro Gln Tyr Ser
385                 390                 395                 400

Cys Val Asp Ser Leu Phe Trp Pro Arg Asn Lys Gly Ala Phe Leu Thr
                405                 410                 415

Ala Ala Lys Ala Ala Lys Ala Pro Tyr Ala Ser
                420                 425

<210> SEQ ID NO 25
<211> LENGTH: 466
<212> TYPE: PRT
<213> ORGANISM: Saccharothrix mutabilis

<400> SEQUENCE: 25

Met Arg Ile Thr Asp Val Gln Arg Cys Glu Val Arg Pro Gly Arg Val
```

-continued

```
1               5                   10                  15
Val Glu Trp Val Leu Arg Pro Val Ala Ala Thr Gly Ala Pro Asp
            20                  25                  30

Asp Ala Arg Pro Pro Ala Tyr Leu Gln Glu Ser His Val Arg Thr Ala
            35                  40                  45

Arg Ser Leu Arg Glu Asp Gly Leu Phe Val Pro Thr Trp Leu Gly Val
            50                  55                  60

Ala Phe Asp Leu Pro Gly Ala Val Asp Leu Asp Ala Leu Glu Glu Ala
65                  70                  75                  80

Leu Arg Val Trp Thr Leu Arg His Glu Thr Leu Arg Ser Gly Phe Arg
                    85                  90                  95

Trp Glu Asp Gly Glu Met Arg Arg Phe Thr Leu Asp Ala Asp Ala Val
                    100                 105                 110

Ala Leu His Arg Glu Asp Val Gly Glu Phe Thr Asp Ala Asp Val Leu
                    115                 120                 125

Val Gln His Leu Gln Asp Arg Phe Asp Val Ala Ala Asp Thr Leu Thr
                    130                 135                 140

Trp Pro Asn Phe Ile Tyr Ala Ala Val Ala Arg Glu Asp Ser Thr Ser
145                 150                 155                 160

Val Tyr Leu Ala Phe Asp His Ser Asn Val Asp Ala Tyr Ser Met Tyr
                    165                 170                 175

Arg Val Pro Ala Glu Leu His Glu Leu Tyr Ala Ala Leu Asp Gly
                    180                 185                 190

Arg Thr Val Asp Ala Ala Pro Ile Ala Ser Tyr Val Asp Phe Cys Ala
                    195                 200                 205

Thr Glu Arg Ala Asp Ala Asp Glu Val Asp Ala Asp His Pro Val Val
                    210                 215                 220

Asp Arg Trp Arg Arg Phe Val Ala Arg Cys Asp Gly Arg Met Pro Asn
225                 230                 235                 240

Phe Pro Phe Asp Leu Gly Leu Ala Pro Gly Gly Pro Leu Pro Thr Gln
                    245                 250                 255

Lys Ser Leu His Glu Met Leu Val Asp Asp Ala Asp Ala Ala Ala Phe
                    260                 265                 270

Glu Arg His Cys Arg Pro Tyr Gly Gly Ser Leu Val Gly Val Leu Ala
                    275                 280                 285

Ala Thr Ala Leu Ile Met Arg Glu Met Thr Gly Asp Asp Val Tyr Arg
                    290                 295                 300

Thr Val Val Pro Phe His Thr Arg Ala Lys Ser Arg Trp Ser Asp Ser
305                 310                 315                 320

Val Gly Trp Tyr Val Gly Gly Val Pro Val Glu Leu Pro Val Ala Thr
                    325                 330                 335

Ala Gly Gly Phe Asp Gly Leu Leu Arg Ala Ala Gln Ala Glu Leu Arg
                    340                 345                 350

Ala Ser Arg Pro Ala Ser Arg Val Pro Ala Arg Val Leu Arg Leu
                    355                 360                 365

Leu Gly Asp Asp Phe Arg Pro Thr Ser Pro Asp Leu Tyr Ser Ile Val
                    370                 375                 380

Ser Phe Met Asp Ala Arg Pro Thr Pro Gly Ser Glu Arg Trp Arg Asp
385                 390                 395                 400

Met Lys Ala Tyr Gly Leu Ile Arg Val Ser Tyr Gly Asp Gln Val Cys
                    405                 410                 415

Val Trp Val Thr Arg Leu His Glu Gly Leu Gln Phe Ala Cys Arg Tyr
                    420                 425                 430
```

```
Pro Asp Asn Asp Val Ala Tyr Lys Asn Ile Arg Leu Tyr Val Asp Arg
        435                 440                 445

Leu Arg Glu Val Ile Leu Ser Val Ala Arg Pro Ala Asp Ala Pro Ala
    450                 455                 460

Ala Gly
465

<210> SEQ ID NO 26
<211> LENGTH: 200
<212> TYPE: PRT
<213> ORGANISM: Saccharothrix mutabilis

<400> SEQUENCE: 26

Met Thr Ser Arg Phe Ala Gln Val Met Phe Thr Pro Asp Val Gln Leu
1               5                   10                  15

His Gln Glu Arg His Gly Ser Arg Asp Ala Tyr Ala Arg Met Ala Asp
            20                  25                  30

Ala Ala Pro Val Arg Asp Arg Ile Gly Pro Asp Glu Ala Ala Phe Ile
        35                  40                  45

Ala Glu Arg Asp Ser Phe Tyr Leu Ala Thr Val Gly Glu Thr Gly Trp
    50                  55                  60

Pro Tyr Ile Gln His Arg Gly Pro Pro Gly Phe Leu Arg Val Leu
65                  70                  75                  80

Asp Glu His Thr Leu Gly Phe Ala Asp Phe Arg Gly Asn Arg Gln Tyr
                85                  90                  95

Ile Thr Arg Gly Asn Leu Asp His Asp Arg Val Ala Leu Phe Leu
            100                 105                 110

Met Asp Tyr Ala Asn Arg Thr Arg Leu Lys Leu Ile Gly His Ala Arg
        115                 120                 125

Ala Asp Asp Ser Pro Glu Val Val Glu Arg Leu Ala Leu Pro Asp Tyr
    130                 135                 140

Arg Ala Lys Val Glu Arg Ala Val Leu Ile Glu Val Glu Ala Thr Ile
145                 150                 155                 160

Trp Asn Cys Arg Gln His Ile Pro Gln Leu Phe Pro Arg Asp Ala Val
                165                 170                 175

Glu Gln Ala Val Gly Ala Leu Arg Asp Arg Ile Thr Glu Leu Glu Gln
            180                 185                 190

Glu Asn Ala Arg Leu Arg Ala Arg
        195                 200

<210> SEQ ID NO 27
<211> LENGTH: 171
<212> TYPE: PRT
<213> ORGANISM: Saccharothrix mutabilis

<400> SEQUENCE: 27

Met Ser Gly Arg Leu His Ala Pro Ala Ile Gly Thr Ala Arg Leu Asp
1               5                   10                  15

Leu Val Pro Leu Arg Val Asp His Ala Glu Glu Met Ala Val Val Leu
            20                  25                  30

Ala Asp Pro Ala Leu His Thr Phe Thr Gly Gly Thr Pro Asp Asp Pro
        35                  40                  45

Arg Ala Leu Arg Ser Arg Tyr Glu Arg Met Leu Ala Gly Ser Pro Asp
    50                  55                  60

Pro Ala Val Ser Trp Leu Asn Trp Val Arg Leu Arg Glu Glu Ser
65                  70                  75                  80

Arg Leu Ala Gly Thr Val Gln Ala Thr Val Gly Pro Thr Asp Gln Gly
```

```
                        85                  90                  95
Pro Val Ala Glu Val Ala Trp Val Val Gly Thr Pro Phe Gln Gly Arg
                100                 105                 110
Gly Ile Ala Arg Glu Ala Ala Arg Gly Leu Val Asp Trp Leu Gly Arg
            115                 120                 125
Gln Gly Val Arg Thr Val Ala His Val His Pro Asp His His Ala
        130                 135                 140
Ser Ala Ala Val Ala Thr Ala Ala Gly Leu Ala Pro Thr Asp Glu Val
145                 150                 155                 160
His Asp Gly Glu Val Arg Trp Arg Leu Ser Arg
                165                 170

<210> SEQ ID NO 28
<211> LENGTH: 398
<212> TYPE: PRT
<213> ORGANISM: Saccharothrix mutabilis

<400> SEQUENCE: 28

Met Ser Leu Asp Glu Arg Lys Leu Phe Ala Ala Arg Leu His Ala Val
1               5                   10                  15
Arg Cys Arg Pro Tyr Leu Ala Thr Ala Leu Phe Ala Leu His Val Val
            20                  25                  30
Glu Ser Arg Arg Val Pro Thr Met Ala Val Asp Arg His Trp Arg Cys
        35                  40                  45
Tyr Val Ser Pro Ala Phe Val Asp Arg Thr Pro Glu Glu Leu Ala
    50                  55                  60
Gly Val Trp Val His Glu Val Ser His Leu Leu Arg Asp His His Gly
65                  70                  75                  80
Arg Gly Asp Arg Phe Ala Ala Glu His Gly Leu Thr Gly Pro Gly Glu
                85                  90                  95
Arg Leu Arg Met Asn Ile Ala Ala Asp Cys Glu Ile Asn Asp Asp Val
            100                 105                 110
Phe Gly Asp Gly Leu Ala Arg Pro Glu Gly Ala Val Glu Pro Glu Leu
        115                 120                 125
Leu Gln Leu Arg Glu Gly Gln Leu Met Glu Asp Tyr Leu Arg Gln Phe
    130                 135                 140
Arg Leu Gly Pro Tyr Thr Asp Ala Phe Thr Trp Leu Asp Cys Gly Ser
145                 150                 155                 160
Gly Ala Asp Gly Leu Glu Arg Glu Trp Asp Leu Gly Pro Asp Gly Ala
                165                 170                 175
His Gly Leu Ser Glu Gln Glu Arg Asp Ala Val Arg Phe Arg Val Ala
            180                 185                 190
Glu Ala Ile Thr Gly Arg Pro Gly Asp Val Pro Leu Gly Trp Arg Arg
        195                 200                 205
Trp Ala Glu Arg Ala Phe His Pro Pro Gln Pro Trp Arg Asp Leu Leu
    210                 215                 220
Gly Ala Ala Val Arg Ser Ala Ser Ala Ala Gly Ala Gly Asp Asp
225                 230                 235                 240
Tyr Thr Tyr Gly Arg Pro Ala Arg Arg Ser Thr Ala Leu Pro Gly Val
                245                 250                 255
Val Leu Pro Ser Leu Arg Arg Pro Pro Arg Val Cys Val Val Val
            260                 265                 270
Asp Thr Ser Gly Ser Val Ser Asp Ala Glu Leu Gly Ser Ala Leu Leu
        275                 280                 285
Glu Ile Ala Ala Ile Ala Arg Ala Val Gly Gly Arg Arg Asp Leu Val
```

```
                290                 295                 300
Ser Val Leu Ser Cys Asp Ala Ala His Val Thr His Pro Leu Cys
305                 310                 315                 320

Arg Ala Glu Gly Ile Pro Leu Met Gly Gly Gly Thr Asp Leu Arg
                325                 330                 335

Thr Gly Phe Thr Arg Ala Leu Arg Thr Arg Pro Asp Val Ile Val Ala
                340                 345                 350

Leu Thr Asp Gly Gln Thr Pro Trp Pro Thr Val Arg Pro Pro Cys Arg
                355                 360                 365

Thr Val Val Gly Leu Phe Arg Arg Pro Lys Pro Gly Asp Tyr Arg
370                 375                 380

Pro Asp Pro Pro Ala Trp Ala Arg Val Val Thr Val Gly
385                 390                 395

<210> SEQ ID NO 29
<211> LENGTH: 404
<212> TYPE: PRT
<213> ORGANISM: Saccharothrix mutabilis

<400> SEQUENCE: 29

Met Pro Thr Ser Leu Ser Ala Arg Pro Leu Asp Val Ala Ala Asp Leu
1               5                   10                  15

Leu Ala Leu Leu Gly Arg Thr Thr Thr Glu Thr Arg Ser Asp Ala Gln
                20                  25                  30

Leu Glu Ala Leu Thr Leu Ala Val Ser Ala Asp Leu Pro Val Leu Leu
            35                  40                  45

Trp Gly Glu Pro Gly Ile Gly Lys Thr Ala Ala Leu Thr Gln Leu Ala
    50                  55                  60

Asp Ala Leu Asp Leu Pro Leu Thr Thr Val Ile Ala Ser Val His Glu
65                  70                  75                  80

Pro Ser Asp Phe Ala Gly Leu Pro Val Val Gly Asp Asp Pro Ala Val
                85                  90                  95

Gln Gly Val Pro Met Ala Pro Pro Asp Trp Ala Val Arg Leu Val Arg
                100                 105                 110

Ala Gly Arg Gly Leu Leu Phe Leu Asp Glu Leu Ser Thr Ala Pro Pro
            115                 120                 125

Ala Val Gln Ala Ala Leu Leu Arg Val Val Leu Glu Arg Arg Ile Gly
        130                 135                 140

Ala Leu Thr Leu Pro Pro Gly Val Arg Ile Val Ala Ala Ala Asn Pro
145                 150                 155                 160

Arg Ser Ser Ala Ala Asp Gly Trp Glu Leu Ser Pro Pro Leu Ala Asn
                165                 170                 175

Arg Phe Val His Leu Gln Trp Ala His Asp His Asp Val Val Val Arg
            180                 185                 190

Gly Leu Gly Gly Thr Trp Pro Arg Ala Glu Leu Pro Arg Leu Asp Pro
        195                 200                 205

Gly Arg Leu Pro Asp Ala Val Ala Tyr Ala Arg Arg Ala Val Cys Glu
    210                 215                 220

Leu Leu Ala Ala Arg Pro Asn Leu Val His Gln Leu Pro Lys Asp Glu
225                 230                 235                 240

Thr Arg Arg Gly Gly Pro Trp Pro Ser Pro Arg Ser Trp Glu Met Ala
                245                 250                 255

Leu Arg Leu Ile Ala Phe Ala Thr Ala Ala Asp Val Ser Arg Asp Val
            260                 265                 270

Leu Ser Met Leu Val Arg Gly Thr Val Gly Asp Gly Pro Gly Leu Glu
```

```
                275                 280                 285
Leu Leu Ala Ser Leu Asp Arg Met Asp Leu Pro Asp Pro Glu Ser Leu
290                 295                 300

Leu Ala Asn Pro Ala Ala Val Leu Pro Glu Arg Gly Asp Leu Arg
305                 310                 315                 320

Gln Ala Val Leu Asp Gly Val Val Glu Ala Val Arg Arg Pro Glu
                325                 330                 335

Ala Ala Arg Trp Asp Ala Ala Trp Ala Leu Leu Val Arg Ala Leu Asp
                340                 345                 350

Thr Gly Ala Pro Asp Leu Val Val Val Pro Ala Ala Thr Leu Ala Ala
                355                 360                 365

Leu Arg Arg Asp Asp Trp Glu Val Pro Ala Ala Ile Glu Arg Leu Ser
370                 375                 380

Gly Ala Val Ser Val Ser Arg Leu Ala Asp Arg Thr Ala Ala Arg Val
385                 390                 395                 400

Gly Ala Gly Arg

<210> SEQ ID NO 30
<211> LENGTH: 222
<212> TYPE: PRT
<213> ORGANISM: Saccharothrix mutabilis

<400> SEQUENCE: 30

Met Ile Thr Val Arg Leu Asn Ala Gly Arg Trp Ala Leu Ala Pro
1               5                   10                  15

Asp Glu Pro Thr Pro Val Leu Thr Ala Ala Pro Arg Arg Asp Pro Thr
                20                  25                  30

Arg Pro Val Leu Pro Asp Ala Ala Thr Arg Thr Pro Pro Asp Leu Asp
                35                  40                  45

Leu Leu Arg Ala Gly Leu Val Asp Ala Asp Arg Leu His Pro Leu Val
50                  55                  60

Ala Ser Ala Leu Val Pro Gly His Arg Arg Thr Thr Gly Ser Pro Asp
65                  70                  75                  80

Pro Ala Thr Gly Pro Arg Leu Val Glu Cys Arg Gly Ala Thr His Arg
                85                  90                  95

Ile Gly Val Val Asp Gly Val Leu Val Pro Leu Asp His Asp Pro Asp
                100                 105                 110

Glu Val Arg Arg Glu Glu Leu Leu Ala Glu Trp Gly Gly Pro Pro Leu
                115                 120                 125

Pro Cys Leu Arg Ala Ile Asp Asp Val His Arg Gln Pro Glu Ser Leu
130                 135                 140

Val Asp Val Arg Ala Arg Leu Asp His Gly Asp Thr Ala Gly Ala Val
145                 150                 155                 160

Ala Ala Val Glu Ala Leu Leu Gly Pro Glu Ala Leu Leu Arg Ala Gly
                165                 170                 175

Ala Leu Arg Asp Glu Leu Asp Ala Ala Val Arg Arg Leu Ala His
                180                 185                 190

Gly Leu Tyr Arg Ala Gly Leu Ala Gly Gly Pro Ala Pro Ser Thr Lys
                195                 200                 205

Asp Gly Arg Arg Arg Val Arg Pro Arg His Ala Phe Ser Arg
210                 215                 220

<210> SEQ ID NO 31
<211> LENGTH: 252
<212> TYPE: PRT
<213> ORGANISM: Saccharothrix mutabilis
```

<400> SEQUENCE: 31

Met Leu Met His His Thr Thr Ala Asp Glu Asn Leu Arg Leu His Phe
1               5                   10                  15

Trp Thr Arg Val Arg Glu Phe Ala Val Pro Pro Ser Met Val Glu Thr
            20                  25                  30

Ala Thr Ala Arg Arg Ser Val Gly Asp Trp Ala Gly Ala Cys Ala Ala
        35                  40                  45

Ala Arg Phe Asp Val Asp Leu Asp Leu Arg Ala Val Gly Arg Thr His
    50                  55                  60

Gly Arg Gln Leu Ala Ala Gln Val Arg Ala Asp Leu His Leu Ala
65                  70                  75                  80

Pro Asp Leu Leu Arg Trp His Phe Pro Arg Ile Gly Pro Asp Gly Leu
                85                  90                  95

Leu Arg Pro Gly Leu Thr Val Ser Leu Ala Arg Tyr Ala Ala Gly Pro
            100                 105                 110

His Leu Val Ala Arg Thr Pro Pro Ala Trp Ala Ala Ala Gly Gln Arg
        115                 120                 125

Ile Ser Leu Ala Trp Trp Asp Pro Ala Glu Pro Arg Ala Gly Ala Gly
    130                 135                 140

Thr His Pro His Pro Arg Pro Asp Arg Arg Phe Arg Leu Asp Leu His
145                 150                 155                 160

Arg His Leu Trp Asp Ala Arg Arg Ala Gly Glu Leu Arg Glu Arg Ser
                165                 170                 175

Ala Gly Gly Asp Pro Pro Pro Gly Phe Asp His Arg Ala Ala Arg Ser
            180                 185                 190

Arg Leu Ala Gly Arg Arg Val Ala Gly Ser Arg Gly Ala Arg Arg Val
        195                 200                 205

Arg Gly Pro Ser Gly Arg Arg Gln Pro Arg Asp Pro Pro Arg Arg Gly
    210                 215                 220

Pro Ser Arg Gly Arg Val Ser Leu Ser Val Val Gly Cys Arg Arg Pro
225                 230                 235                 240

Cys Ser Ser Cys Ala Arg Thr Gly Ala Pro Thr Ala
                245                 250

<210> SEQ ID NO 32
<211> LENGTH: 248
<212> TYPE: PRT
<213> ORGANISM: Saccharothrix mutabilis

<400> SEQUENCE: 32

Met Ala Gly Thr Asp Leu Tyr Asp Asp Ile Gly Thr Gly Tyr Ala Leu
1               5                   10                  15

Gly Arg Arg Thr Asp Pro Arg Trp Met Thr Ala Ile Leu Asp Ala Leu
            20                  25                  30

Gly Gly Ala Arg Thr Ile Ala Asn Val Gly Ala Gly Thr Gly Ser Tyr
        35                  40                  45

Glu Pro Asp Asp Arg Thr Val Val Ala Leu Glu Pro Ser Thr Glu Met
    50                  55                  60

Ile Arg Gln Arg Pro Pro Glu Val Gly Pro Ala Val Arg Ala Val Ala
65                  70                  75                  80

Glu Ala Leu Pro Leu Arg Asp His Ala Val Asp Ala Ala Leu Ala Val
                85                  90                  95

Leu Thr Val His His Trp Thr Asp Trp Arg Ala Gly Leu Ala Glu Leu
            100                 105                 110

```
Arg Arg Ile Ala Pro Arg Arg Val Val Leu Ala Tyr Asp Thr Ser Leu
        115                 120                 125

His Thr Glu Phe Trp Phe Val Arg Glu Tyr Val Pro Glu Ile Ala Asp
130                 135                 140

Leu Glu Arg Thr Arg Pro Ser Ala Ala Asp Ile Ala Gly Glu Leu Gly
145                 150                 155                 160

Ala Asp Ser Val Thr Pro Leu Pro Leu Pro Trp Asp Phe Val Asp Gly
                165                 170                 175

Val Phe Pro Ala Tyr Trp Arg Arg Pro Asp Ala Tyr Leu Asp Pro Arg
            180                 185                 190

Val Arg Arg Ala Cys Ser Ala Leu Ala Gln Thr Asp Pro Ala Ala Val
        195                 200                 205

Asp Arg Gly Val Arg Arg Leu Arg Ala Asp Leu Asp Ser Gly Arg Trp
210                 215                 220

His Asp Asp His Arg Asp Leu Leu Asp Leu Asp Gln Trp Asp Ala Gly
225                 230                 235                 240

Phe Arg Leu Val Val Ser His Thr
                245
```

<210> SEQ ID NO 33
<211> LENGTH: 278
<212> TYPE: PRT
<213> ORGANISM: Saccharothrix mutabilis

<400> SEQUENCE: 33

```
Met Gly Asn Gly Glu Arg Ile Gly Val Phe Tyr Asp Gly Thr Trp Phe
1               5                   10                  15

Ala Tyr Leu Ser Asp Tyr Phe Ala Ser Val His Pro Arg Ala Ala Arg
            20                  25                  30

Val Ser Leu Asp Gly Phe His Asp Ala Leu Arg Trp Tyr Val His Thr
        35                  40                  45

Val Thr His Gln Pro Leu Asp Glu Cys Val Val Ser Glu Ala His Tyr
    50                  55                  60

Val Arg Gly Arg Ile Asp Thr Pro Ala Val Ala Phe Asp Ala Val Leu
65                  70                  75                  80

Ala Ala Ala Gly Val Val Arg His Asp Leu Pro Leu His Ala Gly Lys
                85                  90                  95

Glu Lys Gly Val Asp Val His Leu Ala Leu Glu Ala Trp Glu Arg Ala
            100                 105                 110

Thr Ser Val Pro Leu Arg Trp Val Val Leu Val Thr Gly Asp Ala Asp
        115                 120                 125

Phe Ala Pro Leu Ala Thr Arg Leu Lys Thr Arg Gly Val Arg Val Val
    130                 135                 140

Val Pro Val Asp Gly Gly Val Val Ala Pro Ala Trp Met Pro Arg
145                 150                 155                 160

Thr Ala Ala Pro Leu Arg Ala Ala Ser Ala Thr Pro Thr Phe Asp
                165                 170                 175

Asp Leu Phe Thr Pro Ala Glu Arg Asp Asp Tyr Pro Leu Arg Ala Pro
            180                 185                 190

Phe Val Arg Thr Ser Gly Gly Ala Ser Val Ala Gly Glu Pro Arg
        195                 200                 205

Gly Arg Arg Lys Gly Thr Val Thr Gly Trp Lys Thr Gly Gln Pro His
    210                 215                 220

Gly Phe Ile Thr Asp Thr Arg Gly Ala Ser Trp Phe Val Ser Arg Asp
225                 230                 235                 240
```

```
Asp Leu Pro Leu Gly Leu Val Ala Leu Pro Val Gly Thr Ser Val Ser
            245                 250                 255

Phe Ser Gly Pro Ser Thr Pro Pro Ala Gly Arg Lys Tyr Pro Arg Ala
        260                 265                 270

Tyr Ala Val Gln Thr Glu
        275

<210> SEQ ID NO 34
<211> LENGTH: 245
<212> TYPE: PRT
<213> ORGANISM: Saccharothrix mutabilis

<400> SEQUENCE: 34

Met Ser Lys Gln Pro Asp Ser Leu Arg Thr Thr Val Val Pro Thr
1               5                   10                  15

Tyr Asn Glu Arg Asp Asn Leu Pro Val Leu Val Asp Leu Leu Ala Asp
                20                  25                  30

Leu Gly Val Pro Gly Leu His Val Leu Val Asp Asp Asn Ser Pro
                35                  40                  45

Asp Gly Thr Gly Asp Leu Ala Asp Lys Leu Ala Leu Glu Gly Pro Leu
    50                  55                  60

Pro Leu Ser Val Leu His Arg Thr Glu Lys Asp Gly Leu Gly Arg Ala
65                  70                  75                  80

Tyr Val Ala Gly Ile Leu Lys Ala Leu Asp Asp Gly Ala Asp Leu Val
                85                  90                  95

Val Gln Met Asp Ala Asp Leu Ser His Pro Ala Ser Ala Ile Pro Thr
                100                 105                 110

Met Ile Glu Val Leu Arg Thr Ser Asp Ala Ala Val Val Ile Gly Ser
                115                 120                 125

Arg Tyr Val Pro Gly Gly Ser Val Ser Gly Glu Trp Lys Trp His Arg
    130                 135                 140

Lys Ala Leu Ser Leu Trp Ala Asn Val Tyr Val Asn Ala Ile Leu Arg
145                 150                 155                 160

Leu Arg Val Lys Asp Ala Thr Ala Gly Phe Lys Cys Trp Arg Ala Ala
                165                 170                 175

Thr Leu Arg Arg Ile Asp Val Gly Ser Ile Arg Ser Asn Gly Tyr Ala
                180                 185                 190

Phe Gln Val Glu Met Asn His Arg Val Val Lys Arg Gly Met Arg Ile
                195                 200                 205

Ala Glu Val Pro Ile Arg Phe Glu Glu Arg Ala Glu Gly Ala Ser Lys
    210                 215                 220

Met Ser Phe Gly Val Gln Leu Glu Ser Ala Val Met Pro Trp Lys Leu
225                 230                 235                 240

Leu Phe Lys Lys Gly
            245

<210> SEQ ID NO 35
<211> LENGTH: 19
<212> TYPE: DNA
<213> ORGANISM: Artificial
<220> FEATURE:
<223> OTHER INFORMATION: synthetic construct

<400> SEQUENCE: 35
cccaccttgt tgacgtggt                                                  19

<210> SEQ ID NO 36
<211> LENGTH: 18
```

```
<212> TYPE: DNA
<213> ORGANISM: Artificial
<220> FEATURE:
<223> OTHER INFORMATION: synthetic construct

<400> SEQUENCE: 36
tcagcggtag gcggtcag                                                18

<210> SEQ ID NO 37
<211> LENGTH: 30
<212> TYPE: DNA
<213> ORGANISM: Artificial
<220> FEATURE:
<223> OTHER INFORMATION: synthetic construct

<400> SEQUENCE: 37
aagggccccc atatgccttc ggaaggtctg                                   30

<210> SEQ ID NO 38
<211> LENGTH: 30
<212> TYPE: DNA
<213> ORGANISM: Artificial
<220> FEATURE:
<223> OTHER INFORMATION: synthetic construct

<400> SEQUENCE: 38
ggtgtgtgtt cgaactcaca ctaacgcgcc                                   30

<210> SEQ ID NO 39
<211> LENGTH: 65
<212> TYPE: DNA
<213> ORGANISM: Artificial
<220> FEATURE:
<223> OTHER INFORMATION: synthetic construct

<400> SEQUENCE: 39
gtgcttgacc tctcccccgc gcagcgcagc ctgtgggtgt ctagaattcc ggggatccgt  60
cgacc                                                              65

<210> SEQ ID NO 40
<211> LENGTH: 64
<212> TYPE: DNA
<213> ORGANISM: Artificial
<220> FEATURE:
<223> OTHER INFORMATION: synthetic construct

<400> SEQUENCE: 40
ctattccgcg gtgatctcgt ccagcacggc caggaagtcg ctagctgtag gctggagctg  60
cttc                                                               64

<210> SEQ ID NO 41
<211> LENGTH: 65
<212> TYPE: DNA
<213> ORGANISM: Artificial
<220> FEATURE:
<223> OTHER INFORMATION: synthetic construct

<400> SEQUENCE: 41
gtgaccgcgc tgcaccgcct cgaccagctc gccggcgcgt ctagaattcc ggggatccgt  60
cgacc                                                              65

<210> SEQ ID NO 42
<211> LENGTH: 64
<212> TYPE: DNA
<213> ORGANISM: Artificial
```

```
<220> FEATURE:
<223> OTHER INFORMATION: synthetic construct

<400> SEQUENCE: 42
cacctcgggg tccggctgat caggcccgcc aacgcggtcg ctagctgtag gctggagctg    60
cttc                                                                 64

<210> SEQ ID NO 43
<211> LENGTH: 8
<212> TYPE: PRT
<213> ORGANISM: Artificial Sequence
<220> FEATURE:
<223> OTHER INFORMATION: Synthetic construct

<400> SEQUENCE: 43

Asp Ala Gln Ser Leu Ala Val Val
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic construct

<400> SEQUENCE: 44

Asp Ala Gln Ser Leu Ala Ile Val
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic construct

<400> SEQUENCE: 45

Asp Val Tyr His Phe Ser Leu Val
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic construct

<400> SEQUENCE: 46

Asp Val Tyr His Phe Ser Leu Val
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic construct

<400> SEQUENCE: 47

Asp Val Arg Ser Leu Ser Met Val
1               5

<210> SEQ ID NO 48
<211> LENGTH: 8
<212> TYPE: PRT
<213> ORGANISM: Artificial Sequence
<220> FEATURE:
```

-continued

```
<223> OTHER INFORMATION: Synthetic construct

<400> SEQUENCE: 48

Asp Val Arg His Met Ser Met Val
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic construct

<400> SEQUENCE: 49

Asp Pro Gln Asp Ile Gly Ile Val
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic construct

<400> SEQUENCE: 50

Asp Pro Gln Asp Val Gly Ile Gly
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic construct

<400> SEQUENCE: 51

Asp Thr Glu Asp Val Gly Thr Met
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic construct

<400> SEQUENCE: 52

Asp Thr Glu Asp Val Gly Val Gly
1               5
```

HETEROLOGOUS PRODUCTION OF CAPREOMYCIN AND GENERATION OF NEW CAPREOMYCIN DERIVATIVES THROUGH METABOLIC ENGINEERING

CROSS-REFERENCE TO RELATED APPLICATIONS

This application claims the benefit of U.S. Provisional Application No. 60/917,628, filed May 11, 2007.

STATEMENT REGARDING FEDERALLY SPONSORED RESEARCH OR DEVELOPMENT

This invention was made with government support under AI065850 awarded by the National Institutes of Health. The government has certain rights in the invention.

REFERENCE TO A SEQUENCE LISTING

A Sequence Listing containing SEQ ID NOs:1-52 corresponding to the various sequences disclosed herein, such as the sequences contained within Table 3 and Table 8, is submitted herewith. The Sequence Listing is specifically incorporated by reference.

BACKGROUND OF INVENTION

*Mycobacterium tuberculosis*, the causative agent of tuberculosis, has been causing disease in humans since the beginning of civilization (8). Despite more than 50 years of vaccine and antibiotic development, it has been estimated that 225 million new cases of tuberculosis will arise between the years 1998 and 2030, with 79 million tuberculosis-related deaths (25). One of the challenges in treating this disease is the wide-spread development of multidrug-resistant tuberculosis (MDR-TB), defined as an infection that does not respond to treatment with either first-line drug isoniazid or rifampicin (9). The development of MDR-TB has resulted in an increased emphasis on the use of second-line drugs to treat these infections. One of these second-line drugs is capreomycin (CMN), a collection of four structurally related peptide antibiotics (FIG. 1). The importance of CMN for the treatment of MDR-TB is reflected in this drug being included on the World Health Organization's "List of Essential Medicines" (36). There is additional interest in CMN because of the recent finding that this drug is bactericidal against non-replicating *M. tuberculosis*, suggesting the potential use of CMN to treat latent tuberculosis infections (15). While of most interest for treatment of tuberculosis, capreomycin is known in the art to be more generally active against a number of gram-positive and gram-negative bacteria.

CMN and a structural analog viomycin (VIO) (FIG. 1) (see also U.S. Pat. No. 7,326,782 for details of the VIO cluster and biosynthesis thereof) disrupt the growth of *Mycobacterium* spp. by interfering with the function of the ribosome (22-24, 37-43). This conclusion is based on the isolation and characterization of resistant strains along with in vitro analysis of ribosome binding and disruption of peptide synthesis. There were two surprising results from these studies that emphasize the distinct mechanism of action of CMN and VIO. First, resistance to VIO in *M. smegmatis* was conferred by mutations in either the 16S or 23S rRNA, suggesting this antibiotic interferes with the function of both ribosomal subunits (41). The second result was the recent finding that *M. tuberculosis* resistance to CMN and VIO can also arise from a mutation in the gene tlyA (22). Subsequent analysis determined that the TlyA enzyme likely catalyzes methylation of both the 16S and 23S rRNA, and these methylations are essential for CMN and VIO sensitivity, possibly forming part of the binding site of these antibiotics (18). Thus, resistance to CMN and VIO can arise from point mutations in the 16S or 23S rRNA or from the loss of modifications to these rRNAs.

While the CMN and VIO resistance mechanisms in *Mycobacterium* spp. involve mutations in the rRNA or a gene coding for an rRNA modifying enzyme, the bacteria that naturally produce these antibiotics are proposed to have resistance mechanisms that are independent of ribosome modification (2, 28, 33). VIO resistance by *Streptomyces* sp. strain ATCC11861 (previously known as *Streptomyces vinaceus*) occurs via antibiotic inactivation by Vph, a VIO phosphorylase (2). CMN, while commonly referred to as a single molecule, is actually a mixture of four structural derivatives (FIG. 1). The structural differences between these derivatives are particularly relevant in the context of resistance genes carried by the producing bacterium. For example, a gene coding a homolog of Vph was isolated from the CMN-producer *Saccharothrix mutabilis* subsp. *capreolus* (previously *Streptomyces capreolus*), but this only conferred resistance to CMN IA and IIA, leaving CMN IB and IIB active. This selectivity is due to Cph catalyzing the phosphorylation of the hydroxyl group of residue 2 of CMN IA and IIA that is absent from CMN IB and IIB (FIG. 1) (28, 33). A second gene, cac, was identified and conferred resistance to all four derivatives of CMN (28, 33). The coded enzyme is proposed to catalyze the acetylation of the α-amino group of residue 1 of the cyclic pentapeptide core, thereby inactivating CMN. Consistent with this proposal, Cac did not confer resistance to VIO because of the β-lysine attached to the α-amino group of residue one of VIO.

CMN and VIO are peptide antibiotics with subtly different cyclic pentapeptide cores that can be decorated by carbamoylation, hydroxylation, or acylation with β-lysine (FIG. 1). A series of precursor labeling studies have been performed on CMN and VIO to investigate how these unusual antibiotics are assembled by the producing bacteria (4, 5, 12, 35). We outlined a biosynthetic mechanism for the assembly of VIO using these labeling experiment results in combination with bioinformatic and biochemical analysis of the VIO biosynthetic gene cluster and the enzymes it codes (19, 34) (U.S. Pat. No. 7,326,782). We predict that CMN biosynthesis follows similar mechanisms, but with some differences to account for the structural differences between these antibiotics.

Our interests in deciphering how this family of antibiotics is biosynthesized are in two areas. First, we address the basic biological question of how these unusual cyclic peptides, consisting of rare nonproteinogenic amino acids, are assembled. Second, we explore harnessing of the biosynthetic machinery of CMN and VIO production to generate new structural derivatives of these antibiotics through the use of metabolic engineering. Here we present the isolation and sequencing of the CMN biosynthetic gene cluster from *S. mutabilis* subsp. *capreolus* strain ATCC 23892. Bioinformatics analysis of this gene cluster provides a molecular blueprint for CMN biosynthesis and explains the structural differences between CMN and VIO. The integration of this biosynthetic gene cluster into the chromosome of *Streptomyces lividans* 1326 resulted in the heterologous production of CMN by this naturally non-producing bacterium. This is a significant finding because *S. mutabilis* subsp. *capreolus* has proven intractable to genetic manipulation (27). Thus, metabolic engineering of CMN biosynthesis was not previously possible in the natural producer. The results presented here circumvent this problem. Finally, while previous work suggested that *S.*

*mutabilis* subsp. *capreolus* does not alter its ribosomes to become resistant to CMN, we present data that strongly suggests ribosome modification is a natural CMN resistance mechanism for this bacterium.

SUMMARY OF THE INVENTION

The invention relates to the identification and isolation of DNA sequences encoding the genes of the biosynthetic cluster of capreomycin such as DNA sequences that encode the various gene products summarized in TABLE 2. Provided are expression cassettes, vectors, and uses for such materials, that contain the capreomycin biosynthetic gene cluster from *Saccharothrix mutabilis* subsp. *Capreolus* or any one or more genes of the Cmn gene cluster, such as CmnA-CmnP, CmnR and CmnU.

In an embodiment, the invention provides methods of heterologous production of capreomycin by introduction of such vectors and incorporation of such expression cassettes into a heterologous host organism and growth of such organisms such that they produce capreomycin, or a gene product of interest from the Cmn cluster. Heterologous host organisms include, among others, strains of *Streptomyces* which do not, prior to such introduction, produce capreomycin, particularly strains of *Streptomyces lividans* and *Streptomyces coelicolor*. More specifically the invention relates to production of capreomycin in *Streptomyces lividans* 1326. Accordingly, provided herein is the heterologous production of the capreomycins in a heterologous host that facilitates production of the capreomycins with fewer contaminants.

The identification, isolation and functional analysis of the biosynthetic genes of capreomycin as described herein further facilitates metabolic engineering of the capreomycin biosynthetic gene cluster for the production of new capreomycin derivatives and the improved production of known capreomycin derivatives, such as those derivatives in Tables 5 and 6. More specifically, the biosynthetic gene cluster combined with certain biosynthetic genes of the viomycin biosynthetic gene cluster (see U.S. Pat. No. 7,326,782 for VIO cluster DNA sequence (SEQ ID NO:1) and amino acid sequences of each of VioA-VioT and vph (SEQ ID NOs:2-22, respectively); whose sequences are specifically incorporated by reference), allows the synthesis of capreomycin derivatives in such heterologous hosts. For example, combination of each of vioQ, vioMOP, or vioMOP as well as vioQ, with the genes of the capreomycin biosynthetic gene cluster in such a heterologous host in which the genes are expressed to form functional protein, allows the production of capreomycin derivatives in that host, as discussed in Table 5. Additionally, the combination of vioA with the genes of the capreomycin biosynthetic gene cluster other than cmnA (the cmnA can be excised in whole or in part from the gene cluster or inactivated as is known in the art) in such a heterologous host allows the production of additional capreomycin derivatives as described in Table 5. Further, derivatives such as the 19-OH capreomycins of Table 5 can be employed as intermediates for the synthesis of additional capreomycin derivatives such as those exemplified in Table 6.

The materials and methods provided herein allow production of the capreomycin IIA and IIB components in the absence of the capreomycin IA and IB components. Inactivation and/or excising any one or more of CmnM, CmnO or CmnP in the capreomycin gene cluster will result in the generation of the IIA and IIB components in the absence of the I A and IB capreomycin components. The separated capreomycin IIA and IIB components are useful in the absence of the IA and IB components as antibacterial agents, but are also useful as intermediates for the synthesis of additional capreomycin derivatives. The materials and methods of this invention allow generation of capreomycin derivatives which exhibit renewed activity against resistant bacteria, reduced unwanted side effects, and improved bioavailability for oral intake of the antibiotics rather than the currently used intramuscular injection.

Further, individual genes of the capreomycin biosynthetic cluster can be employed in combination with one or more biosynthetic genes of the viomycin biosynthetic cluster to generate viomycin derivatives.

The invention provides isolated and purified nucleic acid sequences which encode one or more of CmnA, CmnB, CmnC, CmnD, CmnE, CmnF, CmnG, CmnH, CmnI, CmnJ, CmnK, CmnL, CmnM, CmnN, CmnO, CmnP, CmnR, CmnU or Cph gene products (see Table 2). In an aspect, the nucleic acid sequence is not for the Cph gene product alone. The invention provides isolated and purified nucleic acid sequences which encode (1) one or more of CmnA, CmnB, CmnC, CmnD, CmnE, CmnF, CmnG, CmnH, CmnI, CmnJ, CmnK, CmnL, CmnM, CmnN, CmnO, CmnP, CmnR, CmnU or Cph gene products, as well as (2) homologous regulatory sequences sufficient for proper expression of the one or more gene products in a selected heterologous host, such as a strain of *Streptomyces*. The invention provides isolated and purified nucleic acid sequences which encode (1) one or more of CmnA, CmnB, CmnC, CmnD, CmnE, CmnF, CmnG, CmnH, CmnI, CmnJ, CmnK, CmnL, CmnM, CmnN, CmnO, CmnP, CmnR, CmnU or Cph gene products, as well as (2) heterologous regulatory sequences sufficient for proper expression of the one or more gene products in a selected non-*Streptomyces* heterologous host, such as a strain of *Escherichia coli*. Heterologous regulatory sequences which function for expression of coding sequences in such heterologous hosts are known in the art. One of ordinary skill in the art can employ the coding sequences provided herein in combination with known heterologous regulatory sequences and employing known techniques to prepare nucleic acid constructs for introduction into non-Streptomyces heterologous hosts for proper expression of function gene products. Provided herein are nucleotide sequences that encode for a polypeptide or protein having 90% or greater, 95% or greater, 98% or greater or 99% or greater sequence identity to any of the disclosed amino acid sequences (such as SEQ ID NOs:2-34). Optionally, a polypeptide sequence encoded by a nucleotide sequence provided herein are further described in terms of the function of the corresponding protein of the CMN cluster.

In an aspect, the invention provides isolated and purified functional proteins produced by heterologous expression of one or more of the CmnA, CmnB, CmnC, CmnD, CmnE, CmnF, CmnG, CmnH, CmnI, CmnJ, CmnK, CmnL, CmnM, CmnN, CmnO, CmnP, CmnR, CmnU or Cph genes. Certain of these functional proteins are useful for in vitro synthesis or derivatization of peptide antibiotics, such as viomycin and capreomycin, and for regulating gene expression.

Further, the invention provides vectors, including expression vectors which contain a nucleic acid which encodes one or more of the CmnA, CmnB, CmnC, CmnD, CmnE, CmnF, CmnG, CmnH, CmnI, CmnJ, CmnK, CmnL, CmnM, CmnN, CmnO, CmnP or Cph gene products. The invention further provides vectors, including expression vectors, which contain a nucleic acid which encodes each of the CmnA, CmnB, CmnC, CmnD, CmnE, CmnF, CmnG, CmnH, CmnI, CmnJ, CmnK, CmnL, CmnN, or Cph gene products, such that functional products of each of the listed genes are expressed in a selected heterologous host into which the vector is introduced. In a specific embodiment, the invention provides a vector, particularly an expression vector, which comprises nucleic acid sequences which encode all of the gene products of CmnA, CmnB, CmnC, CmnD, CmnE, CmnF, CmnG, CmnH, CmnI, CmnJ, CmnK, CmnL, CmnM, CmnN, CmnO, CmnP or Cph such that functional products of each of the listed genes are expressed in a selected heterologous host into which the vector is introduced. In a specific embodiment, the invention provides a vector, particularly an expression vector, which comprises nucleic acid sequences sufficient for production of all four capreomycin components. In a specific embodiment, the invention provides a vector, particularly an expression vector, which comprises nucleic acid sequences sufficient for production of capreomycin IIA and IIB in the absence of components IA and IB. Such a vector does not contain nucleic acid sequences which allow expression of a functional product of expression of at least one of CmnM, CmnO, or CmnP. In a specific embodiment, the invention provides a vector which comprises only a portion of the functional capreomycin biosynthetic gene cluster from which functional products of the CmnA-CmnL, CmnN and Cph genes can be expressed in a heterologous host. In a specific embodiment, the invention provides a vector which comprises only a portion of the functional capreomycin biosynthetic gene cluster from which functional products of the all of the capreomycin biosynthetic genes other than CmnA can be expressed in a heterologous host. In a specific embodiment, the invention provides vectors which comprise nucleic acid sequence encoding the CmnA gene product.

Isolated nucleic acid molecules of this invention include those encoding the protein having the amino acid sequence of any one of the disclosed sequences of SEQ ID NOs:2-34, 2-20, 2-19, 2-17. Isolated nucleic acid molecules of this invention include those encoding the protein having the amino acid sequence of any one of the disclosed sequences of CmnA, CmnB, CmnC, CmnD, CmnE, CmnF, CmnG, CmnH, CmnI, CmnJ, CmnK, CmnL, CmnM, CmnN, CmnO, or CmnP gene products whose amino acid sequences is provided in TABLE 8. Isolated nucleic acid molecules of this invention include those having the nucleic acid sequences of one or more or CmnA, CmnB, CmnC, CmnD, CmnE, CmnF, CmnG, CmnH, CmnI, CmnJ, CmnK, CmnL, CmnM, CmnN, CmnO, or CmnP genes whose sequences are provided in TABLE 8.

The invention additionally provides heterologous host organisms into which one or more of the nucleic acid sequences or vectors of this invention have been introduced and wherein one or more of the capreomycin biosynthetic genes are expressed therein to form a functional gene product. More specifically the invention provides such heterologous host which are strains of *Streptomyces*, and more specifically which are strains of *Streptomyces lividans* or strains of *Streptomyces coelicolor*. In another embodiment, the invention provides a heterologous host, particularly a strain of *Streptomyces*, which produces one or more of the capreomycin components. The heterologous host organism is one that does not in the absence of introduction of nucleic acid sequences provided herein produce capreomycins. More specifically, the invention relates to such heterologous host organisms which produce all of the capreomycins or which produce capreomycins IIA and IIB in the absence of capreomycins IA and IB.

The invention additionally provides novel derivatives of capreomycin and viomycin which are produced by expression of one or more capreomycin biosynthetic genes of this invention in a heterologous host organism. In specific embodiments, the invention provides 19-OH capreomycin derivatives as described in Table 5.

BRIEF DESCRIPTION OF THE DRAWINGS

FIG. 1. Chemical structures of the four derivatives that make up CMN (left), and the structurally related tuberactinomycin antibiotic VIO (right). For simplicity, throughout this manuscript the four CMN derivatives are referred to as CMN when discussed together. When individual derivatives are discussed, they are identified as CMN IA, IB, IIA, or IIB in the text. Numbering of residues within structures is for guidance for the text.

FIG. 2. A schematic of the thirty-three *S. mutabilis* subsp. *capreolus* ORFs contained on the pCMN-P4C8RF cosmid. The CMN biosynthetic gene cluster consists of ORFs in grey and black. Those ORFs coding for proteins with significant sequence identity with proteins coded by the VIO biosynthetic gene cluster are shown in grey. The newly identified CMN resistance gene is shown in black. The remaining ORFs flanking the CMN biosynthetic gene cluster are shown in white.

FIG. 3. HPLC traces of (A) authentic CMN, (B) metabolites purified from strain EAF1001 (*St. lividans* 1326 containing the integrated pCMN-P4C8RF-436 cosmid), and (C) metabolites purified from EAF1003 (*St. lividans* 1326 containing the integrated pOJ436 cosmid). Metabolite elution was monitored at 268 nm. Arrows above peaks in trace A identify the peaks associated with the co-elution of CMN IA/IB and co-elution of CMN IIA/IIB. Twenty μg of authentic CMN was injected. For EAF1001 and EAF1003 samples, 100 ml of culture was used in the purification. The purified compounds were resuspended in 500 μl of $H_2O$. A portion of these samples was diluted 1:10 $H_2O$, and 20 μl of these diluted samples was injected into the HPLC.

FIG. 4. Schematic for the NRPS for the formation of the cyclic pentapeptide core of CMN (CmnF, CmnA, CmnF, CmnJ, and CmnG), followed by downstream carbamoylation by CmnL and the acylation of CMN IIA and IIB by the combined functions of CmnM and CmnO. The individual domains of the NRPS are noted as circles with the appropriate abbreviation to denote function. Abbreviations are: A, adenylation; PCP, peptidyl carrier protein; C condensation; X, domain of unknown function; C/, modified condensation domain. The arrows above the NRPS components depict the direction of pentapeptide synthesis on the NRPS. The numbering identifies the order in which the residues are incorporated into the cyclic pentapeptide backbone of CMN. The 2,3-L-DAP tethered to the PCP domain of CmnI is believed to be introduced by the A domain of CmnF, analogous to the mechanism described for the VIO NRPS (34); U.S. Pat. No. 7,326,782.

FIG. 5. Schematic for the pathways for L-2,3-DAP, CAM, and β-Lys formation during CMN biosynthesis. Abbreviations: L-2,3-DAP, L-2,3-diaminopropionate; CAM, (2S,3R)-capreomycidine; β-Lys, β-Lysine; βKG, β-ketoglutarate; PLP, pyridoxal phosphate.

DETAILED DESCRIPTION OF THE INVENTION

The term "biologically active agent" is used broadly herein to encompass any functional gene product or expression product generated directly or indirectly from the nucleic acid molecules of this invention. It can be among others an end-product antibiotic, an antibiotic precursor, synthetic intermediate for generation of antibiotic derivatives or an enzyme useful in the production of antibiotics. An antibiotic precursor is a substrate or intermediate involved in the biosynthesis of downstream end-product antibiotics.

The biologically active agent can be generated as a cationic or anionic species. The invention encompasses pharmaceutically acceptable salts of such cationic and anionic species. It is noted that the capreomycins and derivatives thereof can be generated in the form of pharmaceutically acceptable salts such as sulfates. Capreomycins and derivatives thereof of this invention include such pharmaceutically acceptable salt forms.

Suitable pharmaceutically acceptable salts include salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

SEQUENCE VARIATION: Some protein and nucleic acid sequence variation is tolerated without loss of function. In fact, some nucleic acid and protein sequence variation is expected and understood in the art, without substantially affecting protein function.

A variant nucleic acid sequence of the invention has (1) at least about 90%, more preferably at least about 95%, and even more preferably at least about 98%, but less than 100%, contiguous nucleic acid sequence identity to a nucleic acid sequence which encodes a biologically functional amino acid product, or functional fragment thereof, of any of the capreomycin biosynthetic genes whose amino acid sequences are provided herein; (2) has at least about 90%, more preferably at least about 95%, and even more preferably at least about 98%, but less than 100%, contiguous nucleic acid sequence identity to a nucleic acid sequence or functional fragment thereof, of any of the capreomycin biosynthetic genes whose nucleic acid sequences are provided herein; (3) encodes for a gene product having at least about 90%, more preferably at least about 95%, and even more preferably at least about 98%, but less than 100%, contiguous amino acid sequence identity to any of the gene products (SEQ ID Nos:2-20) of the capreomycin biosynthetic gene products. Variant nucleic acid sequences still encode a functional gene product. The amino acid and/or nucleic acid similarity (or homology) of two sequences can be determined manually or using computer algorithms well known to the art. It is noted herein that the genes of the capreomycin biosynthetic gene cluster exhibit organizational, structural and functional similarity to corresponding genes of the viomycin biosynthetic gene cluster (U.S. Pat. No. 7,326,782, specifically incorporated by reference to the extent not inconsistent with the present disclosure). On average the cmn biosynthetic genes exhibit on average about 77% sequence homology with the corresponding vio biosynthetic genes.

The present invention further includes isolated and purified DNA sequences which hybridize under stringent conditions to the nucleic acid molecules of the invention. Hybridization procedures are useful for identifying polynucleotides with sufficient homology to the subject sequences to be useful as taught herein. The particular hybridization techniques are not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}$P, $^{35}$S, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in International Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example in Keller, G. H., M. M. Manak (1987) *DNA Probes*, Stockton Press, New York, N.Y., pp. 169-170, hereby incorporated by reference. For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5 times Denhardt's solution, sonicated salmon sperm DNA (50 μg/ml), 0.1% sodium dodecylsulfate (SDS), and 10% dextran sulfate at 4° C., with washes at 42° C. in 0.2×SSC and 0.1% SDS.

An example of high stringency conditions is hybridizing at 68° C. in 5×SSC/5×Denhardt's solution/0.1% SDS, and washing in 0.2×SSC/0.1% SDS at room temperature. An example of conditions of moderate stringency is hybridizing at 68° C. in 5×SSC/5×Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) supra or Ausubel et al. (1995) *Current Protocols in Molecular Biology*, John Wiley & Sons, NY, N.Y., for further guidance on hybridization conditions.

In general, salt and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

The term "sequence homology" or "sequence identity" means the proportion of base matches between two nucleic acid sequences or the proportion of amino acid matches between two amino acid sequences. When sequence homology or identity is expressed as a percentage, e.g., 95%, the percentage denotes the fraction of matches over the length of sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

"Similarity," when comparing two amino acid sequences, encompasses amino acids that are "identical" and amino acids whose side groups have similar properties (e.g. basic, polar, etc). "Identical" or "identity" only encompasses amino acids that are identical.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 6 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 this volume, pp. 1-10. The two sequences or parts thereof are more preferably homologous if their amino acids are greater than or equal to 50% identical when optimally aligned using the ALIGN program.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence can be a subset of a larger sequence, for example, as a segment of a full-length cDNA or gene sequence given in a sequence listing, or can comprise a complete cDNA or gene sequence. Generally, a reference sequence is at least 20 nucleotides in length, frequently at least 25 nucleotides in length, and often at least 50 nucleotides in length. Since two polynucleotides can each (1) comprise a sequence (i.e., a portion of the complete polynucleotide sequence) that is similar between the two polynucleotides, and (2) can further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window can comprise additions or deletions (i.e., gaps) of 20 percent or less as compared to the reference sequence (which does not comprise additions or deletions) for optimal alignment of the two sequences. Optimal alignment of sequences for aligning a comparison window can be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc; Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide when optimally aligned, such as by the programs GAP or BESTFIT using default gap weights, comprises a sequence that has at least 80 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides. The percentage of sequence identity is calculated by comparing the reference sequence to the polynucleotide sequence which can include deletions or additions which total 20 percent or less of the reference sequence over the window of comparison.

NUCLEOTIDE SEQUENCE VARIATION: The present invention contemplates nucleic acid sequences which hybridize under high stringency hybridization conditions to the exemplified nucleic acid sequences set forth herein. Thus, nucleic acid sequences encoding variant polypeptides, i.e., those having at least one amino acid substitution, insertion, addition or deletion, or nucleic acid sequences having conservative (e.g., silent) nucleotide substitutions, and which exhibit such a hybridization relationship are within the scope of the invention. Preferably, variant polypeptides encoded by the nucleic acid sequences of the invention are biologically active. The present invention also contemplates naturally occurring allelic variations and mutations of the nucleic acid sequences described herein.

Duplex formation and stability depend on substantial complementarity between the two strands of a hybrid, and, as noted above, a certain degree of mismatch can be tolerated. Therefore, the sequences of the subject invention include mutations (both single and multiple), deletions, insertions of the described sequences, and combinations thereof, wherein said mutations, insertions and deletions permit formation of stable hybrids with the target polynucleotide of interest.

Mutations, insertions, and deletions can be produced in a given polynucleotide sequence in many ways, and those methods are known to an ordinarily skilled artisan. Other methods may become known in the future.

These variants can be used in the same manner as the exemplified sequences so long as the variants have substantial sequence homology with the original sequence. As used herein, substantial sequence homology refers to homology sufficient to enable the variant polynucleotide to function in the same capacity as the polynucleotide from which the variant was derived. The degree of homology or identity needed for the variant to function in its intended capacity depends upon the intended use of the sequence. It is well within the skill of a person trained in this art to make mutational, insertional, and deletional mutations which are equivalent in function or are designed to improve the function of the sequence or otherwise provide a methodological advantage.

As is well known in the art, because of the degeneracy of the genetic code, there are numerous other DNA and RNA molecules that can code for the same polypeptides as those encoded by the exemplified biosynthetic genes and fragments thereof. DNA and RNA molecules that have different genetic codes, but encode identical polypeptides, are called "degenerate variants." The present invention, therefore, contemplates those other DNA and RNA molecules which, on expression, encode the polypeptides of the capreomycin biosynthetic genes or polypeptides that have a sequence identity that is greater than 95%, 97% or 99% while maintaining function of the native gene product having the amino acid sequence set forth herein. Having identified the amino acid residue sequence encoded by a capreomycin biosynthetic gene, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid, are within the scope of this invention.

The 20 common amino acids and their representative abbreviations, symbols and codons are well known in the art (see, for example, Molecular Biology of the Cell, Second Edition, B. Alberts et al., Garland Publishing Inc., New York and London, 1989). As is also well known in the art, codons constitute triplet sequences of nucleotides in mRNA molecules and as such, are characterized by the base uracil (U) in place of base thymidine (T) which is present in DNA molecules. A simple change in a codon for the same amino acid residue within a polynucleotide will not change the structure of the encoded polypeptide. By way of example, substitution of the GAG codon with a GAA codon, or vice versa, does not alter the fact that glutamic acid is placed at that location; nor does this type of substitution substantially alter the DNA sequence. Such a substitution results in production of the same polypeptide. In a similar manner, substitutions of the recited codons with other equivalent codons can be made in a like manner without departing from the scope of the present invention.

A nucleic acid molecule, segment or sequence of the present invention can also be an RNA molecule, segment or sequence. An RNA molecule contemplated by the present invention corresponds to, is complementary to or hybridizes under low, moderate or high stringency conditions to, any of the DNA sequences set forth herein. Exemplary and preferred RNA molecules are mRNA molecules that comprise at least one capreomycin biosynthetic gene of this invention.

Mutations can be made to the native nucleic acid sequences of the invention and such mutants used in place of the native sequence, so long as the mutants are able to function with other sequences to collectively catalyze the synthesis of the desired antibiotic. Such mutations can be made to the native sequences using conventional techniques such as by preparing synthetic oligonucleotides including the mutations and inserting the mutated sequence into the gene using restriction endonuclease digestion. (See, e.g., Kunkel, T. A. Proc, Natl. Acad. Sci. USA (1985) 82:448; Geisselsoder et al. BioTechniques (1987) 5:786). Alternatively, the mutations can be effected using a mismatched primer (generally 10-30 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, Methods Enzymol. (1983) 100: 468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al., Proc. Natl. Acad. Sci. USA (1982) 79:6409. PCR mutagenesis will also find use for effecting the desired mutations. Alternatively, in frame deletions can be used (Kieser et al., 2000ab).

Random mutagenesis of the nucleotide sequence can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

PROTEIN SEQUENCE VARIATION: Variation in the amino acid sequence of gene products (proteins) is expected. Proteins can also retain function even after deletion of one or both ends of the protein. Tolerance is also permitted in the precise start and stop locations of the genes encoding functionally equivalent polypeptides. Some adjacent genes can overlap, while others do not. In addition, one or more conservative amino acid substitutions will not substantially affect protein function. Non-conservative amino acid substitutions in regions of the protein that are not functional will not substantially affect protein function.

A preferred functional variant polypeptide includes a variant polypeptide or functional fragment thereof having at least about 10%, more preferably at least about 50% and more preferably at least about 90% of the activity of the polypeptide having the amino acid sequence comprising one of the encoded polypeptides of a capreomycin biosynthetic gene of this invention. For example, the activity of a polypeptide encoded by cmnP can be compared to a variant polypeptide having at least one amino acid substitution, insertion, or deletion relative to the cmnP gene product (cmnP polypeptide). Variant polypeptides are "substantially functionally equivalent" to the polypeptides in this invention, if the variant has at least about 10% the biological activity of the corresponding non-variant polypeptide of this invention. More preferably, the variant polypeptide is "functionally equivalent" and has at least about 50% of the biological activity of the corresponding non-variant polypeptide of this invention, more preferably 90% and greater activity and all subcombinations between.

Similar to nucleotide sequences, the homology between two polypeptide sequences can be determined. Two proteins are substantially identical if they share 90% sequence identity, more preferably 95%, and more preferably at least about 98% or 99% sequence identity. Substantial identity also encompasses two sequences that have conservative amino acid substitutions, as described below. In an aspect, the invention comprises amino acid sequences that are functionally and substantially functionally equivalent to the amino acid sequences of the gene products of this invention.

One or more of the residues of the polypeptides of the cluster (e.g., SEQ ID NOs:2-20) can be altered, so long as the polypeptide variant is biologically active, such as the putative biological function described herein. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major affect on the properties of the resulting variant polypeptide. Whether an amino acid change results in a functional polypeptide can readily be determined by assaying the specific activity of the polypeptide variant.

Amino acid substitutions falling within the scope of the invention, are, in general, accomplished by selecting substitutions that do not differ significantly in their affect on maintaining (a) the structure of the peptide backbone in the area of the substitution, (b) the charge or hydrophobicity of the molecule at the target site, or (c) the bulk of the side chain.

The invention also encompasses polypeptide variants with non-conservative substitutions wherein the variant is functionally equivalent or substantially functionally equivalent to the native protein. Non-conservative substitutions entail exchanging a member of one of the classes described above for another.

Acid addition salts of the polypeptide or variant polypeptide or of amino residues of the polypeptide or variant polypeptide can be prepared by contacting the polypeptide or amine with one or more equivalents of the desired inorganic or organic acid, such as, for example, hydrochloric acid. Esters of carboxyl groups of the polypeptides can also be prepared by any of the usual methods known in the art.

PURIFICATION: The present isolated, biologically active purified polypeptides, variants or fragments thereof, can be further purified by well known techniques in the art, including fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography. These isolated polypeptides are useful as starting compounds or enzymes to generate particular antibiotics, specifically capreomycins, viomycins and novel derivatives thereof.

Heterologous Expression Cassettes (also called chimeric), Vectors and Host Cells of the Invention: As used herein, "heterologous" as applied to DNA sequences means that a vector comprises DNA from at least two different species, or comprises DNA from the same species, which is linked or associated in a manner which does not occur in the "native" or wild type of the species. The recombinant DNA sequence or segment, used for transformation herein, can be circular or linear, double-stranded or single-stranded. Generally, the DNA sequence or segment is in the form of heterologous DNA, such as plasmid DNA, that can also contain coding regions flanked by control sequences which promote the expression of the DNA present in the resultant transformed (recombinant) host cell. Aside from DNA sequences that serve as transcription units for the nucleic acid molecules of the invention or portions thereof, a portion of the DNA can be untranscribed, serving a regulatory or a structural function. For example, the preselected DNA can itself comprise a promoter that is active in a particular host cell.

Other elements functional in the host cells, such as introns, enhancers, polyadenylation sequences and the like, can also be a part of the DNA. Such elements may or may not be necessary for the function of the DNA, but may provide improved expression of the DNA by affecting transcription, stability of the mRNA, or the like. Such elements can be included in the DNA as desired to obtain the optimal performance of the transforming DNA in the cell.

"Control sequences" (also called regulatory sequences) is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers. Other regulatory sequences may also be desirable which allow for regulation of expression of the genes relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements can also be present in the vector, for example, enhancer sequences.

"Operably linked" means that the nucleic acids are placed in a functional relationship with respect to another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The DNA to be introduced into the cells further will generally contain either a selectable marker gene or a reporter gene or both to facilitate identification and selection of transformed cells from the population of cells sought to be transformed. Alternatively, the selectable marker can be carried on a separate piece of DNA and used in a co-transformation procedure. Both selectable markers and reporter genes can be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Expression of the reporter gene is assayed at a suitable time after the DNA has been introduced into the recipient cells.

Prokaryotic expression systems are preferred, and in particular, systems compatible with *Streptomyces* sp. are of particular interest. Control elements for use in such systems include promoters, optionally containing operator sequences, and ribosome binding sites. Particularly useful promoters include control sequences derived from the gene clusters of the invention. Preferred promoters are *Streptomyces* promoters, including but not limited to the ermE, pikA, and tipA promoters. Additional examples include promoter sequences derived from biosynthetic enzymes such as tryptophan (trp), the β-lactamase promoter system, bacteriophage lambda PL, and T5. In addition, synthetic promoters, such as the tac promoter (U.S. Pat. No. 4,551,433), which do not occur in nature, also function in bacterial host cells.

The various nucleic acid molecules of interest can be cloned into one or more recombinant vectors as individual cassettes, with separate control elements, or under the control of, e.g., a single promoter. The nucleic acid molecules can include flanking restriction sites to allow for the easy deletion and insertion of other sequences. The design of such unique restriction sites is known to those of skill in the art and can be accomplished using the techniques, such as site-directed mutagenesis and PCR.

For sequences generated by random mutagenesis, the choice of vector depends on the pool of mutant sequences, i.e., donor or recipient, with which they are to be employed. Furthermore, the choice of vector determines the host cell to be employed in subsequent steps of the claimed method. Any transducible cloning vector can be used as a cloning vector for the donor pool of mutants. It is preferred, however, that phagemids, cosmids, or similar cloning vectors be used for cloning the donor pool of mutant encoding nucleotide sequences into the host cell. Phagemids and cosmids, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted can be identical or can be constructed to harbor and express different genetic markers (see, e.g., Sambrook et al., supra). Vectors containing marker genes are useful to determine whether or not transfection is successful.

The general methods for constructing recombinant DNA which can transform target cells are well known to those skilled in the art, and the same compositions and methods of construction can be utilized to produce the DNA useful herein. For example, J. Sambrook et al., Molecular Cloning: A Laboratory Manual, Cold Spring Harbor Laboratory Press (2d ed., 1989), provides suitable methods of construction.

The recombinant DNA can be readily introduced into the host cells by any procedure useful for the introduction into a particular cell, e.g., calcium phosphate precipitation, protoplast fusion, conjugation, lipofection, electroporation, gene gun and the like.

As used herein, the term "cell line" or "heterologous host cell" is intended to refer to well-characterized homogenous, biologically pure populations of cells. These cells can be eukaryotic cells that are neoplastic or which have been "immortalized" in vitro by methods known in the art, as well as primary cells, or prokaryotic cells. In particular, the cell line or host cell can be of mammalian, plant, insect, yeast, fungal or bacterial origin. Preferred heterologous host cells are prokaryotic cells.

"Transfected" or "transformed" is used herein to include any host cell or cell line, the genome of which has been altered or augmented by the presence of at least one DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The transfected DNA can be maintained as an extrachromosomal element or as an element which is stably integrated into the host chromosome of the host cell. Host cells with transfected DNA maintained as an extrachromosomal element or as an element stable integrated into the host chromosome are referred to as a "recombinant host cell."

Moreover, recombinant polypeptides having a particular activity can be prepared via "gene-shuffling". See, for example, Crameri et al., Nature, 391, 288 (1998); Patten et al., Curr. Op. Biotech., 8, 724 (1997), U.S. Pat. Nos. 5,837,458, 5,834,252, 5,830,727, 5,811,238, 5,605,793).

For phagemids, upon infection of the host cell which contains a phagemid, single-stranded phagemid DNA is produced, packaged and extruded from the cell in the form of a transducing phage in a manner similar to other phage vectors. Thus, clonal amplification of mutant encoding nucleotide sequences carried by phagemids is accomplished by propagating the phagemids in a suitable host cell.

Following clonal amplification, the cloned donor pool of mutants is infected with a helper phage to obtain a mixture of phage particles containing either the helper phage genome or phagemids mutant alleles of the wild-type encoding nucleotide sequence.

Infection, or transfection, of host cells with helper phage is generally accomplished by methods well known in the art (see., e.g., Sambrook et al., supra; and Russell et al. (1986) Gene 45:333-338).

The helper phage can be any phage which can be used in combination with the cloning phage to produce an infective transducing phage. For example, if the cloning vector is a cosmid, the helper phage will necessarily be a lambda phage. Preferably, the cloning vector is a phagemid and the helper phage is a filamentous phage, and preferably phage M13.

If desired after infecting the phagemid with helper phage and obtaining a mixture of phage particles, the transducing phage can be separated from helper phage based on size difference (Barnes et al. (1983) Methods Enzymol. 101:98-122), or other similarly effective techniques.

The entire spectrum of cloned donor mutations can now be transduced into clonally amplified recipient cells into which have been transduced or transformed a pool of mutant encoding nucleotide sequences. Recipient cells which can be employed in the method disclosed and claimed herein can be, for example, E. coli, or other bacterial expression systems which are not recombination deficient. A recombination deficient cell is a cell in which recombinatorial events are greatly reduced, such as rec.sup.-mutants of E. coli (see, Clark et al. (1965) Proc. Natl. Acad. Sci. USA 53:451-459).

These transductants can now be selected for the desired expressed protein property or characteristic and, if necessary or desirable, amplified. Optionally, if the phagemids into which each pool of mutants is cloned are constructed to express different genetic markers, as described above, transductants can be selected by way of their expression of both donor and recipient plasmid markers.

The recombinants generated by the above-described methods can then be subjected to selection or screening by any appropriate method, for example, enzymatic or other biological activity.

The above cycle of amplification, infection, transduction, and recombination can be repeated any number of times using additional donor pools cloned on phagemids. As above, the phagemids into which each pool of mutants is cloned can be constructed to express a different marker gene. Each cycle could increase the number of distinct mutants by up to a factor of $10^6$. Thus, if the probability of occurrence of an interallelic recombination event in any individual cell is f (a parameter that is actually a function of the distance between the recombining mutations), the transduced culture from two pools of $10^6$ allelic mutants will express up to $10^{12}$ distinct mutants in a population of $10^{12}/f$ cells.

In specific embodiments the present invention employs genes and gene products of the viomycin biosynthetic gene cluster. This gene cluster is described in detail in published PCT application publication no. WO 2005/021586 (Thomas et al.) published Mar. 10, 2005. A description of the viomycin biosynthetic cluster is also provided in Thomas et al. (2003) Antimicrobial Agents Chemotherapy (September) pages 2823-2830. Both of these references are specifically incorporated in their entirety herein to provide the details including sequence and functional information on the various viomycin biosynthetic genes and the protein products of such genes.

In specific embodiments of this invention, the materials and methods of this invention are useful for the production of capreomycin or viomycin derivatives. Dirlam et al. in three papers published consecutively in Bioorganic & Medicinal Chem Letters, Vol. 7, No. 9, 1997 on pages (1) 1139-1144; (2) 1145-1148 and (3) 1149-1152 and Yamada et al. (1981) Antimicrob. Agents Chemotherapy 20(6):834-836 provide details of synthetic modifications that can be combined with and applied to the capreomycins and capreomycin derivatives of this invention to generate additional antibiotic derivatives. These references are incorporated by reference herein to provide the details of such methods and derivatives for use in combination with the teachings and descriptions herein.

In specific embodiments of this invention, capreomycin and derivatives thereof are produced in heterologous host organisms. Watanabe et al Nature Chemical Biology (August 2006) 2(8):423-428 provides examples of biosynthesis of antitumor nonribosomal peptides in such a heterologous host (E. coli). This reference is incorporated by reference in its entirety herein to provide details of carrying out production of proteins and polypeptides in such heterologous organisms which can be readily adapted by one of ordinary skill in the art to the biosynthetic genes of this invention.

Examples

Capreomycin (CMN) belongs to the tuberactinomycin family of nonribosomal peptide antibiotics that are essential components of the drug arsenal for the treatment of multidrug-resistant tuberculosis. Members of this antibiotic family target the ribosome of sensitive bacteria and disrupt the function of both subunits of the ribosome. Resistance to these antibiotics in Mycobacterium species arises due to mutations in the genes coding for the 16S or 23S rRNA, but can also arise due to mutations in a gene coding for a rRNA modifying enzyme, TlyA. While Mycobacterium species develop resistance due to alterations in the drug target, it has been proposed that the CMN-producing bacterium, Saccharothrix mutabilis subsp. capreolus, uses CMN modification as a mechanism for resistance, rather than ribosome modification. To better understand CMN biosynthesis and resistance in S. mutabilis subsp. capreolus, we focused on the identification of CMN biosynthetic gene cluster in this bacterium. Here we present the cloning and sequence analysis of the CMN biosynthetic gene cluster from Saccharothrix mutabilis subsp. capreolus ATCC 23892. We provide evidence for the heterologous production of CMN in the genetically tractable bacterium Streptomyces lividans 1326. Finally, we present data supporting the existence of an additional CMN resistance gene. This resistance gene codes for an rRNA modifying enzyme that results in the formation of CMN-resistant ribosomes that are also resistant to the aminoglycoside antibiotic kanamycin. Thus, the results herein support that S. mutabilis subsp. capreolus also uses ribosome modification as a mechanism for CMN resistance.

Bacterial strains, plasmids, and growth medium. The strains and plasmids used in this study are listed in Table 1. S. mutabilis subsp. capreolus (ATCC 23892) was obtained from the American Type Culture Collection. St. lividans 1326 was kindly provided by Dr. Amy Gehring (Williams College). S. mutabilis subsp. capreolus and St. lividans 1326 were propagated on ISP2 medium (Difco, Becton Dickinson Microbiology Systems, Sparks, Md.). St. lividans 1326 was grown in yeast extract-malt extract (YEME) medium (21) to produce mycelia for generating protoplasts. S. mutabilis subsp. capreolus was grown in YEME medium to produce mycelia for chromosomal DNA preparation. For heterologous production of CMN, St. lividans 1326 strains were grown in VIO production medium as previously described (31, 34). All Escherichia coli strains were grown in Luria-Bertani (LB) liquid medium or on LB solid medium with appropriate antibiotics. Kanamycin (50 μg/ml), apramycin (50 μg/ml), ampicillin (100 μg/ml) and chloramphenicol (30 μg/ml) were used in solid and liquid medium for propagation of plasmids or cosmids in E. coli.

Genomic DNA isolation and cosmid library construction. High-molecular weight chromosomal DNA of S. mutabilis subsp. capreolus was prepared from YEME-grown mycelia. Approximately 0.3 g (wet weight) of mycelia was washed with 500 μL of lysis buffer (10.3% [w/v] sucrose, 25 mM Tris-Cl, 25 mM EDTA, pH 8.0), mycelia were collected by centrifugation and resuspended in lysis buffer containing 5 mg/ml of lysozyme. The sample was incubated at 37° C. for 30 min followed by the addition of 250 μl of 2% (w/v) sodium dodecyl sulfate. The sample was mixed and then added to 125 μl of phenol:chloroform:isoamyl alcohol (25:24:1). The sample was vortexed, and then centrifuged (14,000 rpm for 15 min). The aqueous layer was collected and isopropanol and sodium acetate (pH 5.2) were added to precipitate the DNA. The sample was centrifuged (10,000 rpm for 10 min), the supernatant poured off, and the DNA pellet was washed with 70% (v/v) ethanol. The DNA pellet was dried and resuspended in 100 µl of 10 mM Tris-Cl (pH8.0), 1 mM EDTA (pH8.0).

Purified DNA was digested with Sau3AI to give 30-50 kb fragments that were subsequently ligated into the BamHI site of SuperCos1 and packaged into lambda phage using Gigapack III XL Packaging Extract Kit following the manufacturer's instructions (Stratagene, Cedar Creek, Tex.). The packaged cosmid pool was used to infect E. coli XL1-Blue MR according to the manufacturer's instructions (Stratagene). A total of 672 cosmid-containing clones were isolated and individually frozen at −80° C. in microtiter dish wells as well as in pools of 8 clones consisting of 25 µl from each member of a microtiter dish column. Thus, column pools could be screened for the CMN gene cluster first, followed by individual clones of the targeted column.

Screening of cosmid library. Column pools of the cosmid library were screened by PCR amplification for cph, one of the known CMN resistance genes (33). The primers used for this screen were: Cph/For (5'-CCCACCTTGT-TGACGTGGT-3') (SEQ ID NO:35) and Cph/Rev (5'-TCAGCGGTAGGCGGTCAG-3') (SEQ ID NO:36). Boiled cells of each cosmid pool were used as a source of template DNA for PCR amplification. Individual members of each cph-positive cosmid pool were subsequently screened by PCR amplification to identify the specific positive clone. Cosmid PCMN-P4C8RF was identified as a cph-positive cosmid. The two primers described above and two primers that were the reverse complement to these primers were used in sequencing reactions to confirm that the entire cph was contained on pCMN-P4C8RF.

Sequencing and annotation of pCMN-P4C8RF. Two- to three-kb fragments of DNA from pCMN-P4C8RF were subcloned into pSMARTLCKan by Lucigen Corp. (Middleton, Wis.). The subclones were sequenced at the University of Wisconsin Biotechnology Center (five-fold coverage, two-fold minimum). Contigs were assembled using the SeqMan program (Lasergene, Madison, Wis.). Annotation of the ORFs and putative gene functions were assigned using a combination of MapDraw (Lasergene), FramePlot 3.0 (17), and blastp, PSI-BLAST, and RPS-BLAST programs (National Center for Biotechnology Information) (1). The accession number for the DNA sequence from the insert of pCMNP4C8RF is EF472579 (which is hereby specifically incorporated by reference).

Construction of pCMN-P4C8RF-436 and Integration into the St. lividans 1326 Chromosome. The 6.7 kb DraI fragment of pOJ436 (3), containing the oriT, aac(3)IV (apramycin resistance), φC31 attP, and φC31 int genetic information, was cloned into the HpaI site of the SuperCos1 backbone of pCMN-P4C8RF. The resulting cosmid (pCMN-P4C8RF-436) was capable of integration into the φC31 attB site of the St. lividans 1326 genome and selection for this integration using apramycin. This cosmid was transformed into St. lividans 1326 using the established protocols for protoplast formation and transformation (20). Integrants were selected by flooding transformation plates with apramycin (40 µg/ml). Integrants from each plate were streaked for isolation on R2YE (21) and ISP2 plates supplemented with apramycin (40 µg/ml). Two integrant-containing strains (EAF1001 and EAF1002) were characterized further. Two other strains (EAF1003 and EAF1004) containing the integrated pOJ436 cosmid alone were constructed as a control for analyzing heterologous production of CMN. To confirm integration of the CMN biosynthetic gene cluster into St. lividans 1326, all strains were screened by PCR amplification for the presences of cmnR, cmnI, and cph. These genes were used because cmnR and cph are at opposite ends of the gene cluster, and cmnI is at the center of the gene cluster. The presence of all three genes in St. lividans 1326 indicates that the entire CMN biosynthetic gene cluster is present in EAF1001 and EAF1002.

Analysis of EAF1001, EAF1002, EAF1003, and EAF1004 for CMN Production. Single colonies of EAF1001, EAF1002, EAF1003, and EAF1004 were used to inoculate 50 ml of YEME supplemented with apramycin (40 µg/ml). The cultures were grown at 30° C. at 200 rpm until cultures were saturated (8-14 days). The cells were subsequently harvested by centrifugation, washed with 10.3% (w/v) sucrose, resuspended in 5 ml of 10.3% (w/v) sucrose, and frozen at −20° C. until use.

To test for CMN production, 50 µl of the frozen stock of each strain was used to inoculate 100 ml of VIO production medium (31) in 1 L unbaffled flasks. The cultures were grown at 30° C. at 200 rpm for 7 days. Any potential CMN produced was purified using a previously described protocol for purification of the structurally related antibiotic VIO (31, 34). After purification, UV-visible spectrophotometry analysis was performed (Beckman Coulter DU640) and spectra were compared to an authentic CMN standard. To identify whether one or more of the CMN derivatives were produced, the samples were analyzed by high-performance liquid chromatography (HPLC) and electrospray ionization-mass spectrometry (ESI-MS). Briefly, purified samples were run on a C18 small pore column (Vydack) on a Beckman System Gold HPLC with a 1 ml/min flow rate. Buffer A was $H_2O$+0.1% trifluoroacetic acid and buffer B was acetonitrile+0.1% trifluoroacetic acid. The separation profile was 5 min isocratic development at 100% A/O % B, 15 min linear gradient of 100% A/O % B to 50% A/50% B, 1 min linear gradient of 50% A/50% B to 0% A/100% B, 5 min isocratic development at 0% A/100% B. Elution of metabolites was monitored at 268 nm, the $\lambda_{max}$ characteristic of tuberactinomycins (4). For ESI-MS, samples eluting from the HPLC were collected, the solvent evaporated under vacuum, and the samples submitted to the University of Wisconsin Biotechnology Center mass spectrometry facility. Authentic CMN was obtained from MB Biomedicals Inc.

Analysis of cmnU in E. coli. The gene cmnU was PCR amplified from pCMN-P4C8RF using the following primers: CmnU-NdeI (5'-AAGGGCCCC CATATGCCTTCGGAAGGTCTG-3') (SEQ ID NO:37) and CmnU-HindIII (5'-GGTGTGTGTTCGAACTCACAC-TAACGCGCC-3') (SEQ ID NO:38). The amplicon was cloned into pCR-BluntII-TOPO according to manufacturer's instructions (Invitrogen), resulting in pCR-BluntII-TOPO-cmnU. The NdeI/HindIII fragment of pCR-Blunt-TOPO-cmnU containing cmnU was subcloned into the corresponding restriction sites of pET22b (Novagen), resulting in pET22b-cmnU. The XbaI/HindIII fragment of pET22b-cmnU containing the optimized ribosome-binding site and cmnU was subcloned into the corresponding sites of pBAD33 (14) resulting in pBAD33-cmnU. This construct results in the expression of cmnU under the control of the arabinose promoter of pBAD33. pBAD33 and pBAD33-cmnU were transformed into DH5α strains containing either pLJ102 (empty vector) or pSJ101 (tlyA inserted into pLJ102 and expression controlled by IPTG induction) (18). Each of these strains was grown in LB medium containing chloramphenicol (15 µg/ml) and ampicillin (100 µg/ml) for plasmid maintenance, isopropyl-beta-D-thiogalactopyranoside (40 µg/ml) and arabinose (2% w/v) for induced expression of tlyA and cmnU, respectively, and varying concentrations of CMN (12.5-100 µg/ml) or kanamycin (6-96 µg/ml). Similar colony forming units of each strain were added to the media and the $OD_{600}$ was determined after 16 hrs of incubation at 37° C. The value reported as the minimum inhibitory concentration is the antibiotic concentration in which the $OD_{600}$ was <0.1 after 16 hrs.

Analysis of cmnU in *St. lividans* 1326. The XbaI/HindIII fragment of pET22b-cmnU was cloned into the corresponding sites of pSE34 (29) to generate pSE34-cmnU. This vector construct results in the constitutive expression of cmnU when pSE34-cmnU is introduced into *St. lividans* 1326. pSE34-cmnU and pSE34 were introduced into *St. lividans* 1326 by transformation, and successful transformants were selected by using an overlay of thiostrepton (8 μg/ml). Transformants were streaked for isolation on ISP2 medium containing thiostrepton. To test for CMN or kanamycin resistance, $10^5$ spores of *St. lividans* 1326 containing either pSE34-cmnU or pSE34 were plated onto ISP2 plates supplemented with CMN (25-1600 μg/ml) or kanamycin (3-1600 μg/ml). The plates were incubated at 30° C. for 2 days, and the minimum inhibitory concentration was defined as the lowest antibiotic concentration at which no growth was observed.

Isolation and Sequence Analysis of the CMN Biosynthetic Gene Cluster from *S. mutabilis* subsp. *capreolus*. To isolate the CMN biosynthetic gene cluster from *S. mutabilis* subsp. *capreolus*, a cosmid library of its chromosomal DNA was constructed. Cosmids containing at least a portion of the CMN biosynthetic pathway were identified by PCR-based screening of cosmid pools and individual cosmids for the presence of cph, one of the previously identified CMN resistance genes (28, 33). The focus on cph rather than cac, the other known CMN resistance gene, was due to our prior finding that a homolog of cph in the VIO-producing bacterium *Streptomyces* sp. strain ATCC11861 is associated with the VIO biosynthetic gene cluster (34). Thus, it was hypothesized that cph would be associated with the CMN biosynthetic gene cluster. Using cph-specific primers for PCR-based screening and subsequent sequencing, cosmid PCMN-P4C8RF was identified as containing cph. This cosmid was sequenced in its entirety, and thirty-three ORFs were identified on the DNA inserted into pCMN-P4C8RF (FIG. 2).

Figure 2:
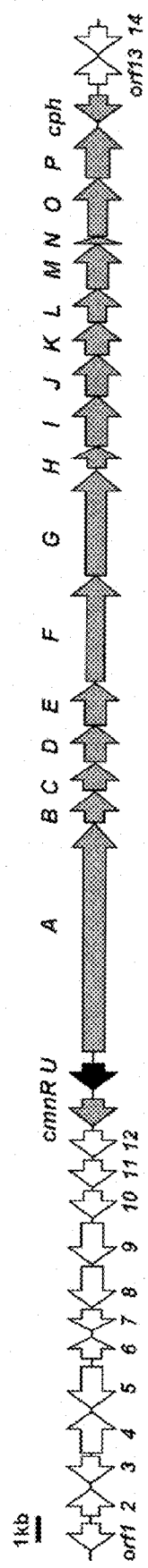

A comparison of these thirty-three ORFs with those involved in VIO biosynthesis identified eighteen ORFs coding proteins showing significant sequence identity with proteins coded by genes associated with the VIO biosynthetic gene cluster (FIG. 2, Table 2). Additionally, seventeen of these ORFs (cmnA-cmnP and cph) were arrayed in an identical order as their respective homologs in the VIO biosynthetic gene cluster. The one ORF not in a similar location as its homolog in the VIO biosynthetic gene cluster was cmnR, coding a putative transcriptional regulator. This gene was upstream of cmnA but separated from cmnA by an additional ORF (cmnU) that did not have a homolog in the VIO biosynthetic gene cluster. However, based on the sequence similarity of CmnU with rRNA modifying enzymes, cmnU was hypothesized to be a newly identified CMN resistance gene. Based on these similarities with the VIO biosynthetic gene cluster and a gene coding a putative rRNA modifying enzyme, nineteen ORFs are identified as involved in CMN production. The remaining ORFs contained on pCMNP4C8RF that surround the nineteen CMN-associated genes did not display any sequence similarity to genes that would play any clear role in CMN biosynthesis (Table 7). Of particular interest was the absence of cac, the second previously identified CMN-resistance gene.

Heterologous Production of CMN in *St. lividans* 1326. *S. mutabilis* subsp. *capreolus* has proven to be intractable to genetic manipulation (27). This eliminated the possibility of using targeted gene disruption followed by metabolite analysis as a means to confirm that the CMN biosynthetic gene cluster had been identified. To address this issue, it was investigated whether the introduction of a modified form of pCMN-P4C8RF into *St. lividans* 1326 would result in the heterologous production of the CMN by this non-producing bacterium. The pCMN-P4C8RF cosmid was modified to contain the genetic information from pOJ436 that enables conjugal transfer between *E. coli* and St. lividans 1326, integration into the φC31 site of the *St. lividans* 1326 genome, and apramycin resistance. The resulting cosmid, pCMN-P4C8RF-436, was transformed into *St. lividans* 1326, and integrants were selected for using apramycin resistance. Two of the isolated integrants were characterized further. Of particular interest was the finding that the integrants were resistant not only to apramycin, but also to CMN. The isolation of CMN-resistant colonies was an important finding because while the integrating cosmid contained cph, conferring resistance to CMN IA and IIA (28, 33), it did not contain the other reported resistance gene cac to give resistance to CMN IB and IIB (28, 33). Importantly, when pOJ436 alone was introduced into *St. lividans* 1326, it did not convey CMN resistance. The fact that the integrants were resistant to a mixture of all four CMN derivatives suggested there was an additional mechanism of CMN resistance coded by the DNA inserted into *St. lividans* 1326. Analysis of this additional resistance gene will be discussed in more detail below.

Figure 3:
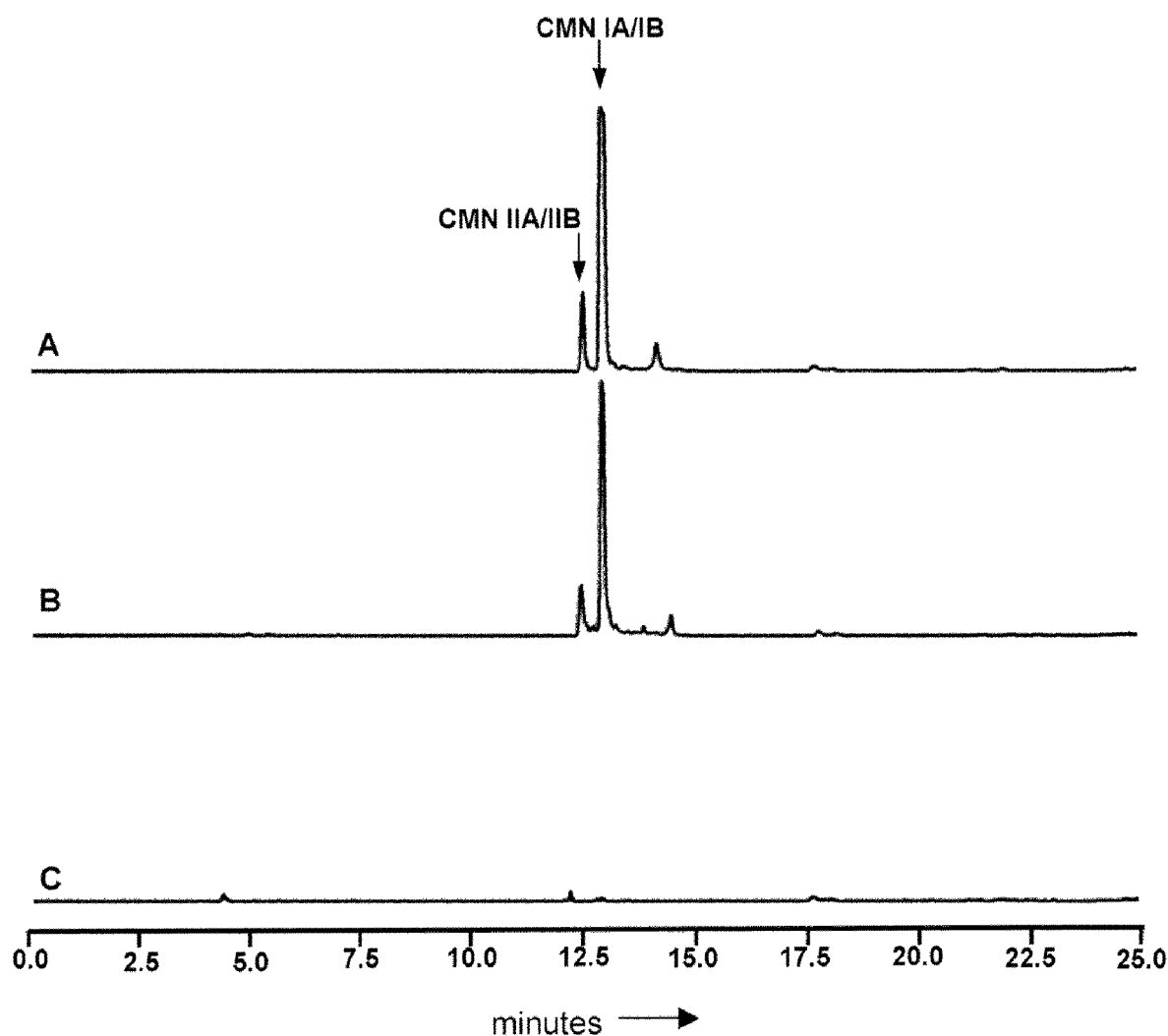

Two successful integrants from the apramycin selection were analyzed for CMN production. Each of these strains (EAF1001 and EAF1002), along with two negative control strains that were integrated with just pOJ436 (EAF1003 and EAF1004), was first grown in YEME medium containing apramycin. These cells were washed to remove the antibiotic and were subsequently used to inoculate VIO production medium lacking antibiotic selection. After seven days of growth, the strains were analyzed for CMN production by purifying metabolites from the culture supernatant using an established protocol for VIO purification (31, 34) and analyzing the purified metabolites by HPLC and ESI-MS. FIG. 3 shows the HPLC traces of the metabolites purified from EAF1001 and EAF1003 in comparison to authentic CMN. Strains EAF1002 and EAF1004 showed similar results as EAF1001 and EAF1003, respectively (data not shown). These data clearly showed that strains carrying the integrated PCMN-R4C8RF-436 produced metabolites with the same retention times as authentic CMN IA/IB and CMN IIA/IIB, but the strains carrying the integrated pOJ436 did not. To confirm that all four CMN derivatives were generated by EAF1001, the metabolites eluting from the HPLC at 12.5 min and 13 min were collected from the HPLC, dried to completion under vacuum, and were then analyzed by ESI-MS. The results from this analysis determined the metabolites eluting at 12.5 min had masses consistent with both CMN IIA (theoretical mass $[M+H]^+=541.25$; experimental mass average $[M+H]^+=541.59$) and CMN IIB (theo. $[M+H]^+=525.26$; exp. $[M+H]^+=525.32$). Additionally, the metabolites eluting at 13 min had masses consistent with both CMN IA (theo. $[M+H]^+=669.35$; exp. $[M+H]^+=669.27$) and CMN IB (theo. $[M+H]^+=653.35$; exp. $[M+H]^+=653.26$). Further analysis of the purified metabolites by strong-cation exchange HPLC determined that CMN IA and IB were produced at a nearly 1:1 ratio; however the ratio of CMN IIA to CMN IIB could not be determined by this approach (data not shown). From these data, we concluded that all the necessary genetic information for the production of and resistance to CMN was contained on pCMN-P4C8RF-436. Furthermore, strain EAF1001 produced CMN at approximately 50 mg/l based on HPLC trace comparisons of known concentrations of authentic CMN versus purified CMN from EAF1001 (data not shown).

Analysis of the CMN Biosynthetic Gene Cluster. Based on bioinformatic analysis and comparisons with the previously identified VIO biosynthetic gene cluster, nineteen ORFs were indicated to be involved in CMN production (FIG. 2, Table 2). A comparison of the CMN biosynthetic gene cluster with the analogous VIO biosynthetic gene cluster gave insights into the putative functions of each ORF and the molecular reasons for the structural differences between CMN and VIO (FIG. 1).

First, three proteins (VioQ, VioS, and VioT) from the VIO biosynthetic gene cluster are not coded by the CMN biosynthetic gene cluster. It was not surprising that VioQ was missing. We previously indicated that this enzyme catalyzed the hydroxylation of the capreomycidine ring of residue five of the cyclic pentapeptide core, and this has been confirmed (10). Since none of the CMN derivatives are hydroxylated at this position, it was not surprising that the CMN biosynthetic gene cluster did not code for a VioQ homolog. The two remaining enzymes, VioS and VioT, were indicated to be a VIO exporter and a transcriptional regulator, respectively, involved in VIO production. The nineteen ORFs designated herein with cmn nomenclature as highlighted in FIG. 2 and Table 2 code for all the proteins needed for CMN biosynthesis, transcriptional regulation of the biosynthetic genes, export of CMN, and resistance to all four CMN derivatives.

Figure 5:
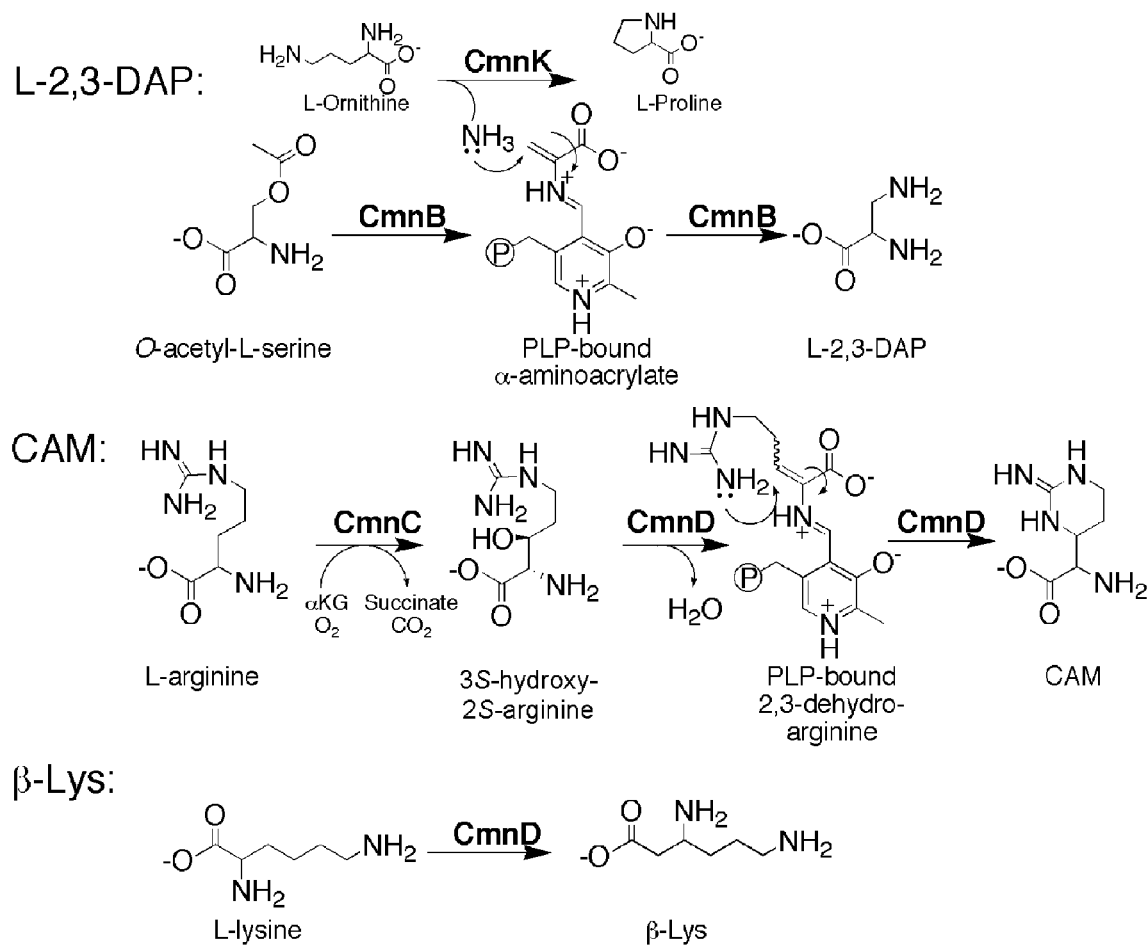

(i) Precursor Biosynthesis. Based on prior analysis of the VIO biosynthetic gene cluster, formation of CMN required three nonproteinogenic amino acids to be synthesized. These amino acids are L-2,3-diaminopropionate (L-2,3-DAP), 2S,3R-capreomycidine (CAM), and β-lysine (β-Lys). We have previously described (34, 19) how each of these precursors is formed during VIO biosynthesis. Certain of these findings have been independently confirmed (44, 45). Homologues for each of the precursor biosynthetic enzymes from the VIO system are coded within the CMN biosynthetic gene cluster (Table 2), indicating that similar mechanisms occur during CMN biosynthesis. The mechanisms for the formation of these precursors are shown in FIG. 5.

(ii) Assembly of the Cyclic Pentapeptide Core of CMN. There are two differences in the cyclic pentapeptide cores of CMN and VIO. First, residue 2 of CMN can be either L-serine (CMN IA or IIA) or L-alanine (CMN IB or IIB), while in VIO it is only L-serine (FIG. 1). Second, residue 3 of CMN is L-2,3-DAP while the corresponding residue of VIO is L-serine. Based on these structural differences, it was anticipated that a comparison of the NRPSs for these two systems would uncover variations in the enzymology that controls the incorporation of the amino acids at these positions.

Figure 4:
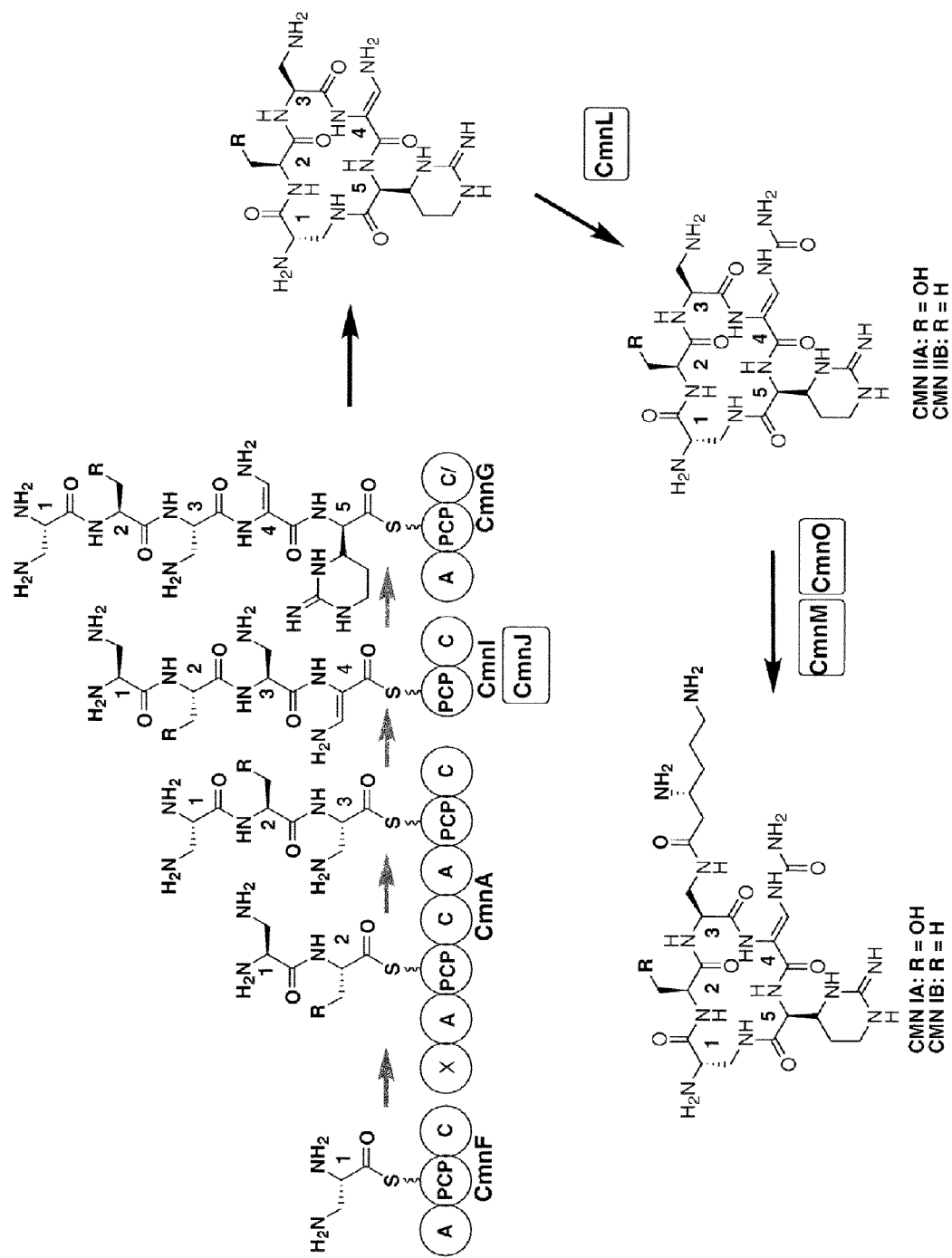

The cyclic pentapeptide core of CMN was predicted to be synthesized by an enzyme complex consisting of CmnF, CmnA, CmnI, and CmnG NRPS subunits along with CmnJ as an additional modifying enzyme that catalyzes the α,β-desaturation of residue 4 (FIG. 4). CmnF, CmnI, and CmnG all showed similar domain organizations as their homologs in the VIO NRPS, and the adenylation (A) domain specificity codes for CmnF and CmnG were nearly identical to those seen in the VIO components (FIG. 4, Table 3). Thus, it was reasonable to presume they function in a similar manner as previously described for VIO (34). The NRPS modules contained on CmnA and VioA control the incorporation of residues 2 and 3 into the cyclic pentapeptide core of their respective antibiotic. As expected, the key differences between the CMN and VIO NRPS systems came from a comparison of CmnA with VioA.

The first A domain of CmnA had a substrate specificity code that was identical to that seen in VioA (Table 3), and this code is for L-serine, the amino acid found in VIO and in CMN IA and IIA (FIG. 1). However, for CMN biosynthesis, the amino acid at residue 2 of the cyclic pentapeptide core is either L-serine or L-alanine (FIG. 1). The answer to how two different amino acids can be found at this position is believed to come from the finding of an extra enzymatic domain at the N-terminus of CmnA, referred to as domain "X" (FIG. 4). This domain showed a low level of amino acid sequence similarity with epimerase domains of NRPSs. With this in mind, one could envision a mechanism whereby L-serine is first activated and tethered to the first PCP domain of CmnA. A catalytic base within the X domain would subsequently abstract the α-carbon proton as if it were functioning as an epimerase; however, this instead results in the dehydration of L-serine to form dehydroalanine. The conversion of dehydroalanine to L-alanine would then require hydride transfer to the desaturated C3 carbon, likely from NADH, with the catalytic base returning the abstracted proton back to the molecule with retention of the initial stereochemistry. This process would not be fully efficient since the ratio of L-serine to L-alanine at residue 2 was observed to be approximately 1:1. This mechanism is analogous to that seen for L-serine to D-alanine conversion during lantibiotic biosynthesis (7). The alternative explanation that the first A domain of CmnA incorporates either L-serine or L-alanine regardless of the specificity code of the A domain cannot be eliminated.

The internal module of CmnA (consisting of the second C-A-PCP set of domains) controls the incorporation of residue three of the cyclic pentapeptide (FIG. 4). A comparison between this region of CmnA with that of VioA finds that while the domain architecture was the same, the specificity code of the A domain in CmnA was different than that from VioA (Table 3). Most significant was the residue at position four of the specificity code, which in CmnA is a seryl residue but is a histidinyl residue in VioA. Residues at this position of an A domain are believed to be at the base of the substrate binding pocket and to interact with the side chain of the bound amino acid (6, 30). One possibility is that a histidinyl residue at this position, as seen in VioA, would hinder the binding of L-2,3-DAP due to the unfavorable interactions between the F-amino group of L-2,3-DAP and the histidinyl residue. However, a change to a seryl residue would allow such a substrate to bind. This subtle difference between CmnA and VioA likely explains the different amino acids found at this position in CMN and VIO. The other steps involved in synthesizing the cyclic peptapeptide core of CMN are believed to proceed in an analogous manner as previously described for VIO (FIG. 4) (34).

(iii) Modification of the Cyclic Pentapeptide Core to Generate the Cmn. There are two possible modifications to the cyclic pentapeptide core once it has been synthesized. First, CmnL, a homolog of ornithine carbamoyltransferases, catalyzes the carbamoylation of the amino group of residue four, resulting in the formation of the β-ureidodehydroalanine moiety. If the molecule is not processed any further, CMN IIA and IIB are generated (FIG. 4). The second possible modification is the addition of β-Lys to the β-amino group of residue three to generate CMN IIA or CMN IIB (FIG. 4). The activation and tethering of β-Lys to this position is believed to be catalyzed by a monomodular NRPS. CmnO is a didomain protein consisting of an N-terminal A domain with a specificity code for β-Lys (Table 3) and a C-terminal PCP domain. This indicated that CmnO recognized β-Lys and catalyzed the covalent tethering of β-Lys to its PCP domain. The β-Lys would then be transferred to CMN IIA or IIB by the action of CmnM, a homolog of condensation domains of NRPSs. Thus, CmnO and CmnM work in unison as a monomodular NRPS to acylate CMN IIA or CMN IIB, producing CMN IA or CMN IB, analogous to how VioO and VioM are described to work during VIO biosynthesis (34).

(iv) Transcriptional Regulation and Export of CMN. CmnR is a homolog of VioR, and both proteins show sequence similarity with the LuxR family of transcriptional regulators (11). Finally, CmnE is a homolog of VioE, and both show sequence similarity to the major facilitator superfamily MFS_1 (DUF894) involved in the efflux of various metabolites (26).

Analysis of CMN and Kanamycin Resistance. The *St. lividans* 1326 strains containing the pCMNP4C8RF-436 cosmid integrated into the *St. lividans* 1326 genome conferred resistance to all four CMN derivatives. Since pCMNP4C8RF-436 only codes for Cph, this suggested there was an additional resistance gene coded within pCMNP4C8RF. The most likely candidate for conferring this resistance activity was the gene cmnU. CmnU is a homolog of 16S rRNA methyltransferases that are known to confer resistance to kanamycin and apramycin by modifying residue A1408 (*E. coli* numbering) of the 16S rRNA (16). The relevance of this finding is that mutations in the analogous residue in *M. tuberculosis* and *M. smegmatis* 16S rRNA result in VIO and kanamycin resistance (32), and a mutation in the analogous residue of *Thermus thermophilus* results in CMN resistance (13). Furthermore, the enzyme TlyA from *M. tuberculosis* that methylates both 16S and 23S rRNA to make the ribosome more sensitive to CMN methylates residue C1409 of the 16S rRNA (18). From these results, it was reasonable to hypothesize that CmnU modifies the 16S rRNA of *S. mutabilis* subsp. *capreolus*, likely at the equivalent position to A1408, resulting in CMN-resistant ribosomes. To investigate whether cmnU confers antibiotic resistance to bacteria expressing this gene, cmnU was cloned into vectors that enabled expression of the gene in *E. coli* or *St. lividans* 1326. The strains carrying these expression constructs were analyzed for both CMN and kanamycin resistance. The latter was tested based on the amino acid similarity between CmnU and aminoglycoside methyltransferases.

*E. coli* does not methylate its ribosomes in a similar manner to *M. tuberculosis* or *M. smegmatis* because it lacks a TlyA homolog, and this results in *E. coli* being less sensitive to CMN (18). Therefore we evaluated whether expression of cmnU in *E. coli* resulted in increased CMN resistance in the presence and absence of tlyA from *M. smegmatis*. As seen previously (18), the expression of tlyA in *E. coli* resulted in increased sensitivity to CMN but had no effect on kanamycin resistance (Table 4). However, regardless of the methylation state of the *E. coli* ribosomes, the expression of cmnU in *E. coli* resulted in increased resistance to CMN (Table 4). Expression of cmnU in *E. coli* also resulted in kanamycin resistance; however, the coexpression of tlyA resulted in a decrease in the kanamycin resistance compared to a strain lacking tlyA (Table 4). It is not clear at this time why the expression of tlyA impairs the ability to cmnU to confer full kanamycin resistance.

When cmnU was expressed in *St. lividans* 1326, it resulted in increased resistance to both CMN and kanamycin (Table 4). The observed resistance to all four CMN derivatives indicated that cmnU was a newly identified CMN resistance gene from *S. mutabilis* subsp. *capreolus*. Furthermore, expression of cmnU also conferred resistance to the aminoglycoside kanamycin (Table 4). CmnU is a homolog of the proteins coded by kamB and kamC, two genes isolated for their ability to confer kanamycin resistance to *St. lividans* 1326 (16). It has been shown that expression of kamB or kamC in *E. coli* results in the modification of A1408 of the 16S rRNA. Based on the similarity between CmnU, KamB, and KamC, it is believed that CmnU will catalyze the modification of the 16S rRNA of the ribosome, resulting in CMN and kanamycin resistant ribosomes. Thus, ribosome modification in *S. mutabilis* subsp. *capreolus* is believed to be a mechanism for resistance to the CMN produced by this bacterium.

We have isolated and sequenced the CMN biosynthetic gene cluster from *S. mutabilis* subsp. *capreolus*. These data provided a molecular blueprint for how CMN is biosynthesized by this organism and gives some insights into the reasons for the structural differences between CMN and VIO. We also showed that transfer of this gene cluster into *St. lividans* 1326 resulted in the heterologous production of the CMN antituberculosis drug, providing an important first step toward the metabolic engineering of CMN biosynthesis. Finally, we have provided evidence that ribosome modification by CmnU confers CMN resistance to *E. coli* and *St. lividans* 1326, and this is likely to be true for *S. mutabilis* subsp. *capreolus*. The similarity between CmnU and aminoglycoside resistance genes gives further support that the ribosome binding sites of CMN and aminoglycosides are overlapping on the ribosome.

Construction of pCMN-P4C8RF-436-ΔcmnM and pCMN-P4C8RF-436-ΔcmnO and integration into the *S. lividans* 1326 chromosome. The spectinomycin resistance cassette (aadA) from plasmid pIJ778-nooriT was PCR amplified with either primers cmnMdelXba (5'-GTGCTTGAC-CTCTCCCCCGCGCAGCGCAGC CTGTGGGTGTCTA-GAATTCCGGGGATCCGTCGACC-3') (SEQ ID NO:39) and cmnMdelNhe (5'-CTATTCCGCGGTGATCTCGTC-CAGCACGGCCAGGAAGTCGCTAGCTGTAGGCTGG AGCTGCTTC-3') (SEQ ID NO:40) or cmnOdelXba (5'-GT-GACCGCGC TGCACCGCCT CGACCAGCTCGCCG-GCGCGTCTAGAATTCCGGGGATCCGTCGAC C-3') (SEQ ID NO:41) and cmnOdelNhe (5'-CACCTCGGGGTC-CGGCTGATCAGGCC CGCCAACGCGGTCGCTAGCT-GTAGGCTGGAGCTGCTTC-3') (SEQ ID NO:42). The resulting products contained the spectinomycin resistance cassette flanked by 39 bp of homology to the 5' and 3' regions of cmnM or cmnO, as well as XbaI and NheI restriction sites. The PCR products were then electroporated into electrocompetent *E. coli* BW2113 containing the temperature sensitive plasmid pIJ790 and pCMN-P4C8RF. Transformants were plated on LB with kanamycin (50 µg/mL), carbenicillin (100 µg/mL), and spectinomycin (50 µg/mL) at 37° C. to select for integration of the PCR product into the cosmid and loss of pIJ790.

To remove the resistance cassette, pCMN-P4C8RF-cmnM::aadA and pCMN-P4C8RF-cmnO::aadA were digested with XbaI and NheI, ligated together (thus destroying both restriction sites), and electroporated into XL-1 Blue MR. Transformants were screened for spectinomycin sensitivity. To confirm loss of the cassette, clones were screened by restriction digest with PstI. The resulting cosmids, pCMN-P4C8RF-ΔcmnM and pCMN-P4C8RF-ΔcmnO, contained a nonpolar, inframe deletion of all but the first and last 13 codons of cmnM or cmnO, respectively.

The 6.7-kb DraI fragment of pOJ436, containing the oriT, aac(3)IV (apramycin resistance), φC31 attP, and φC31 int genetic information, was cloned into the HpaI site of the SuperCos1 backbone of pCMN-P4C8RF-ΔcmnM and pCMN-P4C8RF-ΔcmnO. The resulting cosmids were not stable in XL-1 Blue MR and frequently underwent rearrangement. To confirm correct integration and desired orientation of the pOJ436 DraI fragment, clones were screened by restriction digest with EcoRI, HindIII, and PstI. Approximately 1 in 12 clones contained the desired construct. To maintain the cosmids in an XL-1 Blue MR background, strains were always streaked fresh from freezer stocks and screened for rearrangement before subsequent transformation into S. lividans.

The resulting cosmids (pCMN-P4C8RF-436-ΔcmnM and pCMN-P4C8RF-436-ΔcmnM) were capable of integration into the φC31 attB site of the S. lividans 1326 genome, and selection for this integration was performed using apramycin. S. lividans 1326 was transformed with these cosmids by using established protocols for protoplast formation and transformation. Transformants were selected by flooding transformation plates with apramycin (40 μg/ml). Transformants from each plate were streaked for isolation onto R2YE and ISP2 plates supplemented with apramycin (40 μg/ml).

TABLE OF REFERENCES

1. Altschul, S. F., T. L. Madden, A. A. Schäffer, J. Zhang, Z. Zhang, W. Miller, and D. J. Lipman. 1997. Gapped BLAST and PSI-BLAST: a new generation of protein database search programs. Nucleic Acids Res. 25:3389-3402.
2. Bibb, M. J., J. M. Ward, and S, N. Cohen. 1985. Nucleotide sequences encoding and promoting expression of three antibiotic resistance genes indigenous to Streptomyces. Mol. Gen. Genet. 199:26-36.
3. Bierman, M., R. Logan, K. O'Brien, E. T. Seno, R. N. Rao, and B. E. Schoner. 1992. Plasmid cloning vectors for the conjugal transfer of DNA from Escherichia coli to Streptomyces spp. Gene 116:43-9.
4. Carter, J. H., 2nd, R. H. Du Bus, J. R. Dyer, J. C. Floyd, K. C. Rice, and P. D. Shaw. 1974. Biosynthesis of viomycin. I. Origin of alpha, beta-diaminopropionic acid and serine. Biochemistry 13:1221-7.
5. Carter, J. H., 2nd, R. H. Du Bus, J. R. Dyer, J. C. Floyd, K. C. Rice, and P. D. Shaw. 1974. Biosynthesis of viomycin. II. Origin of beta-lysine and viomycidine. Biochemistry 13:1227-33.
6. Challis, G. L., J. Ravel, and C. A. Townsend. 2000. Predictive, structure-based model of amino acid recognition by nonribosomal peptide synthetase adenylation domains. Chem. Biol. 7:211-24.
7. Cotter, P. D., P. M. O'Connor, L. A. Draper, E. M. Lawton, L. H. Deegan, C. Hill, and R. P. Ross. 2005. Posttranslational conversion of L-serines to D-alanines is vital for optimal production and activity of the lantibiotic lacticin 3147. Proc. Natl. Acad. Sci. USA 102:18584-9.
8. Daniels, T. M., J. H. Bates, and K. A. Downes. 1994. History of tuberculosis, p. 13-24. In B. R. Bloom (ed.), Tuberculosis: Pathogenesis, protection, and control. ASM Press, Washington, D.C.
9. Dye, C., M. A. Espinal, C. J. Watt, C. Mbiaga, and B. G. Williams. 2002. Worldwide incidence of multidrug-resistant tuberculosis. J. Infect. Dis. 185:1197-202.
10. Fei, X., X. Yin, L. Zhang, and T. M. Zabriskie. 2007. Roles of VioG and VioQ in the incorporation and modification of the capreomycidine residue in the peptide antibiotic viomycin. J. Nat. Prod. 70:618-22.
11. Fuqua, C., S. C. Winans, and E. P. Greenberg. 1996. Census and consensus in bacterial ecosystems: the LuxR-LuxI family of quorum-sensing transcriptional regulators. Annu. Rev. Microbiol. 50:727-51.
12. Gould, S. J., and D. A. Minott. 1992. Biosynthesis of Capreomycin: 1. Incorporation of Arginine. J. Org. Chem. 57:5214-5217.
13. Gregory, S. T., J. F. Carr, and A. E. Dahlberg. 2005. A mutation in the decoding center of Thermus thermophilus 16S rRNA suggests a novel mechanism of streptomycin resistance. J. Bacteriol. 187:2200-2.
14. Guzman, L. M., D. Belin, M. J. Carson, and J. Beckwith. 1995. Tight regulation, modulation, and high-level expression by vectors containing the arabinose PBAD promoter. J. Bacteriol. 177:4121-30.
15. Heifets, L., J. Simon, and V. Pham. 2005. Capreomycin in active against non-replicating M. tuberculosis. Ann. Clin. Microbiol. Antimicrob. 1:6.
16. Holmes, D. J., D. Drocourt, G. Tiraby, and E. Cundliffe. 1991. Cloning of an aminoglycoside-resistance-encoding gene, kamC, from Saccharopolyspora hirsuta: comparison with kamB from Streptomyces tenebrarius. Gene 102:19-26.
17. Ishikawa, J., and K. Hotta. 1999. FramePlot: a new implementation of the frame analysis for predicting protein-coding regions in bacterial DNA with a high G+C content. FEMS Microbiol. Lett. 174:251-3.
18. Johansen, S. K., C. E. Maus, B. B. Plikaytis, and S. Douthwaite. 2006. Capreomycin binds across the ribosomal subunit interface using tlyA-encoded 2'-O-methylations in 16S and 23S rRNAs. Mol. Cell. 23:173-82.
19. Ju, J., S. G. Ozanick, B. Shen, and M. G. Thomas. 2004. Conversion of (2S)-arginine to (2S,3R)-capreomycidine by VioC and VioD from the viomycin biosynthetic pathway of Streptomyces sp. strain ATCC11861. ChemBioChem 5:1281-1285.
20. Kieser, T., M. J. Bibb, M. J. Buttner, K. F. Chater, and D. A. Hopwood. 2000. Introduction of DNA into Streptomyces, p. 229-252. Practical Streptomyces genetics. The John Innes Foundation, Norwich, UK.
21. Kieser, T., M. J. Bibb, M. J. Buttner, K. F. Chater, and D. A. Hopwood. 2000. Media, buffers and suppliers, p. 405-420. In T. Kieser, M. J. Bibb, M. J. Buttner, K. F. Chater, and D. A. Hopwood (ed.), Practical Streptomyces Genetics. Crowes, Norwich, England, Norwich, England.
22. Maus, C. E., B. B. Plikaytis, and T. M. Shinnick. 2005. Mutation of tlyA confers capreomycin resistance in Mycobacterium tuberculosis. Antimicrob. Agents Chemother. 49:571-577.
23. Mizuguchi, Y., K. Suga, K. Masuda, and T. Yamada. 1974. Genetic and biochemical studies on drug-resistant mutants in Mycobacterium smegmatis. Jpn. J. Microbiol. 18:457-62.
24. Mizuguchi, Y., K. Suga, and T. Yamada. 1979. Interaction between 30 S ribosomal components in a viomycin resistant mutant of Mycobacterium smegmatis. Microbiol. Immunol. 23:595-604.
25. Murray, C. J. L., and J. A. Salomon. 1998. Modeling the impact of global tuberculosis control strategies. Proc. Natl. Acad. Sci. USA 95:13881-13886.
26. Saier, M. H., Jr., J. T. Beatty, A. Goffeau, K. T. Harley, W. H. Heijne, S. C. Huang, D. L. Jack, P. S. Jahn, K. Lew, J. Liu, S. S. Pao, l. T. Paulsen, T. T. Tseng, and P. S. Virk. 1999. The major facilitator superfamily. J. Mol. Microbiol. Biotechnol. 1:257-79.
27. Saugar, I., E. Sanz, M. A. Rubio, J. C. Espinosa, and A. Jimenez. 2002. Identification of a set of genes involved in the biosynthesis of the aminonucleoside moiety of antibiotic A201A from Streptomyces capreolus. Eur. J. Biochem. 269:5527-35.
28. Skinner, R. H., and E. Cundliffe. 1980. Resistance to the antibiotics viomycin and capreomycin in the Streptomyces species which produce them. J. Gen. Microbiol. 120:95-104.

29. Smirnova, N., and K. A. Reynolds. 2001. Engineered fatty acid biosynthesis in *Streptomyces* by altered catalytic function of beta-ketoacyl-acyl carrier protein synthase III. J. Bacteriol. 183:2335-42.
30. Stachelhaus, T., H. D. Mootz, and M. A. Marahiel. 1999. The specificity-conferring code of adenylation domains in nonribosomal peptide synthetases. Chem. Biol. 6:493-505.
31. Tam, A. H.-K., and D. C. Jordan. 1972. Laboratory production and $^{14}$C-labelling of viomycin. J. Antibiot. 25:524-529.
32. Taniguchi, H., B. Chang, C. Abe, Y. Nikaido, Y. Mizuguchi, and S. I. Yoshida. 1997. Molecular analysis of kanamycin and viomycin resistance in *Mycobacterium smegmatis* by use of the conjugation system. J. Bacteriol. 179:4795-801.
33. Thiara, A. S., and E. Cundliffe. 1995. Analysis of two capreomycin-resistance determinants from *Streptomyces capreolus* and characterization of the action of their products. Gene 167:121-6.
34. Thomas, M. G., Y. A. Chan, and S. G. Ozanick. 2003. Deciphering tuberactinomycin biosynthesis: Isolation, sequencing, and annotation of the viomycin biosynthetic gene cluster. Antimicrob. Agents Chemother. 47:2823-2830.
35. Wang, M., and S. J. Gould. 1993. Biosynthesis of Capreomycin. 2. Incorporation of L-Serine, L-Alanine, and L-2,3-diaminopropionic acid. J. Org. Chem. 58:5176-5180.
36. World Health Organization. 2005. World Health Organization Model List of Essential Medicines. World Health Organization.
37. Yamada, T. 1987. The role of ribosomes in sensitivity of mycobacteria to tuberactinomycin. Microbiol. Immunol. 31:179-181.
38. Yamada, T., and K. H. Bierhaus. 1978. Viomycin favours the formation of 70S ribosome couples. Mol. Gen. Genet. 161:261-5.
39. Yamada, T., K. Masuda, Y. Mizuguchi, and K. Suga. 1976. Altered ribosomes in antibiotic-resistant mutants of *Mycobacterium smegmatis*. Antimicrob. Agents Chemother. 9:817-23.
40. Yamada, T., K. Masuda, K. H. Nierhaus, and H. G. Wittmann. 1972. Analysis of ribosomes from viomycin-sensitive and -resistant *Mycobacterium smegmatis*. J. Bacteriol. 112:1-6.
41. Yamada, T., Y. Mizugichi, K. H. Nierhaus, and H. G. Wittmann. 1978. Resistance to viomycin conferred by RNA of either ribosomal subunit. Nature 275:460-1.
42. Yamada, T., Y. Mizugichi, and K. Suga. 1976. Localization of co-resistance to *streptomyces*, kanamycin, capreomycin and tuberctinomycin in core particles derived from ribosomes of viomycin resistant *Mycobacterium smegmatis*. J. Antibiot. 29:1124-1126.
43. Yamada, T., A. Nagata, Y. Ono, Y. Suzuki, and T. Yamanouchi. 1985. Alteration of ribosomes and RNA polymerase in drug-resistant clinical isolates of *Mycobacterium tuberculosis*. Antimicrob. Agents Chemother. 27:921-4.
44. Yin, X., K. L. McPhail, K.-j. Kim, and T. M. Zabriskie. 2004. Formation of the nonproteinogenic Amino Acid 2S,3R-capreomycidine by VioD from the viomycin biosynthesis pathway. ChemBioChem 5:1278-1281.
45. Yin, X., and T. M. Zabriskie. 2004. VioC is a non-heme iron, a-ketoglutarate-dependent oxygenase that catalyzes the formation of 3S-hydroxy-L-arginine during viomycin biosynthesis. ChemBioChem 5:1274-1277.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 1

Bacterial strains and plasmids used in this study

| Strain or Plasmid | Relevant characteristic | Source or reference |
|---|---|---|
| *Escherichia coli* | | |
| DH5α | F-/φ80ΔlacZM15(lacZYA-argF)U169 recA1 endA1 hsdR17($r_{k-}$, $m_{k+}$) phoA supE44 λ-thi-1 gyrA96 relA1 | Laboratory strain |
| XL1-Blue MR | Δ(mcrA)183 Δ(mcrCB-hsdSMR-mrr)173 endA1 supE44 thi-1 recA1 gyrA96 relA1 lac | Stratagene |
| *Saccharothrix mutabilis* subsp. *capreolus* | Wild type (ATCC 23892) | ATCC |
| *Streptomyces lividans* 1326 | Wild type | A. Gehring |
| EAF1001 | *St. lividans* with pCMN-P4C8RF-436 integrated into φC31 attB site, clone #1 | This study |
| EAF1002 | *St. lividans* with pCMN-P4C8RF-436 integrated into φC31 attB site, clone #2 | This study |
| EAF1003 | *St. lividans* with pOJ436 inserted into φC31 attB site, clone #1 | This study |
| EAF1004 | *St. lividans* with pOJ436 inserted into φC31 attB site, clone #2 | This study |
| Plasmids | | |
| SuperCos1 | $Kan^R$ $Amp^R$ cloning cosmid | Stratagene |
| pOJ436 | $Apr^R$, oriT, φC31 int, φC31 attP cosmid vector | (3) |
| pCR-BluntII TOPO | $Kan^R$ cloning vector | Invitrogen |
| pCMN-P4C8RF | *S. mutabilis* subsp. *capreolus* genomic DNA cloned into SuperCos1; contains CMN gene cluster | This study |
| pCMN-P4C8RF-436 | pCMN-P4C8RF with $Apr^R$, oriT, φC31 int, φC31 attP DraI fragment of pOJ436 inserted into HpaI site | This study |
| pTOPO-cmnU | cmnU cloned into pCR-BluntII TOPO cloning vector | This study |
| pBAD33 | Arabinose-inducible expression vector | (14) |
| pET22b | $Kan^R$ cloning vector | Novagen |
| pET22b-cmnU | cmnU cloned into NdeI/HindIII site of pET22b | This study |
| pBAD33-cmnU | XbaI/HindIII fragment of pET22b-cmnU cloned into XbaI/HindIII site of pBAD33 | This study |

TABLE 1-continued

Bacterial strains and plasmids used in this study

| Strain or Plasmid | Relevant characteristic | Source or reference |
|---|---|---|
| pLJ102 | IPTG-inducible expression vector | (18) |
| pSJ101 | pLJ102 derivative with tlyA insert | (18) |
| pSE34 | *Streptomyces* sp. expression vector | (29) |
| pSE34-cmnU | pSE34 with cmnU cloned into the XbaI/HindIII site | This study |

TABLE 2

Analysis of ORFs involved in CMN production.

| Predicted ORF (AA length) | SEQ ID NO: | Homolog from VIO biosynthesis (AA length) | % Identity | Predicted Function[a] |
|---|---|---|---|---|
| CmnR (238) | 18 | VioR (263) | 49 | Transcriptional regulator (LuxR family) |
| CmnU (240) | 19 | — | — | CMN resistance-rRNA methyltransferase |
| CmnA (2402) | 2 | VioA (2123) | 53 | NRPS (X-A-PCP-C-A-PCP-C) |
| CmnB (370) | 3 | VioB (346) | 65 | L-2,3-DAP formation |
| CmnC (339) | 4 | VioC (358) | 62 | CAM formation |
| CmnD (374) | 5 | VioD (389) | 65 | CAM formation |
| CmnE (416) | 6 | VioE (447) | 63 | CMN efflux |
| CmnF (1057) | 7 | VioF (1073) | 56 | NRPS (A-PCP-C) |
| CmnG (953) | | VioG (1088) | 48 | NRPS (C-A-PCP-C/) |
| CmnH (249) | 9 | VioH (262) | 52 | Type II thioesterase |
| CmnI (549) | 10 | VioI (550) | 52 | NRPS (C-PCP) |
| CmnJ (384) | 11 | VioJ (390) | 62 | L-2,3-DAP α,β-desaturase |
| CmnK (333) | 12 | VioK (360) | 62 | L-2,3-DAP formation |
| CmnL (296) | 13 | VioL (308) | 65 | Carbamoyltransferase |
| CmnM (402) | 14 | VioM (457) | 45 | NRPS (C)-β-Lys attachment |
| CmnN (63) | 15 | VioN (63) | 75 | Unknown function |
| CmnO (585) | 16 | VioO (610) | 52 | NRPS (A-PCP)-β-Lys attachment |
| CmnP (449) | 17 | VioP (445) | 77 | β-Lys formation |
| Cph (282) | 20 | Vph (293) | 53 | CMN Resistance-CMN phosphotransferase |

[a]Abbreviations: A, adenylation domain; PCP, peptidyl carrier protein domain; C, condensation domain; X, domain of unknown function; C/ modified condensation domain; NRPS, nonribosomal peptide synthetase; L-2,3-DAP, L-2,3-diaminopropionate; CAM, 2S,3R-capreomycidine; β-Lys, β-lysine.

TABLE 3

Comparison of A domain specificity codes from CMN and VIO NRPSs

| NRPS component[a] (CMN or VIO) | Specificity Code[b] | | Amino Acid Activated[c] |
|---|---|---|---|
| CmnF | D A Q S L A V V | SEQ ID NO: 43 | L-2,3-DAP |
| VioF | D A Q S L A I V | SEQ ID NO: 44 | L-2,3-DAP |
| CmnA-A1[d] | D V Y H F S L V | SEQ ID NO: 45 | L-Ser (or L-Ala) |
| VioA-A1 | D V Y H F S L V | SEQ ID NO: 46 | L-Ser |
| CmnA-A2 | D V R S L S M V | SEQ ID NO: 47 | L-2,3-DAP |
| VioA-A2 | D V R H M S M V | SEQ ID NO: 48 | L-Ser |
| CmnG | D P Q D I G I V | SEQ ID NO: 49 | CAM |
| VioG | D P Q D V G I G | SEQ ID NO: 50 | CAM |
| CmnO | D T E D V G T M | SEQ ID NO: 51 | β-Lys |
| VioO | D T E D V G V G | SEQ ID NO: 52 | β-Lys |

[a]NRPSs components are groups according to homology (e.g. VioF is the homolog of CmnF)
[b]Specificity code as described in references 6 and 30. Alignment program to identify the substrate-specificity code: world wide web page: tigr.org/jravel/nrps
[c]This proposal is based on the results of the A domain substrate-specificity code and the chemical structures of CMN and VIO.
[d]CmnA and VioA each contain more than one A domain. The code for the first A domain is noted as A1, the second as A2.

TABLE 4

Changes in CMN and kanamycin sensitivity upon expression of cmnU.[a]

| Strain (relevant genotype) | CMN (μg/ml) | Kanamycin (μg/ml) |
|---|---|---|
| *E. coli* DH5α/pBAD33/pLJ102 (cmnU⁻, tlyA⁻) | 50 | 12 |
| *E. coli* DH5α/pBAD33-cmnU/pLJ102 (cmnU⁺, tlyA⁻) | 100 | 96 |
| *E. coli* DH5α/pBAD33/pSJ101 (cmnU⁻, tlyA⁺) | 25 | 12 |
| *E. coli* DH5α/pBAD33-cmnU/pSJ101 (cmnU⁺, tlyA⁺) | 50 | 24 |
| *St. lividans* 1326/pSE34 (cmnU⁻) | 200 | 6 |
| *St. lividans* 1326/pSE34-cmnU (cmnU⁺) | >1600 | >1600 |

[a]Values reported are the minimum inhibitory concentration (MIC). For *E. coli* strains, this was defined as the lowest antibiotic concentration in which $OD_{650}$ < 0.1 after 16 hrs of incubation at 37° C. in LB medium. For *St. lividans* 1326 strains, this was defined as the lowest antibiotic concentration at which no growth was observed on ISP2 plates after 2 days of incubation at 30° C. MICs reported are from three separate experiments. See Materials and Methods for details.

TABLE 5
Exemplary Capreomycin Derivatives that can be produced by Metabolic Engineering
A. By adding vioQ into heterologous host, e.g., S. lividans, containing the CMN biosynthetic gene cluster the following can be produced:
C19hydroxy-CMN IA
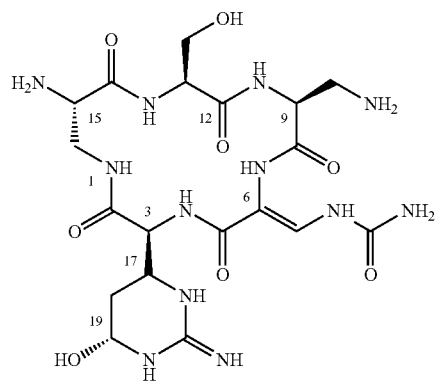
C19hydroxy-CMN IB
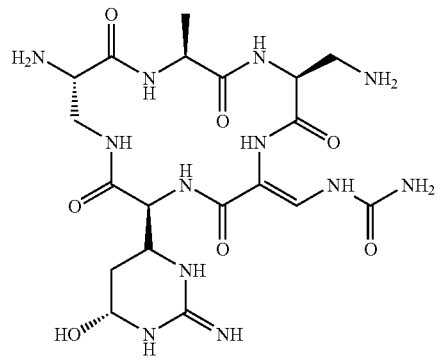
C19hydroxy-CMN IIA
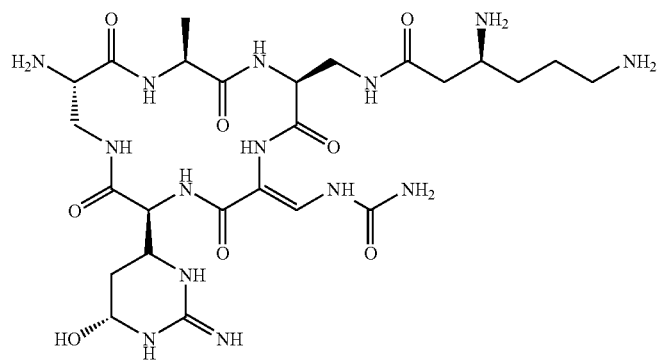

TABLE 5-continued

| Exemplary Capreomycin Derivatives that can be produced by Metabolic Engineering |
| --- |
| C19hydroxy-CMN IIB 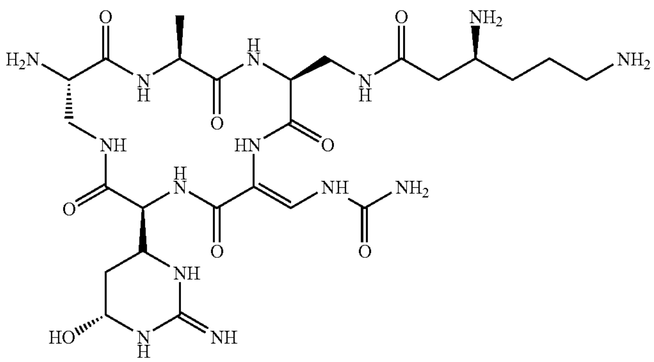  |
| B. By adding vioMOP into heterologous host, e.g., S. lividans, containing the CMN biosynthetic gene cluster the following can be produced: |
| Pseudocapreomycin IA 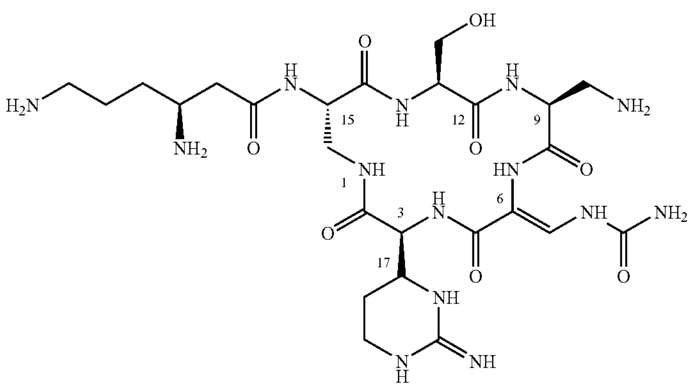  |
| Pseudocapreomycin IB (previously made by chemical modification) 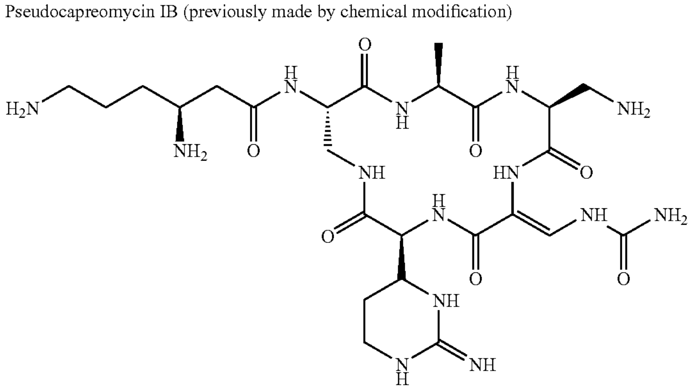  |

TABLE 5-continued
Exemplary Capreomycin Derivatives that can be produced by Metabolic Engineering
Di-beta-lysyl-CMN IIA (previously made chemical modification)
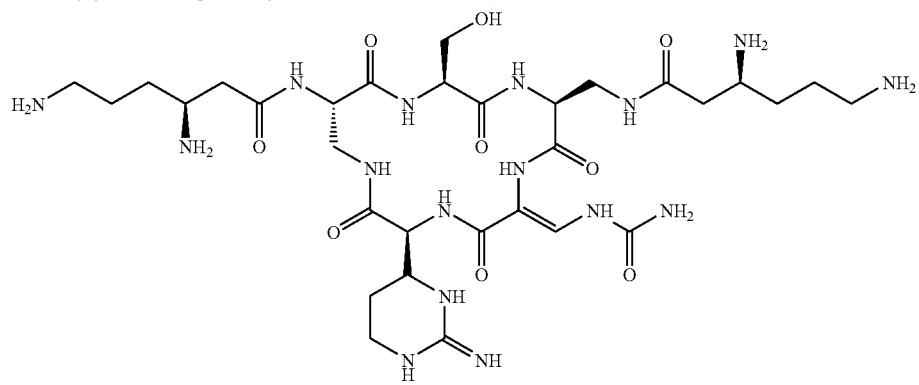
Di-beta-lysyl-CMN IIB
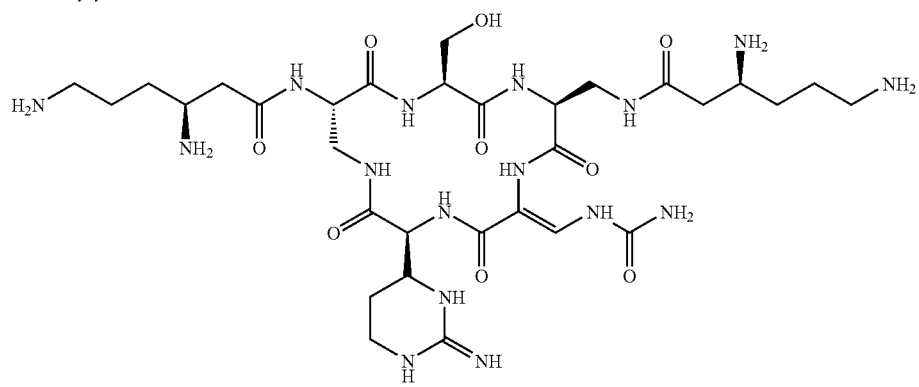
C. By adding vioMOP and vioQ into heterologous host, e.g., S. lividans, containing the CMN biosynthetic gene cluster the following can be produced:
C19-hydroxy-pseudo-CMN IA
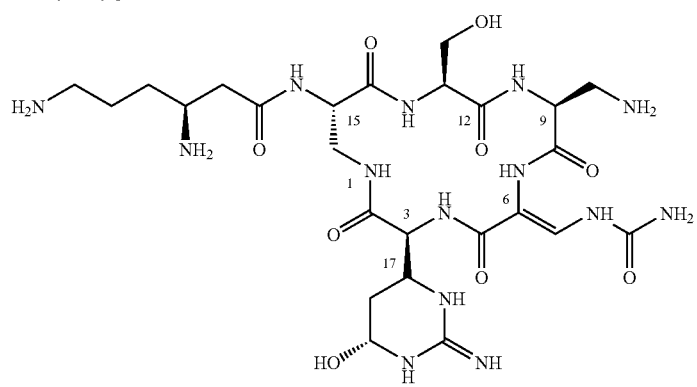

TABLE 5-continued
Exemplary Capreomycin Derivatives that can be produced by Metabolic Engineering
C19-hydroxy-pseudo-CMN IB
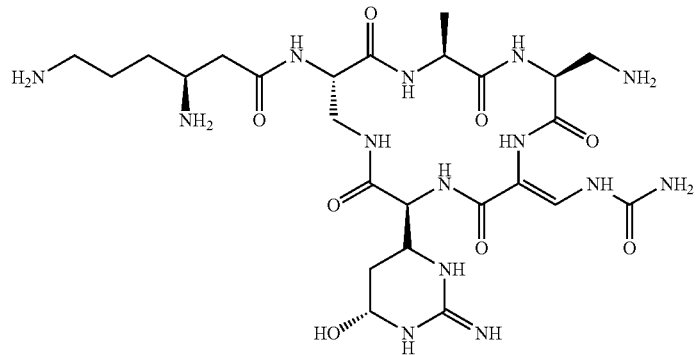
C19-hydroxy-di-beta-lysyl-CMN IIA
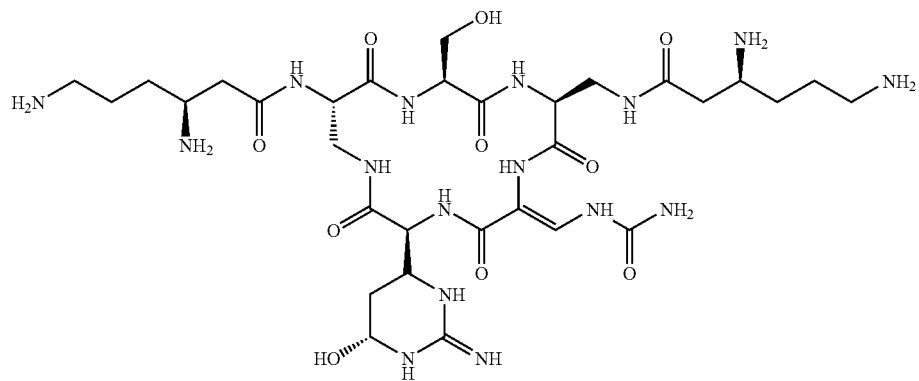
C19-hydroxy-di-beta-lysyl-CMN IIB
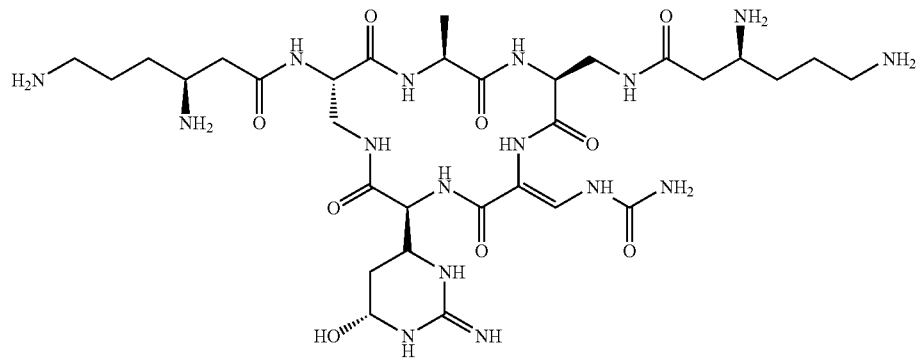

TABLE 5-continued

Exemplary Capreomycin Derivatives that can be produced by Metabolic Engineering

D. By adding vioA into a heterologous host, e.g., S. lividans, containing the CMN biosynthetic gene cluster in which cmaA is inactivated the following can be produced:

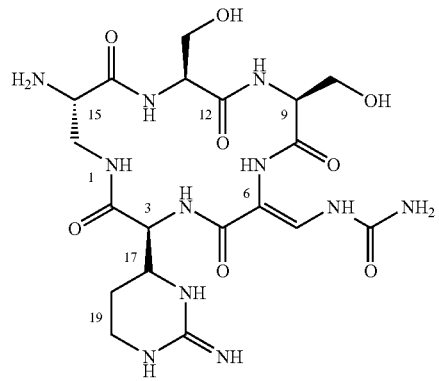

TABLE 6

Chemical modification of C19-hydroxy-CMN derivatives (based on analogous methods from Bioorg. Medicin. Chem. Lett. 7:1145-1148)

C19-3,4-dihydroxy(or dimethoxy)-CMN IA

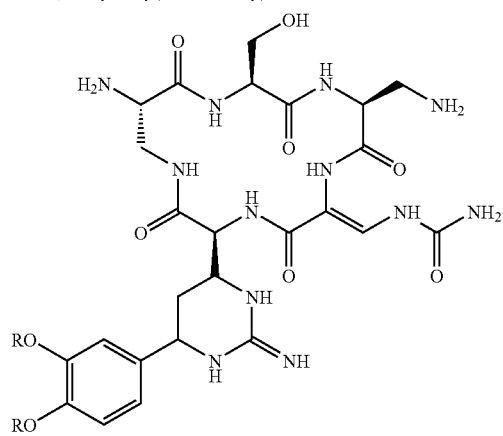

R = H, CH$_3$

C19-3,4-dihydroxy(or dimethoxy)-CMN IB

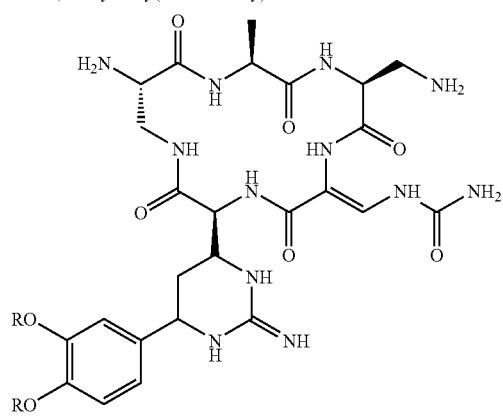

R = H, CH$_3$

TABLE 6-continued

Chemical modification of C19-hydroxy-CMN derivatives (based on analogous methods from Bioorg. Medicin. Chem. Lett. 7:1145-1148)

C19-3,4-dihydroxy(or dimethoxy)-CMN IIB

R = H, CH₃

C19-3,4-dihydroxy(or dimethoxy)-CMN IB

R = H, CH₃

40

TABLE 7

Analysis of ORFs neighboring the CMN biosynthetic gene cluster.

| Predicted ORF (Amino Acids) | BLAST Homolog | % Identity |
|---|---|---|
| Orf1 (168 aa) SEQ ID NO: 21 | AAM78425 Hypothetical protein EcaE (*Streptomyces coelicolor* A3(2), 515 aa) | 39 |
| Orf2 (191 aa) SEQ ID NO: 22 | NP_001037080 Putative calcium-binding protein JhdK (*Bombyx mori*, 183 aa) | 28 |
| Orf3 (247 aa) SEQ ID NO: 23 | EAY34418 Hypothetical β-galactosidase (*Vibrio cholera* V51, 1029 aa) | 31 |
| Orf4 (428 aa) SEQ ID NO: 24 | ZP_01426479 Carboxypeptidase A-like (*Herpetosiphon aurantiacus* ATCC 23779, 1061) | 45 |
| Orf5 (467 aa) SEQ ID NO: 25 | SCO4476 Hypothetic protein (*Streptomyces coelicolor* A3(2), 473 aa) | 68 |
| Orf6 (201 aa) SEQ ID NO: 26 | YP_824735 Hypothetical pyridoxine 5'-phosphate oxidase GOG3576 (*Solibacter usitatus* Ellin6076, 208 aa) | 50 |
| Orf7 (172 aa) SEQ ID NO: 27 | NP_826435 Putative acetyltransferase (GNAT) family (*Streptomyces avermitilis* MA-4680, 202 aa) | 68 |
| Orf8 (399 aa) SEQ ID NO: 28 | ZP_01431759 Conserved hypothetical COG3864 (*Salinispora tropica* CNB-440, 416 aa) | 80 |
| Orf9 (405 aa) SEQ ID NO: 29 | ZP_01431758 ATPase associated with various cellular activities, AAA_3 (*Salinispora tropica* CNB-440, 414 aa) | 84 |
| Orf10 (223 aa) SEQ ID NO: 30 | ZP_01431757 Conserved hypothetical (*Salinispora tropica* CNB-440, 466 aa) | 65 |
| Orf11 (253 aa) SEQ ID NO: 31 | ZP_01431757 Conserved hypothetical (*Salinispora tropica* CNB-440, 466 aa) | 65 |

TABLE 7-continued

Analysis of ORFs neighboring the CMN biosynthetic gene cluster.

| Predicted ORF (Amino Acids) | BLAST Homolog | % Identity |
|---|---|---|
| Orf12 (249 aa) SEQ ID NO: 32 | ZP_01431485 Methyltransferase Type 11 (*Salinispora tropica* CNB-440, 429 aa) | 52 |
| Orf13 (279 aa) SEQ ID NO: 33 | YP_380276 Putative cold-shock protein (*Chlorobium chlorochromatii* CaD3, 310 aa) | 38 |
| Orf14 (246 aa) SEQ ID NO: 34 | YP_116825 Putative glycosyltransferase (*Nocardia farcinica* IFM 10152, 253 aa) | 73 |

TABLE 8

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces capreolus*)

SEQ ID NO:1-nucleotide sequence that comprises cmn cluster

```
   1 cttatcgatg ataagcggtc aaacatgaga attcgcggcc gcataatacg actcactata
  61 gggatccgca gcgcgccggg ctcggtcggg tccgggtggt cgtccacggc cggcaggcta
 121 ccggaccgga gcaccggtga tcatcggcct tgtgccgggg tgtcgcccca cgtctgcgcg
 181 ggcgccacgt gcgagggacg gctctgaccg gcgaggaacg cctccgccca caccgtcttg
 241 tgctccgggt ggcggaccac gccccagtcg gtggacagcg cctgcacgat caccaggccg
 301 cgaccaccgg aggcgtccgc ggtgcggatg cggggctggc cggagccggc gtcgtccacc
 361 tcgacgcgca ggcgctgccc ggcccggacc aggcggcacc ggcggggcgg ctcgccgtgc
 421 cgcaacgcgt tgctgaccag ttcgtccacc acgagcacgg cgtcgtccac cgcgaccccg
 481 gcgcggtccg agagcagatc acgcacaagg tcacgcacct cgcgcacggc gaccccgtcc
 541 agcgcgagca ccacctcgtc gccagactcg tctcccgcgt cccacgactg cgaggacatg
 601 accacatcac ccccatcggg catcccgccg caccagcggc tcacgcgacg acatacccc g
 661 cgcggcgacc cgcgaatccg ccgggatgcg gactgcgcgc cctctcacgc cctcgacgtg
 721 cgtgcggctg accgggtgag ggcgggttcc cgatccggtg atcttgcttg cccgcaccca
 781 ccgccgaccc gagactccgc cctatgacct ccacggagaa cgacctgctc ctcgacaaga
 841 tcgggcgggg attcgaccac ctcgacgccg acggtgacgg gctgctcgac gagcgggacc
 901 acgtcctcat gggcgagcgc gtcgcggcgg cgctcgggca cgggtccggg tcggcggaag
 961 aggagcggat cgtggacatg tacgtccgcg tctggcacga cgtgcacctc ccccacctgc
1021 cggccgggac caccgccatc ggccgggacg agttcatcgc cgccaccgc gacctcgccg
1081 acgacccggc cgccgcggac gccacgctcg gcgccctcgc ccgggagttc ctccggatcg
1141 ccgacatcga cgccgacggc cgggtcacgc ccgccgagtt cctgaccttc cagcgcggcc
1201 acttcccga cctgagcgac gaggacgccg ccgccgcgtt cgagcacctc gacaccgacg
1261 gcgacggctc gctgtccccg gaggagttca tccgggccac cgtcgagtac tggaccagca
1321 ccgaccccga ctcgcccgcc aactggtgga tcggtcggcc gcggccgacc gcctgaggcg
1381 gatcagcagc cgggtttcgg gcagggcaac cgggacgccg cgccggtgag cagccgcagg
1441 gcgccctcgc ggctctcgtc ggcgggcatg ccctgccgtc tggcgttgcc gttcgcccccg
1501 ccgtactcga ccgtcaggaa cacgttgtgg tccacggccc tgacccggct gtagctctgc
1561 accccgttgt acttgtgcat gacgtcgccg tcgtccaggc cggcgcccgt gatgccgggg
1621 tccttcgcct gcgggtccga cgcgaggtgg tggcgggcgt tcccggtggc cgaccggccg
1681 tcgccggcgc ggtagcgcat gaccgtgacc gtgacgtagc ggtacagggg agtgccgggc
1741 gtgtcgggcg cccagtcgtc gtgcggcaac accggcacgt tgccggaatc gccgaactcg
1801 tggcggcact cgaccatgtc gaccggtcg tcagaaaacc ggaccggctc ccggctcggc
1861 ggtgcggcgg ggaggccgcg cgacagcgcg gtgaccgtcc ccgggtccac gaggtcgcac
1921 gcctcgatga gcgaaacgta ctcgggctct tccgccgacg aaccgatgc caccgtcgcc
1981 aacaacaggg cgacgacccc cagtctcacc atgccgcgaa cctagcgcg atcacgctcc
2041 agatgcggct gaccaccgat agtaggtgtt gatcgtgacc gggtcggccc catactcgcg
2101 agcggagcgg cggtcacccc caccctgcac cgaccgccgg ctcgtctgga ggtcttccat
2161 gaaactacgg gcgggacttc tcaccgcggc cctgttgctg ctgggaacca acgcgatggc
2221 cgccgcaccg gactcgacgc cgttctactg gcaggtcccg ggagccgatg agcgcacgct
2281 ccaggacgcc gggttcgacg tcgaacacgg cgtggacggc ggcgtgcagg tggtcgggga
2341 cgcgcgggtg gccggccggc tgaccgcgct gggctaccag ccgaagaagt tcgacaccgt
2401 ctacaagccg gtgccgcccg gccgcagcgg cgacatcggc gtccagacgt tctccggcgg
2461 ctaccacacg gtcgccgagc acgagaagca cctgaccgac gtggccgccg cgtaccccgc
2521 gctgacgcag gtgttcgaca tcgcgacag ttggcgcaag acccgcggcc tgggcgggca
2581 cgacatcaag gccatctgca tcaccaagaa gcaggccggc gactgcgcgt tgagcccac
2641 ctcccccaag ccccggttcg ccatgatcgc gcagttgcac gcgcgggaac tggccaccgg
2701 tgaactcgcg tggcgctgga tcgaccatgt caccgcccgc tacggcaccg acgccggagt
2761 gacgtccatc ctggacacca ccgagctgtg ggtggtcccg atcgtcaacc ccgacggcgt
2821 ggacatcgtc gcctccggcg gcagccggcc gctgatgcag cgcaagaacg ccaacaacac
2881 cggcgcgtcc tgctcggtgc cgagctacgg cgtggacctc aaccgcaact ccacgttcaa
2941 gtggggcggc gcgggcacga accgtgcgg cgaacctac cagggcacgg cggccgggtc
3001 ggagcggag accagggcgc tggaggcgtg gttcaagcag ctgttcccgg accagcgcgg
3061 ccccggtgac accgacccg cgccggtgac caccaagggc gtgatgatca cgatccacag
3121 ctacgcaac ctgatcatgc cgccgtgggg ctggacgtgg aacgcgaacc cgaacgccgc
3181 gcaactggcc gcgctgggca agaagatggc ggcgttcaac gggtacacgg tggtggccga
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces
capreolus*)

```
3241 gggcgacacg acgggcacga ccgacgactt cacctacggc accctgggca tcgccagcta
3301 cacgttcgag atcgggtcca gcagcggcag ctgcggcggg ttcttcccgc agtactcgtg
3361 cgtggacagc ctgttctggc cgcggaacaa gggcgctttc ctgacggcgg cgaaggccgc
3421 caaggcccct tacgcgagct gacgccggcg gccggtggac gctacccgc cgcgggtgcg
3481 tccgccggcc gcgcgacgga caggatgacc tcgcgcagcc ggtccacgta gaggcggatg
3541 ttcttgtacg ccacgtcgtt gtccgggtac cggcacgcga actggagccc ttcgtgcagc
3601 cgggtcaccc acacgcacac ctggtcgccg taggacacgc ggatcagccc gtacgccttc
3661 atgtcccgcc agcgctccga acccggcgtg gggcgggcgt ccatgaacga gacgatcgag
3721 tacaggtcgg gcgaggtggg gcggaagtcg tcgcccagca ggcgcagcac gcgcgcgacc
3781 ggcacccgcg acgccgggcg gctcgcgcgc agttcggcct gggccgcgcg cagcaggccg
3841 tcgaaaccgc ccgccgtggc cacgggcagt tccaccggca cgccgccgac gtaccagccg
3901 accgagtccg accaccgcga cttggcccgc gtgtgaacg gcacgaccgt gcggtagacg
3961 tcgtcgccgg tcatctcgcg catgatcagc gcggtggcgg cgaggacgcc gaccagggaa
4021 ccgccgtagg gccggcagtg ccgctcgaac gccgccgct cggcgtcgtc caccagcatc
4081 tcgtgcaacg acttctgcgt gggcagcggg ccgccggcg ccaggcccag gtcgaacggg
4141 aagttcggca tccggccgtc gcagcgcgcc acgaaccgcc gccaccggtc caccaccggg
4201 tggtcggcgt ccacctcgtc ggcgtcggcg cgctcggtgg cgcagaagtc gacgtagctg
4261 gcgatcggcg cggcgtccac ggtgcggccg tcgagcgcga cggcgtacag ctcgtgcagc
4321 tcggcgggga cgcggtacat ggagtaggcg tcgacgttgc tgtggtcgaa cgcggaggtag
4381 acgctcgtgc tgtcctcgcg ggccacggcc gcgtagatga agttgggcca ggtgagggtg
4441 tcggcggcga cgtcgaaccg gtcctggagg tgctgcacga gcacgtcggc gtcggtgaac
4501 tcgccgacgt cctctcggtg cagcgcgacg gcgtcggcgt cgagggtgaa ccggcgcatc
4561 tcgccgtcct cccaccggaa accgctgcgc agcgtctcgt gccgcaacgt ccacacccgc
4621 aacgcctcct ccagggcgtc gaggtccacc gcgcccggca ggtcgaacgc gacgcccagc
4681 cacgtcggga cgaacaggcc gtcctcgcgc aggctccggg ccgtgcgcac gtgcgactcc
4741 tgcaggtacg ccggcggtcg cgcgtcgtcc ggcgcgccgg tcgcggcggc cacggggcgc
4801 agcacccact ccacgacgcg ccctggccgg acctcacaac gctggacatc ggtgatgcgc
4861 atgaccttct ccgtctgcct gccggtgcgg cacaaggcgg cgcgcaggcg tacctgaaac
4921 cttcgggggg agggtggctc gtctcacgac cacacggcgg aatgtcgccg tacccgagcg
4981 aggaccttaa cgacggcccg atcaagaaac caccgccgaa gacccgagcc acgctatcga
5041 gtgaactcgt gatgtgactg ccgtcacaga tcaccggcaa ccggaatgac catgaccgat
5101 ctaacggttg gaccctaggt caaacgttag aacgcgcccg gaggccgaga tgaccagccg
5161 cttcgcccaa gtcatgttca ccccggacgt ccagctccac caggagcggc acggcagccg
5221 cgacgcctac gcccggatgg ccgacgccgc gccggtccgg gaccgcatcg gccccgacga
5281 ggcggcgttc atcgccgagc gcgacagctt ctacctgccg ccgtcggggg agaccgggtg
5341 gccctacatc cagcaccgcg gcggcccgcc cgggttcctg cgcgtgctgg acgagcacac
5401 gctcggcttc gccgacttcc gcggcaaccg gcagtacatc acccgcggca acctcgacca
5461 cgacgaccgc gtggcgctgt tcctgatgga ctacgccaac cgcacgcgcc tcaagctcat
5521 cggccacgcc cgcgccgacg actcgcccga ggtcgtcgaa cggctcgcgc tgccggacta
5581 ccgggcgaag gtcgaacgcg cggtgctcat cgaggtcgag gctacgatct ggaactgccg
5641 ccagcacatc ccgcaactgt ccccgcgcga cgccgtggag caggccgtcg gcgcgctgcg
5701 cgaccggatc accgagctgg aacaggaaaa cgcccgcctg cgcgcgaggt gacgcgggcc
5761 ggccggggc gtcgccgggg ccggccggat cggccgggt cgccgggtca ggcgggggcg
5821 tcaccgggtc aggcgggacg tcaccgggac agccggggcg tcatcgggac agccgccacc
5881 ggacctcgcc gtcgtgcacc tcgtcggtgg gcgcgagtcc ggcggcggtc gcgacggcgg
5941 ccgacgcgtg gtggtcgggg tggacgtggg cgacgaccgt gcgcacgccc tgccgcccga
6001 gccagtccac gagccccgg gcggcttcac gggcgatccc ccgccccctgg aacggcgtcc
6061 ccaccaccca ggcgacctcc gcgaccgggc cctggtccgt ggggccgacc gtcgcctgga
6121 ccgtgcccgc caggcggac tcctcgcgca gccggacgac ccagttcagc caggagaccg
6181 cgggatcggg cgagccggcg agcatgcgtt cgtagcgtga ccgcagggct cgcgggtcgt
6241 ccggggtgcc gccggtgaac gtgtgcaacg cgggatcggc caacacgacg gccatctcct
6301 ccgcgtggtc caccgcaac ggcaccaggt cgaggcgggc ggtgccgatg gctgggcgt
6361 ggaggcggcc ggacatgtgg gccaacagta gtgctcaccc cacggtcacc acccgggccc
6421 acgccggcgg tgggtccggt cggtagtcgc ccggtttcgg tgggcggcgg aacaggccca
6481 cgaccgttcg gcacggcggt cgcacggtgg gccacgggt ctggccgtcg gtcagggcga
6541 cgatgacgtc cgggcgggtg cgcagggccc gggtgaagcc ggtgcgcagg tcggtcccgc
6601 cgccgcccat caggggatg ccctcggctc ggcacagcgg gtgcgtcacg tgggcggcgg
6661 cgtcgcagga caggaccgac accaggtcgc gccggccgcc cacggcgcgg gcgatggcgg
6721 cgatctccag cagcgcgctg cccagttccg cgtcgctcac cgacccgag gtgtccacga
6781 ccacgcacac gcgcggcggc ctgcggcgca ggctgggcag cagcacacg ggcaggggcg
6841 tggaccggcg cgccgggcgg ccgtaggtgt agtcgtcgcc cgcgcccgcg gccgacgcgg
6901 ccgagcggac cgccgcgccc agcaggtcgc gccacggctg gggcgggtgg aacgcccgct
6961 ccgcccaccg ccgccagccc agcggcacgt cgcccggccg gccggtgatg gcctcggcga
7021 cccggaaccg caccgcgtcc cgctcctgct cgctgagccc gtgcgcccg tccggcccca
7081 ggtccactc gcgctccagg ccgtccgcg cgctgccgca gtccagccac gtgaacgcgt
7141 cggtgtacgg gccgagccgg aactggcgca ggtagtcctc catcaactgc ccctcgcgca
7201 actgcagcag ttccggctcc accgcgccct cgggccgtgc caacccgtcc ccgaacacgt
7261 cgtcgttgat ctcgcagtca cgggcgatgt tcatccgcaa ccgctccccc ggccccgtca
7321 gcccgtgctc cgcgcgaac cggtccgccgc cgccgtggtg gtcgcgcagc aggtcggaca
7381 cctcgtgcac ccacaccccg gccaactcct cctccgcgcgt gcggtccacg aaggccgggg
7441 agacgtaaca acgccagtgc cggtccacgg ccatcgtcgg caccgcgcc gactccacca
7501 cgtgcagcgc gaacaacgcc gtcgccaggt acggcggca gcgcaccgcg tgcagccggg
7561 cggcgaacag cttgcgctcg tccaggctca ccggcccgcc ccgacgcgcg ccgccgtccg
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces capreolus*)

```
 7621 gtcggccagc cgcgacaccg acaccgcgcc ggagagccgc tcgatcgccg ccggcacctc
 7681 ccagtcgtcg cggcgcaacg cggcgagcgt cgccgccggc acgacgacca ggtccggcgc
 7741 gccggtgtcc aacgcccgca ccaacaacgc ccacgccgcg tcccaccgcg ccgcctccgg
 7801 acgtcgccgc accgcctcca ccacaccgtc gagcaccgct ggcgcaggt cgccgcgctc
 7861 gggcagcacg gccgccgccg ggttcgcgag cagcgactcg gggtcgggca ggtccatccg
 7921 gtccaggctc gccagcagct ccaggcccgg cccgtcgccc acggtcccccc gcacgagcat
 7981 cgacagcacg tcccgggaca cgtccgccgc ggtggcgaag gcgatcagcc gcaacgccat
 8041 ctcccagctg cgcggcgacg gccacggacc accgcgccgg gtctcgtcct gggcagttg
 8101 gtgcaccagg ttggggcggg cggccagcag ttcgcacacc gcccgacgcg cgtaggccac
 8161 ggcgtccggc aagcggcccg ggtccaggcg cggcagctcg gcccgcggcc acgtcccgcc
 8221 cagcccgcgg accaccacgt cgtggtcgtg ggcccactgg aggtggacga accggttggc
 8281 cagcggcggg ctgagctccc agccgtcggc ggcggacgag cgcgggttgg cggcggccac
 8341 gatccgcacg cccggcggga gggtcagcgc gccgatccgg cgttcgagga cgacccgcag
 8401 gagcgcggcc tggaccgccg gcggcgcggt ggacagctcg tccaggaaca gcagtccgcg
 8461 gccggcgcgg accaggcgca ccgcccagtc cggcggggcc atcggaacgc cctgcaccgc
 8521 cgggtcgtcg ccgacgacgg gcaggccggc gaagtcggac ggttcgtgca cgctcgcgat
 8581 gaccgtggtc agcggcaggt cgagggcgtc ggcgagctgg gtgagggcgg cggtcttgcc
 8641 gatccccggc tcgccccaca gcagcaccgg caggtcgggca gacacggcca gggtcagggc
 8701 ttcgagctgg gcgtcggaac gggtttcggt ggtcgtgcgg ccgagcaggg cgagcaggtc
 8761 ggcggcgacg tcgagcggtc gcgcggacag ggaagtgggc atattcgggc accctcgggt
 8821 tgcgtaggga cgtgcgtcgg ccgagcgagc acgcgggggg attcagcgag agaacgcgtg
 8881 gcgcgggcgg acccgtcgcc gaccgtcctt tgtggaggga gccgggccgc cggcgagtcc
 8941 ggcccggtac aggccgtgcg ccagccggcg gcggaccgcc gcgtccagct cgtcgcgcag
 9001 cgcgccggcg cgcaggagcg cctccgggcc gagcagggct tcgacggccg cgacggcgcc
 9061 ggcggtgtcg ccgtggtcga gccgggcgcg aacgtccaca agggactccg gttgtcggtg
 9121 cacgtcgtcg atcgcccgca ggcacggcaa cggcggaccg ccccactcgg ccagcagctc
 9181 ctcgcggcgg acctcgtcgg ggtcgtggtc cagcggccag aggacccgt ccacgacgcc
 9241 gatccggtgc gtcgcgccgc ggcactcgac caggcgcgga cccgttgcgg ggtcgggact
 9301 tccggttgtt cgccggtggc cggggaccag ggccgacgcg accagcgggt gcagccggtc
 9361 ggcgtcgacc aggccggcgc ggagcaggtc gaggtcgggt ggtgtgcggg tggcggcgtc
 9421 gggcaggacg ggcgggtgg ggtctcgtcg gggagcggcc gtgagcaggg gtgtcggctc
 9481 gtccggggcc agcgccaacc accgaccggc gttgagccgc acggtgatca cgcggtcggc
 9541 gcaccggtcc gcgcgcagga ggagcaaggc ctccggcacc caacgaccga cagcgaaacc
 9601 ctccccctcg acgggcccacg gcgcggcggg tccctcggct ggcggcggcc cgacggccca
 9661 cgaacgcggc gggcccctcg gctgccggcg acccgaccgc ccgcgagccg gctgcgcgca
 9721 gcgcggtggt caaacccggg cggggatcg ccgcccgcgg accgttcccg cagctcgccg
 9781 gcccggcgcg cgtcccacag gtggcggtgc aggtccaggc ggaaccgccg gtccggccgg
 9841 gggtgcgggt gcgtgccgc gccggcccgg ggttcggccg ggtcccacca cgccaggctg
 9901 atccgctgcc cggctgccgc ccacgccggt ggcgtgccgc ccacgaggtg cgggcccgcc
 9961 gcgtaccggg ccagggacac ggtgagcccc gggcgcagca agccgtccgg accgatcctc
10021 gggaagtgcc agcgcagcag gtcggggggcc aggtgccgca ggtcggcgcg gacctgtgcc
10081 gcgagctgcc gaccgtgggt ccggcccacg gcccgcaggt ccaggtccac gtcgaagcgc
10141 gcggcggcac aggcccccggc ccagtcgccc accgagccgg gggcggtcgc tgtctcgacc
10201 atcgacggcg gcacggcgaa ctcgcgcacg cgcgtccaga agtgaaggcg aaggttctca
10261 tccgcggtgg tgtggtgcat cagcactcac cttgcgcgaa tgaaaccccc gatctaccag
10321 agaaggtgat catcgcggcc gagcgtacca gcaaacggcg ctcaggtgtg cgagacgacg
10381 agccggaaac cggcgtccca ctggtcgagg tcgacaggt cgcggtggtc gtcgtgccac
10441 cggccgctgt cgaggtccgc gcgcaggcgg cggacgccgc ggtccacggc ggcgggggtcg
10501 gtctgggcca gggcggagca cgcgcggcgg acgcgcgggt cgaggtaggc gtccgggcgt
10561 cgccagtacg cggggaagac gccgtcgacg aagtcccacg gcagcggcag cggcgtgacg
10621 ctgtccgcgc ccagttcgcc cgcgatgtcg gccgccgacg ggcgggtgcg ttccaggtcg
10681 gcgatctcgg gcacgtactc gcggacgaac cagaactcgg tgtcaggct cgtgtcgtag
10741 gccagcacga cccggcgcgg cgcgatccgg cgcagttcgg cgagcccggc ccgccagtcg
10801 gtccagtggt ggacggtgag cacggccagc gcggcgtcca cggcgtggtc gcgcagcggc
10861 agggcctcgg cgaccgcgcg cacggccggt ccgacctccg gcgggcgttg gcggatcatc
10921 tccgtggacg gttcgagggc gaccaccgtc cggtcgtccg gctcgtagga gccggtgccc
10981 gcgcccacgt tggcgatcgt ccgccgcgcc ccgagcgcgt cgaggatcgc ggtcatccac
11041 cgcgggtcgg tgcggcggcc cagcgcgtaa cccgtgccga tgtcgtcgta gagatccgtg
11101 ccggccactg tcccccagt gctcaagcgg aaagtttcga cgtgggcggc gacgggccgg
11161 tccgggaggg cccggatcgg ccgtcgtcac ccgcgggttc ggccccggcg gtcacgccga
11221 cgcgcccgg ggcttcacca cctcgggggc ctcgcgcgcg gtcaccaggc ccaggcgcca
11281 ggccagcaga gcggcctgga cgcggtctcg cagctccagc ttggccagca cccgggacac
11341 gtggctcttc accgtggtct cgctgacctc gaactcgcgg gcgatctcgc ggttggaccg
11401 cccctggccg atggcgcgca gcacctggcc ctcccgttcg gtcaacgaca gcagggccgg
11461 cgccgacggg tcgggcagcg ggatgatctg gaagctctcg aacacccgct tggtgacgtg
11521 cgcggggcagg tacgcgccgc cctcggccac cgccggatc gcgcgcggga actcctcccc
11581 cggcgaccc agcggcaggt agccgctcac acccgccgcg atcgcggaca ccagcagctc
11641 gtccgagtcg tcctgggtgg ccaccacgac ccgctgcccc gccagcagcc gcgccaccccg
11701 gaaatcgtcc acccgcaaca acgacgcccc gaccagcacc agtccggcgt ggtcgcggcc
11761 gatccggtcc agcagttccg gcacgccgtg caccgcgccg accacgtga tcgcgtcgtc
11821 ccgcgcgagc acgggcccgca ggccgtccag gatcacctcg tggtcgtcgg cgagcagcac
11881 ggcgatcccc cgccgcgccc gccccgcccc ggcggcgtc agcacgctta tcgcccccggt
11941 ctcccgacgg taccgggcc cgactgaata tcgtccgac acttctccgg tcacgttctt
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces
capreolus*)

```
12001  ccgaccccct cggccacggg ttttccccac ggcgtttcga aacagtcgcg gcgggcgcga
12061  aaacaccacc ggaaccgcga gccgcccggg accaccgacc cgcggcaccc cggccgtctg
12121  cttcaccatc cccaggcgcc gccggcaatc cggatcgacg ccacccagt tgcaaacaat
12181  atgcattaac acccaaccta ccggaccacc ggacgggcgg caacctccgc acggtgtgtg
12241  cacgcactca cactaacgcg ccaattaggc ggggagacat gccgctttag aagtaatccc
12301  ggcaacgccg ggcgtcgatc cgccacgcgc cgcgccctcc acgccgagca cgtcgaactc
12361  ctcccggcag gcccccagcc gacgggtcca cgtgctggtc aactcgctcg cgccgacatc
12421  ggccaggtac ccggcccggg taacgcgcag gcccgcctcg gcgtagacgt gggccagttc
12481  ccggcgcacc cattcgggtg tcggttcggc gatcccggtg acggcggggg ccgccggccg
12541  ccaggcgtgg aggttcacgg tgatgtggaa ccgggcgccg gcgcggcacg cgccgccag
12601  gccggcgagc acggcggggt cgcgcccgag gacaccgcgc agcaggctgc cccacggcat
12661  caacacgtgc atttcgtcca catcgcccag acaggccggc atctcctcgg cggcggcgtg
12721  gaccagcacc aggttgggca gcccgccgcg cgcgggtttg gcggcggcgc gcgcggacac
12781  gccccgcatc cggtcgggt tggcgtccac gccgaccacc agccggtcgg ggtcggcgcg
12841  ggcgagccgg taggcgtgct tgccgtcgcc ggtgcccacg tcgagcagga ccgaccggtg
12901  acgggcgcgc aactcggcga actcggcgtc ggcgagcggc acgcaccgct tgccgacgac
12961  cttgaccaga ccttcggaag gcatgacggg gcccttcgcg tgagtgggtg aggacctgcg
13021  ggaaacggcc ggcgacggac cgcagaatta cggggaaaca ccctccggga catcgccgga
13081  ggacccttgt caatcgttgc cggaaatacc ggccgctgcc caccctccg gagcagccgg
13141  gagcccggtc ctgggaaaat gtggccgtaa atcacgccaa tgggggaagt gaacccgtc
13201  aaaatcactc tgcgtgatta gttttctcct accagcggac gagacgtcac cctacttcgg
13261  aaggaacggt gctcgttcga aatatccgca ccgggcattc gccggaatga gccggcgggc
13321  cacccaaaga agtctgtcga aaacggcgga gtcgctcata ggctgagcgg cgtccccaat
13381  tcgcgacgac cggagggcca tttgcccggc ccgggtcgga tcgacatcag ccggagacgc
13441  caccatgacc gttgacccca cgatcgagct gcgcctgacg ctgaacggcg acccggacgt
13501  gcccgcgctg acccgggcgt gggcggcgct gcgcgcccgg caccgcgccc tggccggtcc
13561  gctgggtgcg caccgggacg tcgccgcgtt cgaggacgcg gtgcgccgcg gccccggctg
13621  ccacctgctg cgcgcccccg gccggcacga gttcgcgctg accgccgggt gcgacgcggc
13681  gtcggtgccc gcggtcctgg ccgagctgtc cgcgctctac gcccgcgagc tgggccaccc
13741  ctccgagggg ctgccgcgc cggcccggc cgtcccgcac gaccgcccgc cgcacgacgt
13801  tccccgccc ggaccggagc tgccgggct ggagctgttc gggcgcggcg aaccgggccg
13861  gcgcgtggtg acccgcgtgg acctcggcca cccgaccgc cggcacgtct ccgcgctggc
13921  ccgccggcac ggcgtgaccc gcgaggtcgt cgtggtcacc gcgtgggcgc tgctgctggg
13981  cgagctggcc gagcgggacg agttcgtgct gggcctggtc accgatcccc gcgacccggc
14041  gcgcaccga cccgccgtgg gcgcgctgcg cgaggcccgc ccgctgcggg tggacctgac
14101  cggccggccg tcgttcgccg acgcggtgcg ccgcaccacc gccgccgtgg cgaccgcccg
14161  gtcccgcccc ggtgacgcgc ccgccgacgt ggcggtgcag tacgcgagc agccggcggc
14221  ggcgctgcgg ctggccggcc tcgaccccgc cgaggtcccc gccgccttct ggctggccga
14281  cgacctcccc ggcccgcacc gggtcgtgct gcgcctgcg gacaccccg acggctgct
14341  cgccggcgtc gcgcaccacc ccgacgcccct ggacgggccc ggcgcgcggc gctgggtgtc
14401  ccggctggcc gcgctgctgg ccggcgcgca cgacgagtcg cccgagcccg tggtgatgtc
14461  cgaggacgag caccgccggg tcgtgctcgc gcccaacgcg accgccgtgg acctcggcgc
14521  gcccgccgacg gtccacgacc tggtcgccga gcaggcccgc cgcaccccgg accgaccgc
14581  gctggtcttc gccggcgccg aggtcggcta cgccgagctg gacgcccgcg ccaaccgcct
14641  cgcccacgag ctgcgcgagc gcggcgtgcg gcgggagacg ccggtcgcgg tgtgcctgga
14701  acgcgagacg ggcctggtgg tcgcgctgct ggcggtgctc aaggcgggcg gcgcgttcgt
14761  gccgctggac ccgcagtacc cgcggcagcg cctgcccac atgctcggcg actcgggcg
14821  ggccgtggtg ctcacccagg gtcggctgcg cgaccggttc gccgccgacg gcccgcccgt
14881  gctggtgacc gacgacgacg cgacccggtt cgcccaccac ccgagcagcg cgccgccggc
14941  gtcgtccggc ccggacgacc tcgcctacgt cgtctacacc tcgggatcga ccgggcggcc
15001  caagggcgtg atggtcgagc accggggcat cgcgtcctac ctgcgcggaa tgcagcacga
15061  cttcccgctc acgcccgagg accgcgtgct ccaggcgacc tcgctgtcct tcgacgtgtc
15121  ggtgtacgag atcttctggc cgttgcaggt gggcgcgggg gtggtgctgc ccgcgcccgg
15181  cgggcacacc gaccgtacc acctgtcgga gctgatccag cggcacggcg tgacgtgcct
15241  gcacttcgtg ccgtcgctga tgcggttgtt cgtggaggag gccgacccgg gggcgggcgc
15301  cgggctgcgg cgggtgttcg tgtccggtga ggcgctggac ccgtcgctgg tggcgctggt
15361  gcacgagcgg acctcggcgg agctggtgaa cctgtacggg gcgacggagg tgtcggtcga
15421  ctcgacctac tggaccgccg accgcgccaa gccgaccgc ccggtgctgg tggggcggcc
15481  gatggccaac gccacggcgt acgtgctgga ccagcggttg cgacccaagc ccgcgggcgt
15541  ggtcggcgag gtcttcctgg gcggcgcgag cgtcacccgc ggctaccacg cgcggccggc
15601  gctgacgcgc gagcggttcg tgcccgaccc gttcgggcca cccggggtcg gctgtaccgg
15661  gaccgcgac ctgggccggg tgacccggga cggcgagctg gagttcctgg ggcgcgcga
15721  ccaccagttc aagctgcgcg ggtggcgggt ggaggccggc gagatcgagg cggcgatcac
15781  cgcgcacccc ggcgtgaacg gcgcggtcgt ggtgaccgag ggggcgcacg agcacgcgac
15841  cctgctggcc tacgtgggcg cggacgcggg gctggaccag gcggcgctgc gggagttcct
15901  ggcgcggcgc ctgccccgac cgctggtgcc ggcgcggttc atccgcctgg accgcctgcc
15961  gatctccccc aacggcaagg tggaccgcgc cgccctgccc aagcccgacc aggcgcccgc
16021  cgagccgcg ccgaccaccg ccgacaccgc gacgcacgcc gcggacggtc ggccgcgtt
16081  ggagcacgcc gcggacggtc ggccggcgct ggagcgcgcg tcggacggcg ggccggtgtt
16141  ggaggtggtg ctggcggtcg cggccgaggt gctgggcgcg ccgatcgggc cggaggacag
16201  cttcttcggc tccggcgcca actccatcca ggccaccgg ctggccgccc gcctgcgcgc
16261  cgccctgcgc accgacgtcc cggtgcggct ggcgttcgag gcgcccacgc cggccgcgat
16321  ggcggcgctg ctgtccccgc cgtcccccga gcccgtcgcc gaggtctccc gggccgagca
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces capreolus*)

```
16381 acggatctgg ctgctcagcc ggctcggcgg ccaccccgcc gagtacgcga tccccgtggc
16441 gctgcgcctg gccggcccgc tggacgtcgc caagctcaag aacgccgtgg acgcggtcgt
16501 gcgccgccac gaaggcctgc ggcacgtctt ccccgaggtc gacggctccc cgacgcgggc
16561 cgtgctcgac ccgggctcga tcaccgtggc cgaggaggcg aaccggtcgg tgcgcgaggt
16621 gctcgccgag ggtgtcgccg cgctggaccc cgcgaccggc ccactggccc gcttcacgct
16681 ggtcaaccag ggccgcagg accacgtgct ggccatcgtg ctgcaccacc tcatcgccga
16741 cggctggtcg gtggacgtgc tgctgcgcga catcgccgcc cactacaccg gcgcgccgac
16801 cgccaccccc ggccgctacg ccgactacct cgccctggaa cgggccgagg agcaggacgg
16861 cgccctgggc gcgcgcctgg agcacttcgt caccgcgctg gacggcgtgc cgacgaggt
16921 cagcttcccg cccgaccacc cccgccccgc gcaacgcacg ggggcgggcg acgtcgtgcg
16981 ccaccggatc gacgccgcgc cggtcaccgc gctggccgaa cgcctgcgca ccacgccgtt
17041 cgcggtgctg ctggcggcgg tgggcgtgct gctgcaccgc gtcggcggcc accgggacgt
17101 ggtggtcggc acggccgtcg cccgccggcc cgacgccggg ctggaccacc tggtcggcct
17161 gtgcctgaac acgctcgccc tgcgctggcc cgtgcagccg cacgacacgc tgggcgaggt
17221 ggtccgcgcc gtgaccgacc ggctcgccga cggcctccag cacgacgccg cgtcgttcga
17281 ccgggtggtg gacaagctcg ccccgccccg cgacagcggt cgcacccccg tgttccaggt
17341 gatggccctg tacgaggagc cgtacgagac cgcgctggcg ctgccggacg tgacgaccac
17401 cgacgtgacc gtccactgtg gatccgcgca ggcggacgcg gcgttcgggt tcgtgccgcg
17461 cgagggcggg atcgacctca ccctccagtt ctccaccgac gtgttccacc gcgccacggc
17521 gagccggtgg gcgcgccgcc tggcgaccct gctggccggc gcgcgggcgg acaccagggt
17581 cgcggacctg ccgctgctgc cggaggacga aagccaggac ctggaacgct ggagcggcac
17641 cacaggggaa gcgccgacca ccacgctgca cgccctcgcc cacgagatcg cccaacgcca
17701 ccccgaccgc ccggcgatcc acttcggaca gaacagcctg acctacggcg agttcgacgc
17761 gcgatccgct cagctcgccc acgagttgcg cgcccgcggc gtccgagccg aaacccggt
17821 cgtggtgtgc ctggaacgct ctcccgaggc gctgatcgcc gtctacggcg tgctgaaggc
17881 cggcggcgcg tacgtgccgg tggagaccag caaccccgac ctgccggatcg ccgagctgat
17941 cgccgactcc ggagcgggcg tggtcctcac ccagcggcga ctcgccgacc gcctggccgc
18001 gctgggcgcg gaggtcgtgg tggtggacga gccgctgccc cggcaccca ccaccgaccc
18061 ggagccgctc accggtcccg accacctggc gtacgtgatc tacacgtccg gctccaccgg
18121 ccgccccaag ggcgtgatgg tgcagcacg gtcggtgctg aacttcctcg acgcgctgga
18181 ccgccgcttc gacctcaccc ccgacgaccg gctgctgcac aagtccccgc tggcgttcga
18241 cgtgtcggtg cgcgaggtct tctgggcgct gacccggggc gcgtcggtcg tcgtcgccga
18301 acccgccgg cacgccgacc ccggccacct ggtggacctg gtcgagcggg agcgggtcac
18361 cgtcgcgcac ttcgtgccca gctcgctggc ggtgttcctg gagggcctgc ccggaccggg
18421 ccggtgcccg accctgccgc acgtcctcac cagcggcgag acgctgcccg tgaccacggc
18481 ccgagccgcg cgcgacctgc tgggagcccg gctgcgcaac atgtacgccc ccaccgagac
18541 cacagtcgag atgaccgacc acgacgtcgt ggacgacacc gtggaccggc tgccgatcgg
18601 ccaccgtc gagggcgcgg tcgtgcgcgt gctggacgcg gacctgcggc cggtgccgcc
18661 gggcagcacc ggtgagctgt gcgtcggcgg cctgccggtg gcgcgcgct acctgggccg
18721 cccggcgctg accgccgagc ggttcgtgcc cgacccgctg gggccggcgg gcgcgcggct
18781 gtaccgcacc ggcgacctgg cccggctgct gcccgacggg caactggact tcctgggccg
18841 caacgacttc caggtcaagg tgcgcgggca ccggatcgag cccggcgagg tcgaggcggt
18901 gctcggccgcg ctgcccggcg tgcacgggc gctggtcacc gcgcacgacg accggctcat
18961 cggctacgcc gtcaccgacc gggacggcga ggagctgcgg acggcgctgg ccgagcggct
19021 gcccgagcac ctggtgccct cggtggtgct gaccctggac cggttcccgt tgaccggcaa
19081 cggcaagctc gaccgcgcgg cgctgcccac cccaccggc cggcacaccg gcgacagccg
19141 cccgctgacc gcgaccgagg cggcgctggc cgcgatctgg cgcgacctgc tggacgtgcc
19201 ggaggtgcgg gcggacgacc acttcttcgc gctgggcgtc cactcgtcg tcgcggcccg
19261 ggtcgccgcc cgcgccggcg ccgcgctggg cgtggcgctg cccttgccga ccgtgctgcg
19321 cttccccgc ctcgcggacc tggcgaccgc ggtggacggc acgcgcgccg accgcgaacc
19381 cgtccggccc cggcccgacc ggcggcgccg cgcgccgctg tcgtccgcgc agcgccggct
19441 gtggatcgag gagaacctgc gacccggcac cgccacctac accgtcgccg aggcgttccg
19501 cctgcgcggc gagctggacg aggaggcgtt cgcggcggcc gtgacgacg tgctgcgccg
19561 ccacgacgcg ctgccgcgcc acgtcgagtc cgtcgaggac ggtgaaccgg agctggtggt
19621 cgcgcccgag ccgcgcaccg cgctgcgcgt cggcgacctg ccggccgacc gggtgcggga
19681 cgcgctggcc gccgagtcgg cccgggtgtt cgacccgccc ggcccgctgg tggccacgag
19741 cctgcaccgg ctcgcgcccg acgagtggcg gttccagttc accgcgcacc acctggtggt
19801 ggacgctgg tcgctggacg tgctgtggcg cgacctggcc gcctgctacc acgaccgccg
19861 cgcaggccgc gcgccgcgac cgcgcgacgg gctgaccttc accgactaca cgtggtggga
19921 gcgggacgtg cggtcccgcg acctggaacc gcaactggcg ttctggcgcg gggaactggc
19981 cgggttgcgc ccgcagcccc cggccgacgc gcacggcccc ggcgcggtgc tggacttcgc
20041 gctcggcgcg gcgctgtccg acgagctgcg cgccaccgcc gccggcctgg gcgtctcgcc
20101 gttcgtgctc gggctgaccg cgttcgcgct ggcgctgggc gaggactcgc cgggcgcgat
20161 cggcgtggag gtggccaacc ggcgcctccgc cgagaccgcg gacctggtgg ggctgttcgt
20221 caaccacgtg ccggtgcggg tggcgccgac cggcaccggc cgggcggcgg tggcggcgt
20281 ggacgaggcc cgccggcgcg tcctgccgca cgagcacgtg ccgttcgacc tggtggtgga
20341 cctgctgggg cccggagggg cgccgacgag cgtggcgttc tcgcacctgg acgtgcgcgg
20401 gcactcgccg cggctggacg gcgtcaccgc caccgcctc accccgcccg acaacggcac
20461 cgccaagttc gacctcctgc tggaggtgct ggacaccgag cacgccctga ccggggcgtt
20521 cgagtaccgg cccgagcggt tcaccgccgc ccgcgtcgcg caggtccgca accactggga
20581 ggccgcgctg ctgacgctgc tggccgaccc ggacctgccg gtgacgcccg ccgacccgga
20641 tttcgcgtga tgtcgagggg gaacgacgtg ctgtcaacgg tcgatccggc ggcggagctg
20701 agcaccaccg ccgccgaggt cctggaacac gtggacgccg cggtggcggc gtacccggag
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces
capreolus*)

```
20761 gtgccgatcg cccgcgtgcg ggtcgaggtc gcgggcatcc cgcgcaccct gctgctgaag
20821 ctggagggcc gctcgccgtg gcggtccatc aagggccgca ccgcgctggg cctggtccgc
20881 tcgatcgcgc cgcgcatggc gtcgcgggac gtcacggtcg tggagtccac ctcgggcaac
20941 ctgggcgtgg cgctgtcggc gatctgccgc gacctgggcc tgccgttcgt ggccgtggtg
21001 gacctcaagc agtcgccggt gatccaggcg gcgatcgagg ccaacggcgc gcggctggag
21061 gtcgtgccgga cgccggcggc ggccaccacg cacctgctgg accggctgga ccgggtgcgc
21121 aagctggtcg ccgagatccc cggcgcggtg tggcccaacc agtacgagaa cgacgccaac
21181 cggcacgtgc acgagacgtg gaccgcgccg gagatcgacc gccaggtcgg cggcgaggcg
21241 caggcggtgt tcgtcgcggt gtccaccggg ggcacgctgg cgggcctggc cgcccacttc
21301 cgccgcgccc gcccggcgac gcgcctggtg gccgtggacg tcgagggctc gacggtgttc
21361 ggcggcgtgc ccggcgggcg cgtgctgacc ggcatcggcg cgagccgccg ctccaccttc
21421 ctgacccgcg ccgagtgcga cgacctggtg tacgtgcggg aggcggcggc gatcgccgcg
21481 tgccacgtgc tgcgcgccga caccgggatc gcggtcggcg ggtccagcgg cgcggtcgtc
21541 gcaggcgcgc tggaccacct cgccgcccac cccgggcgga ccaccgccgt gtgcgtgtgc
21601 gccgacctcg gcgagaacta cgccgcgcacg gtctacgacc ccgactggct ggcgccgctg
21661 cgcctcaccg acgacccecgg actcctgcgg tcccgcctgc gcggggcgcg cttccaccac
21721 gccgaaccgg acaccggaca ggagagcacc ccatgaccgc catccgcgag atccggctca
21781 gcgagccgga gtccgcgcag gccgcgctgc tcgcgctgga gtgcgcgcag cgctacgccg
21841 aacccgactc cgccgacttc ctcgccgacg ccgccgtgct ggcccacgac ctgccccggg
21901 cggtgcgccg ggaggtcgag cgcgcccgcc tggacgaccg gctgcacgcg ctggtcgtgc
21961 gcggcaacga cgtcgaccag gacgcgctcg gcccgacccc gccgcattgg cggcaggcgc
22021 gcaccgccgc gtcccgccgc tacggcttcc tcctggtgct ctacgcctcg ctgctcggcg
22081 acgtggtcgg ctgggccacc cagcaggacg gccgcgtggt gaccgacgtg ctgcccatcg
22141 aggggcagga ggactcgctg tcagcgctcca gcagcagcgt ggagctgggc tggcacaccg
22201 aggacgcgtt ctccccctac cgggccgact acgtgggcct gttctcgctg cgcaacccecg
22261 actcggtggc caccaccgtg gccgggctgg acccccgacct ggtcgggccg gccgtggtgg
22321 acgtgctgtt cggcgagcgc ttccacatcc gcccgacaa ctcccacctg cccacgcaca
22381 acagcggcgg ccggttgagc gactacttcg ccggcatcgt cgaggcggtg gagaacccgc
22441 gcgcggtgtc gatcctgcgc gggcaccgcg acgcgccgca gttgtgcgtg gacagcgact
22501 tcaccaccgc cgtggacggc gacgccgagg ccgcgggcgc gttggacacg ctcatcaagc
22561 acctcggccgg cgcgctgtac gagtggtgc tgggcccggg tgacgtgcg ttcctggaca
22621 accgcaacgt cgtgcacggc cgccgcccgt tccgggcccg gttcgacggc acggaccgct
22681 ggctcaagcg catcaacgtg accgcggacc tgcgcaagtc gcgggcggcg cggcgcgacg
22741 cccaggcgcg cgtgctgggt gaggcgtgat ggtgcgcgac ctgccggccg ccgcgctgga
22801 ggactggttg cgcgagcggt acttcaccgc ccgcgtggac gtctccagca gcggtgtggc
22861 cgaccaccgg ctggcggacc tgcggcggtt gggcgggatc ccgtcgagg agctcgacgc
22921 ggtggtgttc cgcgacgggc cgtcgctggg cgcggagcgg ctgcgggcgg cgctggcgga
22981 ccggctgcgg cccggacccg accacgtcgt gatgaccgcg cacgggtcca gcgaggcgtt
23041 gttcctggcg atgaccgcgc tggtgcggcc cggtgacgag gtggtggtgc ccgaccccgc
23101 ctaccactcg ctgtcggcgc tggcgcgggc gtgcgggcg gtgctgcggc cgtcgccggt
23161 gctgggcgcg gcacccgacc cggcggacct gcgggcgttg ttgacgccc gcacccggct
23221 ggtcgtggtg aacttcccgc acaaccccac cggggtgacc gtggacgcgg cggtgcaggc
23281 cgaactgctc gacgtggtcg ggcgcagcgg ggcgtacctg ttgtgggaca acgcgttccg
23341 cgacctggtc tacgacgcgc cgccgctgcc ggagccgacc gcgctgggcg ggcgggtgct
23401 gtccaccggc acgctgtcca aggcccacgg gctgcccggc ctgcgggtcg ggtggtgcgt
23461 gctgcccgcc gacctcgcgc cggagctggt ccgcgtccgg gactacctga cgctgagcct
23521 gtcgccgctg accgaactgc tcgccgcggt cgccgtggag cacgccgacg agctgatcgc
23581 gccccggctg gcggaggcga ccgccaaccg gcggcggctg ctggactggg ccgccgcgca
23641 cggcgtggac tgccccgcgc cggcggcgg ggtgaccgcg ttccccecggt tcccggggct
23701 ggccgacgtg acgccgctgt gcgaccggct gatgtccgaa cacggcgtcc tgaccgttcc
23761 gggcggttgt ttcggattcc ccgatcgaat gcggatcgga ttcggctgcg accccgcggt
23821 gttcgcggcc gggttgaccg cgctgggcgc cgtgctgggcg gaaaaacggt tgccggcaaa
23881 actgtgactg gttgactacg cagcgcaaca tcgccgttttc gagaggaatc accgtggcag
23941 ccatcgagaa cgcgccacgc aggctgcgcg acaacaggga cttccggttc tggtggggcg
24001 gcaccgtgct gtcggccatc ggcgacgagg tcacgctgat cgcgtttccc ctgctcgtgc
24061 tgttcctgac cgggtcgccg acgcacgcgg gctggtcgg cggcgtgggcg gccgtgccgc
24121 cgctgctgct gagcgtgccg atcggcgtgc tggccgaccg gacgtcccgg cgggcgctca
24181 tgctcggcgg ttcggtggtc agcgcgatct ccatcacgtc cattccggtc gtgcacctcc
24241 tgggtgaact cacccttccg catttgtacg tggtcgcatt tgtcaacagc gttgcggcga
24301 ccgtgtaccg gatcgccgac accgccgcgc tgccccggat cgcgggcgag gagaaactgg
24361 gcgaggcggc gtcccagagc gagacgatct gggcatctc ggccatcgtc gcgccgccgc
24421 tggccggtct gctgttcgag accgccggcc cgacctcgcc gttctggatc gacgccgtgt
24481 cgttcgtcgc gatcatggtg tgcgtcctgg cgatccgggc ccggctcggc gcggacaagc
24541 cctacccgga ggtgtcctgg cggcaggacc tcaccaccgg ccgcgcgctc acgttgagcc
24601 ggccgctggt gcgggccctg acgatcctga ccgtcgcggg cgacttcctg ttcgcgggca
24661 tcggcctgct gctgatcgtc atggtgcggg agaacggcgc gtcgggcctg gagaccggca
24721 cggtgttcac cgccgccgcg gtgggcggca tcctcggctc gatgctcgcc ggccgggtcg
24781 aaggaccggat cgggatggtc ccggccgtgc tgacccagca ctggctgacc gccgcgtcgt
24841 tcccgctgct gctggtggac ctgccccgct gggccaccgg gctggtctgg ggcctgatct
24901 cgttccagat ctcgatcctc aacgtgatcc agatgaagta cctgatgagc gtcatcccca
24961 acagcaagct cggccgcgtc gaggggttcc tgacgttcat cgagcagggc agcctgccgc
25021 tgggctacgc gctcaccggc gtgctgctgg gcctgctcgg caccacgtcc acgctgctgg
25081 cctacgaggc cgtgctgctg gtcctggccg tcttcgcgac ggtcagccgg ggcctgcgca
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces capreolus*)

```
25141  ccccgcgca  ccccgacgag  cccgccgat  catcgggctg  acgccaggag  agctgatgac
25201  ccaggtcgac  ttcaccggt  gggacctgcg  caccgacgcc  gagaagcacg  ccaccccgac
25261  cgtcctgagt  ggaccgccgc  cggcgtggtc  gccggacacc  acgttggcgc  ggctggtgct
25321  ggaccaggcc  gaccgcaccc  cggacgcgga  cgcggtccgc  atcggcccgg  acgccctgac
25381  ctaccgcgag  ttggccgccg  gcgcgcggcg  ggtcgcggcc  tgggtggccc  ggcagccgca
25441  caccgggccg  ccgcgcgtcg  gcgtgctcgg  cgagcggtcc  cttgcgacct  acccggtgct
25501  gctgggggtg  ctgctggcgg  gcggcgcgta  cgtccgctg  gaccggcgg  cgccgcccgc
25561  ccggctgcgc  gcggtgctgt  cccgggccga  cgcgcacgcc  gtggtgacga  ccgcggagag
25621  ctgggcgttg  ttggagcagc  cggggctgcc  cgcgctgctg  accgaccagc  cgctgccgtt
25681  ccagcggtcc  aaggtggaca  gcgggcgggt  cgcggtgctg  gcgggcctgc  ccgacgcggg
25741  cgagccggtc  gggccgacgc  cggacgacgt  ggcctacgtg  atcttcacgt  ccggttcgac
25801  cggcacgccc  aagggtgtgg  tggtgcagca  ccgggcggcg  gtgaacctga  cctgctgggc
25861  ccgcgacctg  gtgccgatgg  ggccgggcag  ccgggtcacc  cagaacgcgt  cgctgcactt
25921  cgacgcctcg  gtgcaacaga  tcttcccggc  gctggcctcg  ggggcgacgc  tgttcccggt
25981  gccggagcgg  gtgcgactgt  ccgggccgga  gctggccgcg  tggctggccc  ggcaccggat
26041  cacgcactgg  gactcggtgc  cctcgctgtg  gacgcccgtg  gtggagcacc  tggccgaccg
26101  gatcgccgcg  ggacaacggg  tgctgcccga  cctgcgggcc  gtgctgctgg  ccggcgagcc
26161  gctgccgcg  cggcaggtgg  accggtggcg  gtcgtgggag  caggggcacc  ggctgttcaa
26221  cgtctacggg  cccaccgagg  tgaccgtgaa  cgcgaccgcg  ttcgaggtga  ccgggccggt
26281  gggcgcggtg  gtgccgatcg  ggcggccgtt  gccggggatc  accgcgtccg  tgctggacgc
26341  gcacggcaac  ccctgcccgg  tggacgccga  cggtgagctg  ttcctgggcg  gggtggggct
26401  ggcgcgcggc  tacctggacg  acccggaggg  caccgcgcgg  tcgttcgtgg  agcgcggcgg
26461  cgagccggttc  taccggaccg  gtgacgtggt  gcgggtcggc  gcggacggcc  tgctggtgtt
26521  cgtgggccgc  cgggacgacc  aggtgaagct  caacggcgtc  cgcgtcgagc  cggccgagat
26581  cgagcacgcc  ctgctggcgc  accccggcgt  gaccgaggcg  gtggcggtgg  tgctgcgcga
26641  ggagggccgg  gcggagctgg  tggcctgcgt  ggcctcggcg  gtcgagctgt  ccacggagga
26701  catccgggcc  gggctggcgg  aagagctgcc  cggcgtcgc  gtgccgtcgc  gggtggtggt
26761  cgtggagtcg  ttgccgcaca  acgccaacgg  caagctggac  cgggccgcgt  gcgcggagct
26821  ggcgcgcgac  ctgtccggcc  cgtcgggcgg  cgccgggccg  ctcggggcga  cggcggcgac
26881  gctgctgggc  atctggcgga  gcgtgctggg  ccgtgacgac  atcggcccgg  acgacgagtt
26941  cttccaggtc  ggcggcaact  cgatcaccag  catccggctg  cgccgggagt  gcgtggaggc
27001  ggggttgccg  atccgggcgg  tggacgtgtt  cctgcaccg  accgtgcggc  ggctggcccg
27061  gtacgtggac  gacaaccgga  ccacgctggc  cgcccgcgcc  cgtcccgcgc  cggaggagtc
27121  gccgaccgac  ggcgagttcc  ccctgctgcc  cgcccaacgg  ccgctcgccc  tgacggcgct
27181  gctcagcgac  ggcggcgcgc  agcgcggtct  ggtgcaggag  accgtcacct  accgggtgcc
27241  gctggacgtg  gacgccgtgc  gcggcgcgct  ggaggtgctg  ctggagcggc  acgaagtgct
27301  gcggacggcg  gtcacccgg  ggctggcgca  gcgggtgctg  ccgaaggtgc  cggtgccgtt
27361  ggaggtggtg  gacctgaccg  gcgtggccga  ccagtggggt  gcggtgctgg  aggccgccga
27421  ccgggactac  gcgaccccgt  tcgacctggc  cgagccgccg  ctggtgcggg  tgcgggcgtt
27481  cgaccggggc  gaggtgttct  cgctgacctg  gaccctgcac  cacgtcatct  cggacgggtg
27541  gtcgtgggag  atcgtgcaac  gcgagttcga  ccggctgcac  gtggccctgc  gagcgggccg
27601  gttccgcccg  ctgccgcac  cggtgctgcc  cctgcgcgcg  ctggcccgcc  gctggggtc
27661  gggcgggacg  ccggacccgg  agtgggtggc  gcgcctggcc  gccacgcccg  ccctgctgct
27721  gcccgccgac  ggcagcggcg  tcggcggtga  gcacatcgag  tggccgatcg  accccgggac
27781  gcaccgcgag  ttggccgccc  gcgcgcaggc  cgcggaggcg  tcgccggccg  cgatccacct
27841  cctcgccttc  accgaggccc  tgcggcgggt  gtgccggcag  gactcgttcc  cgtcggcgt
27901  cgtgtcgtcg  ggccgcaacg  tggacgtgcc  gggcgtcgga  gaggccgtcg  cgtgcctggc
27961  ccggaccgtg  ccgctgccgg  tggacgccgt  gggcggcgcc  gaggcccgcc  tggcgcggct
28021  gcaccgcgac  ctcgccgtgg  tggtcggcat  ggacgacgtg  gacaccgacg  tgctcccggc
28081  cgacgtgccc  gccggcgtcc  gccaccggt  ggcgaccttc  gtcttccaga  actacccgga
28141  cgccgccgtg  ccgcccgcc  accggccgct  gcccgaggtg  cccgaggagg  gccgctggcg
28201  cgaggccggg  tccgacccgc  tggcgctggt  gtgcttcgag  gacgacgggc  tgccccggctg
28261  ccggctggag  ttcgacaccg  ccgcggtgtc  ccgggcgacc  gccgagctgg  tcgccaggga
28321  ggtccgccgg  gcccagaacc  gactcgcgaa  ggggatgcag  ccgtgaccgc  ggacgccgcg
28381  ctcgaacccg  acgaacgggc  cgcctggctg  gcctacaacg  acaccgccga  ggacttcccc
28441  ggcccgcacc  tgctcgcccg  cctcgacgcc  gtggccgcg  agcaccccga  ccgccccgcc
28501  gtgcacgccg  tcgacggcgt  gtggacctac  cgcgaactgc  accgccgcgc  cgaccgggtg
28561  gccgccttcc  tggccgcgcg  gggcgtccgg  ccgggttcgg  tggtggcgat  cgcggccacc
28621  cgcgcgctcg  ccccgtacgc  cgcgctgctc  ggcgtcctga  aggccgggtg  cgcctacgtg
28681  ccggtcaacc  cggacgaccc  cgccgaccgg  gtggcgttcg  tgctggccga  cgccggcgcc
28741  acgccgctgc  tgctggacac  cgaccggcg  agcctgcccg  ccgcgcccgc  gccggacgtg
28801  ccgcacgagc  cggaccgggt  ctgctacgtc  atctacacct  ccggcagcac  cggccgcccc
28861  aagggcgtgg  tgatggccga  acgcgccgtg  gacaacctca  cgcactgggt  ggtgcggcgg
28921  cacgacgtgc  gccccgacga  ccggctgggc  cagaccgcgc  gctgacgtt  cgacccgtcc
28981  gtgcaacagg  tcttcccgc  ctgggcgacc  ggcgcgtgcc  tggtcaccgt  gcccgacgac
29041  gtccagcgcg  acccggccgc  cttcctggac  tggctgcgcg  ccgagccgt  cacccacctg
29101  gacctggtga  cctcgcactg  ggtccacctg  ctcaacgccg  ccgaggcgcg  cccggcggag
29161  ctgccggacc  tgctgcggat  catcatcggc  ggcgagacgt  actactacca  ccagaccac
29221  cgctggcacc  gggtcgtgtc  ctcccccgcg  ccgctgaaca  cgatctacgg  ccccaccgag
29281  gcggccgtca  acgccaccga  gcacctcacc  gaacccgacc  tggaccacgg  ccaggtgccc
29341  atcggcgtcc  cgctgcccaa  ctaccgcctc  tacgcctgg  acgacgacgg  cggctgtgc
29401  ccgccgggca  tcaccggcga  gatccacatc  gccggcgccg  gcctcgcgcg  cggctaccgg
29461  tccgccgagg  ccaccgcgaa  ggcgttccac  gagctggaag  tccacagtgg  acggaccgag
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces capreolus*)

```
29521  cggctgtacc ggaccggcga cctcgcccgg ctggtgcgcc acgccgaccg gtgggcgctg
29581  gagttccagg gccgggtgga cagccaggtc aagatctccg gctaccgcgt cgagctggag
29641  gaggtggacg cggcggtcaa ggccgtgccg ggcgtgcggg acgcggccgt cgtggtgcgc
29701  ggcgaaccgg ccgagcagct cgtgtgctgc tacgtcggcg acgtgccgcc ggaccggctg
29761  cggtcgcgcc tgaccgagcg gttgcccgcc tacctggtgc cgcacctgct ggtgccggtg
29821  gaggcgttgc cgttcacccg caacgggaag atggacaccg ccgagctggc cgagctggtg
29881  cggcggttcg cgcgcgactc cgccggccgc gcgccgcgcc ccggcgtgga gtccgtggtc
29941  gcggcggtgt gggccgaggt gctggacctg ccggaggtgt cggcggacgc ggacttcctg
30001  ggccacggcg ggtcgtcgct gctggcgttc cgggtcgtgg accggctgcg ccggcgcggg
30061  atccgggtgc ggccggccga cgtgctgcgc gagcgcacgg tcgcgggcct ggccgccgtc
30121  gccgaagagg acctggtgct gacgccctcg acgcggctgg cgctgcgccg gccgggcggc
30181  aacgccaccc tcgacatcgg cctccccgcc gacgtgcccg ccgaacgggg ccgcgccgtg
30241  ctgaggacac tcgtgcggcg gcacccccgtg ctgcgcgccc ggatcgacga cgacggcccg
30301  cgcgcggtgc cggtggaccg gttcgagctg cacacccccg acggcccggt ggacgacgcc
30361  aaggcccggc tcgccgagtc caccgacctg acgaccgggc tgcccacggc agccgcgctg
30421  gtggcgggcc ggctgctggt gtcgatccgg cacgaactgg tcgacggcgc ggcgctgcgc
30481  cgggtcgccg aggaggtcgc ggccggcctg ggtcgcgcgc gcggccccc cccggtcgtg
30541  cccgtggccg accagccgct gggcggaccg gcccccggacg ggctgcgcgg gcacctggtc
30601  cgcttccttg aggccgagaa ggccgcgttg gccgcgctgc cgcgcgagca ccgcgaccgg
30661  gtggtggagg tggacctggg gcacgcgccc gacgcgctgc tggacacccc gccgacccgg
30721  tggcacgccc gcctggtcgc cgccgccgcg acggccgcgc ggtcctggct ggggctggtc
30781  gacgtgccgg tgggcgtgcc ccggcactgg ccgggcgcgg gcgggtcggt cgcgaacctg
30841  gccgacgtgc tgccccttggt cgtcgcggac gacgacgagg ccgacgcgca gtggcgggcg
30901  ttcgccgacc cggccgtgca ctggggcgcg gcgctgctgg acgcctgccc cgacctcgcc
30961  gacgactggc ccgcgccccg gatcgcgccg cagggctcgt tccggctcgt ggtgaccgcc
31021  gacgacgaac cgctcgcgcc cgacctcccg ctgcacgaga gcccgaccgc gttcgacccg
31081  gcgtcggcgg gcgcggtgga gttcgcggtc gtcgcgggcg accgcctgcg gctgcacgtc
31141  accggctggg acctgcccgc cgacgaggtc aaggccgtgg ccgccggctg ggtcgaggcg
31201  ttggcgggtg agcggcggtg acgccggacc cgcactggct gcgcccggtg ggcgggcggt
31261  ccggcggccc ggtgctgctg tgcctgccgc acgcgggcgc cggcgccttc gcctacgccg
31321  gctgggaccg gcaggacgcg ttcgacgtcg tggccgtgca accgcccggc cggggaggacc
31381  ggttcgccga gcagccgatc accgaccccg agcacctcgt ccgcgagatc gccgacgcgc
31441  tgggcgacct cgccgagcag ccgctggcgc tgttcgggca cagcctgggc gcgctgatcg
31501  cccacgacct ggcccgcgag ctggaccgcc ggggcgcgcc cgacccgctg ctgctcgcgg
31561  tgtccgggca cgtgccgccg caccggctcg accccgaccg ggcgcgcgac cggtccgacg
31621  ccgaactggt cgagcacgtc cgcgaactcg acgacgaccc cctgacgac gtgctggccg
31681  acccggagtg gcgcgcgatg ctgctgcgcc cgctgcgcgg cgacctggcc ctgcacgacg
31741  cccacaccca ccgccccggc ccccggctgc gcgtgcccgt gctcgcgctg accggcgcgg
31801  acgacgacgc caccccggcc gaggacacgg cggcgtgggc ggagctgacc gagggccccct
31861  tcgcccaccg ggtccacccc ggcgggcact tctacctccg cgccgccagg tcggccgtcc
31921  tcgacgacct cgcgcaccac ctcgaaggag cgtggcgacc atgaccaccg agaccccagc
31981  gaccaccggc gccccggcga ccaccggcgc ccccgccccca ccgggccggg ccgagatcgt
32041  cgccgccgtg ctgccggtat tcgccgaggt gctcgacgcg cggacctca cccccgacag
32101  cgacttcttc gtccacggcg gcaactcgct gctggccatc cgggtcgccg ggcgggtggg
32161  ccgcaggctg gccggcaggt tccgcccgcg cggcgtgctc aagcaccccga ccccggacct
32221  gctggccgcc cacctggagg aggagttccg cggcggcggc gcgccgccga tccccgcgcc
32281  gcgcgccggg gcggaggccg accgccggcc gtccaccgcc caggaacggg tgtggctgct
32341  gcaccagctc gaccccgacc ggctcgacca cctggtcacc gtggcgctgg acgtggccgg
32401  gacggtggac ccggcggcgt tcaccgcggc gtggaccgcg gtcgtgcgcc ggcacgaggc
32461  gctgcgcagc cggttcgtca aggccgacga cgaccgggtc gcggtcgtcg tggacgccga
32521  ggccgcgccg gagatcagcg tgctggacct cgcccgcttc cccgcccggg tgcgcgaccg
32581  gctcgcggag aacgggtcc ggctcctgcg caccaccccg atccggctgg acaccggccc
32641  gctcgcccgg ttcgcgctgc tgcgcctggc cgaccggcgg taccggatcg agctggccgt
32701  gcaccacatc gtgtgcgacg gctggagcct ggacaccctg ctcgccgact tcctcgacgc
32761  ctacgccgc gcgctggcgg gccgctcccc cgccgctgccg ccgccggcgg tgggcttcgc
32821  cgactacgtg gcgtgggagc gggacgtgga gtcctcgcgg tggccggaca tggccgtgcg
32881  gctggcccgc cggttcgccg accggcccgc cgacctgccg ctgccggtgg accggtgga
32941  cgtgccggcg cacgaggacg gcgacgacgt gaccgtgcac gccccgcccg gcctcgcggc
33001  ggcggtggag cgggcccgga cctccttcgg gcacaccgcg ctgacgttcc acctgaccgc
33061  gctgggcgtc ctgctcgccc ggatcaccgg ggtggacgac ctggtggtgg cggtgccggt
33121  cgcggggccgc gcgcagaccg agcacgagga cctggtgggg ctgttcgtca acacgcccct
33181  ggcgcgggtg cggctgggcg gcacctcgga cgtgcgggtg ctgctggagc gcaaccgcga
33241  cgaggtggac gagctggtgg actgccagac cttcccgttc gaccgcctgg tggacctgct
33301  cggccgccgc cgcgcgggca ccagggtgcc gctggcccgg gtgtcgctgg cggtgcagaa
33361  cttcgacgac cccgcacgc ccgcgcccga gctgggcttc acctggcagt tccgcgaccc
33421  gccggagcgg cagagcaagt tcgacctggc cttcaccgtc tccgacaccg acggcctgcg
33481  gttgacggtc acctaccggc cgtcgctgtt ccgccgggcc accgtcgccg cgtgggccgg
33541  ccagtacctc gtggcgctgg agcacgtcgt ggccgaccgg gccgaccccgg agggagcgc
33601  gcggtgaagc tcaaccggca gcacgagttg ttccgcgagt ccgtgcggat ggtgctcgac
33661  cgcgagtgcg tcgagctggt cgacgactgg gagcgcgacg gcgtcatgcc cgtgcaccag
33721  ctgtgcaaga ccctggccgc cgaaggggctg ctgggcctga ccatgccggt ggaggacggc
33781  gggctggggcc tggacctggg ctactcctac gtgtgggcgc aggagctggg ccgcgtcccg
33841  gccggcgcgc ccgcgatggc gctgtccgtg cagaccgaca tcgtcgcgcc gctgctggcc
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces
capreolus*)

```
33901  cgcgccggca cgcccgaggt gcgccgggac gtgctgcggc cggccatccg gggcgagctg
33961  gtggcggcgc tggccggcgac cgagccggcg ggcgggtccg acctgggcgc gctcaccacc
34021  accgccgtgc gcaccgagcg cggcttcacc gtcaacggca ccaaggcgtt catcaccaac
34081  gggtcggtcg cggacttcgc cgtggtgctg tgccgcaccg gcgaggcggc cggcatcggc
34141  gacctggcgc tgctggtggt gccgaccaac ctggccgggg tgcggcaggt ccgccacacc
34201  ggcaagctcg gccaccgctc gtgcgaccac ggcacgctga ccttcaccga cgtggaggtg
34261  cccgcggcct acctgctggg cgaggtcggc gagggctacg agctgcagac ccgcacgttc
34321  acccgggagc gctgcttcct ggccgtggtc gcgctcggcc aggccgaacg ggtgctgcgc
34381  gcgaccgtgc accacgcgcg ccgccgccgc gtcctgggcc gcgcgctgac cgaccaccag
34441  gcgatcgggt tccggctcgc cgaactcgac gccgaactcg acctcgtgcg cagctacgcg
34501  ggcgaggcct accaactgct cgccgacggc gcgcagtgcc tgcgcgaggc cagcatcgcc
34561  aagctgcgcg ccacccgcct gctgcgcgag gtcgccgacg tcgggctcca ggtccggggc
34621  gcggcgggct acctgggcgt ggacgacgtc gagcgcacct accgcgacgc ccgcgcgggc
34681  agcttcgcgg gcggcgcgga cgaagcgctg ctgcacctca tcgcggggcca cctgaccggc
34741  accgaacagg agtgaccatg acgccgagcg aagaactgct gttcctggac cgcgagaccg
34801  tgcgggcctg cgtcgcgggc gtggaccccg tcgaggtggt cgagtccgtg ctgcgcagcc
34861  acgccgccgg ccgcaccacc ctgcccgccg agggctacct gccgtgggag aacgaccagg
34921  gcgcgtactg ccggtccatc gccatgctgg gcgcggtgga cggcgaacgc ggccccacct
34981  acggcatcaa gctgatcaac gccgccgtct ccaacccctc gatcggcctg gaccgggccg
35041  gcggctgcgg gttcctgttc gacccgcgga ccgcccggcc cgtggtgctg gcggaggcgg
35101  cctacctgtc gggactgcgc accgccgcct acacgatggc gagcctgcgc cacctggggc
35161  cggtggggtt cgacgcggtg agcttcatcg gcacggggc gcaggcgcgc gtgcacgccg
35221  cgctgctggc ccgctacttc ccggccgtgc gggacctgca cgtgttcgac accgagcgct
35281  ccagggccga ggcgttcacc ggcgcgtccg ggcacaccgt gcacgtcac gacaccgccg
35341  aggccgccgt gcgcgcgagt cacgtcctgg tcaccctgac caccgtcgac gacgggtaca
35401  tcccgcacga ctggttccgg cccgggtcgt tcgtcgcgca cgtgtcgctg gacgacctgc
35461  tgcccgaggt gttcttcaag tccgaggcgc tgttcgtgga cgacctggag ctgatccggg
35521  agaacccgcg ccgggtgctg ggcgcgctgc tggccgacgg cgacgtcccg gtcaccgggt
35581  cgctgggcgg ggtgctgacc ggggcggtgg ccccggtgcg gccccgggac ggggtggtgg
35641  tcagcaaccc gttcggcatg gccgtgctgg acgtgggcct gctggcggag gtcgccgcgc
35701  acgcccgctc cgccgggctg ggcacgaccc tcgacctgct gggcgcggcc cgatgaccgg
35761  cctgtactcg ctggcggacc tgtccccggc ggacgtcctc gcctggcgg accggtcggt
35821  gcagctgcac cgcgaccgga ccgcgcacga ccgcccgctg accgacctgg tggtgggcac
35881  cctgttcacc aagacctcca cccgcaccag gaccgcgttc accacggcgg cgctgcggct
35941  gggcgcgtcg gtggtcgcgt tcggcccgga cgagctgcag accgccaccg gcgagtccac
36001  cgcggacacc ggccgggtcc tggcgtccat gctggacggg ctggtcgtgc gcaccgccgg
36061  gccggtcgcg cggcaacggg agttgtccgg cggcggcgtg ctgccggtgg tcaacgccat
36121  gagccgcgag gagcacccca cccaggggcct gaccgacctc gcggtgctgc gccaccactt
36181  cggcgacctg gcgggcgtgc gggtgctgta cgtgggcgag ggcaacaaca ccgccgccgc
36241  cctggtgcac gcgctggccg ccgtcccggg ctgcgagctg gtgctggcct gccccaaggg
36301  ctacggggccg cgcgaccccg gcccgtggcg ggaggtcgcg gacctgccgg aggtcaccgg
36361  ggacgtggac gtcgtctaca ccacccggtg gcagaccacc ggcacggcca aggccgaccc
36421  ggactggcgc gaggcgttcc ggccttcca cgtggacacc gcgctgatgg accggtggcc
36481  ggacgcggtg ttcctgcacg acctgcccgc ccaccggggc gaggaggtgg ccggcgcggt
36541  gctggacggc gcgcggtcgc tggcctggac gcaggccgcg atgaaggcgg cgagcgcgat
36601  ggcggtgctg gagcggttcg tcgggggtcg tcgtgcttga cctctccccc gcgcagcgca
36661  gcctgtgggt gctgcaccaa ctggacgaca ccgggttcac gctgtcgtcg gcgcaccggc
36721  tgcgcgggcc gttcgacctc ggcgcgttca cggcggcggt ggacggggtg gtggcccggc
36781  actcgccgtt gcgcaccccg ttcccggtcg ggacggacgg cgggcccgac cccgtggtgg
36841  acccgccggg gccggtggtg gtcgaggcgg tcgcggcgga ggggttcacg gccgcgcacg
36901  ccgaagccgc gcggttctgc gcccggccgt tcgacctggc gcgggagtgg ccgctacggg
36961  tgctcgtggt gcgtctgtcc acagaggacc atgtggtgac gttggcggtg caccacatct
37021  cctgtgacgg cgtgtcgctg gggctgttgc acgacgagct gtcccggctc tacgacgtg
37081  cggagctgcc gccggtcgcc gaccaccggg agctggtggc tcggcgcgcg gtgacccggg
37141  cggcggtggc ccggtgccgg gaccggctgg cgggcgtgcc gccgctggcc gccgaccggc
37201  ccgcggtgcg gtcgggcaag ggcgaccagg tgtggttcac cgtgcccgcc gacctgaccg
37261  gcgcggtgcg ggcgtgcgcg cggcggcacc gcgtcaccgc gttcatggtg ttgctggccg
37321  cgttccagct cgtcctgcac cggcggaccg gcagaccga cttcgccgtc ggcgtgccgg
37381  tggccgggcg cggcgacccg gacagcgaga cgtcatcgg cctgttcacc aacaccgtcg
37441  tggtgccgggc cgacctggcc ggcgagccgg gcccggcgga ggtgctgcgc cgggtgcggg
37501  aggccgcgtt cgacgcgttc gccgaccagg acgtcccgct gggcgcggtg gtggcggccg
37561  tgggcgaacc gcccgacccg gcgcgcaccc cgttgttcca ggccctgttc accttccagg
37621  acgcgccggt cgggcggctg gcgctgcccg gcgtgcggtg cgtggaactg gacctgccca
37681  ccggccgccgc cgcctccgac ctggagctgg agctggtgcg cgacggcgag gagctgaccg
37741  ggtccctgga gtactcgacc gacctgcacg acagcggcac ggccgcggcc ctgaccgccg
37801  acttcctggc cgtgctggac gagatcaccg cggaataggg ggaaacgtgg acacgtacct
37861  ggtggtcgtc aaccacgagg agcagtactc ggtgtggccg gccgaccggc cgctgcccgc
37921  cgggtggcgt gccgagggca cgtccggcga caaggagcag tgcctcgcga acatcgagac
37981  cgtgtggacc gacatgcgcc cgctcagcgt gcgccgccgc gcggaggcgg tgtgaccgcg
38041  ctgcaccgcc tcgaccagct cgccggcgcg cggcccgacg cgccggcgtt gctggacgag
38101  gcggagacgg tgtcctacgg cggctgtgg cgcgagctga ccggcgtggc gggcgcgttg
38161  cggcggcgg gcgtgcgcg cggggaccgg gtggtggtgc cggcggaccg gacgtggcag
38221  ggcatcgtgt cgatgctcgg tgtgctgcgg gcggggggcgg cgtacgtgcc ggtggacgcc
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces
capreolus*)

```
38281 ggcgacccgg tcgagcggtt gcggcacgtc gtgcggacgg cgggcgcggc gtgggtgacc
38341 gggcgggcgg aggcgctggc ggcgttgccg gacctgggcc tgcacccgat cccgttcggc
38401 tcggcccccag actcggcctc acgctcggcc tcaggctcgg actcgggttc gcactcggct
38461 tccggaggcg tcggcgggtt gcccgatccg gaggacttgg cgtacgtgat gttcacctcc
38521 gggtccacgg gcacggcgaa ggcggtcatg gtgccgcacc ggtcgatcgc gcacgccgcc
38581 ccgtcgctgg cgcggcggtc cgggatcacg ccggacgacc ggttcctgag ctgggcgtcg
38641 ctcgtgtggg acaccagcgg cgaggagctg tactcgacgc tgctgtccgg cgcgggcctg
38701 gtgctcgacc gcgaggccac ctccgggtcg gtcccggcgc tgctgcgcgc ggtcgaacgc
38761 cggtcggtgt cggtcgtgga cctgccgacc gcgttctgga accaggtggt cgactacctg
38821 gagacgaccg gcgaggcggt gccggagtgc ctgcggctgg tcgtcgtggg cggcgaggag
38881 gtgcgggcgc ggcaggtgcg ggtctgggcc gagcgcgcgc cggacgtccg gctgctcaac
38941 acctacgggc agaccgagac cgtcatggtc acccacgcgg ccgacatcgg cggtctcgcg
39001 ccgccggacg ggggcgcggt gccgatcggg cacccgctgc cgcacgtccg ccagcacctc
39061 gaaccggtcg gcgacggcct gttcgagctg cacgtcggcg gtcccaccct cgcgtggggc
39121 taccgggacc ggcccgcggc gaccgccgag cggttcccgc ccgacgagcg cgggcggcgg
39181 ttccgcaccg gggacctggt gcgggtggcc gacgacggcg cactggtgtt cgtgggtcgg
39241 gcggaccggc aggtcaaggt gcgcggggtg cgggtcgagc cggccgaggt ggaacgcgcg
39301 ctcatggcgt gccccgggat gaccgcgcg gcggcgttcg tggtggacaa cgcgtcggac
39361 ggcgtcctgc tggtcggcgc gttcgtgccc ggcgacggcg acgccacgcc cgcgacggtc
39421 gcggcggccc tgcgcaccag gttgtcgccc gcgctgctgc cgcaccgcct ggtgtccgtg
39481 cccagcatgc cgctgctcac cacgggcaag atcgaccagg ccgcgctggt ggagcggttc
39541 gcgcggtccg acgtcgcgcc gggcgccggc ctggcggggc agctcgcggt ggtgttcagc
39601 gaagtcctgg gcacgccgtg cgcggccgac gacgacttct tcgaccaggg cggtgactcc
39661 gtggtcgcga cccggctgct gacgcgcatc cggcgcagct accgggtgga gctgacgttc
39721 cgcgacgtgt tcgaccaccc gagcccgacc gcgttggcgg gcctgatcag ccggacccccg
39781 aggtgagcgc ggtgcccgtc cagccgcacg agcacgtccg gcgcacgccg gtggagccgt
39841 cctggcggcg gttccccggc tggcgggacg gcagtgggcg gacccgcggt
39901 ggcagcgcgt gcactgcgtc cggaacaccc ggcagttgcg cgcggtcgtc ggtgacctgc
39961 tcgacgagcg gttctacgac gacctggcgg ccgaccagga gtcgttcgcc acgatgtcga
40021 tgctgctgcc cccgcagatg ctcaacacga tggtgcccga gggggcggcg gacttcaccg
40081 gggcgttcta cgccgacccg gtgcgccggt acatgctgcc ggtgcggtcc gaccgcgacc
40141 ccgagtggcc gagccacccg tactcgtcac gggactcgtt gcacgaggcc gagatgtggg
40201 tggtggaggg cctgacccac cggtacccga cgaaggtgct ggcggagctg gtgtccacgt
40261 gcccccagta ctgcgggcac tgcacgcgga tggacctggt cggcaactcg accccgcagg
40321 tgcgcaagca caagctggag ctcaaaccgg tggaccggca ggaccggatg ctggactacc
40381 tgcgccggac gccggccgtg cgggacgtgg tggtctccgg cggtgacgtg gcgaacgtgc
40441 cgtggccgca actggagtcg ttcctggccgc ggctgctgga gatcgagacc gtgcgcgaca
40501 tccggttggc caccaaggcg ctcgccggcc tgccccagca ctggctccaa ccgcaggtgg
40561 tggagggcat gtcccgcgtc gcccgcacgg ccgcgagccg gggcgtgaac ctggccgtgc
40621 acacgcacgt gaaccacgcc cagtccgtga cgccgttggt ggccgagggc gcgcgggcgc
40681 tgctggacgc gggggtgcgg gacgtgcgca accagggcgt gctgatgagg ggcgtgaacg
40741 cgacgccgga cgacctgctg gagctgtgct tcgcgttgca gggcgaggcg aacatcctgc
40801 cgtactactt ctacctgtgc gacatgatcc cgaacgccga gcactggcgg acgtcggtgg
40861 ccgaggcgca ggacctgcag gcggcgatca tgggttactt acccggctac gcgacgccgc
40921 gcatcgtgtg cgacgtgccg tacgtgggga agcggtgggt gcaccaggtg gtcgagtacg
40981 accgcgagct gggcgtctcg tactggacga agaactaccg gacgggtatc gaatcagacg
41041 acccgaacgc cctggaccgc cggtacccct actacgacc gatctccacg ttgggcgaga
41101 cggggccggcg gtggtggcgc aaacacgaac gagcctgacc cgcacgcgcc ccgacggctc
41161 aacggtcgtc ggggcgcggc accggcacgg gcgggcgcgg ggtgggccgg cctggcgtgc
41221 gcgggcctgc ggcgagtgtg ggcgtgcggg tgggctatgg cggagcggtg gactcagcgg
41281 taggcggtca ggccgtcttc cagttcttcg tcgtcgccgt cctcggcacc cgccagcgcc
41341 tgctgcaacg cgaacgtccc ctggtaagcc cggatccggg gccacaggtc ccccgccccg
41401 agcagcgcga ccacccgctc caccagctca ggcccataac tggccccccac cgccgccagg
41461 tcctccgccg ggtcgcccac cttggcctcg tccagtccca cgatcccggt cagccgcggc
41521 agctcctcga cctgctgcca caacacgttc tccccgccga gatccccgtg caccaacccg
41581 gtggcgacgt ggtccatcgc cacggccgcc gccaactcgc gctcggccgc cgcccgggccg
41641 tcctccgaca tcagcgggaa cagcgtcgcc cggacccgcc ggcgaaccc gcgccaccgc
41701 ccggcgtcgg cgaccggcag caccagccgc aacttctcca catcagcgcc ggccatcgcc
41761 cgcaacaccc gcgcgaactc ggcgccacg acgtcgatca cctcgggcga cgtcgcgtcc
41821 cccgctcca acggcgtgcc ggcgacccgg ctgacccacca ggaaccgtg cggaccgccg
41881 tcccgcacct ccgacagcgg aaccggcacc cccaccccca gctccaccgc gtcgaccgcc
41941 gtcagcaccg ccacccgacc cggcagctcc gccgccgcgc cagccgtctt gggaaaccgg
42001 aacacccgt cacgcgcgat caacacgtcc tggaactggc cggagtgcac accggcaccc
42061 tcaagatcga catccggtg ggcacgccga accacgtcaa caaggtggga caaggtcatg
42121 ccccacata gtgccgaccc accgaagcca ccgcgaccga tttatctcac ggtccgcacc
42181 cgtccacta ctcagtgaaa tcccttacaa cgatcgggtg aatcgccgca cagcacccga
42241 accgaaccca cgcccgcgca cgaaccactg gagccgtccg gcgcacggcc gaatcgtgcg
42301 ccggacgggc ctgcgcgtgc cgccgtttag agttccgtag tgggaatgg cgagcggatc
42361 ggggtgttct acgacggcac ctggttcgcg tatttgagcg actacttcgc gtccgtgcac
42421 ccgcgggccg cccggggtctc gctggacggg ttccacgacg ccctgcgctg gtacgtgcac
42481 accgtcaccc accagccgtt ggacgagtgc gtggtcagtg aggcgcatta cgtccgcggc
42541 cggatcgaca cgccggcggt ggcgttcgac gccgtgttgg cggcggccgg ggtggtgcgg
42601 cacgacctgc cgctgcacgc gggcaaggag aagggggtgg acgtccacct cgcgctggag
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces
capreolus*)

```
42661 gcctgggagc gggccacctc cgtgccgttg cggtgggtcg tgctggtgac cggcgacgcg
42721 gacttcgcac ccctcgccac ccgcctcaag acacgcggcg tccgggtcgt ggtgccggtc
42781 gtggacggcg gggtcgtcgc gccggcgtgg atgccgcgca cggcggcgcc gctgcgcgcg
42841 gcggcgtcgg ccacgcccac gttcgacgac ctgttcacac ccgcggaacg cgacgactac
42901 ccgctgcggg cgccgttcgt gcggacctcc gggggcggcg cgtccgtcgc cggcgaaccc
42961 cgcggccggc gcaagggcac cgtcaccggg tggaaaacgg gccagccgca cgggttcatc
43021 accgacacgc gcggcgcgtc ctggttcgtc tcgcgcgacg acctcccgct ggggctggtg
43081 gccctgccgg tcggcacgtc cgtgtcgttc tccggcccgt ccactccccc ggccggacgc
43141 aagtacccgc gggcgtacgc ggtgcagacg gagtgatcag cccttcttga acagcagctt
43201 ccacggcatg accgcggact ccaactgcac cccgaagctc atcttggacg cgccctccgc
43261 ccgctcctcg aaccggatcg gcacctcggc gatgcgcatc ccgcgcttga ccacgcggtg
43321 gttcatctcg acctggaagg cgtaccgtt gctgcggatc gagccgacgt cgatcctgcg
43381 gagcgtcgcg gcgcgccagc acttgaagcc ggcggtggcg tccttgacgc gcagccgcag
43441 gatcgcgttg acgtagacgt tggcccacag ggaaagcgcc ttgcggtgcc acttccactc
43501 gccggacacc gaccccgccgg gcacgtaacg cgaaccgatg acgaccgccg cgtccgacgt
43561 ccgcagcacc tcgatcatcg tcgggatggc gctcgccggg tcgacaggt cggcgtccat
43621 ctggacgacc aggtcggcgc cgtcgtccag ggcttcagg atccccgcga cgtacgcgcg
43681 cccgaggccg tccttctccg tgccggtgcaa cacggaaagc ggaagcgggc cttcgagcgc
43741 caacttgtcc gcgaggtcgc cggtgccgtc gggggaattg tcgtcgacca ccaggacgtg
43801 caggcccggc acacccaggt cggcgagcag gtcgaccagg acgggcaggt tgtcccgctc
43861 gttgtaggtc ggcacgacga cggtggtcct gagcgagtcc ggttgtttcg acattccccc
43921 gagcttaccc gcgcgcggac gccgggaagt gcgcgaccgc ctcagtcgtg ccaggggagt
43981 tcgtcacgta gtccggtgtg gatcgcataa gcgttcttga tggcggctt caccgagcct
44041 tccgcccaac gccggtgccg gcggtcacag gcgtcgttgg cgaaccacac ccggttcacc
44101 gggcggatcc ctttagtgag ggttaattgc ggccgcgaat t
```

SEQ ID NO:2-CmnA amino acid sequence

```
MTVDPTIELRLTLNGDPDVPALTRAWAALRARHRALAGPLGAHRDVAAFEDAVRAGPGCHLLRAPGRHEFA
LTAGCDAASVPAVLAELSALYARELGHPSEGLPAPAPAVPHDRPPHDVPPPGPELPGLELFGRGEPGPRVV
TRVDLGHPTRRHVSALARRHGVTREVVVVTAWALLLGELAERDEFVLGLVTDPRDPAAHRPAVGALREARP
LRVDLTGRPSFADAVRRTTAAVATARSRPGDAPADVAVQYGEQPAAALRLAGLDPAEVPAAFWLADDLPGP
HRVVLRLLDTPDGLLAGVAHHPDALDGPGARRWVSRLAALLAGAHDESPEPVVMSEDEHRRVVLAPNATAV
DLGAPATVHDLVAEQARRTPDRTALVFAGAEVGYAELDARANRLAHELRERGVRRETPVAVCLERETGLVV
ALLAVLKAGGAPVPLDPQYPRQRLAHMLADSGAAVVLTQGRLGRDFPAADGPVPVLVTDDDATRFAHHPSSAP
PASSGPDDLAYVVYTSGSTGRPKGVMVEHRGIASYLRGMQHDFPLTPEDRVLQATSLSFDVSVYEIFWPLQ
VGAAVVLPAPGGHTDPYHLSELIQRHGVTCLHFVPSLMRLFVEEADPGAGAGLRRVFVSGEALDPSLVALV
HERTSAELVNLYGATEVSVDSTYWTADRAKPDRPVLVGRPMANATAYVLDQRLRPKPAGVVGEVFLGGASV
TRGYHARPALTAERFVPDPFGPPGSRLYRTGDLGRVTPDGELEFLGRRDHQFKLRGWRVEAGEIEAAITAH
PGVNGAVVVTEGAHEHATLLAYVGADAGLDQAALREFLLARRLPRPLVPARFIRLDRLPISPNGKVDRAALP
KPDQAPAEPAPTTAAPPTHAADGRPALEHAADGRPALERGSDGRPVLEVVLAVAAEVLGAPIGPEDSFFGS
GGNSIQATRLAARLRAALRTDVPVRLAFEAPTPAAMAALLSPPSPEPVAEVSRAEQRIWLLSRLGGHPAEY
AIPVALRLAGPLDVAKLKNAVDAVVRRHEGLRHVFPEVDGSPTRAVLDPGSITVAEEANRSVREVLAEGVA
ALDPATGPLARFTLVNQGPQDHVLAIVLHHLIADGWSVDVLLRDIAAHYTGAPTATPGRYADYLALERAEE
QDGALGRALEHFVTALDGVPDEVSFPPDHPRPAQRTGRGDVVRHRIDAAPVTALAERLRTTPFAVLLAAVG
VLLHRVGGHRDVVVGTAVARRPDAGLDHLVGLCLNTLALRWPVQPHDTLGEVVRAVTDRLADGLQHDAASF
DRVVDKLAPARDSGRTPVFQVMALYEEPYETALALPDVTTTDVTVHCGSAQADAAFGFVPREGGIDLTLQF
STDVFTRATASRWARRLATLLAGARADTRVADLPLLPEDESQDLERWSGTTGEAPTTTLHALAHEIAQRHP
DRPAIHFGQNSLTYGEFDARSAQLAHELRARGVRAETPVVVCLERSPEALIAVYGVLKAGGAYVPVETSNP
DLRIAELIADSGAALVLTQRRLADRLAALGAEVVVVDEPLPRHPTTDPEPLTGPDHLAYVIYTSGSTGRPK
GVMVQHGSVLNFLDALDRRFDLTPDDRLLHKSPLAFDVSVREVFWALTRGASVVVAEPGRHADPGHLVDLV
ERERVTVAHFVPSSLAVFLEGLPGPGRCPTLRHVLTSGETLPVTTARAARDLLGARLRNMYGPTETTVEMT
DHDVVDDTVDRLPIGHPFEGAVVRVLDADLRPVPPGSTGELCVGGLPVARGYLGRPALTAERFVPDPLGPA
GARLYRTGDLARLLPDGQLDFLGRNDFQVKVRGHRIEPGEVEAVLGALPGVHGALVTAHDDRLIGYAVTDR
DGEELRTALAERLPEHLVPSVVLTLDRFPLTGNGKLDRAALPTPTGRHTGDSRPLTATEAALAAIWRDLLD
VPEVRADDHFFALGGHSLLAARVAARAGAALGVALPLPTVLRFPRLADLATAVDGTRADREPVRPRPDRRR
RAPLSSAQRRLWIEENLRPGTATYTVAEAFRLRGELDEEAFAAAVDDVLRRHDALRAHVESVEDGEPELVV
APEPRTALRVGDLPADRVRDALAAESARVFDPAGPLVATSLHRLAPDEWLFQFTAHHLVVDGWSLDVLWRD
LAACYHDRRAGRAPRPRDGLTFTDYTWWERDVRSRDLEPHLAFWRGELAGLRPQPPADAHGPGAVLDFALG
AALSDELRATAAGLGVSPFVLGLTAFALALGEDSPGAIGVEVANRASAETADLVGLFVNHVPVRVAPRGTG
RAAVAAVDEARRRVLPHEHVPFDLVVDLLGPGRAPTSVAFSHLDVRGHSPRLDGVTATRLTPPHNGTAKFD
LLLEVLDTEHGLTGAFEYRPERFTAARVAQVRNHWEAALLTLLADPDLPVDARRPDFA
```

SEQ ID NO:3-CmnB amino acid sequence

```
MLSTVDPAAELSTTAAEVLEHVDAAVAAYPEVPIARVRVEVAGIPRTLLLKLEGRSPWRSIKGRTALGLVR
SIAPRMASRDVTVVESTSGNLGVALSAICRDLGLPFVAVVDLKQSPVIQAAIEANGARLEVVRTPAAATTH
LLDRLDRVRKLVAEIPGAVWPNQYENDANRHVHETWTAPEIDRQVGGEAQAFVAVSTGGTLAGLAAHFRR
ARPATRLVAVDVEGSTVFGGVPGGRVLTGIGASRRSTFLTRAECDDLVYVREAAAIAACHVLRADTGIAVG
GSSGAVVAGALDHLAAHPGLTTAVCVCADLGENYARTVYDPDWLAPLRLTDDPGLLRSRLRGARFHHAEPD
TGQESTP
```

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces capreolus*)

SEQ ID NO:4-CmnC amino acid sequence

MTAIREIRLSEPESAQAALLALECAQRYAEPDSADFLADAAVLAHDLPRAVRREVERARLDDRLHALVVRG
NDVDQDALGPTPPHWRQARTAASRRYGFLLVLYASLLGDVVGWATQQDGRVVTDVLPIEGQEDSLVSSSSS
VELGWHTEDAFSPYRADYVGLFSLRNPDSVATTVAGLDPDLVGPAVVDVLFGERFHIRPDNSHLPTHNSGG
RLSDYFAGIVEAVENPRAVSILRGHRDAPQLCVDSDFTTAVDGDAEAAGALDTLIKHLGGALYEVVLGPGD
VAFLDNRNVVHGRRPFRARFDGTDRWLKRINVTADLRKSRAARRDAQARVLGEA

SEQ ID NO:5-CmnD amino acid sequence

MMVRDLPAAALEDWLRERYFTARVDVSSSGVADHRLADLRRLGGITVEELDAVVFRDGPSLGAERLRAALA
DRLRPGPDHVVMTAHGSSEALFLAMTALVRPGDEVVVPDPAYHSLSALARACGAVLRPWPVLGAAPDPADL
RALLTPRTRLVVVNFPHNPTGVTVDAAVQAELLDVVGRSGAYLLWDNAFRDLVYDAPPLPEPTALGGRVLS
TGTLSKAHGLPGLRVGWCVLPADLAPELVRVRDYLTLSLSPLTELLAAVAVEHADELIAPRLAEATANRRR
LLDWAAAHGVDCPAPGGGVTAFPRFPGVADVTPLCDRLMSEHGVLTVPGGCFGFPDRMRIGFGCDPAVFAA
GLTALGAVLAEKRLPAKL

SEQ ID NO:6-CmnE amino acid sequence (23934 . . . 25181)

MAAIENAPRRLRDNRDFRFWWGGTVLSAIGDEVTLIAFPLLVLFLTGSPTHAGLVGGVAAVPPLLLSVPIG
VLADRTSRRALMLGGSVVSAISITSIPVVHLLGELTLPHLYVVAFVNSVAATVYRIADTAALPRIAGEEKL
GEAASQSETIWGISAIVAPPLAGLLFETAGPTSPFWIDAVSFVAIMVCVLAIRARLGADKPYPEVSWRQDL
TTGARVTLSRPLVRALTILTVAGDFLFAGIGLLLIVMVRENGASGLETGTVFTAAAVGGILGSMLAGRVED
RIGMVPAVLTKHWLTAALFPLLLVDLPGWATGLVWGLISFQISILNVIQMKYLMSVIPNSKLGRVEGFLTF
IEQGSLPLGYALTGVLLGLLGTTSTLLAYEAVLLVLAVFATVSRGLRTPAHPDEPARSSG

SEQ ID NO:7-CmnF amino acid sequence (25196 . . . 28366)

MTQVDFTRWDLRTDAEKHATPTVLSGPPPAWSPDTTLARLVLDQADRTPDADAVRIGPDALTYRELAAGAR
RVAAWVARQPHTGPPRVGVLGERSLATYPVLLGVLLAGGAYVPLDPAAPPARLRAVLSRADAHAVVTTAES
WALLEQPGLPALLTDQPLPFQRSKVDSGRVAVLAGLPDAGEPVGPTPDDVAYVIFTSGSTGTPKGVVVQHR
AAVNLTCWARDLVPMGPGSRVTQNASLHFDASVQQIFPALASGATLFPVPERVRLSGPELAAWLARHRITH
WDSVPSLWTPVVEHLADRIAAGQRVLPDLRAVLLAGEPLPARQVDRWRSWEQGHRLFNVYGPTEVTVNATA
FEVTGPVGAVVPIGRPLPGITASVLDAHGNPCPVDADGELFLGGVGLARGYLDDPEGTARSFVERGGERFY
RTGDVVRVGADGLLVFVGRRDDQVKLNGVRVEPAEIEHALLAHPGVTEAVAVVLREEGRAELVACVASAVE
LSTEDIRAGLAEELPAALVPSRVVVVESLPHNANGKLDRAACAELARDLSGPSGGAGPLGATAATLLGIWR
SVLGRDDIGPDDEFFQVGGNSITSIRLRRECVEAGLPIRAVDVFLHPTVRRLARYVDDNRTTLAARARPAP
EESPTDGEFPLLPAQRPLALTALLSDGGAQRGLVQETVTYRVPLDVDAVRGALEVLLERHEVLRTAVTPGL
AQRVLPKVPVPLEVVDLTGVADQWGAVLEAADRDYATPFDLAEPPLVRVRAFDRGEVFSLTWTLHHVISDG
WSWEIVQREFDRLHVALRAGRFRPLPPPVLPLRALARRLGSGGTPDPEWVARLAATPALLLPADGSGVGGE
HIEWPIDPGTHRELAARAQAAEASPAAIHLLAFTEALRRVCRQDSFAVGVVSSGRNVDVPGVEEAVACLAR
TVPLPVDAVGGAEARLARLHRDLAVVVGMDDVDTDVLPADVPAGVRHPVATFVFQNYPDAAVPPGHRPLPE
VPEEGRWREAGSDPLALVCFEDDGVPGCRLEFDTAAVSRATAELVAREVRRAQNRLAKGMQP

SEQ ID NO:8-CmnG amino acid sequence (28363 . . . 31221)

MTADAALEPDERAAWLAYNDTAEDFPGPHLLARLDAVAREHPDRPAVHAVDGVWTYRELHRRADAVAAFLA
ARGVRPGSVVAIAATRALAPYAALLGVLKAGCAYVPVNPDDPADRVAFVLADAGATPLLLDTDPASLPAAP
APDVPHEPDRVCYVIYTSGSTGRPKGVVMAERAVDNLTHWVVRRHDVRPDDRLGQTAPLTFDPSVQQVFPA
WATGACLVTVPDDVQRDPAAFLDWLRAERVTHLDLVTSHWVHLLNAAEARPAELPDLRWIIIGGETYYYHQ
THRWHRVVSSPARLNTIYGPTEAAVNATEHLTEPDLDHGQVPIGVPLPNYRLYALDDDGRLCPPGITGEIH
IAGAGLARGYRSAEEATAKAFHELEVHSGRTERLYRTGDLARLVRHADRWALEFQGRVDSQVKISGYRVELE
EVDAAVKAVPGVRDAAVVVRGEPAEQLVCCYVGDVPPDRLRSRLTERLPAYLVPHLLVPVEALPFTRNGKM
DTAELAELVRRFARDSAGRAPRPGVESVVAAVWAEVLDLPEVSADADFLGHGGSSLLAFRVVDRLRRRGIR
VRPADVLRERTVAGLAAVAEEDLVLTPSTRLALRRPGGNATLDIGLPADVPAERVRAVLEDIVRRHPVLRA
RIDDDGPRAVPVDRFELHTPDGPVDDAKARLAESTDLTTGLPTAAALVAGRLLVSIRHELVDGAALRRVAE
EVAAGLGRAPRPRPVVPVADQPLGGPAPDGLRGHLVRFLEAEKAALAALPREHRDRVVEVDLGHAPDALLD
TPPTRWHARLVAAAATAARSWLGLVDVPVGVPRHWPGAGGSVANLADVLPLVVADDDEADAQWRRFADPAV
HWGAALLDACPDLADDWPAPRIAPQGSFRLVVTADDEPLAPDLPLHESPTAFDPASAGAVEFAVVAGDRLR
LHVTGWDLPADEVKAVAAGWVEALAGERR

SEQ ID NO:9-CmnH amino acid sequence (31218 . . . 31964)

MTPDPHWLRPVGGRSGGPVLLCLPHAGAGAFAYAGWDRQDAFDVVAVQPPGREDRFAEQPITDPEHLVREI
ADALGDLAEQPLALFGHSLGALIAHDLARELDRRGAPDPLLLAVSGHVPPHRLDPDRARDRSDAELVEHVR
ELDDDPLDDVLADPEWRAMLLRPLRGDLALHDAHTHRPGPRLRVPVLALTGADDDATPAEDTAAWAELTEG
PFAHRVHPGGHFYLRAARSAVLDDLAHHLEGAWRP

SEQ ID NO:10-CmnI amino acid sequence (31961 . . . 33607)

MTTETPATTGAPATTGAPAPPGRAEIVAAVLPVFAEVLDAPDLTPDSDFFVHGGNSLLAIRVAGRVGRRLG
RQVPPAGVLKHPTPDLLAAHLEEEFRGGGAPPIPAPRAGAEADRRPSTAQERVWLLHQLDPDRLDHLVTVA

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces capreolus*)

LDVAGTVDPAAFTAAWTAVVRRHEALRSRFVKADDDRVAVVVDAEAAPEISVLDLARFPAPVRDRLAEERV
RLLRTTPIRLDTGPLARFALLRLADRRYRIELAVHHIVCDGWSLDTLLADFLDAYGRALAGRSPALPPPAV
GFADYVAWERDVESSRWPDMAVRLARRFADRPADLPLPVDPVDVPAHEDGDDVTVHAPPGLAAAVERARTS
FGHTALTFHLTALGVLLARITGVDDLVVAVPVAGRAQTEHEDLVGLFVNTALARVRLGGTSDVRVLLERNR
DEVDELVDCQTPFFDRLVDLLGARRAGTRVPLARVSLAVQNFDDPGTPAPELGFTWQFRDPPERQSKFDLA
FTVSDTDGLRLTVTYRPSLFRRATVAAWAGQYLVALEHVVRGVADPEGSAR

SEQ ID NO:11-CmnJ amino acid sequence (33604 . . . 34755)

MKLNRQHELFRESVRMVLDRECVELVDDWERDGVMPVHQLCKTLAAEGLLGLTMPVEDGGLGLDLGYSYVW
AQELGRVPAGAPAMALSVQTDIVAPLLARAGTPEVRRDVLRPAIRGELVAALAATEPAGGSDLGALTTTAV
RTERGFTVNGTKAFITNGSVADFAVVLCRTGEAAGIGDLALLVVPTNLAGVRQVRHTGKLGHRSCDHGTLT
FTDVEVPAAYLLGEVGEGYELQTRTFTRERCFLAVVALGQAERVLRATVHHARRRRVLGRALTDHQAIGFR
LAELDAELDLVRSYAGEAYQLLADGAQCLREASIAKLRATRLLREVADVGLQVRGAAGYLGVDDVERTYRD
ARAGSFAGGADEALLHLIAGHLTGTEQE

SEQ ID NO:12-CmnK amino acid sequence (34758 . . . 35756)

MTPSEELLFLDRETVRACVAGVDPVEVVESVLRSHAAGRTTLPAEGYLPWENDQGAYCRSIAMLGAVDGER
GPTYGIKLINAAVSNPSIGLDRAGGCGFLFDPRTARPVVLAEAAYLSGLRTAAYTMASLRHLGPVGPDAVS
FIGTGAQARVHAALLARYFPAVRDLHVFDTERSRAEAFTGASGHTVHVHDTAEAAVRASHVLVTLTTVDDG
YIPHDWFRPGSPVAHVSLDDLLPEVFFKSEALFVDDLELIRENPRRVLGALLADGDVPVTGSLGGVLTGAV
APVRPRDGVVVSNPFGMAVLDVGLLAEVAAHARSAGLGTTLDLLGAAR

SEQ ID NO:13-CmnL amino acid sequence (35753 . . . 36640)

MTGLYSLADLSPADVLALADRSVQLHRDRTAHDRPLTDLVVGTLFTKTSTRTRTAFTTAALRLGASVVAFG
PDELQTATGESTADTGRVLASMLDGLVVRTAGPVARQRELSGGGVLPVVNAMSREEHPTQGLTDLAVLRHH
FGDLAGVRVLYVGEGNNTAAALVHALAAVPGCELVLACPKGYGPRDPGPWREVADLAEVTGDVDVVYTTRW
QTTGTAKADPDWREAFRPFHVDTALMDRWPDAVFLHDLPAHRGEEVAGAVLDGARSLAWTQAAMKAASAMA
VLERFVGGRRA

SEQ ID NO:14-CmnM amino acid sequence (36633 . . . 37838)

MLDLSPAQRSLWVLHQLDDTGFTLSSAHRLRGPFDLGAFTAAVDAVVARHSPLRTRFPVGTDGGPDPVVDP
PGPVVVEAVAAEGFTAAHAEAARFCARPFDLAREWPLRVLVVRLSTEDHVVALAVHHISCDGVSLGLLHDE
LSRLYDGAELPPVADHRELVARRAVDPAAVARCRDRLAGVPPLAADRPAVRSGKGDQVWFTVPADLTGAVR
ACARRHRVTAFMVLLAAFQLVLHRRTGQTDFAVGVPVAGRGDPDSENVIGLFTNTVVVRADLAGEPGPAEV
LRRVREAAFDAFADQDVPLGAVVAAVGEPPDPARTPLFQALFTFQDAPVGRLALPGVRCVELDLPTGAAAS
DLELELVRDGDELAGSLEYSTDLHDSGTAAALTADFLAVLDEITAE

SEQ ID NO:15-CmnN amino acid sequence (37847 . . . 38035)

MDTYLVVVNHEEQYSVWPADRPLPAGWRAEGTSGDKEQCLAHIETVWTDMRPLSVRRRAEAV

SEQ ID NO:16-CmnO amino acid sequence (38032 . . . 39786)

MTALHRLDQLAGARPDAPALLDEAETVSYGRLWRELTGVAGALRAAGVRRGDRVVVPADRTWQGIVSMLGV
LRAGAAYVPVDAGDPVERLRHVVRTAGAAWVTGRAEALAALPDLGLHPIPFGSAPDSASRSASGSDSGSHS
ASGGVGGLPDPEDLAYVMFTSGSTGTAKAVMVPHRSIAHAAPSLARRCGITPDDRFLSWASLVWDTSGEEL
YSTLLSGAGLVLDREATSGSVPALLRAVERRSVSVVDLPTAFWNQVVDYLETTGEAVPECLRLVVVGGEEV
RARQVRVWAERAPDVRLLNTYGQTETVMVTHAADIGGLAPPDGGAVPIGHPLPHVRQHLEPVGDGLFELHV
GGPTLAWGYRDRPAATAERFPPDERGRRFRTGDLVRVADDGALVFVGRADRQVKVRGVRVEPAEVERALMA
CPGVTAAAAFVVDNASDGVLLVGAFVPGDGDATPATVAAALRTRLSPALLPHRLVSVPSMPLLTTGKIDQA
ALVERFARSDVAPGAGLAGQLAVVFSEVLGTPCAADDDFFDQGGDSVVATRLLTRIRRSYRVELTFRDVFD
HPSPTALAGLISRTPR

SEQ ID NO:17-CmnP amino acid sequence (39792 . . . 41138)

MPVQPHEHVRRTPVEPSWRRFPGWRDVTREQWRDPRWQRVHCVRNTRQLRAVVGDLLDERFYDDLAADQES
FATMSMLLPPQMLNTMVPEGAADFTGAFYADPVRRYMLPVRSDRDPEWPSHPYSSRDSLHEAEMWVVEGLT
HRYPTKVLAELVSTCPQYCGHCTRMDLVGNSTPQVRKHKLELKPVDRQDRMLDYLRRTPAVRDVVVSGGDV
ANVPWPQLESFLARLLEIETVRDIRLATKALAGLPQHWLQPQVVEGMSRVARTAASRGVNLAVHTHVNHAQ
SVTPLVAEEAARALLDAGVRDVRNQGVLMRGVNATPDDLLELCFALQGEANILPYYFYLCDMIPNAEHWRTS
VAEAQDLQAAIMGYLPGYATPRIVCDVPYVGKRWVHQVVEYDRELGVSYWTKNYRTGIESDDPNALDRRYP
YYDPISTLGETGRRWWRKHERA

SEQ ID NO:18-CmnR amino acid sequence (11212 . . . 11925)

MLTPAGAGRARRGIAVLLADDHEVILDGLRAVLARDDAITVVGAVHGVPELLDRIGRDQPDVVLVGASLLR
VDDFRVARLLAGQRVVATQDDSDELLVSAIAAGVSGYLPLGSPGEEFPRAIRAVAEGGAYLPAHVTKRVF
ESFQIIPLPDPSAPALLSLTEREGQVLRAIGQGRSNREIAREFEVSETTVKSHVSRVLAKLELRDRVQAAL
LAWRLGLVTAREAPEVVKPRGASA

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces
capreolus*)

SEQ ID NO:19-CmnU amino acid sequence (12265 . . . 12984)

MPSEGLVKVVGKRCVPLADAEFAELRARHRSVLLDVGTGDGKHAYRLARADPDRLVVGVDANPDRMRGVSA
RAAAKPARGGLPNLVLVHAAAEEMPPCLGDVDEMHVLMPWGSLLRGVLGRDPAVLAGLAGACRAGARFHIT
VNLHAWRPAAPAVTGIAEPTPEWVRRELAHVYAEAGLRVTRAGYLADVGASELTSTWTRRLGACREEFDVL
GVEGAARGGSTPGVAGITSKAACLPA

SEQ ID NO:20-Cph amino acid sequence (42119-41274) (see GenBank Acc.
No. U13078)

MTLSHLVDVVRRAHPDVDLEGAGVHSGQFHDVLIARDRVFRFPKTAGAAAELPGRVAVLTAVDAVELGVGV
PVPLSEVRDGGPHGFLVLSRLHGTPLERGDATSPEVIDVVAAEFARVLRAMAGADVEKLRLVLPVADAGRW
RGFAGRVRATLFPLMSEDGRARAERELAAAVAMDHVATGLVHGDLGGENVLWQQVEELPRLTGIVDWDEAK
VGDPAEDLAAVGASYGPELVERVVALLGAGDLWPRIRAYQGTFALQQALAGAEDGDDEELEDGLTAYR

SEQ ID NO:21-orf 1 (141 . . . 644)

MSRWCGGMPDGGDVVMSSQSWDAGDESGDEVVLALDGVAVREVRDLVRDLLSDRAGVAVDDAVLVVDELVS
NALRHGEPPRRCRLVRAGQRLRVEVDDAGSGQPRIRTADASGGRGLVIVQALSTDWGVVRHPEHKTVWAEV
LLAGQSRPSHVAPAQTWGDTPAQGR

SEQ ID NO:22-orf 2 (804 . . . 1376)

MTSTENDLLLDKIGRGFDHLDADGDGLLDERDHVLMGERVAAALGHGSGSAEEERIVDMYVRVWHDVHLPH
LPAGTTAIGRDEFIAATRDLADDPAAADATLGALAREFLRIADIDADGRVTPAEFLTFQRGHFPDLSDEDA
AAAFEHLDTDGDGSLSPEEFIRATVEYWTSTDPDSPANWWIGRPRPTA

SEQ ID NO:23-orf 3 (1383 . . . 2123)

MGVTAAPLASMGPTRSRSTPTIGGQPHLERDRARVRGMVRLGVVALLLATVASACAAEEPEYVSLIEACDL
VDPGTVTALSRGLPAAPPSREPVRFSDDRVDMVECRHEFGDSGNVPVLPHDDWAPDTPGTPLYRYVTVTVM
RYRAGDGRSATGNARHHLASDPQAKDPAITGAGLDDGDVMHKYNGVQSYSRVRAVDHNVFLTVEYGGANGN
ARPQGMPADESREGALRLLTGAASRLPCPKPGC

SEQ ID NO:24-orf 4 (2159 . . . 3442)

MKLRAGLLTAALLLLGTNAMAAAPDSTPFYWQVPGADERTLQDAGFDVEHGVDGGVQVVGDARVAGRLTAL
GYQPKFDTVYKPVPPGRSGDIGVQTFYGGYHTVAEHEKHLTDVAAAYPALTQVFDIGDSWRKTRGLGGHD
IKAICITKKQAGDCALSPTSPKPRFAMIAQLHARELATGELAWRWIDHVTRGYGTDAEVTSILDTTELWVV
PIVNPDGVDIVASGGSRPLMQRKNANNTGASCSVPSYGVDLNRNSTFKWGGAGTNRCGETYQGTAAGSEPE
TRALEAWFKQLFPDQRGPGDTDPAPVTTKGVMITIHSYGNLIMPPWGWTWNANPNAAQLAALGKKMAAFNG
YTVVAEGDTTGTTDDFTYGTLGIASYTFEIGSSSGSCGGFFPQYSCVDSLFWPRNKGAFLTAAKAAKAPYA
S

SEQ ID NO:25-orf 5 (3462 . . . 4862)

MRITDVQRCEVRPGRVVEWVLRPVAAATGAPDDARPPAYLQESHVRTARSLREDGLFVPTWLGVAFDLPGA
VDLDALEEALRVWTLRHETLRSGFRWEDGEMRRFTLDADAVALHREDVGEFTDADVLVQHLQDRFDVAADT
LTWPNFIYAAVAREDSTSVYLAFDHSNVDAYSMYRVPAELHELYAAALDGRTVDAAPIASYVDFCATERAD
ADEVGADHPVVDRWRRFVARCDGRMPNFPPFDLGLAPGGPLPTQKSLHEMLVDDADAAAFERHCRPYGGSLV
GVLAATALIMREMTGDDVYRTVVPFHTRAKSRWSDSVGWYVGGVPVELPVATAGGFDGLLRAAQAELRASR
PASRVPVARVLRLLGDDFRPTSPDLYSIVSFMDARPTPGSERWRDMKAYGLIRVSYGDQVCVWVTRLHEGL
QFACRYPDNDVAYKNIRLYVDRLREVILSVARPADAPAAG

SEQ ID NO:26-orf 6 (5150 . . . 5752)

MTSRFAQVMFTPDVQLHQERHGSRDAYARMADAAPVRDRIGPDEAAFIAERDSFYLATVGETGWPYIQHRG
GPPGFLRVLDEHTLGFADFRGNRQYITRGNLDHDDRVALFLMDYANRTRLKLIGHARADDSPEVVERLALP
DYRAKVERAVLIEVEATIWNCRQHIPQLFPRDAVEQAVGALRDRITELEQENARLRAR

SEQ ID NO:27-orf 7 (5861 . . . 6376)

MSGRLHAPAIGTARLDLVPLRVDHAEEMAVVLADPALHTFTGGTPDDPRALRSRYERMLAGSPDPAVSWLN
WVVRLREESRLAGTVQATVGPTDQGPVAEVAWVVGTPFQGRGIAREAARGLVDWLGRQGVRTVVAHVHPDH
HASAAVATAAGLAPTDEVHDGEVRWRLSR

SEQ ID NO:28-orf 8 (6395 . . . 7591)

MSLDERKLFAARLHAVRCRPYLATALFALHVVESRRVPTMAVDRHWRCYVSPAFVDRTPEEELAGVWVHEV
SHLLRDHHGRGDRFAAEHGLTGPGERLRMNIAADCEINDDVFGDGLARPEGAVEPELLQLREGQLMEDYLR
QFRLGPYTDAFTWLDCGSGADGLEREWDLGPDGAHGLSEQERDAVRFRVAEAITGRPGDVPLGWRRWAERA
FHPPQPWRDLLGAAVRSAASAAGAGDDYTYGRPARRSTALPGVVLPSLRRRPPRVCVVVDTSGSVSDAELG

TABLE 8-continued

CMC Biosynthetic Gene Cluster Sequence
(corresponding to GENBANK ACC. NO. EF472579; specifically incorporated
by reference for the sequences disclosed therein and start/stop
position for individual genes in the cluster; sequence isolated from
*Saccharothrix mutabilis* subsp. *capreolus* (previously *Streptomyces capreolus*)

SALLEIAAIARAVGGRRDLVSVLSCDAAAHVTHPLCRAEGIPLMGGGGTDLRTGFTRALRTRPDVIVALTD
GQTPWPTVRPPCRTVVGLFRRPPKPGDYRPDPPPAWARVVTVG

SEQ ID NO:29-orf 9 (7588 . . . 8802)

MPTSLSARPLDVAADLLALLGRTTTETRSDAQLEALTLAVSADLPVLLWGEPGIGKTAALTQLADALDLPL
TTVIASVHEPSDFAGLPVVGDDPAVQGVPMAPPDWAVRLVRAGRGLLFLDELSTAPPAVQAALLRVVLERR
IGALTLPPGVRIVAAANPRSSAADGWELSPPLANRFVHLQWAHDHDVVVRGLGGTWPRAELPRLDPGRLPD
AVAYARRAVCELLAARPNLVHQLPKDETRRGGPWPSPRSWEMALRLIAFATAADVSRDVLSMLVRGTVGDG
PGLELLASLDRMDLPDPESLLANPAAAVLPERGDLRQAVLDGVVEAVRRRPEAARWDAAWALLVRALDTGA
PDLVVVPAATLAALRRDDWEVPAAIERLSGAVSVSRLADRTAARVGAGR

SEQ ID NO:30-orf 10 (8863 . . . 9531)

MITVRLNAGRWLALAPDEPTPVLTAAPRRDPTRPVLPDAATRTPPDLDLLRAGLVDADRLHPLVASALVPG
HRRTTGSPDPATGPRLVECRGATHRIGVVDGVLVPLDHDPDEVRREELLAEWGGPPLPCLRAIDDVHRQPE
SLVDVRARLDHGDTAGAVAAVEALLGPEALLRAGALRDELDAAVRRRLAHGLYRAGLAGGPAPSTKDGRRR
VRPRHAFSR

SEQ ID NO:31-orf 11 (9528 . . . 10286)

MLMHHTTADENLRLHFWTRVREFAVPPSMVETATARRSVGDWAGACAAARFDVDLDLRAVGRTHGRQLAAQ
VRADLRHLAPDLLRWHFPRIGPDGLLRPGLTVSLARYAAGPHLVARTPPAWAAAGQRISLAWWDPAEPRAG
AGTHPHPRPDRRFRLDLHRHLWDARRAGELRERSAGGDPPPGFDHRAARSRLAGRRVAGSRGARRVRGPSG
RRQPRDPPRRGPSRGRVSLSVVGCRRPCSSCARTGAPTA

SEQ ID NO:32-orf 12 (10362 . . . 11108)

MAGTDLYDDIGTGYALGRRTDPRWMTAILDALGGARTIANVGAGTGSYEPDDRTVVALEPSTEMIRQRPPE
VGPAVRAVAEALPLRDHAVDAALAVLTVHHWTDWRAGLAELRRIAPRRVVLAYDTSLHTEFWFVREYVPEI
ADLERTRPSAADIAGELGADSVTPLPLPWDFVDGVFPAYWRRPDAYLDPRVRRACSALAQTDPAAVDRGVR
RLRADLDSGRWHDDHRDLLDLDQWDAGFRLVVSHT

SEQ ID NO:33-orf 13 (42340 . . . 43176)

MGNGERIGVFYDGTWFAYLSDYFASVHPRAARVSLDGFHDALRWYVHTVTHQPLDECVVSEAHYVRGRIDT
PAVAFDAVLAAAGVVRHDLPLHAGKEKGVDVHLALEAWERATSVPLRWVVLVTGDADFAPLATRLKTRGVR
VVVPVVDGGVVAPAWMPRTAAPLRAAASATPTFDDLFTPAERDDYPLRAPFVRTSGGGASVAGEPRGRRKG
TVTGWKTGQPHGFITDTRGASWFVSRDDLPLGLVALPVGTSVSFSGPSTPPAGRKYPRAYAVQTE

SEQ ID NO:34-orf 14 (43177 . . . 43914)

MSKQPDSLRTTVVVPTYNERDNLPVLVDLLADLGVPGLHVLVVDDNSPDGTGDLADKLALEGPLPLSVLHR
TEKDGLGRAYVAGILKALDDGADLVVQMDADLSHPASAIPTMIEVLRTSDAAVVIGSRYVPGGSVSGEWKW
HRKALSLWANVYVNAILRLRVKDATAGFKCWRAATLRRIDVGSIRSNGYAFQVEMNHRVVKRGMRIAEVPI
RFEERAEGASKMSFGVQLESAVMPWKLLFKKG

;1

We claim:

1. An isolated and purified nucleic acid molecule that encodes a Capreomycin A (CmnA) gene product having at least 95% sequence identity to the amino acid sequence of SEQ ID NO:2, wherein the CmnA gene product is a non-ribosomal peptide synthetase product capable of forming a peptide bond between a peptide that comprises L-2,3-diaminopropionate and L-serine or L-alanine.

2. The nucleic acid molecule of claim 1 wherein the molecule encodes at least one additional gene product selected from the group consisting of:
   a CmnB gene product having an amino acid sequence at least 95% identical to the amino acid sequence set forth in SEQ ID NO:3 and having 2,3-diaminopropionate synthase activity,
   a CmnC gene product having an amino acid sequence at least 95% identical to the amino acid sequence set forth in SEQ ID NO:4 and having L-arginine hydroxylase activity,
   a CmnD gene product having an amino acid sequence at least 95% identical to the amino acid sequence set forth in SEQ ID NO:5 and having capreomycidine synthase activity,
   a CmnE gene product having an amino acid sequence at least 95% identical to the amino acid sequence set forth in SEQ ID NO:6 and having permease activity,
   a CmnF gene product having the amino acid sequence set forth in SEQ ID NO:7,
   a CmnG gene product having an amino acid sequence at least 95% identical to the amino acid sequence set forth in SEQ ID NO:8 and having non-ribosomal peptide synthetase pentapeptide cyclization activity, a CmnH gene product having an amino acid sequence at least 95% identical to the amino acid sequence set forth in SEQ ID NO:9 and having Type II thioestererase activity, a CmnI gene product having the amino acid sequence set forth in SEQ ID NO:10, a CmnJ gene product having an amino acid sequence at least 95% identical to the amino acid sequence set forth in SEQ ID NO:11 and having 2,3-diaminopropionyl α,β-desaturase activity, a CmnK gene product having an amino acid sequence at least 95% identical to the amino acid sequence set forth in SEQ ID NO:12 and having ornithine cyclodeaminase activity, a CmnL gene product having an amino acid sequence at least 95% identical to the amino acid sequence set forth in SEQ ID NO:13 and having carbamoyltransferase activity, a CmnM gene product having an amino acid sequence at least 95% identical to the amino acid sequence set forth in SEQ ID NO:14 and having non-ribosomal peptide synthetase condensation β-lysine transferase activity, a CmnN gene product having the amino acid sequence set forth in SEQ ID NO:15, a CmnO gene product having an amino acid sequence at least 95% identical to the amino acid sequence set forth in SEQ ID NO:16 and having non-ribosomal peptide synthetase carrier protein β-lysine thioesterification activity, a CmnP gene product having an amino acid sequence at least 95% identical to the amino acid sequence set forth in SEQ ID NO:17 and having lysine 2,3-aminomutase activity, a CmnR gene product having an amino acid sequence at least 95% identical to the amino acid sequence set forth in SEQ ID NO:18 and having transcriptional regulator activity, a CmnU gene product having an amino acid sequence at least 95% identical to the amino acid sequence set forth in SEQ ID NO:19 and having capreomycin resistance activity, and a Cph gene product having an amino acid sequence at least 95% identical to the amino acid sequence set forth in SEQ ID NO:20 and having capreomycin resistance activity.

3. The nucleic acid molecule of claim 1 which further encodes a CmnF gene product having the amino acid sequence set forth in SEQ ID NO:7, a CmnG gene product having an amino acid sequence at least 95% identical to the amino acid sequence set forth in SEQ ID NO:8 and having non-ribosomal peptide synthetase pentapeptide cyclization activity, a CmnI gene product having the amino acid sequence set forth in SEQ ID NO:10, and a CmnJ gene product having an amino acid sequence at least 95% identical to the amino acid sequence set forth in SEQ ID NO:11 and having 2,3-diaminopropionyl α,β-desaturase activity.

4. The nucleic acid molecule of claim 1 which further encodes:

a CmnM gene product having an amino acid sequence at least 95% identical to the amino acid sequence set forth in SEQ ID NO:14 and having non-ribosomal peptide synthetase condensation β-lysine transferase activity, a CmnO gene product having an amino acid sequence at least 95% identical to the amino acid sequence set forth in SEQ ID NO:16 and having non-ribosomal peptide synthetase carrier protein β-lysine thioesterification activity, and a CmnP gene product having an amino acid sequence at least 95% identical to the amino acid sequence set forth in SEQ ID NO:17 and having lysine 2,3-aminomutase activity.

5. The nucleic acid molecule of claim 1 which further encodes:

a CmnB gene product having an amino acid sequence at least 95% identical to the amino acid sequence set forth in SEQ ID NO:3 and having 2,3-diaminopropionate synthase activity, a CmnC gene product having an amino acid sequence at least 95% identical to the amino acid sequence set forth in SEQ ID NO:4 and having L-arginine hydroxylase activity, a CmnD gene product having an amino acid sequence at least 95% identical to the amino acid sequence set forth in SEQ ID NO:5 and having capreomycidine synthase activity, a CmnE gene product having an amino acid sequence at least 95% identical to the amino acid sequence set forth in SEQ ID NO:6 and having permease activity, a CmnF gene product having the amino acid sequence set forth in SEQ ID NO:7, a CmnG gene product having an amino acid sequence at least 95% identical to the amino acid sequence set forth in SEQ ID NO:8 and having non-ribosomal peptide synthetase pentapeptide cyclization activity, a CmnH gene product having an amino acid sequence at least 95% identical to the amino acid sequence set forth in SEQ ID NO:9 and having Type II thioestererase activity, a CmnI gene product having the amino acid sequence set forth in SEQ ID NO:10, a CmnJ gene product having an amino acid sequence at least 95% identical to the amino acid sequence set forth in SEQ ID NO:11 and having 2,3-diaminopropionyl α,β-desaturase activity, a CmnK gene product having an amino acid sequence at least 95% identical to the amino acid sequence set forth in SEQ ID NO:12 and having ornithine cyclodeaminase activity, a CmnL gene product having an amino acid sequence at least 95% identical to the amino acid sequence set forth in SEQ ID NO:13 and having carbamoyltransferase activity, a CmnM gene product having an amino acid sequence at least 95% identical to the amino acid sequence set forth in SEQ ID NO:14 and having non-ribosomal peptide synthetase condensation β-lysine transferase activity, a CmnN gene product having the amino acid sequence set forth in SEQ ID NO:15, a CmnO gene product having an amino acid sequence at least 95% identical to the amino acid sequence set forth in SEQ ID NO:16 and having non-ribosomal peptide synthetase carrier protein β-lysine thioesterification activity, a CmnP gene product having an amino acid sequence at least 95% identical to the amino acid sequence set forth in SEQ ID NO:17 and having lysine 2,3-aminomutase activity, a CmnR gene product having an amino acid sequence at least 95% identical to the amino acid sequence set forth in SEQ ID NO:18 and having transcriptional regulator activity, a CmnU gene product having an amino acid sequence at least 95% identical to the amino acid sequence set forth in SEQ ID NO:19 and having capreomycin resistance activity, and a Cph gene product having an amino acid sequence at least 95% identical to the amino acid sequence set forth in SEQ ID NO:20 and having capreomycin resistance activity.

6. An expression cassette comprising the isolated and purified nucleic acid molecule of claim 1 operably linked to a functional promoter which permits capreomycin production in a host cell when said host cell is transformed with said expression cassette.

7. An isolated, recombinant, host cell transformed with at least the isolated and purified nucleic acid molecule of claim 1 and capable of expressing the encoded CmnA gene product.

8. The isolated, recombinant, host cell of claim 7 in which capreomycin levels are increased relative to the levels in a corresponding nonrecombinant host cell.

9. The isolated, recombinant, host cell of claim 7 wherein the recombinant host cell is a prokaryote or a eukaryote host cell.

10. The isolated, recombinant, host cell of claim 7 wherein the recombinant host cell is a cell of the genus *Streptomyces*.

11. The isolated, recombinant, host cell of claim 7 wherein the recombinant host cell is *Streptomyces coelicolor*.

12. A bacterial strain, other than a strain of *Saccharothrix mutabilis* subsp. *capreolus*, transformed with at least the isolated and purified nucleic acid molecule of claim 1.

13. The bacterial strain of claim 12 which is a strain of *Streptomyces*.

14. The bacterial strain of claim 12 which is a strain of *Streptomyces lividans*.

15. The bacterial strain of claim 12 which is a strain of *Streptomyces coelicolor*.

16. The bacterial strain of claim 12 which produces one or more of Capreomycin IA, IB, IIA and IIB.

17. The bacterial strain of claim 12 which produces Capreomycin IA, IB, IIA and IIB.

18. The bacterial strain of claim 12 which produces a derivative of capreomycin.

19. The bacterial strain of claim 18, wherein the derivative is selected from the group consisting of: C19hydroxy-CMN IA, C19hydroxy-CMN IB, C19hydroxy-CMN IIA, C19hydroxy-CMN IIB, Pseudocapreomycin IA, Pseudocapreomycin IB, Di-beta-lysyl-CMN IIA, Di-beta-lysyl-CMN IIB, C19-hydroxy-pseudo-CMN IA, C19-hydroxy-pseudo-CMN IB, C19-hydroxy-di-beta-lysyl-CMN IIA, C19-hydroxy-di-beta-lysyl-CMN IIB, and

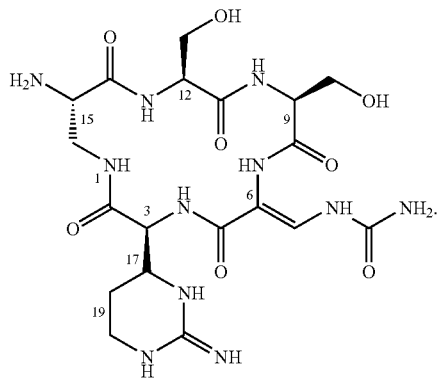

20. An isolated and purified nucleic acid molecule that encodes a polypeptide having the amino acid sequence set forth in SEQ ID NO:2 (CmnA) and which further encodes a polypeptide selected from one or more of the group consisting of SEQ ID NO:3 (CmnB), SEQ ID NO:4 (CmnC), SEQ ID NO:5 (CmnD), SEQ ID NO:6 (CmnE), SEQ ID NO:7 (CmnF), SEQ ID NO:8 (CmnG), SEQ ID NO:9 (CmnH), SEQ ID NO:10 (CmnI), SEQ ID NO:11 (CmnJ), SEQ ID NO:12 (CmnK), SEQ ID NO:13 (CmnL), SEQ ID NO:14 (CmnM), SEQ ID NO:15 (CmnN), SEQ ID NO:16 (CmnO), SEQ ID NO:17 (CmnP), SEQ ID NO:18 (CmnR), SEQ ID NO:19 (CmnU), and SEQ ID NO:20 (Cph).

21. An isolated and purified nucleic acid molecule that encodes a CmnA gene product having the amino acid sequence set forth in SEQ ID NO:2.

22. The nucleic acid molecule of claim 21 further comprising a nucleic acid sequence which further encodes one or more polypeptides having an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

23. The nucleic acid molecule of claim 21 comprising the nucleic acid sequence set forth in SEQ ID NO:1 from position 13445 through position 20650.

24. The nucleic acid molecule of claim 21 comprising the nucleic acid sequence set forth in SEQ ID NO:1 from position 11212 through position 42119.

25. The nucleic acid molecule of claim 21 comprising a capreomycin gene cluster.

* * * * *